(12) United States Patent
Mohan et al.

(10) Patent No.: US 11,136,329 B2
(45) Date of Patent: Oct. 5, 2021

(54) JAK INHIBITORS

(71) Applicant: Vimalan Biosciences, Inc., Encinitas, CA (US)

(72) Inventors: Raju Mohan, Encinitas, CA (US); John Nuss, Encinitas, CA (US); Jason Harris, Encinitas, CA (US); Shendong Yuan, Encinitas, CA (US)

(73) Assignee: VIMALAN BIOSCIENCES, INC., Encinitas, CA (US)

( * ) Notice: Subject to any disclaimer, the term of this patent is extended or adjusted under 35 U.S.C. 154(b) by 0 days.

(21) Appl. No.: 16/869,433

(22) Filed: May 7, 2020

(65) Prior Publication Data

US 2020/0369669 A1   Nov. 26, 2020

Related U.S. Application Data

(60) Provisional application No. 62/845,119, filed on May 8, 2019, provisional application No. 62/884,588, filed on Aug. 8, 2019.

(51) Int. Cl.
 *C07D 487/04* (2006.01)

(52) U.S. Cl.
 CPC .................. *C07D 487/04* (2013.01)

(58) Field of Classification Search
 CPC .................. C07D 487/04; C07D 471/04
 See application file for complete search history.

(56) References Cited

U.S. PATENT DOCUMENTS

| | | |
|---|---|---|
| 8,580,802 B2 | 11/2013 | Salituro et al. |
| 9,642,855 B2 | 5/2017 | Galatsis et al. |
| 2009/0203688 A1 | 8/2009 | Gaul et al. |
| 2010/0190787 A1 | 7/2010 | Kasibhatla et al. |
| 2012/0207763 A1 | 8/2012 | Brain et al. |
| 2012/0252779 A1 | 10/2012 | Ramsden et al. |
| 2018/0186800 A1 | 7/2018 | Yamamoto et al. |
| 2021/0040100 A1 | 2/2021 | Mohan et al. |

FOREIGN PATENT DOCUMENTS

| | | |
|---|---|---|
| WO | WO-2011048082 A1 | 4/2011 |
| WO | WO-2012143320 A1 | 10/2012 |
| WO | WO-2020227563 A1 | 11/2020 |

OTHER PUBLICATIONS

Berge et al. Pharmaceutical Salts. Journal of Pharmaceutical Sciences 66(1):1-19 (Jan. 1977).
Morshed et al.: Computational approach to the identification of novel Aurora-A inhibitors. Bioorg Med Chem.19(2): 907-916 (2011).
National Center for Biotechnology Information (2020). PubChem Compound Summary for CID 11847933. Retrieved Sep. 25, 2020 from https://pubchem.ncbi.nlm.nih.gov/compound/11847933. (8 pages).
National Center for Biotechnology Information (2020). PubChem Compound Summary for CID 68948833. Retrieved Sep. 26, 2020 from https://pubchem.ncbi.nlm.nih.gov/compound/68948833. (8 pages).
PCT/US2020/031925 International Search Report and Written Opinion dated Sep. 16, 2020.
PCT/US2020/045431 International Search Report and Written Opinion dated Dec. 15, 2020.
PCT/US2020/045431 Invitation to Pay Additional Fees dated Oct. 6, 2020.
PCT/US2020/052556 International Search Report and Written Opinion dated Feb. 8, 2021.
PCT/US2020/052556 Invitation to Pay Additional Fees dated Nov. 19, 2020.

*Primary Examiner* — Susanna Moore
(74) *Attorney, Agent, or Firm* — Wilson Sonsini Goodrich & Rosati

(57) ABSTRACT

Described herein are Janus kinase (JAK) inhibitors of Formula (I'):

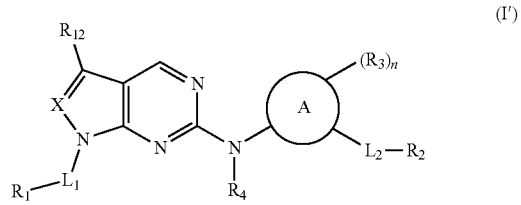

Also described herein are methods of utilizing JAK inhibitors of Formula (I') in the treatment of diseases, disorders or conditions and pharmaceutical compositions containing such compounds.

19 Claims, No Drawings

JAK INHIBITORS

CROSS-REFERENCE

This application claims benefit of U.S. Provisional Application No. 62/845,119, filed on May 8, 2019 and U.S. Provisional Application No. 62/884,588, filed on Aug. 8, 2019, both of which are herein incorporated by reference in their entirety.

BACKGROUND OF THE INVENTION

Janus kinase (JAK) is a family of intracellular, nonreceptor tyrosine kinases that transduce cytokine-mediated signals via the JAK-STAT pathway. The four JAK family members are Janus kinase 1 (JAK1), Janus kinase 2 (JAK2), Janus kinase 3 (JAK3), and Tyrosine kinase 2 (TYK2) and have been shown to be key components of cytokine-mediated effects. The critical function of JAKs in cytokine signaling has implicated JAK inhibitors as potential therapeutics for a variety of diseases, including autoimmune and inflammatory diseases.

SUMMARY OF THE INVENTION

In one aspect, provided herein are compounds of Formula (I'):

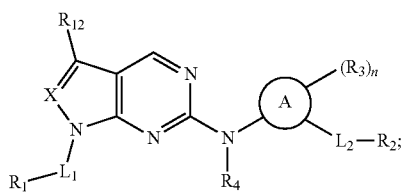

Formula (I')

wherein:

is phenyl or a $C_2$-$C_9$heteroaryl ring;
$X$ is $C(R_{11})$ or $N$;
$L_1$ is $C_1$-$C_6$alkyl or $C_1$-$C_6$heteroalkyl;
$L_2$ is a bond, $C_1$-$C_6$alkyl, or $C_1$-$C_6$heteroalkyl;
$R_1$ is $C_3$-$C_9$alkyl, $C_2$-$C_6$alkenyl, $C_2$-$C_6$alkynyl, $C_3$-$C_6$cycloalkyl, $C_2$-$C_9$heterocycloalkyl, or $C_2$-$C_9$heteroaryl, wherein $C_3$-$C_9$alkyl, $C_2$-$C_6$alkenyl, $C_2$-$C_6$alkynyl, $C_3$-$C_6$cycloalkyl, $C_2$-$C_9$heterocycloalkyl, or $C_2$-$C_9$heteroaryl are optionally substituted with 1, 2, or 3 $R_5$;
$R_2$ is —C(=O)O$R_6$,

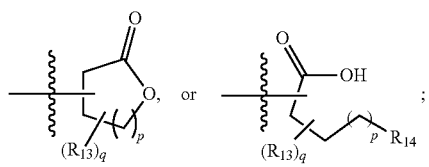

each $R_3$ is independently selected from halogen, $C_1$-$C_6$alkyl, $C_1$-$C_6$haloalkyl, $C_1$-$C_6$heteroalkyl, —O$R_7$, —N($R_7$)$_2$, —CN, —C(=O)$R_8$, —C(=O)O$R_7$, —C(=O)N($R_7$)$_2$, —N$R_7$C(=O)$R_8$, —N$R_7$S(=O)$_2$$R_8$, —S(=O)$_2$$R_8$, and —S(=O)$_2$N($R_7$)$_2$;

$R_4$ is hydrogen, $C_1$-$C_6$alkyl, or $C_1$-$C_6$heteroalkyl;
each $R_5$ is independently selected from halogen, oxo, $C_1$-$C_6$alkyl, $C_1$-$C_6$haloalkyl, $C_1$-$C_6$heteroalkyl, —O$R_7$, —N($R_7$)$_2$, —CN, —C(=O)$R_8$, —C(=O)O$R_7$, —C(=O)N($R_7$)$_2$, —N$R_7$C(=O)$R_8$, —N$R_7$S(=O)$_2$$R_8$, —S(=O)$_2$$R_8$, and —S(=O)$_2$N($R_7$)$_2$;

$R_6$ is hydrogen, $C_1$-$C_6$alkyl optionally substituted with 1 or 2 Y, $C_3$-$C_6$cycloalkyl optionally substituted with 1 or 2 Y, $C_2$-$C_9$heterocycloalkyl optionally substituted with $C_1$-$C_6$alkyl, or —$C_1$-$C_6$alkyl-$C_2$-$C_9$heterocycloalkyl optionally substituted with $C_1$-$C_6$alkyl;

each Y is independently selected from —CN, —O$R_9$, —S$R_9$, and —N($R_{10}$)$_2$;

each $R_7$ is independently selected from hydrogen, $C_1$-$C_6$alkyl, $C_2$-$C_6$alkenyl, $C_1$-$C_6$haloalkyl, and $C_1$-$C_6$heteroalkyl;

each $R_8$ is independently selected from $C_1$-$C_6$alkyl, $C_2$-$C_6$alkenyl, $C_1$-$C_6$heteroalkyl, $C_3$-$C_6$cycloalkyl, and $C_2$-$C_9$heterocycloalkyl;

each $R_9$ is independently selected from hydrogen and $C_1$-$C_6$alkyl;

each $R_{10}$ is independently selected from hydrogen and $C_1$-$C_6$alkyl;

$R_{11}$ is hydrogen or $C_1$-$C_6$alkyl optionally substituted with 1, 2, or 3 $R_5$;
$R_{12}$ is hydrogen, halogen, or $C_1$-$C_6$alkyl;
$R_{13}$ is $C_1$-$C_6$alkyl;
$R_{14}$ is —OH, —C(=O)H, or —C(=O)O$R_{15}$;
$R_{15}$ is hydrogen or $C_1$-$C_6$alkyl;
n is 0, 1, 2, or 3;
p is 0, 1, or 2; and
q is 0, 1, or 2;
or a pharmaceutically acceptable salt or solvate thereof.

In another aspect, provided herein are compounds of Formula (I):

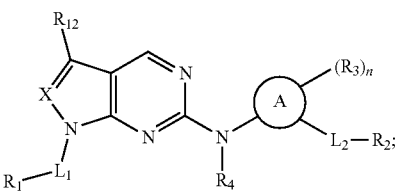

Formula (I)

wherein:

is phenyl or a $C_2$-$C_9$heteroaryl ring;
$X$ is $C(R_{11})$ or $N$;
$L_1$ is $C_1$-$C_6$alkyl or $C_1$-$C_6$heteroalkyl;
$L_2$ is a bond, $C_1$-$C_6$alkyl, or $C_1$-$C_6$heteroalkyl;
$R_1$ is $C_3$-$C_9$alkyl, $C_2$-$C_6$alkenyl, $C_2$-$C_6$alkynyl, $C_3$-$C_6$cycloalkyl, $C_2$-$C_9$heterocycloalkyl, or $C_2$-$C_9$heteroaryl, wherein $C_3$-$C_9$alkyl, $C_2$-$C_6$alkenyl, $C_2$-$C_6$alkynyl, $C_3$-$C_6$cycloalkyl, $C_2$-$C_9$heterocycloalkyl, or $C_2$-$C_9$heteroaryl are optionally substituted with 1, 2, or 3 $R_5$;
$R_2$ is —C(=O)O$R_6$ or

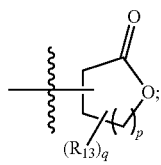

each $R_3$ is independently selected from halogen, $C_1$-$C_6$alkyl, $C_1$-$C_6$haloalkyl, $C_1$-$C_6$heteroalkyl, —$OR_7$, —$N(R_7)_2$, —CN, —C(=O)$R_8$, —C(=O)$OR_7$, —C(=O)N$(R_7)_2$, —$NR_7$C(=O)$R_8$, —$NR_7$S(=O)$_2R_8$, —S(=O)$_2R_8$, and —S(=O)$_2$N$(R_7)_2$;

$R_4$ is hydrogen, $C_1$-$C_6$alkyl, or $C_1$-$C_6$heteroalkyl;

each $R_5$ is independently selected from halogen, oxo, $C_1$-$C_6$alkyl, $C_1$-$C_6$haloalkyl, $C_1$-$C_6$heteroalkyl, —$OR_7$, —$N(R_7)_2$, —CN, —C(=O)$R_8$, —C(=O)$OR_7$, —C(=O)N$(R_7)_2$, —$NR_7$C(=O)$R_8$, —$NR_7$S(=O)$_2R_8$, —S(=O)$_2R_8$, and —S(=O)$_2$N$(R_7)_2$;

$R_6$ is hydrogen, $C_1$-$C_6$alkyl optionally substituted with 1 or 2 Y, $C_3$-$C_6$cycloalkyl optionally substituted with 1 or 2 Y, $C_2$-$C_9$heterocycloalkyl optionally substituted with $C_1$-$C_6$alkyl, or —$C_1$-$C_6$alkyl-$C_2$-$C_9$heterocycloalkyl optionally substituted with $C_1$-$C_6$alkyl;

each Y is independently selected from —CN, —$OR_9$, —$SR_9$, and —$N(R_{10})_2$;

each $R_7$ is independently selected from hydrogen, $C_1$-$C_6$alkyl, $C_2$-$C_6$alkenyl, $C_1$-$C_6$haloalkyl, and $C_1$-$C_6$heteroalkyl;

each $R_8$ is independently selected from $C_1$-$C_6$alkyl, $C_2$-$C_6$alkenyl, $C_1$-$C_6$heteroalkyl, $C_3$-$C_6$cycloalkyl, and $C_2$-$C_9$heterocycloalkyl;

each $R_9$ is independently selected from hydrogen and $C_1$-$C_6$alkyl;

each $R_{10}$ is independently selected from hydrogen and $C_1$-$C_6$alkyl;

$R_{11}$ is hydrogen or $C_1$-$C_6$alkyl optionally substituted with 1, 2, or 3 $R_5$;

$R_{12}$ is hydrogen, halogen, or $C_1$-$C_6$alkyl;

$R_{13}$ is $C_1$-$C_6$alkyl;

n is 0, 1, 2, or 3;

p is 0, 1, or 2; and q is 0, 1, or 2;

or a pharmaceutically acceptable salt or solvate thereof.

In some embodiments is a compound of Formula (I') or (I), or a pharmaceutically acceptable salt or solvate thereof, wherein

is phenyl. In some embodiments is a compound of Formula (I') or (I), or a pharmaceutically acceptable salt or solvate thereof, wherein

is a $C_2$-$C_9$heteroaryl ring. In some embodiments is a compound of Formula (I') or (I), or a pharmaceutically acceptable salt or solvate thereof, wherein

is selected from oxazolyl, thiazolyl, pyrazolyl, furanyl, thienyl, pyrrolyl, imidazolyl, triazolyl, tetrazolyl, isoxazolyl, isothiazolyl, oxadiazolyl, thiadiazolyl, pyridinyl, pyrimidinyl, pyrazinyl, pyridazinyl, and triazinyl. In some embodiments is a compound of Formula (I') or (I), or a pharmaceutically acceptable salt or solvate thereof, wherein

is selected from pyrazolyl, pyrrolyl, and imidazolyl. In some embodiments is a compound of Formula (I') or (I), or a pharmaceutically acceptable salt or solvate thereof, wherein

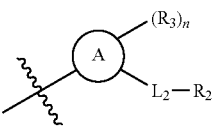

is selected from

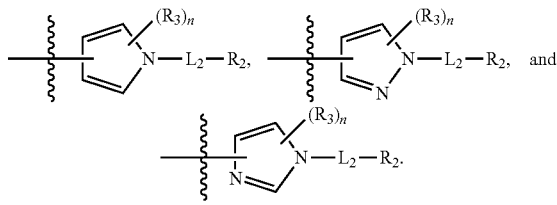

In some embodiments is a compound of Formula (I') or (I), or a pharmaceutically acceptable salt or solvate thereof, wherein

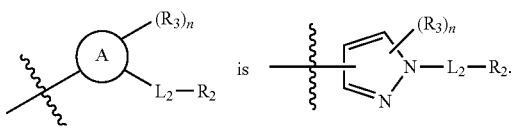

In some embodiments is a compound of Formula (I') or (I), or a pharmaceutically acceptable salt or solvate thereof, wherein $L_2$ is $C_1$-$C_6$alkyl. In some embodiments is a compound of Formula (I') or (I), or a pharmaceutically acceptable salt or solvate thereof, wherein $L_2$ is a bond. In some embodiments is a compound of Formula (I') or (I), or a pharmaceutically acceptable salt or solvate thereof, wherein $L_1$ is $C_1$-$C_6$alkyl. In some embodiments is a compound of Formula (I') or (I), or a pharmaceutically acceptable salt or solvate thereof, wherein $R_1$ is $C_3$-$C_9$alkyl, $C_3$-$C_6$cycloalkyl, or $C_2$-$C_9$heteroaryl, wherein $C_3$-$C_9$alkyl, $C_3$-$C_6$cycloalkyl, or $C_2$-$C_9$heteroaryl are optionally substituted with 1, 2, or 3 $R_5$ and $C_2$-$C_9$heteroaryl is selected from oxazolyl, thiazolyl, pyrazolyl, furanyl, thienyl, pyrrolyl, imidazolyl, triazolyl, tetrazolyl, isoxazolyl, isothiazolyl, oxadiazolyl, and thiadiazolyl. In some embodiments is a compound of Formula (I')

or (I), or a pharmaceutically acceptable salt or solvate thereof, wherein each $R_5$ is independently selected from halogen, $C_1$-$C_6$alkyl, $C_1$-$C_6$haloalkyl, —$OR_7$, and —$N(R_7)_2$. In some embodiments is a compound of Formula (I') or (I), or a pharmaceutically acceptable salt or solvate thereof, wherein $R_1$ is unsubstituted $C_3$-$C_9$alkyl. In some embodiments is a compound of Formula (I') or (I), or a pharmaceutically acceptable salt or solvate thereof, wherein $R_1$ is unsubstituted $C_3$-$C_6$cycloalkyl. In some embodiments is a compound of Formula (I') or (I), or a pharmaceutically acceptable salt or solvate thereof, wherein $R_1$ is unsubstituted $C_2$-$C_9$heteroaryl selected from oxazolyl, thiazolyl, pyrazolyl, furanyl, thienyl, pyrrolyl, imidazolyl, triazolyl, tetrazolyl, isoxazolyl, isothiazolyl, oxadiazolyl, and thiadiazolyl.

In some embodiments is a compound of Formula (II'):

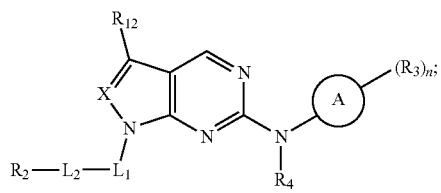

Formula (II')

wherein:

is a $C_2$-$C_9$heteroaryl ring;
X is $C(R_{11})$ or N;
$L_1$ is a bond or $C_1$-$C_6$alkyl;
$L_2$ is $C_1$-$C_6$alkyl, $C_2$-$C_9$heteroaryl, or —C(H)(phenyl)-;
$R_2$ is —C(=O)$OR_6$,

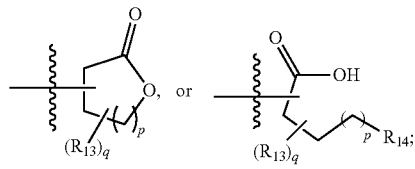

each $R_3$ is independently selected from halogen, $C_1$-$C_6$alkyl, $C_1$-$C_6$haloalkyl, $C_1$-$C_6$alkoxy, $C_1$-$C_6$heteroalkyl, —$OR_7$, —$N(R_7)_2$, —CN, —C(=O)$R_8$, —C(=O)$OR_7$, —C(=O)N($R_7$)$_2$, —$NR_7$C(=O)$R_8$, —$NR_7$S(=O)$_2R_8$, —S(=O)$_2R_8$, and —S(=O)$_2$N($R_7$)$_2$;
$R_4$ is hydrogen, $C_1$-$C_6$alkyl, or $C_1$-$C_6$heteroalkyl;
each $R_5$ is independently selected from halogen, oxo, $C_1$-$C_6$alkyl, $C_1$-$C_6$haloalkyl, $C_1$-$C_6$heteroalkyl, —$OR_7$, —$N(R_7)_2$, —CN, —C(=O)$R_8$, —C(=O)$OR_7$, —C(=O)N($R_7$)$_2$, —$NR_7$C(=O)$R_8$, —$NR_7$S(=O)$_2R_8$, —S(=O)$_2R_8$, and —S(=O)$_2$N($R_7$)$_2$;
$R_6$ is hydrogen, $C_1$-$C_6$alkyl optionally substituted with 1 or 2 Y, $C_3$-$C_6$cycloalkyl optionally substituted with 1 or 2 Y, $C_3$-$C_6$cycloalkyl optionally substituted with 1 or 2 Y, $C_2$-$C_9$heterocycloalkyl optionally substituted with $C_1$-$C_6$alkyl, or —$C_1$-$C_6$alkyl-$C_2$-$C_9$heterocycloalkyl optionally substituted with $C_1$-$C_6$alkyl;

each Y is independently selected from —CN, —$OR_9$, —$SR_9$, and —N($R_{10}$)$_2$;
each $R_7$ is independently selected from hydrogen, $C_1$-$C_6$alkyl, $C_2$-$C_6$alkenyl, $C_1$-$C_6$haloalkyl, and $C_1$-$C_6$heteroalkyl;
each $R_8$ is independently selected from $C_1$-$C_6$alkyl, $C_2$-$C_6$alkenyl, $C_1$-$C_6$heteroalkyl, $C_3$-$C_6$cycloalkyl, and $C_2$-$C_9$heterocycloalkyl;
each $R_9$ is independently selected from hydrogen and $C_1$-$C_6$alkyl;
each $R_{10}$ is independently selected from hydrogen and $C_1$-$C_6$alkyl;
$R_{11}$ is hydrogen or $C_1$-$C_6$alkyl optionally substituted with 1, 2, or 3 $R_5$;
$R_{12}$ is hydrogen, halogen, or $C_1$-$C_6$alkyl;
$R_{13}$ is $C_1$-$C_6$alkyl;
$R_{14}$ is —OH, —C(=O)H, or —C(=O)$OR_{15}$;
$R_{15}$ is hydrogen or $C_1$-$C_6$alkyl;
n is 0, 1, 2, or 3;
p is 0, 1, or 2; and
q is 0, 1, or 2;
or a pharmaceutically acceptable salt or solvate thereof.

In some embodiments is a compound of Formula (II):

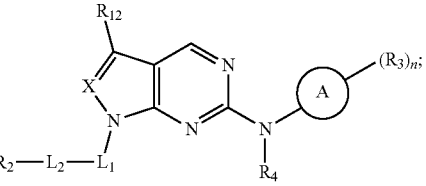

Formula (II)

wherein:

is a $C_2$-$C_9$heteroaryl ring;
X is $C(R_{11})$ or N;
$L_1$ is a bond or $C_1$-$C_6$alkyl;
$L_2$ is $C_1$-$C_6$alkyl, $C_2$-$C_9$heteroaryl, or —C(H)(phenyl)-;
$R_2$ is —C(=O)$OR_6$ or

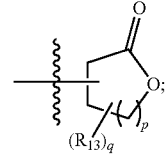

each $R_3$ is independently selected from halogen, $C_1$-$C_6$alkyl, $C_1$-$C_6$haloalkyl, $C_1$-$C_6$alkoxy, $C_1$-$C_6$heteroalkyl, —$OR_7$, —$N(R_7)_2$, —CN, —C(=O)$R_8$, —C(=O)$OR_7$, —C(=O)N($R_7$)$_2$, —$NR_7$C(=O)$R_8$, —$NR_7$S(=O)$_2R_8$, —S(=O)$_2R_8$, and —S(=O)$_2$N($R_7$)$_2$;
$R_4$ is hydrogen, $C_1$-$C_6$alkyl, or $C_1$-$C_6$heteroalkyl;
each $R_5$ is independently selected from halogen, oxo, $C_1$-$C_6$alkyl, $C_1$-$C_6$haloalkyl, $C_1$-$C_6$heteroalkyl, —$OR_7$, —$N(R_7)_2$, —CN, —C(=O)$R_8$, —C(=O)$OR_7$, —C(=O)N($R_7$)$_2$, —$NR_7$C(=O)$R_8$, —$NR_7$S(=O)$_2R_8$, —S(=O)$_2R_8$, and —S(=O)$_2$N($R_7$)$_2$;

$R_6$ is hydrogen, $C_1$-$C_6$alkyl optionally substituted with 1 or 2 Y, $C_3$-$C_6$cycloalkyl optionally substituted with 1 or 2 Y, $C_2$-$C_9$heterocycloalkyl optionally substituted with $C_1$-$C_6$alkyl, or —$C_1$-$C_6$alkyl-$C_2$-$C_9$heterocycloalkyl optionally substituted with $C_1$-$C_6$alkyl;

each Y is independently selected from —CN, —$OR_9$, —$SR_9$, and —$N(R_{10})_2$;

each $R_7$ is independently selected from hydrogen, $C_1$-$C_6$alkyl, $C_2$-$C_6$alkenyl, $C_1$-$C_6$haloalkyl, and $C_1$-$C_6$heteroalkyl;

each $R_8$ is independently selected from $C_1$-$C_6$alkyl, $C_2$-$C_6$alkenyl, $C_1$-$C_6$heteroalkyl, $C_3$-$C_6$cycloalkyl, and $C_2$-$C_9$heterocycloalkyl;

each $R_9$ is independently selected from hydrogen and $C_1$-$C_6$alkyl;

each $R_{10}$ is independently selected from hydrogen and $C_1$-$C_6$alkyl;

$R_{11}$ is hydrogen or $C_1$-$C_6$alkyl optionally substituted with 1, 2, or 3 $R_5$;

$R_{12}$ is hydrogen, halogen, or $C_1$-$C_6$alkyl;

$R_{13}$ is $C_1$-$C_6$alkyl;

n is 0, 1, 2, or 3;

p is 0, 1, or 2; and q is 0, 1, or 2;

or a pharmaceutically acceptable salt or solvate thereof.

In some embodiments is a compound of Formula (II') or (II), or a pharmaceutically acceptable salt or solvate thereof, wherein

Ⓐ is oxazolyl, thiazolyl, pyrazolyl, furanyl, thienyl, pyrrolyl, imidazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl. In some embodiments is a compound of Formula (II') or (II), or a pharmaceutically acceptable salt or solvate thereof, wherein

Ⓐ is pyrazolyl. In some embodiments is a compound of Formula (II') or (II), or a pharmaceutically acceptable salt or solvate thereof, wherein $L_2$ is $C_1$-$C_6$alkyl. In some embodiments is a compound of Formula (II') or (II), or a pharmaceutically acceptable salt or solvate thereof, wherein $L_2$ is —C(H)(phenyl)-. In some embodiments is a compound of Formula (II') or (II), or a pharmaceutically acceptable salt or solvate thereof, wherein $L_2$ is $C_2$-$C_9$heteroaryl. In some embodiments is a compound of Formula (II') or (II), or a pharmaceutically acceptable salt or solvate thereof, wherein $L_1$ is a bond. In some embodiments is a compound of Formula (II') or (II), or a pharmaceutically acceptable salt or solvate thereof, wherein Li is $C_1$-$C_6$alkyl.

In some embodiments is a compound of Formula (I'), (I), (II'), or (II), or a pharmaceutically acceptable salt or solvate thereof, wherein $R_4$ is hydrogen. In some embodiments is a compound of Formula (I'), (I), (II'), or (II), or a pharmaceutically acceptable salt or solvate thereof, wherein $R_4$ is $C_1$-$C_6$alkyl. In some embodiments is a compound of Formula (I'), (I), (II'), or (II), or a pharmaceutically acceptable salt or solvate thereof, wherein $R_{12}$ is hydrogen. In some embodiments is a compound of Formula (I'), (I), (II'), or (II), or a pharmaceutically acceptable salt or solvate thereof, wherein $R_{12}$ is halogen. In some embodiments is a compound of Formula (I'), (I), (II'), or (II), or a pharmaceutically acceptable salt or solvate thereof, wherein $R_{12}$ is $C_1$-$C_6$alkyl. In some embodiments is a compound of Formula (I'), (I), (II'), or (II), or a pharmaceutically acceptable salt or solvate thereof, wherein n is 0. In some embodiments is a compound of Formula (I'), (I), (II'), or (II), or a pharmaceutically acceptable salt or solvate thereof, wherein n is 1. In some embodiments is a compound of Formula (I'), (I), (II'), or (II), or a pharmaceutically acceptable salt or solvate thereof, wherein $R_3$ is selected from halogen, $C_1$-$C_6$alkyl, $C_1$-$C_6$haloalkyl, —$OR_7$, and —$N(R_7)_2$. In some embodiments is a compound of Formula (I'), (I), (II'), or (II), or a pharmaceutically acceptable salt or solvate thereof, wherein each $R_7$ is independently selected from hydrogen and $C_1$-$C_6$alkyl. In some embodiments is a compound of Formula (I'), (I), (II'), or (II), or a pharmaceutically acceptable salt or solvate thereof, wherein $R_3$ is $C_1$-$C_6$alkyl. In some embodiments is a compound of Formula (I'), (I), (II'), or (II), or a pharmaceutically acceptable salt or solvate thereof, wherein X is $C(R_{11})$. In some embodiments is a compound of Formula (I'), (I), (II'), or (II), or a pharmaceutically acceptable salt or solvate thereof, wherein X is C(H). In some embodiments is a compound of Formula (I'), (I), (II'), or (II), or a pharmaceutically acceptable salt or solvate thereof, wherein X is N.

In another aspect, provided herein are compounds of Formula (Ia'):

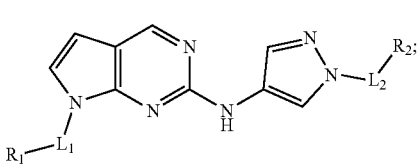

Formula (Ia')

wherein:

$L_1$ is a bond or $C_1$-$C_6$alkyl;

$L_2$ is $C_1$-$C_6$alkyl;

$R_1$ is $C_1$-$C_9$alkyl, $C_3$-$C_6$cycloalkyl, $C_2$-$C_9$heterocycloalkyl, or $C_2$-$C_9$heteroaryl, wherein $C_1$-$C_9$alkyl, $C_3$-$C_6$cycloalkyl, $C_2$-$C_9$heterocycloalkyl, or $C_2$-$C_9$heteroaryl are optionally substituted with 1, 2, or 3 $R_5$;

$R_2$ is —C(=O)$OR_6$,

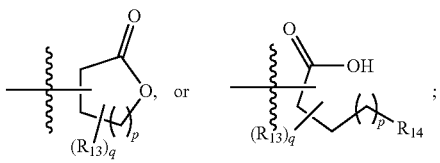

each $R_5$ is independently selected from halogen, $C_1$-$C_6$alkyl, $C_1$-$C_6$haloalkyl, $C_1$-$C_6$heteroalkyl, —$OR_7$, —$N(R_7)_2$, —CN, —C(=O)$R_8$, —C(=O)$OR_7$, —C(=O)N$(R_7)_2$, —$NR_7$C(=O)$R_8$, —$NR_7$S(=O)$_2R_8$, —S(=O)$_2R_8$, and —S(=O)$_2$N$(R_7)_2$;

$R_6$ is hydrogen, $C_1$-$C_6$alkyl optionally substituted with 1 or 2 Y, $C_3$-$C_6$cycloalkyl optionally subsituted with 1 or 2 Y, $C_2$-$C_9$heterocycloalkyl optionally substituted with $C_1$-$C_6$alkyl, or —$C_1$-$C_6$alkyl-$C_2$-$C_9$heterocycloalkyl optionally substituted with $C_1$-$C_6$alkyl;

each Y is independently selected from —CN, —$OR_9$, —$SR_9$, and —$N(R_{10})_2$;

each $R_7$ is independently selected from hydrogen, $C_1$-$C_6$alkyl, $C_2$-$C_6$alkenyl, $C_1$-$C_6$haloalkyl, and $C_1$-$C_6$heteroalkyl;

each $R_8$ is independently selected from $C_1$-$C_6$alkyl, $C_2$-$C_6$alkenyl, $C_1$-$C_6$heteroalkyl, $C_3$-$C_6$cycloalkyl, and $C_2$-$C_9$heterocycloalkyl;

each $R_9$ is independently selected from hydrogen and $C_1$-$C_6$alkyl; and each $R_{10}$ is independently selected from hydrogen and $C_1$-$C_6$alkyl;

$R_{13}$ is $C_1$-$C_6$alkyl;

$R_{14}$ is —OH, —C(=O)H, or —C(=O)$OR_{15}$;

$R_{15}$ is hydrogen or $C_1$-$C_6$alkyl;

p is 0, 1, or 2; and q is 0, 1, or 2 or a pharmaceutically acceptable salt or solvate thereof.

In another aspect, provided herein are compounds of Formula (Ia):

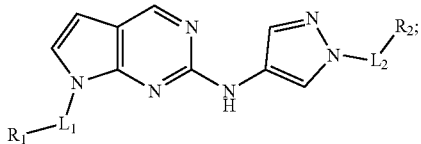

Formula (Ia)

wherein:

$L_1$ is a bond or $C_1$-$C_6$alkyl;

$L_2$ is $C_1$-$C_6$alkyl;

$R_1$ is $C_1$-$C_9$alkyl, $C_3$-$C_6$cycloalkyl, $C_2$-$C_9$heterocycloalkyl, or $C_2$-$C_9$heteroaryl, wherein $C_1$-$C_9$alkyl, $C_3$-$C_6$cycloalkyl, $C_2$-$C_9$heterocycloalkyl, or $C_2$-$C_9$heteroaryl are optionally substituted with 1, 2, or 3 $R_5$;

$R_2$ is —C(=O)$OR_6$ or

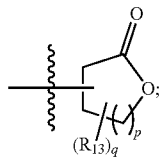

each $R_5$ is independently selected from halogen, $C_1$-$C_6$alkyl, $C_1$-$C_6$haloalkyl, $C_1$-$C_6$heteroalkyl, —$OR_7$, —$N(R_7)_2$, —CN, —C(=O)$R_8$, —C(=O)$OR_7$, —C(=O)N$(R_7)_2$, —$NR_7$C(=O)$R_8$, —$NR_7$S(=O)$_2R_8$, —S(=O)$_2R_8$, and —S(=O)$_2$N$(R_7)_2$;

$R_6$ is hydrogen, $C_1$-$C_6$alkyl optionally subsituted with 1 or 2 Y, $C_3$-$C_6$cycloalkyl optionally subsituted with 1 or 2 Y, $C_2$-$C_9$heterocycloalkyl optionally substituted with $C_1$-$C_6$alkyl, or —$C_1$-$C_6$alkyl-$C_2$-$C_9$heterocycloalkyl optionally substituted with $C_1$-$C_6$alkyl;

each Y is independently selected from —CN, —$OR_9$, —$SR_9$, and —$N(R_{10})_2$;

each $R_7$ is independently selected from hydrogen, $C_1$-$C_6$alkyl, $C_2$-$C_6$alkenyl, $C_1$-$C_6$haloalkyl, and $C_1$-$C_6$heteroalkyl;

each $R_8$ is independently selected from $C_1$-$C_6$alkyl, $C_2$-$C_6$alkenyl, $C_1$-$C_6$heteroalkyl, $C_3$-$C_6$cycloalkyl, and $C_2$-$C_9$heterocycloalkyl;

each $R_9$ is independently selected from hydrogen and $C_1$-$C_6$alkyl; and each $R_{10}$ is independently selected from hydrogen and $C_1$-$C_6$alkyl;

$R_{13}$ is $C_1$-$C_6$alkyl;

p is 0, 1, or 2; and q is 0, 1, or 2 or a pharmaceutically acceptable salt or solvate thereof.

In some embodiments is a compound of Formula (Ia') or (Ia), or a pharmaceutically acceptable salt or solvate thereof, wherein $L_1$ is $C_1$-$C_6$alkyl. In some embodiments is a compound of Formula (Ia') or (Ia), or a pharmaceutically acceptable salt or solvate thereof, wherein $R_1$ is $C_1$-$C_9$alkyl, $C_3$-$C_6$cycloalkyl, or $C_2$-$C_9$heteroaryl, wherein $C_1$-$C_9$alkyl, $C_3$-$C_6$cycloalkyl, or $C_2$-$C_9$heteroaryl are optionally substituted with 1, 2, or 3 $R_5$ and $C_2$-$C_9$heteroaryl is selected from oxazolyl, thiazolyl, pyrazolyl, furanyl, thienyl, pyrrolyl, imidazolyl, triazolyl, tetrazolyl, isoxazolyl, isothiazolyl, oxadiazolyl, and thiadiazolyl. In some embodiments is a compound of Formula (Ia') or (Ia), or a pharmaceutically acceptable salt or solvate thereof, wherein each $R_5$ is independently selected from halogen, $C_1$-$C_6$alkyl, $C_1$-$C_6$haloalkyl, —$OR_7$, and —$N(R_7)_2$. In some embodiments is a compound of Formula (Ia') or (Ia), or a pharmaceutically acceptable salt or solvate thereof, wherein $R_1$ is unsubstituted $C_1$-$C_9$alkyl. In some embodiments is a compound of Formula (Ia') or (Ia), or a pharmaceutically acceptable salt or solvate thereof, wherein $R_1$ is unsubstituted $C_3$-$C_6$cycloalkyl. In some embodiments is a compound of Formula (Ia') or (Ia), or a pharmaceutically acceptable salt or solvate thereof, wherein $R_1$ is unsubstituted $C_2$-$C_9$heteroaryl selected from oxazolyl, thiazolyl, pyrazolyl, furanyl, thienyl, pyrrolyl, imidazolyl, triazolyl, tetrazolyl, isoxazolyl, isothiazolyl, oxadiazolyl, and thiadiazolyl.

In some embodiments is a compound of Formula (I'), (I), (Ia'), (Ia), (II'), or (II), or a pharmaceutically acceptable salt or solvate thereof, wherein $R_2$ is —C(=O)$OR_6$. In some embodiments is a compound of Formula (I'), (I), (Ia'), (Ia), (II'), or (II), or a pharmaceutically acceptable salt or solvate thereof, wherein $R_6$ is unsubstituted $C_1$-$C_6$alkyl. In some embodiments is a compound of Formula (I'), (I), (Ia'), (Ia), (II'), or (II), or a pharmaceutically acceptable salt or solvate thereof, wherein $R_6$ is $C_2$-$C_9$heterocycloalkyl optionally substituted with $C_1$-$C_6$alkyl. In some embodiments is a compound of Formula (I'), (I), (Ia'), (Ia), (II'), or (II), or a pharmaceutically acceptable salt or solvate thereof, wherein $R_6$ is —$C_1$-$C_6$alkyl-$C_2$-$C_9$heterocycloalkyl optionally substituted with $C_1$-$C_6$alkyl. In some embodiments is a compound of Formula (I'), (I), (Ia'), (Ia), (II'), or (II), or a pharmaceutically acceptable salt or solvate thereof, wherein $R_6$ is hydrogen. In some embodiments is a compound of Formula (I'), (I), (Ia'), (Ia), (II'), or (II), or a pharmaceutically acceptable salt or solvate thereof, wherein $R_2$ is

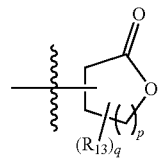

In some embodiments is a compound of Formula (I'), (I), (Ia'), (Ia), (II'), or (II), or a pharmaceutically acceptable salt or solvate thereof, wherein $R_2$ is

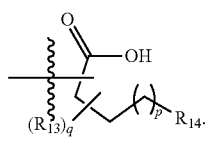

In some embodiments is a compound of Formula (I'), (I), (Ia'), (Ia), (II'), or (II), or a pharmaceutically acceptable salt or solvate thereof, wherein $R_{14}$ is —OH. In some embodiments is a compound of Formula (I'), (I), (Ia'), (Ia), (II'), or (II), or a pharmaceutically acceptable salt or solvate thereof, wherein $R_{14}$ is —C(=O)H. In some embodiments is a compound of Formula (I'), (I), (Ia'), (Ia), (II'), or (II), or a pharmaceutically acceptable salt or solvate thereof, wherein $R_{14}$ is —C(=O)O$R_{15}$. In some embodiments is a compound of Formula (I'), (I), (Ia'), (Ia), (II'), or (II), or a pharmaceutically acceptable salt or solvate thereof, wherein $R_{15}$ is hydrogen. In some embodiments is a compound of Formula (I'), (I), (Ia'), (Ia), (II'), or (II), or a pharmaceutically acceptable salt or solvate thereof, wherein q is 0. In some embodiments is a compound of Formula (I'), (I), (Ia'), (Ia), (II'), or (II), or a pharmaceutically acceptable salt or solvate thereof, wherein p is 1. In some embodiments is a compound of Formula (I'), (I), (Ia'), (Ia), (II'), or (II), or a pharmaceutically acceptable salt or solvate thereof, wherein $R_2$ is

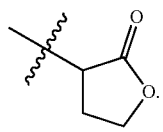 [SMILES: *C1CCOC1=O]

In another aspect described herein is a pharmaceutical composition comprising a compound of Formula (I'), (I), (Ia'), (Ia), (II'), or (II), or a pharmaceutically acceptable salt or solvate thereof, and a pharmaceutically acceptable excipient.

In another aspect described herein is a method of treating an inflammatory or autoimmune disease in a patient in need thereof, comprising administering to the patient a therapeutically effective amount of a compound of Formula (I'), (I), (Ia'), (Ia), (II'), or (II), or a pharmaceutically acceptable salt or solvate thereof. In some embodiments is a method of treating an inflammatory or autoimmune disease in a patient in need thereof, comprising administering to the individual a therapeutically effective amount of a compound of Formula (I'), (I), (Ia'), (Ia), (II'), or (II), or a pharmaceutically acceptable salt or solvate thereof, wherein the disease is selected from rheumatoid arthritis, multiple sclerosis, psoriasis, lupus, intestinal bowel disease, Crohn's disease, ulcerative colitis, ankylosing spondylitis, vitiligo, and atopic dermatitis.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

In the context of this disclosure, a number of terms shall be utilized.

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "Advanced Organic Chemistry $4^{th}$ Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

An "alkyl" group refers to a straight or branched hydrocarbon chain radical consisting solely of carbon and hydrogen atoms, containing no unsaturation. In some embodiments, the "alkyl" group may have 1 to 6 carbon atoms (whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated). The alkyl group of the compounds described herein may be designated as "$C_1$-$C_6$alkyl" or similar designations. By way of example only, "$C_1$-$C_6$alkyl" indicates that there are one to six carbon atoms in the alkyl chain, i.e., the alkyl chain is selected from the group consisting of methyl, ethyl, n-propyl, iso-propyl, n-butyl, iso-butyl, sec-butyl, t-butyl, n-pentyl, iso-pentyl, neo-pentyl, and hexyl. Alkyl groups can be substituted or unsubstituted. Depending on the structure, an alkyl group can be a monoradical or a diradical (i.e., an alkylene group).

An "alkoxy" refers to a "—O-alkyl" group, where alkyl is as defined herein.

The term "alkenyl" refers to a straight or branched hydrocarbon chain radical group consisting solely of carbon and hydrogen atoms, containing at least one carbon-carbon double bond. Non-limiting examples of an alkenyl group include —CH=CH$_2$, —C(CH$_3$)=CH$_2$, —CH=CHCH$_3$, —CH=C(CH$_3$)$_2$ and —C(CH$_3$)=CHCH$_3$. In some embodiments, an alkenyl groups may have 2 to 6 carbons. Alkenyl groups can be substituted or unsubstituted. Depending on the structure, an alkenyl group can be a monoradical or a diradical (i.e., an alkenylene group).

The term "alkynyl" refers to a straight or branched hydrocarbon chain radical group consisting solely of carbon and hydrogen atoms, containing at least one carbon-carbon triple bond. Non-limiting examples of an alkynyl group include —C≡CH, —C≡CCH$_3$, —C≡CCH$_2$CH$_3$ and —C≡CCH$_2$CH$_2$CH$_3$. In some embodiments, an alkynyl group can have 2 to 6 carbons. Alkynyl groups can be substituted or unsubstituted. Depending on the structure, an alkynyl group can be a monoradical or a diradical (i.e., an alkynylene group).

"Amino" refers to a —NH$_2$ group.

The term "alkylamine" or "alkylamino" refers to the —N(alkyl)$_x$H$_y$ group, where alkyl is as defined herein and x and y are selected from the group x=1, y=1 and x=2, y=0. When x=2, the alkyl groups, taken together with the nitrogen to which they are attached, can optionally form a cyclic ring system. "Dialkylamino" refers to a —N(alkyl)$_2$ group, where alkyl is as defined herein.

The term "aromatic" refers to a planar ring having a delocalized π-electron system containing 4n+2 π electrons, where n is an integer. Aromatic rings can be formed from five, six, seven, eight, nine, or more than nine atoms. Aromatics can be optionally substituted. The term "aromatic" includes both aryl groups (e.g., phenyl, naphthalenyl) and heteroaryl groups (e.g., pyridinyl, quinolinyl).

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, and naphthalenyl. Depending on the structure, an aryl group can be a monoradical or a diradical (i.e., an arylene group).

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to,

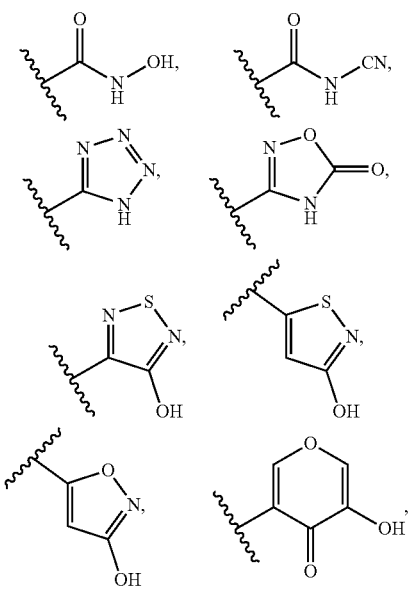

and the like.

The term "cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). In some embodiments, cycloalkyl groups include groups having from 3 to 10 ring atoms.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom.

A "heterocycloalkyl" group or "heteroalicyclic" group refers to a cycloalkyl group, wherein at least one skeletal ring atom is a heteroatom selected from nitrogen, oxygen and sulfur. The radicals may be fused with an aryl or heteroaryl. The term heteroalicyclic also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring).

The term "halo" or, alternatively, "halogen" means fluoro, chloro, bromo and iodo.

The term "haloalkyl" refers to an alkyl group that is substituted with one or more halogens. The halogens may the same or they may be different. Non-limiting examples of haloalkyls include —$CH_2Cl$, —$CF_3$, —$CHF_2$, —$CH_2CF_3$, —$CF_2CF_3$, and the like.

The terms "fluoroalkyl" and "fluoroalkoxy" include alkyl and alkoxy groups, respectively, that are substituted with one or more fluorine atoms. Non-limiting examples of fluoroalkyls include —$CF_3$, —$CHF_2$, —$CH_2F$, —$CH_2CF_3$, —$CF_2CF_3$, —$CF_2CF_2CF_3$, —$CF(CH_3)_3$, and the like. Non-limiting examples of fluoroalkoxy groups, include —$OCF_3$, —$OCHF_2$, —$OCH_2F$, —$OCH_2CF_3$, —$OCF_2CF_3$, —$OCF_2CF_2CF_3$, —$OCF(CH_3)_2$, and the like.

The term "heteroalkyl" refers to an alkyl radical where one or more skeletal chain atoms is selected from an atom other than carbon, e.g., oxygen, nitrogen, sulfur, phosphorus, silicon, or combinations thereof. The heteroatom(s) may be placed at any interior position of the heteroalkyl group. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —$CH_2$—NH—$OCH_3$, —$CH_2$—O—$Si(CH_3)_3$, —$CH_2$—CH=N—$OCH_3$, and —CH=CH—N($CH_3$)—$CH_3$. In addition, up to two heteroatoms may be consecutive, such as, by way of example, —$CH_2$—NH—$OCH_3$ and —$CH_2$—O—$Si(CH_3)_3$. Excluding the number of heteroatoms, a "heteroalkyl" may have from 1 to 6 carbon atoms.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

As used herein, the substituent "R" appearing by itself and without a number designation refers to a substituent selected from among from alkyl, haloalkyl, heteroalkyl, alkenyl, cycloalkyl, aryl, heteroaryl (bonded through a ring carbon), and heterocycloalkyl.

"Optional" or "optionally" means that a subsequently described event or circumstance may or may not occur and that the description includes instances when the event or circumstance occurs and instances in which it does not.

The term "optionally substituted" or "substituted" means that the referenced group may be substituted with one or more additional group(s) individually and independently selected from alkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halo, acyl, acyloxy, —$CO_2H$, —$CO_2$-alkyl, nitro, haloalkyl, fluoroalkyl, and amino, including mono- and di-substituted amino groups (e.g. —$NH_2$, —NHR, —N(R)$_2$), and the protected derivatives thereof. By way of example, an optional substituents may be $L^sR^s$, wherein each L is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, —($C_1$-$C_6$alkyl)-, or —($C_2$-$C_6$alkenyl)-; and each $R_s$ is independently selected from among H, ($C_1$-$C_6$alkyl), ($C_3$-$C_8$cycloalkyl), aryl, heteroaryl, heterocycloalkyl, and $C_1$-$C_6$heteroalkyl. The protecting groups that may form the protective derivatives of the above substituents are found in sources such as Greene and Wuts, above.

As used herein, the term "about" or "approximately" means within 20%, preferably within 10%, and more preferably within 5% of a given value or range.

The term a "therapeutically effective amount" as used herein refers to the amount of a JAK inhibitor that, when administered to a mammal in need, is effective to at least partially ameliorate or to at least partially prevent conditions related to skin aging.

As used herein, the term "expression" includes the process by which polynucleotides are transcribed into mRNA and translated into peptides, polypeptides, or proteins.

The term "modulate" encompasses either a decrease or an increase in activity or expression depending on the target molecule.

The term "activator" is used in this specification to denote any molecular species that results in activation of the indicated receptor, regardless of whether the species itself binds to the receptor or a metabolite of the species binds to the receptor when the species is administered topically. Thus, the activator can be a ligand of the receptor or it can be an activator that is metabolized to the ligand of the receptor, i.e., a metabolite that is formed in tissue and is the actual ligand.

The term "patient" or "mammal" refers to a human, a non-human primate, canine, feline, bovine, ovine, porcine, murine, or other veterinary or laboratory mammal. Those skilled in the art recognize that a therapy which reduces the severity of a pathology in one species of mammal is predictive of the effect of the therapy on another species of mammal.

The term "soft-drug" as used herein, refers to drug substance and/or a chemical compound that is biologically active in the desired target tissue and that is metabolized, after exerting its effect in the target tissue, to a compound that is inactive against the biological target. In some embodiments, the soft-drug has no target biological activity in systemic circulation.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts, and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts, and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins, and the like. See Berge et al., supra.

As used herein, "treatment" or "treating" or "palliating" or "ameliorating" are used interchangeably herein. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

JAK Inhibitors

Cytokines are critical for host defense and immunoregulation, but are also major players in the immunopathogenesis of autoimmune diseases. Based on structure, several major families of cytokines can be recognized. Two major classes are the so-called Type I and Type II cytokine receptors. Type I receptors bind several interleukins (ILs), colony stimulating factors, and hormones such erythropoietin, prolactin, and growth hormone. Type II receptors bind interferons and IL-10 related cytokines. In contrast to other receptors, whose intracellular domains encode kinase or other enzymatically active domains, these receptors lack such elements. Instead, the cytoplasmic domain of Type I and II cytokine receptors bind to members of a specific kinase family, known as the Janus kinases (JAKs) which include JAK1, JAK2, JAK3, and TYK2. Cytokine receptors are paired with different JAKs, which are activated upon cytokine binding. Because JAKs are phosphotransferases, they catalyze the transfer of phosphate from ATP to various substrates such as cytokine receptors. This modification allows the recruitment of various signaling molecules including members of the signal transducer and activator of transcription (STAT) family of DNA binding proteins. STATs are another important JAK substrate. Phosphorylation of STATs promotes their nuclear accumulation and regulation of gene expression. In addition, studies with knockout mice support the critical and specific role of JAKs signaling by Type I/I cytokines and not other pathways. The critical function of JAKs in cytokine signaling suggests the therapeutic potential of JAK inhibitors.

The compounds of Formula (I'), (I), (Ia'), (Ia), (Ib), (II'), (II), (IIa), (III), (IIIa), or (IV) described herein are JAK inhibitors. The compounds of Formula (I'), (I), (Ia'), (Ia), (Ib), (II'), (II), (IIa), (III), (IIIa), or (IV) described herein, and compositions comprising these compounds, are useful for the treatment of an inflammatory or autoimmune disease.

In some embodiments, provided herein is a compound of Formula (I'), or a pharmaceutically acceptable salt or solvate thereof:

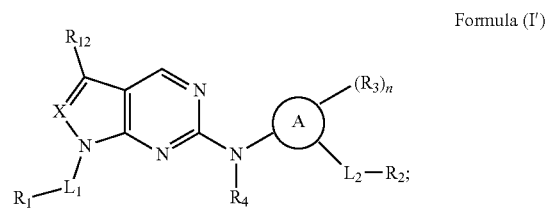

Formula (I')

wherein:

is phenyl or a $C_2$-$C_9$heteroaryl ring;
X is $C(R_{11})$ or N;
$L_1$ is $C_1$-$C_6$alkyl or $C_1$-$C_6$heteroalkyl;
$L_2$ is a bond, $C_1$-$C_6$alkyl, or $C_1$-$C_6$heteroalkyl;
$R_1$ is $C_3$-$C_9$alkyl, $C_2$-$C_6$alkenyl, $C_2$-$C_6$alkynyl, $C_3$-$C_6$cycloalkyl, $C_2$-$C_9$heterocycloalkyl, or $C_2$-$C_9$heteroaryl, wherein $C_3$-$C_9$alkyl, $C_2$-$C_6$alkenyl, $C_2$-$C_6$alkynyl, $C_3$-$C_6$cycloalkyl, $C_2$-$C_9$heterocycloalkyl, or $C_2$-$C_9$heteroaryl are optionally substituted with 1, 2, or 3 $R_5$;
$R_2$ is —C(=O)O$R_6$,

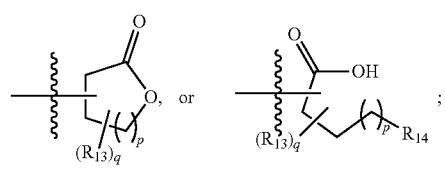

each $R_3$ is independently selected from halogen, $C_1$-$C_6$alkyl, $C_1$-$C_6$haloalkyl, $C_1$-$C_6$heteroalkyl, —O$R_7$, —N(R$_7$)$_2$, —CN, —C(=O)R$_8$, —C(=O)OR$_7$, —C(=O)N(R$_7$)$_2$, —NR$_7$C(=O)R$_8$, —NR$_7$S(=O)$_2$R$_8$, —S(=O)$_2$R$_8$, and —S(=O)$_2$N(R$_7$)$_2$;

R$_4$ is hydrogen, C$_1$-C$_6$alkyl, or C$_1$-C$_6$heteroalkyl;

each R$_5$ is independently selected from halogen, oxo, C$_1$-C$_6$alkyl, C$_1$-C$_6$haloalkyl, C$_1$-C$_6$heteroalkyl, —OR$_7$, —N(R$_7$)$_2$, —CN, —C(=O)R$_8$, —C(=O)OR$_7$, —C(=O)N(R$_7$)$_2$, —NR$_7$C(=O)R$_8$, —NR$_7$S(=O)$_2$R$_8$, —S(=O)$_2$R$_8$, and —S(=O)$_2$N(R$_7$)$_2$;

R$_6$ is hydrogen, C$_1$-C$_6$alkyl optionally subsituted with 1 or 2 Y, C$_3$-C$_6$cycloalkyl optionally subsituted with 1 or 2 Y, C$_2$-C$_9$heterocycloalkyl optionally substituted with C$_1$-C$_6$alkyl, or —C$_1$-C$_6$alkyl-C$_2$-C$_9$heterocycloalkyl optionally substituted with C$_1$-C$_6$alkyl;

each Y is independently selected from —CN, —OR$_9$, —SR$_9$, and —N(R$_{10}$)$_2$;

each R$_7$ is independently selected from hydrogen, C$_1$-C$_6$alkyl, C$_2$-C$_6$alkenyl, C$_1$-C$_6$haloalkyl, and C$_1$-C$_6$heteroalkyl;

each R$_8$ is independently selected from C$_1$-C$_6$alkyl, C$_2$-C$_6$alkenyl, C$_1$-C$_6$heteroalkyl, C$_3$-C$_6$cycloalkyl, and C$_2$-C$_9$heterocycloalkyl;

each R$_9$ is independently selected from hydrogen and C$_1$-C$_6$alkyl;

each R$_{10}$ is independently selected from hydrogen and C$_1$-C$_6$alkyl;

R$_{11}$ is hydrogen or C$_1$-C$_6$alkyl optionally substituted with 1, 2, or 3 R$_5$;

R$_{12}$ is hydrogen, halogen, or C$_1$-C$_6$alkyl;

R$_{13}$ is C$_1$-C$_6$alkyl;

R$_{14}$ is —OH, —C(=O)H, or —C(=O)OR$_{15}$;

R$_{15}$ is hydrogen or C$_1$-C$_6$alkyl;

n is 0, 1, 2, or 3;

p is 0, 1, or 2; and q is 0, 1, or 2.

In some embodiments, provided herein is a compound of Formula (I), or a pharmaceutically acceptable salt or solvate thereof:

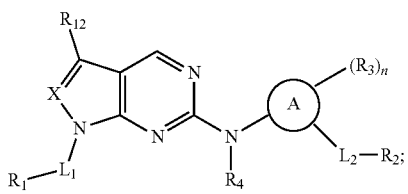

Formula (I)

wherein:

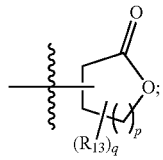

A is phenyl or a C$_2$-C$_9$heteroaryl ring;

X is C(R$_{11}$) or N;

L$_1$ is C$_1$-C$_6$alkyl or C$_1$-C$_6$heteroalkyl;

L$_2$ is a bond, C$_1$-C$_6$alkyl, or C$_1$-C$_6$heteroalkyl;

R$_1$ is C$_3$-C$_9$alkyl, C$_2$-C$_6$alkenyl, C$_2$-C$_6$alkynyl, C$_3$-C$_6$cycloalkyl, C$_2$-C$_9$heterocycloalkyl, or C$_2$-C$_9$heteroaryl, wherein C$_3$-C$_9$alkyl, C$_2$-C$_6$alkenyl, C$_2$-C$_6$alkynyl, C$_3$-C$_6$cycloalkyl, C$_2$-C$_9$heterocycloalkyl, or C$_2$-C$_9$heteroaryl are optionally substituted with 1, 2, or 3 R$_5$;

R$_2$ is —C(=O)OR$_6$ or each R$_3$ is independently selected from halogen, C$_1$-C$_6$alkyl, C$_1$-C$_6$haloalkyl, C$_1$-C$_6$heteroalkyl, —OR$_7$, —N(R$_7$)$_2$, —CN, —C(=O)R$_8$, —C(=O)OR$_7$, —C(=O)N(R$_7$)$_2$, —NR$_7$C(=O)R$_8$, —NR$_7$S(=O)$_2$R$_8$, —S(=O)$_2$R$_8$, and —S(=O)$_2$N(R$_7$)$_2$;

R$_4$ is hydrogen, C$_1$-C$_6$alkyl, or C$_1$-C$_6$heteroalkyl;

each R$_5$ is independently selected from halogen, oxo, C$_1$-C$_6$alkyl, C$_1$-C$_6$haloalkyl, C$_1$-C$_6$heteroalkyl, —OR$_7$, —N(R$_7$)$_2$, —CN, —C(=O)R$_8$, —C(=O)OR$_7$, —C(=O)N(R$_7$)$_2$, —NR$_7$C(=O)R$_8$, —NR$_7$S(=O)$_2$R$_8$, —S(=O)$_2$R$_8$, and —S(=O)$_2$N(R$_7$)$_2$;

R$_6$ is hydrogen, C$_1$-C$_6$alkyl optionally subsituted with 1 or 2 Y, C$_3$-C$_6$cycloalkyl optionally subsituted with 1 or 2 Y, C$_2$-C$_9$heterocycloalkyl optionally substituted with C$_1$-C$_6$alkyl, or —C$_1$-C$_6$alkyl-C$_2$-C$_9$heterocycloalkyl optionally substituted with C$_1$-C$_6$alkyl;

each Y is independently selected from —CN, —OR$_9$, —SR$_9$, and —N(R$_{10}$)$_2$;

each R$_7$ is independently selected from hydrogen, C$_1$-C$_6$alkyl, C$_2$-C$_6$alkenyl, C$_1$-C$_6$haloalkyl, and C$_1$-C$_6$heteroalkyl;

each R$_8$ is independently selected from C$_1$-C$_6$alkyl, C$_2$-C$_6$alkenyl, C$_1$-C$_6$heteroalkyl, C$_3$-C$_6$cycloalkyl, and C$_2$-C$_9$heterocycloalkyl;

each R$_9$ is independently selected from hydrogen and C$_1$-C$_6$alkyl;

each R$_{10}$ is independently selected from hydrogen and C$_1$-C$_6$alkyl;

R$_{11}$ is hydrogen or C$_1$-C$_6$alkyl optionally substituted with 1, 2, or 3 R$_5$;

R$_{12}$ is hydrogen, halogen, or C$_1$-C$_6$alkyl;

R$_{13}$ is C$_1$-C$_6$alkyl;

n is 0, 1, 2, or 3;

p is 0, 1, or 2; and q is 0, 1, or 2.

In some embodiments is a compound of Formula (I') or (I), or a pharmaceutically acceptable salt or solvate thereof, wherein X is C(R$_{11}$). In some embodiments is a compound of Formula (I') or (I), or a pharmaceutically acceptable salt or solvate thereof, wherein X is C(H). In some embodiments is a compound of Formula (I') or (I), or a pharmaceutically acceptable salt or solvate thereof, wherein X is N.

In some embodiments is a compound of Formula (I') or (I), or a pharmaceutically acceptable salt or solvate thereof, wherein

A is phenyl.

In some embodiments is a compound of Formula (I') or (I), or a pharmaceutically acceptable salt or solvate thereof, wherein

A is a $C_2$-$C_9$heteroaryl ring. In some embodiments is a compound of Formula (I') or (I), or a pharmaceutically acceptable salt or solvate thereof, wherein

is a $C_2$-$C_9$heteroaryl ring selected from oxazolyl, thiazolyl, pyrazolyl, furanyl, thienyl, pyrrolyl, imidazolyl, triazolyl, tetrazolyl, isoxazolyl, isothiazolyl, oxadiazolyl, thiadiazolyl, pyridinyl, pyrimidinyl, pyrazinyl, pyridazinyl, and triazinyl. In some embodiments is a compound of Formula (I') or (I), or a pharmaceutically acceptable salt or solvate thereof, wherein

is a $C_2$-$C_9$heteroaryl ring selected from pyrazolyl, pyrrolyl, and imidazolyl. In some embodiments is a compound of Formula (I') or (I), ARA or a pharmaceutically acceptable salt or solvate thereof, wherein

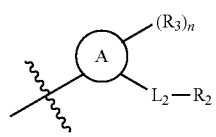

is a $C_2$-$C_9$heteroaryl ring selected from

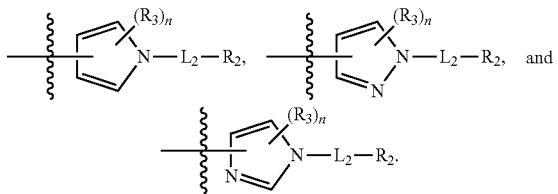

In some embodiments is a compound of Formula (I') or (I), or a pharmaceutically acceptable salt or solvate thereof, wherein

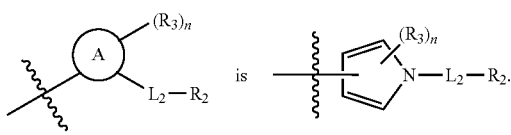

In some embodiments is a compound of Formula (I') or (I), or a pharmaceutically acceptable salt or solvate thereof, wherein

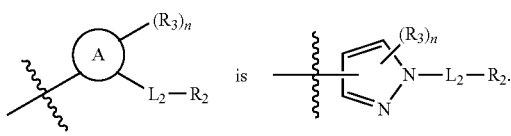

In some embodiments is a compound of Formula (I') or (I), or a pharmaceutically acceptable salt or solvate thereof, wherein

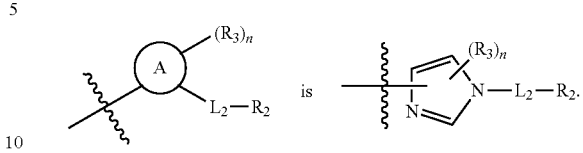

In some embodiments, provided herein is a compound of Formula (I') or (I), or a pharmaceutically acceptable salt or solvate thereof, wherein $L_1$ is $C_1$-$C_6$alkyl. In some embodiments, provided herein is a compound of Formula (I') or (I), or a pharmaceutically acceptable salt or solvate thereof, wherein $L_1$ is —$CH_2$—. In some embodiments, provided herein is a compound of Formula (I') or (I), or a pharmaceutically acceptable salt or solvate thereof, wherein $L_1$ is —$CH_2CH_2$—. In some embodiments, provided herein is a compound of Formula (I') or (I), or a pharmaceutically acceptable salt or solvate thereof, wherein $L_1$ is $C_1$-$C_6$heteroalkyl.

In some embodiments, provided herein is a compound of Formula (I') or (I), or a pharmaceutically acceptable salt or solvate thereof, wherein $R_1$ is $C_3$-$C_9$alkyl optionally substituted with 1, 2, or 3 $R_5$. In some embodiments, provided herein is a compound of Formula (I') or (I), or a pharmaceutically acceptable salt or solvate thereof, wherein $R_1$ is unsubstituted $C_3$-$C_9$alkyl. In some embodiments, provided herein is a compound of Formula (I') or (I), or a pharmaceutically acceptable salt or solvate thereof, wherein $R_1$ is $C_3$-$C_6$cycloalkyl optionally substituted with 1, 2, or 3 $R_5$. In some embodiments, provided herein is a compound of Formula (I') or (I), or a pharmaceutically acceptable salt or solvate thereof, wherein $R_1$ is $C_3$-$C_6$cycloalkyl optionally substituted with 1, 2, or 3 $R_5$, wherein each $R_5$ is independently selected from halogen, $C_1$-$C_6$alkyl, $C_1$-$C_6$haloalkyl, —$OR_7$, and —$N(R_7)_2$. In some embodiments, provided herein is a compound of Formula (I') or (I), or a pharmaceutically acceptable salt or solvate thereof, wherein $R_1$ is $C_3$-$C_6$cycloalkyl optionally substituted with 1, 2, or 3 $R_5$, wherein each $R_5$ is independently selected from halogen and $C_1$-$C_6$alkyl. In some embodiments, provided herein is a compound of Formula (I') or (I), or a pharmaceutically acceptable salt or solvate thereof, wherein $R_1$ is unsubstituted $C_3$-$C_6$cycloalkyl. In some embodiments, provided herein is a compound of Formula (I') or (I), or a pharmaceutically acceptable salt or solvate thereof, wherein $R_1$ is $C_2$-$C_9$heterocycloalkyl optionally substituted with 1, 2, or 3 $R_5$. In some embodiments, provided herein is a compound of Formula (I') or (I), or a pharmaceutically acceptable salt or solvate thereof, wherein $R_1$ is $C_2$-$C_9$heterocycloalkyl optionally substituted with 1, 2, or 3 $R_5$, wherein each $R_5$ is independently selected from halogen, $C_1$-$C_6$alkyl, $C_1$-$C_6$haloalkyl, —$OR_7$, and —$N(R_7)_2$. In some embodiments, provided herein is a compound of Formula (I') or (I), or a pharmaceutically acceptable salt or solvate thereof, wherein $R_1$ is $C_2$-$C_9$heterocycloalkyl optionally substituted with 1, 2, or 3 $R_5$, wherein each $R_5$ is independently selected from halogen and $C_1$-$C_6$alkyl. In some embodiments, provided herein is a compound of Formula (I') or (I), or a pharmaceutically acceptable salt or solvate thereof, wherein $R_1$ is unsubstituted $C_2$-$C_9$heterocycloalkyl. In some embodiments, provided herein is a compound of Formula (I') or (I), or a pharmaceutically acceptable salt or solvate thereof, wherein $R_1$ is $C_2$-$C_9$heteroaryl optionally substituted with 1, 2, or 3 $R_5$. In some embodiments, provided herein is a compound of Formula (I') or (I), or a pharmaceutically acceptable salt or solvate thereof, wherein $R_1$ is $C_2$-$C_9$heteroaryl optionally substituted with 1, 2, or 3 $R_5$, wherein each $R_5$ is independently selected from halogen, $C_1$-$C_6$alkyl, $C_1$-$C_6$haloalkyl, —$OR_7$, and —$N(R_7)_2$. In some embodiments, provided herein is a compound of Formula (I') or (I), or a pharmaceutically acceptable salt or solvate thereof, wherein $R_1$ is $C_2$-$C_9$heteroaryl optionally substituted with 1, 2, or 3 $R_5$, wherein each $R_5$ is independently selected from halogen and $C_1$-$C_6$alkyl. In some embodiments, provided herein is a compound of Formula (I') or (I), or a pharmaceutically acceptable salt or solvate thereof, wherein $R_1$ is unsubstituted $C_2$-$C_9$heteroaryl. In some embodiments, provided herein is a compound of Formula (I') or (I), or a pharmaceutically acceptable salt or solvate thereof, wherein $C_2$-$C_9$heteroaryl is selected from oxazolyl, thiazolyl, pyrazolyl, furanyl, thienyl, pyrrolyl, imidazolyl, triazolyl, tetrazolyl, isoxazolyl, isothiazolyl, oxadiazolyl, and thiadiazolyl.

In some embodiments, provided herein is a compound of Formula (I') or (I), or a pharmaceutically acceptable salt or solvate thereof, wherein $L_2$ is a bond. In some embodiments, provided herein is a compound of Formula (I') or (I), or a pharmaceutically acceptable salt or solvate thereof, wherein $L_2$ is $C_1$-$C_6$alkyl. In some embodiments, provided herein is a compound of Formula (I') or (I), or a pharmaceutically acceptable salt or solvate thereof, wherein $L_2$ is —$CH_2$—. In some embodiments, provided herein is a compound of Formula (I') or (I), or a pharmaceutically acceptable salt or solvate thereof, wherein $L_2$ is —$CH_2CH_2$—. In some embodiments, provided herein is a compound of Formula (I') or (I), or a pharmaceutically acceptable salt or solvate thereof, wherein $L_2$ is —$CH_2CH_2CH_2$—. In some embodiments, provided herein is a compound of Formula (I') or (I), or a pharmaceutically acceptable salt or solvate thereof, wherein $L_2$ is $C_1$-$C_6$heteroalkyl.

In some embodiments, provided herein is a compound of Formula (I') or (I), or a pharmaceutically acceptable salt or solvate thereof, wherein $R_2$ is —C(=O)$OR_6$. In some embodiments, provided herein is a compound of Formula (I') or (I), or a pharmaceutically acceptable salt or solvate thereof, wherein $R_2$ is —C(=O)$OR_6$ and $R_6$ is $C_1$-$C_6$alkyl optionally subsituted with 1 or 2 Y. In some embodiments, provided herein is a compound of Formula (I') or (I), or a pharmaceutically acceptable salt or solvate thereof, wherein $R_2$ is —$CO_2C_1$-$C_6$alkyl. In some embodiments, provided herein is a compound of Formula (I') or (I), or a pharmaceutically acceptable salt or solvate thereof, wherein $R_2$ is —$CO_2CH_3$. In some embodiments, provided herein is a compound of Formula (I') or (I), or a pharmaceutically acceptable salt or solvate thereof, wherein $R_2$ is —$CO_2CH_2CH_3$. In some embodiments, provided herein is a compound of Formula (I') or (I), or a pharmaceutically acceptable salt or solvate thereof, wherein $R_2$ is —$CO_2H$. In some embodiments, provided herein is a compound of Formula (I') or (I), or a pharmaceutically acceptable salt or solvate thereof, wherein $R_2$ is —$CO_2C_1$-$C_6$alkyl-Y. In some embodiments, provided herein is a compound of Formula (I') or (I), or a pharmaceutically acceptable salt or solvate thereof, wherein $R_2$ is —$CO_2C_1$-$C_6$alkyl-$OR_9$. In some embodiments, provided herein is a compound of Formula (I') or (I), or a pharmaceutically acceptable salt or solvate thereof, wherein $R_2$ is —C(=O)$OR_6$ and $R_6$ is $C_2$-$C_9$heterocycloalkyl optionally substituted with $C_1$-$C_6$alkyl. In some embodiments, provided herein is a compound of Formula (I') or (I), or a pharmaceutically acceptable salt or solvate thereof, wherein $R_2$ is —C(=O)$OR_6$ and $R_6$ is unsubstituted $C_2$-$C_9$heterocycloalkyl. In some embodiments, provided herein is a compound of Formula (I') or (I), or a pharmaceutically acceptable salt or solvate thereof, wherein $R_2$ is —C(=O)$OR_6$ and $R_6$ is —$C_1$-$C_6$alkyl-$C_2$-$C_9$heterocycloalkyl optionally substituted with $C_1$-$C_6$alkyl. In some embodiments, provided herein is a compound of Formula (I') or (I), or a pharmaceutically acceptable salt or solvate thereof, wherein $R_2$ is —C(=O)$OR_6$ and $R_6$ is unsubstituted —$C_1$-$C_6$alkyl-$C_2$-$C_9$heterocycloalkyl.

In some embodiments, provided herein is a compound of Formula (I') or (I), or a pharmaceutically acceptable salt or solvate thereof, wherein $R_2$ is

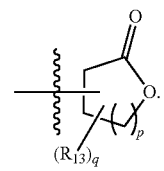

In some embodiments, provided herein is a compound of Formula (I') or (I), or a pharmaceutically acceptable salt or solvate thereof, wherein $R_2$ is

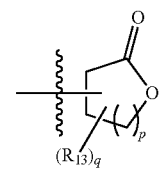

and p is 1. In some embodiments, provided herein is a compound of Formula (I') or (I), or a pharmaceutically acceptable salt or solvate thereof, wherein $R_2$ is

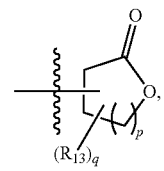

p is 1, and q is 0. In some embodiments, provided herein is a compound of Formula (I') or (I), or a pharmaceutically acceptable salt or solvate thereof, wherein $R_2$ is

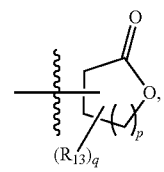

p is 1, and q is 2. In some embodiments, provided herein is a compound of Formula (I') or (I), or a pharmaceutically acceptable salt or solvate thereof, wherein $R_2$ is In some embodiments, provided herein is a compound of Formula (I') or (I), or a pharmaceutically acceptable salt or solvate thereof, wherein $R_2$ is

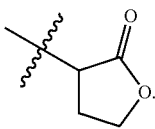 [SMILES: *C1CCOC1=O]

In some embodiments, provided herein is a compound of Formula (I') or (I), or a pharmaceutically acceptable salt or solvate thereof, wherein $R_2$ is

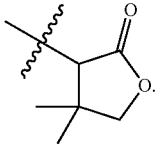 [SMILES: *C1C(=O)OCC1(C)C]

In some embodiments, provided herein is a compound of Formula (I') or (I), or a pharmaceutically acceptable salt or solvate thereof, wherein $R_2$ is

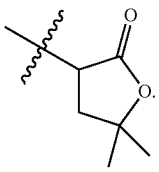 [SMILES: *C1CC(C)(C)OC1=O]

In some embodiments, provided herein is a compound of Formula (I'), or a pharmaceutically acceptable salt or solvate thereof, wherein $R_2$ is

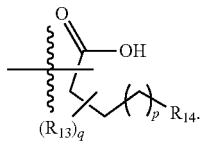

In some embodiments, provided herein is a compound of Formula (I'), or a pharmaceutically acceptable salt or solvate thereof, wherein $R_2$ is

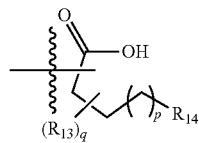

and p is 1. In some embodiments, provided herein is a compound of Formula (I'), or a pharmaceutically acceptable salt or solvate thereof, wherein $R_2$ is

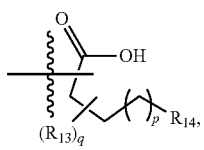

p is 1, and q is 0. In some embodiments, provided herein is a compound of Formula (I'), or a pharmaceutically acceptable salt or solvate thereof, wherein $R_2$ is

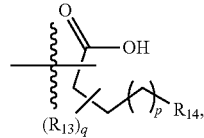

p is 1, and q is 2. In some embodiments, provided herein is a compound of Formula (I'), or a pharmaceutically acceptable salt or solvate thereof, wherein $R_{14}$ is —OH. In some embodiments, provided herein is a compound of Formula (I'), or a pharmaceutically acceptable salt or solvate thereof, wherein $R_{14}$ is —C(=O)H. In some embodiments, provided herein is a compound of Formula (I'), or a pharmaceutically acceptable salt or solvate thereof, wherein $R_{14}$ is —C(=O)OR$_{15}$. In some embodiments, provided herein is a compound of Formula (I'), or a pharmaceutically acceptable salt or solvate thereof, wherein $R_{14}$ is —C(=O)OR$_{15}$ and $R_{15}$ is hydrogen.

In some embodiments, provided herein is a compound of Formula (I') or (I), or a pharmaceutically acceptable salt or solvate thereof, wherein n is 0.

In some embodiments, provided herein is a compound of Formula (I') or (I), or a pharmaceutically acceptable salt or solvate thereof, wherein n is 1. In some embodiments, provided herein is a compound of Formula (I') or (I), or a pharmaceutically acceptable salt or solvate thereof, wherein n is 2. In some embodiments, provided herein is a compound of Formula (I') or (I), or a pharmaceutically acceptable salt or solvate thereof, wherein n is 3. In some embodiments, provided herein is a compound of Formula (I') or (I), or a pharmaceutically acceptable salt or solvate thereof, wherein n is 1 or 2 and each $R_3$ is independently selected from halogen, $C_1$-$C_6$alkyl, $C_1$-$C_6$haloalkyl, $C_1$-$C_6$heteroalkyl, —OR$_7$, —N(R$_7$)$_2$, —CN, —C(=O)R$_8$, —C(=O)OR$_7$, —C(=O)N(R$_7$)$_2$, —NR$_7$C(=O)R$_8$, —NR$_7$S(=O)$_2$R$_8$, —S(=O)$_2$R$_8$, and —S(=O)$_2$N(R$_7$)$_2$. In some embodiments, provided herein is a compound of Formula (I') or (I), or a pharmaceutically acceptable salt or solvate thereof, wherein n is 1 or 2 and each $R_3$ is independently selected from halogen, $C_1$-$C_6$alkyl, $C_1$-$C_6$haloalkyl, $C_1$-$C_6$heteroalkyl, —OR$_7$, —N(R$_7$)$_2$, —CN, —C(=O)R$_8$, —C(=O)OR$_7$, —C(=O)N(R$_7$)$_2$, —NR$_7$C(=O)R$_8$, —NR$_7$S(=O)$_2$R$_8$, —S(=O)$_2$R$_8$, and —S(=O)$_2$N(R$_7$)$_2$. In some embodiments, provided herein is a compound of Formula (I') or (I), or a pharmaceutically acceptable salt or solvate thereof, wherein n is 1 or 2 and each $R_3$ is independently selected from halogen, $C_1$-$C_6$alkyl, $C_1$-$C_6$haloalkyl, —OR$_7$, and —N(R$_7$)$_2$. In some embodiments, provided herein is a compound of Formula (I') or (I), or a pharmaceutically acceptable salt or solvate thereof, wherein n is 1 or 2 and each $R_3$ is independently selected from halogen and $C_1$-$C_6$alkyl. In some embodiments, provided herein is a compound of Formula (I') or (I), or a pharmaceutically acceptable salt or solvate thereof, wherein n is 1 and $R_3$ is selected from halogen, $C_1$-$C_6$alkyl, $C_1$-$C_6$haloalkyl, —OR$_7$, and —N(R$_7$)$_2$. In some embodiments, provided herein is a compound of Formula (I') or (I), or a pharmaceutically acceptable salt or solvate thereof, wherein n is 1 and $R_3$ is selected from halogen and $C_1$-$C_6$alkyl. In some embodiments, provided herein is a compound of Formula (I') or (I), or a pharmaceutically acceptable salt or solvate thereof, wherein n is 1 and $R_3$ is halogen. In some embodiments, provided herein is a compound of Formula (I') or (I), or a pharmaceutically acceptable salt or solvate thereof, wherein n is 1 and $R_3$ is $C_1$-$C_6$alkyl.

In some embodiments, provided herein is a compound of Formula (I') or (I), or a pharmaceutically acceptable salt or solvate thereof, wherein $R_4$ is hydrogen. In some embodiments, provided herein is a compound of Formula (I') or (I), or a pharmaceutically acceptable salt or solvate thereof, wherein $R_4$ is $C_1$-$C_6$alkyl. In some embodiments, provided herein is a compound of Formula (I') or (I), or a pharmaceutically acceptable salt or solvate thereof, wherein $R_4$ is —$CH_3$. In some embodiments, provided herein is a compound of Formula (I') or (I), or a pharmaceutically acceptable salt or solvate thereof, wherein $R_4$ is $C_1$-$C_6$heteroalkyl.

In some embodiments is a compound of Formula (I') or (I), or a pharmaceutically acceptable salt or solvate thereof, wherein $R_{12}$ is hydrogen. In some embodiments is a compound of Formula (I') or (I), or a pharmaceutically acceptable salt or solvate thereof, wherein $R_{12}$ is halogen. In some embodiments is a compound of Formula (I') or (I), or a pharmaceutically acceptable salt or solvate thereof, wherein $R_{12}$ is $C_1$-$C_6$alkyl. In some embodiments, provided herein is a compound of Formula (I') or (I), or a pharmaceutically acceptable salt or solvate thereof, wherein $R_{12}$ is —$CH_3$.

In some embodiments, provided herein is a compound of Formula (Ia'), or a pharmaceutically acceptable salt or solvate thereof:

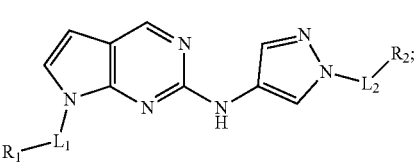

Formula (Ia')

wherein:
$L_1$ is a bond or $C_1$-$C_6$alkyl;
$L_2$ is $C_1$-$C_6$alkyl;
$R_1$ is $C_1$-$C_9$alkyl, $C_3$-$C_6$cycloalkyl, $C_2$-$C_9$heterocycloalkyl, or $C_2$-$C_9$heteroaryl, wherein $C_1$-$C_9$alkyl, $C_3$-$C_6$cycloalkyl, $C_2$-$C_9$heterocycloalkyl, or $C_2$-$C_9$heteroaryl are optionally substituted with 1, 2, or 3 $R_5$;
$R_2$ is —C(=O)$OR_6$,

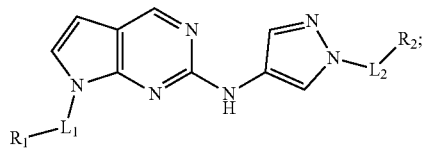

each $R_5$ is independently selected from halogen, $C_1$-$C_6$alkyl, $C_1$-$C_6$haloalkyl, $C_1$-$C_6$heteroalkyl, —$OR_7$, —N($R_7$)$_2$, —CN, —C(=O)$R_8$, —C(=O)$OR_7$, —C(=O)N($R_7$)$_2$, —$NR_7$C(=O)$R_8$, —$NR_7$S(=O)$_2$$R_8$, —S(=O)$_2$$R_8$, and —S(=O)$_2$N($R_7$)$_2$;
$R_6$ is hydrogen, $C_1$-$C_6$alkyl optionally subsituted with 1 or 2 Y, $C_3$-$C_6$cycloalkyl optionally subsituted with 1 or 2 Y, $C_2$-$C_9$heterocycloalkyl optionally substituted with $C_1$-$C_6$alkyl, or —$C_1$-$C_6$alkyl-$C_2$-$C_9$heterocycloalkyl optionally substituted with $C_1$-$C_6$alkyl;

each Y is independently selected from —CN, —$OR_9$, —$SR_9$, and —N($R_{10}$)$_2$;
each $R_7$ is independently selected from hydrogen, $C_1$-$C_6$alkyl, $C_2$-$C_6$alkenyl, $C_1$-$C_6$haloalkyl, and $C_1$-$C_6$heteroalkyl;
each $R_8$ is independently selected from $C_1$-$C_6$alkyl, $C_2$-$C_6$alkenyl, $C_1$-$C_6$heteroalkyl, $C_3$-$C_6$cycloalkyl, and $C_2$-$C_9$heterocycloalkyl;
each $R_9$ is independently selected from hydrogen and $C_1$-$C_6$alkyl; and
each $R_{10}$ is independently selected from hydrogen and $C_1$-$C_6$alkyl;
$R_{13}$ is $C_1$-$C_6$alkyl;
$R_{14}$ is —OH, —C(=O)H, or —C(=O)$OR_{15}$;
$R_{15}$ is hydrogen or $C_1$-$C_6$alkyl;
p is 0, 1, or 2; and
q is 0, 1, or 2.

In some embodiments, provided herein is a compound of Formula (Ia), or a pharmaceutically acceptable salt or solvate thereof:

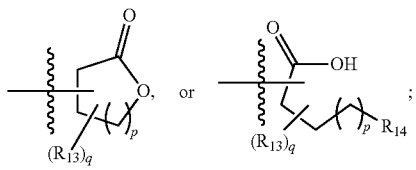

Formula (Ia)

wherein:
$L_1$ is a bond or $C_1$-$C_6$alkyl;
$L_2$ is $C_1$-$C_6$alkyl;
$R_1$ is $C_1$-$C_9$alkyl, $C_3$-$C_6$cycloalkyl, $C_2$-$C_9$heterocycloalkyl, or $C_2$-$C_9$heteroaryl, wherein $C_1$-$C_9$alkyl, $C_3$-$C_6$cycloalkyl, $C_2$-$C_9$heterocycloalkyl, or $C_2$-$C_9$heteroaryl are optionally substituted with 1, 2, or 3 $R_5$;
$R_2$ is —C(=O)$OR_6$ or

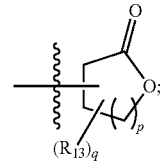

each $R_5$ is independently selected from halogen, $C_1$-$C_6$alkyl, $C_1$-$C_6$haloalkyl, $C_1$-$C_6$heteroalkyl, —$OR_7$, —N($R_7$)$_2$, —CN, —C(=O)$R_8$, —C(=O)$OR_7$, —C(=O)N($R_7$)$_2$, —$NR_7$C(=O)$R_8$, —$NR_7$S(=O)$_2$$R_8$, —S(=O)$_2$$R_8$, and —S(=O)$_2$N($R_7$)$_2$;
$R_6$ is hydrogen, $C_1$-$C_6$alkyl optionally subsituted with 1 or 2 Y, $C_3$-$C_6$cycloalkyl optionally subsituted with 1 or 2 Y, $C_2$-$C_9$heterocycloalkyl optionally substituted with $C_1$-$C_6$alkyl, or —$C_1$-$C_6$alkyl-$C_2$-$C_9$heterocycloalkyl optionally substituted with $C_1$-$C_6$alkyl;
each Y is independently selected from —CN, —$OR_9$, —$SR_9$, and —N($R_{10}$)$_2$;
each $R_7$ is independently selected from hydrogen, $C_1$-$C_6$alkyl, $C_2$-$C_6$alkenyl, $C_1$-$C_6$haloalkyl, and $C_1$-$C_6$heteroalkyl;
each $R_8$ is independently selected from $C_1$-$C_6$alkyl, $C_2$-$C_6$alkenyl, $C_1$-$C_6$heteroalkyl, $C_3$-$C_6$cycloalkyl, and $C_2$-$C_9$heterocycloalkyl;

each $R_9$ is independently selected from hydrogen and $C_1$-$C_6$alkyl; and each $R_{10}$ is independently selected from hydrogen and $C_1$-$C_6$alkyl;

$R_{13}$ is $C_1$-$C_6$alkyl;

n is 0, 1, 2, or 3;

p is 0, 1, or 2; and q is 0, 1, or 2.

In some embodiments, provided herein is a compound of Formula (Ia') or (Ia), or a pharmaceutically acceptable salt or solvate thereof, wherein $L_1$ is $C_1$-$C_6$alkyl. In some embodiments, provided herein is a compound of Formula (Ia') or (Ia), or a pharmaceutically acceptable salt or solvate thereof, wherein $L_1$ is —$CH_2$—. In some embodiments, provided herein is a compound of Formula (Ia') or (Ia), or a pharmaceutically acceptable salt or solvate thereof, wherein $L_1$ is —$CH_2CH_2$—. In some embodiments, provided herein is a compound of Formula (Ia') or (Ia), or a pharmaceutically acceptable salt or solvate thereof, wherein $L_1$ is a bond.

In some embodiments, provided herein is a compound of Formula (Ia') or (Ia), or a pharmaceutically acceptable salt or solvate thereof, wherein $R_1$ is $C_1$-$C_6$alkyl optionally substituted with 1, 2, or 3 $R_5$. In some embodiments, provided herein is a compound of Formula (Ia') or (Ia), or a pharmaceutically acceptable salt or solvate thereof, wherein $R_1$ is $C_3$-$C_9$alkyl optionally substituted with 1, 2, or 3 $R_5$. In some embodiments, provided herein is a compound of Formula (Ia') or (Ia), or a pharmaceutically acceptable salt or solvate thereof, wherein $R_1$ is unsubstituted $C_1$-$C_9$alkyl. In some embodiments, provided herein is a compound of Formula (Ia') or (Ia), or a pharmaceutically acceptable salt or solvate thereof, wherein $R_1$ is unsubstituted $C_3$-$C_9$alkyl. In some embodiments, provided herein is a compound of Formula (Ia') or (Ia), or a pharmaceutically acceptable salt or solvate thereof, wherein $R_1$ is $C_3$-$C_6$cycloalkyl optionally substituted with 1, 2, or 3 $R_5$. In some embodiments, provided herein is a compound of Formula (Ia') or (Ia), or a pharmaceutically acceptable salt or solvate thereof, wherein $R_1$ is $C_3$-$C_6$cycloalkyl optionally substituted with 1, 2, or 3 $R_5$, wherein each $R_5$ is independently selected from halogen, $C_1$-$C_6$alkyl, $C_1$-$C_6$haloalkyl, —$OR_7$, and —$N(R_7)_2$. In some embodiments, provided herein is a compound of Formula (Ia') or (Ia), or a pharmaceutically acceptable salt or solvate thereof, wherein $R_1$ is $C_3$-$C_6$cycloalkyl optionally substituted with 1, 2, or 3 $R_5$, wherein each $R_5$ is independently selected from halogen and $C_1$-$C_6$alkyl. In some embodiments, provided herein is a compound of Formula (Ia') or (Ia), or a pharmaceutically acceptable salt or solvate thereof, wherein $R_1$ is unsubstituted $C_3$-$C_6$cycloalkyl. In some embodiments, provided herein is a compound of Formula (Ia') or (Ia), or a pharmaceutically acceptable salt or solvate thereof, wherein $R_1$ is $C_2$-$C_9$heterocycloalkyl optionally substituted with 1, 2, or 3 $R_5$. In some embodiments, provided herein is a compound of Formula (Ia') or (Ia), or a pharmaceutically acceptable salt or solvate thereof, wherein $R_1$ is $C_2$-$C_9$heterocycloalkyl optionally substituted with 1, 2, or 3 $R_5$, wherein each $R_5$ is independently selected from halogen, $C_1$-$C_6$alkyl, $C_1$-$C_6$haloalkyl, —$OR_7$, and —$N(R_7)_2$. In some embodiments, provided herein is a compound of Formula (Ia') or (Ia), or a pharmaceutically acceptable salt or solvate thereof, wherein $R_1$ is $C_2$-$C_9$heterocycloalkyl optionally substituted with 1, 2, or 3 $R_5$, wherein each $R_5$ is independently selected from halogen and $C_1$-$C_6$alkyl. In some embodiments, provided herein is a compound of Formula (Ia') or (Ia), or a pharmaceutically acceptable salt or solvate thereof, wherein $R_1$ is unsubstituted $C_2$-$C_9$heterocycloalkyl. In some embodiments, provided herein is a compound of Formula (Ia') or (Ia), or a pharmaceutically acceptable salt or solvate thereof, wherein $R_1$ is $C_2$-$C_9$heteroaryl optionally substituted with 1, 2, or 3 $R_5$. In some embodiments, provided herein is a compound of Formula (Ia') or (Ia), or a pharmaceutically acceptable salt or solvate thereof, wherein $R_1$ is $C_2$-$C_9$heteroaryl optionally substituted with 1, 2, or 3 $R_5$, wherein each $R_5$ is independently selected from halogen, $C_1$-$C_6$alkyl, $C_1$-$C_6$haloalkyl, —$OR_7$, and —$N(R_7)_2$. In some embodiments, provided herein is a compound of Formula (Ia') or (Ia), or a pharmaceutically acceptable salt or solvate thereof, wherein $R_1$ is $C_2$-$C_9$heteroaryl optionally substituted with 1, 2, or 3 $R_5$, wherein each $R_5$ is independently selected from halogen and $C_1$-$C_6$alkyl. In some embodiments, provided herein is a compound of Formula (Ia') or (Ia), or a pharmaceutically acceptable salt or solvate thereof, wherein $R_1$ is unsubstituted $C_2$-$C_9$heteroaryl. In some embodiments, provided herein is a compound of Formula (Ia') or (Ia), or a pharmaceutically acceptable salt or solvate thereof, wherein $C_2$-$C_9$heteroaryl is selected from oxazolyl, thiazolyl, pyrazolyl, furanyl, thienyl, pyrrolyl, imidazolyl, triazolyl, tetrazolyl, isoxazolyl, isothiazolyl, oxadiazolyl, and thiadiazolyl.

In some embodiments, provided herein is a compound of Formula (Ia') or (Ia), or a pharmaceutically acceptable salt or solvate thereof, wherein $L_2$ is —$CH_2$—. In some embodiments, provided herein is a compound of Formula (Ia') or (Ia), or a pharmaceutically acceptable salt or solvate thereof, wherein $L_2$ is —$CH_2CH_2$—. In some embodiments, provided herein is a compound of Formula (Ia') or (Ia), or a pharmaceutically acceptable salt or solvate thereof, wherein $L_2$ is —$CH_2CH_2CH_2$—.

In some embodiments, provided herein is a compound of Formula (Ia') or (Ia), or a pharmaceutically acceptable salt or solvate thereof, wherein $R_2$ is —$C(=O)OR_6$. In some embodiments, provided herein is a compound of Formula (Ia') or (Ia), or a pharmaceutically acceptable salt or solvate thereof, wherein $R_2$ is —$C(=O)OR_6$ and $R_6$ is $C_1$-$C_6$alkyl optionally subsituted with 1 or 2 Y. In some embodiments, provided herein is a compound of Formula (Ia') or (Ia), or a pharmaceutically acceptable salt or solvate thereof, wherein $R_2$ is —$CO_2C_1$-$C_6$alkyl. In some embodiments, provided herein is a compound of Formula (Ia') or (Ia), or a pharmaceutically acceptable salt or solvate thereof, wherein $R_2$ is —$CO_2CH_3$. In some embodiments, provided herein is a compound of Formula (Ia') or (Ia), or a pharmaceutically acceptable salt or solvate thereof, wherein $R_2$ is —$C_2CH_2CH_3$. In some embodiments, provided herein is a compound of Formula (Ia') or (Ia), or a pharmaceutically acceptable salt or solvate thereof, wherein $R_2$ is —$CO_2H$. In some embodiments, provided herein is a compound of Formula (Ia') or (Ia), or a pharmaceutically acceptable salt or solvate thereof, wherein $R_2$ is —$CO_2C_1$-$C_6$alkyl-Y. In some embodiments, provided herein is a compound of Formula (Ia') or (Ia), or a pharmaceutically acceptable salt or solvate thereof, wherein $R_2$ is —$CO_2C_1$-$C_6$alkyl-$OR_9$. In some embodiments, provided herein is a compound of Formula (Ia') or (Ia), or a pharmaceutically acceptable salt or solvate thereof, wherein $R_2$ is —$C(=O)OR_6$ and $R_6$ is $C_2$-$C_9$heterocycloalkyl optionally substituted with $C_1$-$C_6$alkyl. In some embodiments, provided herein is a compound of Formula (Ia') or (Ia), or a pharmaceutically acceptable salt or solvate thereof, wherein $R_2$ is —$C(=O)OR_6$ and $R_6$ is unsubstituted $C_2$-$C_9$heterocycloalkyl. In some embodiments, provided herein is a compound of Formula (Ia') or (Ia), or a pharmaceutically acceptable salt or solvate thereof, wherein $R_2$ is —$C(=O)OR_6$ and $R_6$ is —$C_1$-$C_6$alkyl-$C_2$-$C_9$heterocycloalkyl optionally substituted with $C_1$-$C_6$alkyl. In some embodiments, provided herein is a compound of Formula (Ia') or (Ia), or a pharmaceutically acceptable salt or solvate thereof, wherein $R_2$ is —C(=O)OR$_6$ and $R_6$ is unsubstituted —$C_1$-$C_6$alky-$C_2$-$C_9$heterocycloalkyl.

In some embodiments, provided herein is a compound of Formula (Ia') or (Ia), or a pharmaceutically acceptable salt or solvate thereof, wherein $R_2$ is

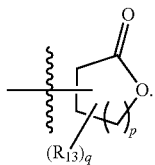

In some embodiments, provided herein is a compound of Formula (Ia') or (Ia), or a pharmaceutically acceptable salt or solvate thereof, wherein $R_2$ is

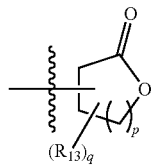

and p is 1. In some embodiments, provided herein is a compound of Formula (Ia') or (Ia), or a pharmaceutically acceptable salt or solvate thereof, wherein $R_2$ is

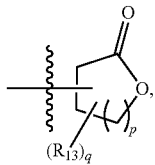

p is 1, and q is 0. In some embodiments, provided herein is a compound of Formula (Ia') or (Ia), or a pharmaceutically acceptable salt or solvate thereof, wherein $R_2$ is

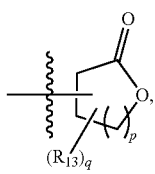

p is 1, and q is 2. In some embodiments, provided herein is a compound of Formula (Ia') or (Ia), or a pharmaceutically acceptable salt or solvate thereof, wherein $R_2$ is

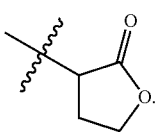 [SMILES: *C1CCOC1=O]

In some embodiments, provided herein is a compound of Formula (Ia') or (Ia), or a pharmaceutically acceptable salt or solvate thereof, wherein $R_2$ is

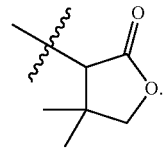 [SMILES: *C1C(=O)OCC1(C)C]

In some embodiments, provided herein is a compound of Formula (Ia), or a pharmaceutically acceptable salt or solvate thereof, wherein $R_2$ is

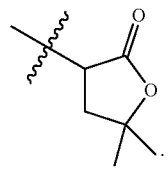 [SMILES: *C1CC(C)(C)OC1=O]

In some embodiments, provided herein is a compound of Formula (Ia'), or a pharmaceutically acceptable salt or solvate thereof, wherein $R_2$ is

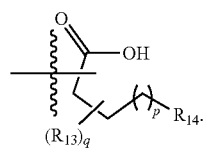

In some embodiments, provided herein is a compound of Formula (Ia'), or a pharmaceutically acceptable salt or solvate thereof, wherein $R_2$ is

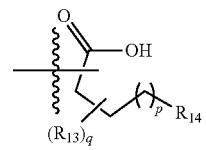

and p is 1. In some embodiments, provided herein is a compound of Formula (Ia'), or a pharmaceutically acceptable salt or solvate thereof, wherein $R_2$ is

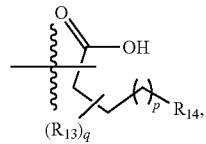

p is 1, and q is 0. In some embodiments, provided herein is a compound of Formula (Ia'), or a pharmaceutically acceptable salt or solvate thereof, wherein $R_2$

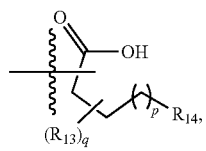

p is 1, and q is 2. In some embodiments, provided herein is a compound of Formula (Ia'), or a pharmaceutically acceptable salt or solvate thereof, wherein $R_{14}$ is —OH. In some embodiments, provided herein is a compound of Formula (Ia'), or a pharmaceutically acceptable salt or solvate thereof, wherein $R_{14}$ is —C(=O)H. In some embodiments, provided herein is a compound of Formula (Ia'), or a pharmaceutically acceptable salt or solvate thereof, wherein $R_{14}$ is —C(=O)OR$_{15}$. In some embodiments, provided herein is a compound of Formula (Ia'), or a pharmaceutically acceptable salt or solvate thereof, wherein $R_{14}$ is —C(=O)OR$_{15}$ and $R_{15}$ is hydrogen.

In some embodiments, provided herein is a compound of Formula (Ib), or a pharmaceutically acceptable salt or solvate thereof:

Formula (Ib)

wherein:
$L_1$ is $C_1$-$C_6$alkyl;
$L_2$ is a bond or $C_1$-$C_6$alkyl;
$R_1$ is $C_1$-$C_6$alkyl, $C_3$-$C_6$cycloalkyl, $C_2$-$C_9$heterocycloalkyl, or $C_2$-$C_9$heteroaryl, wherein $C_3$-$C_6$alkyl, $C_3$-$C_6$cycloalkyl, $C_2$-$C_9$heterocycloalkyl, or $C_2$-$C_9$heteroaryl are optionally substituted with 1, 2, or 3 $R_5$;
$R_2$ is —C(=O)OR$_6$ or

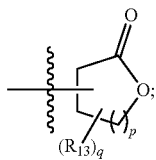

each $R_5$ is independently selected from halogen, $C_1$-$C_6$alkyl, $C_1$-$C_6$haloalkyl, $C_1$-$C_6$heteroalkyl, —OR$_7$, —N(R$_7$)$_2$, —CN, —C(=O)R$_8$, —C(=O)OR$_7$, —C(=O)N(R$_7$)$_2$, —NR$_7$C(=O)R$_8$, —NR$_7$S(=O)$_2$R$_8$, —S(=O)$_2$R$_8$, and —S(=O)$_2$N(R$_7$)$_2$;
$R_6$ is hydrogen, $C_1$-$C_6$alkyl, $C_2$-$C_9$heterocycloalkyl optionally substituted with $C_1$-$C_6$alkyl, or —$C_1$-$C_6$alkyl-$C_2$-$C_9$heterocycloalkyl optionally substituted with $C_1$-$C_6$alkyl;
each $R_7$ is independently selected from hydrogen, $C_1$-$C_6$alkyl, $C_2$-$C_6$alkenyl, $C_1$-$C_6$haloalkyl, and $C_1$-$C_6$heteroalkyl; and
each $R_8$ is independently selected from $C_1$-$C_6$alkyl, $C_2$-$C_6$alkenyl, $C_1$-$C_6$heteroalkyl, $C_3$-$C_6$cycloalkyl, and $C_2$-$C_9$heterocycloalkyl;
$R_{13}$ is $C_1$-$C_6$alkyl;
p is 0, 1, or 2; and
q is 0, 1, or 2.

In some embodiments, provided herein is a compound of Formula (Ib), or a pharmaceutically acceptable salt or solvate thereof, wherein $L_1$ is —CH$_2$—. In some embodiments, provided herein is a compound of Formula (Ib), or a pharmaceutically acceptable salt or solvate thereof, wherein $L_1$ is —CH$_2$CH$_2$—.

In some embodiments, provided herein is a compound of Formula (Ib), or a pharmaceutically acceptable salt or solvate thereof, wherein $R_1$ is $C_1$-$C_6$alkyl optionally substituted with 1, 2, or 3 $R_5$. In some embodiments, provided herein is a compound of Formula (Ib), or a pharmaceutically acceptable salt or solvate thereof, wherein $R_1$ is unsubstituted $C_1$-$C_6$alkyl. In some embodiments, provided herein is a compound of Formula (Ib), or a pharmaceutically acceptable salt or solvate thereof, wherein $R_1$ is $C_3$-$C_6$cycloalkyl optionally substituted with 1, 2, or 3 $R_5$. In some embodiments, provided herein is a compound of Formula (Ib), or a pharmaceutically acceptable salt or solvate thereof, wherein $R_1$ is $C_3$-$C_6$cycloalkyl optionally substituted with 1, 2, or 3 $R_5$, wherein each $R_5$ is independently selected from halogen, $C_1$-$C_6$alkyl, $C_1$-$C_6$haloalkyl, —OR$_7$, and —N(R$_7$)$_2$. In some embodiments, provided herein is a compound of Formula (Ib), or a pharmaceutically acceptable salt or solvate thereof, wherein $R_1$ is $C_3$-$C_6$cycloalkyl optionally substituted with 1, 2, or 3 $R_5$, wherein each $R_5$ is independently selected from halogen and $C_1$-$C_6$alkyl. In some embodiments, provided herein is a compound of Formula (Ib), or a pharmaceutically acceptable salt or solvate thereof, wherein $R_1$ is unsubstituted $C_3$-$C_6$cycloalkyl. In some embodiments, provided herein is a compound of Formula (Ib), or a pharmaceutically acceptable salt or solvate thereof, wherein $R_1$ is $C_2$-$C_9$heterocycloalkyl optionally substituted with 1, 2, or 3 $R_5$. In some embodiments, provided herein is a compound of Formula (Ib), or a pharmaceutically acceptable salt or solvate thereof, wherein $R_1$ is $C_2$-$C_9$heterocycloalkyl optionally substituted with 1, 2, or 3 $R_5$, wherein each $R_5$ is independently selected from halogen, $C_1$-$C_6$alkyl, $C_1$-$C_6$haloalkyl, —OR$_7$, and —N(R$_7$)$_2$. In some embodiments, provided herein is a compound of Formula (Ib), or a pharmaceutically acceptable salt or solvate thereof, wherein $R_1$ is $C_2$-$C_9$heterocycloalkyl optionally substituted with 1, 2, or 3 $R_5$, wherein each $R_5$ is independently selected from halogen and $C_1$-$C_6$alkyl. In some embodiments, provided herein is a compound of Formula (Ib), or a pharmaceutically acceptable salt or solvate thereof, wherein $R_1$ is unsubstituted $C_2$-$C_9$heterocycloalkyl. In some embodiments, provided herein is a compound of Formula (Ib), or a pharmaceutically acceptable salt or solvate thereof, wherein $R_1$ is $C_2$-$C_9$heteroaryl optionally substituted with 1, 2, or 3 $R_5$. In some embodiments, provided herein is a compound of Formula (Ib), or a pharmaceutically acceptable salt or solvate thereof, wherein $R_1$ is $C_2$-$C_9$heteroaryl optionally substituted with 1, 2, or 3 $R_5$, wherein each $R_5$ is independently selected from halogen, $C_1$-$C_6$alkyl, $C_1$-$C_6$haloalkyl, —OR$_7$, and —N(R$_7$)$_2$. In some embodiments, provided herein is a compound of Formula (Ib), or a pharmaceutically acceptable salt or solvate thereof, wherein $R_1$ is $C_2$-$C_9$heteroaryl optionally substituted with 1, 2, or 3 $R_5$, wherein each $R_5$ is independently selected from halogen and $C_1$-$C_6$alkyl. In some embodiments, provided herein is a compound of Formula (Ib), or a pharmaceutically acceptable salt or solvate thereof, wherein $R_1$ is unsubstituted $C_2$-$C_9$heteroaryl. In some embodiments, provided herein is a compound of Formula (Ib), or a pharmaceutically acceptable salt or solvate thereof, wherein $C_2$-$C_9$heteroaryl is selected from oxazolyl, thiazolyl, pyrazolyl, furanyl, thienyl, pyrrolyl, imidazolyl, triazolyl, tetrazolyl, isoxazolyl, isothiazolyl, oxadiazolyl, and thiadiazolyl.

In some embodiments, provided herein is a compound of Formula (Ib), or a pharmaceutically acceptable salt or solvate thereof, wherein $L_2$ is a bond. In some embodiments, provided herein is a compound of Formula (Ib), or a pharmaceutically acceptable salt or solvate thereof, wherein $L_2$ is —CH$_2$—. In some embodiments, provided herein is a compound of Formula (Ib), or a pharmaceutically acceptable salt or solvate thereof, wherein $L_2$ is —CH$_2$CH$_2$—. In some embodiments, provided herein is a compound of Formula (Ib), or a pharmaceutically acceptable salt or solvate thereof, wherein $L_2$ is —CH$_2$CH$_2$CH$_2$—.

In some embodiments, provided herein is a compound of Formula (Ib), or a pharmaceutically acceptable salt or solvate thereof, wherein $R_2$ is —C(=O)OR$_6$. In some embodiments, provided herein is a compound of Formula (Ib), or a pharmaceutically acceptable salt or solvate thereof, wherein $R_2$ is —C(=O)OR$_6$ and $R_6$ is $C_1$-$C_6$alkyl optionally subsituted with 1 or 2 Y. In some embodiments, provided herein is a compound of Formula (Ib), or a pharmaceutically acceptable salt or solvate thereof, wherein $R_2$ is —CO$_2$C$_1$-C$_6$alkyl. In some embodiments, provided herein is a compound of Formula (Ib), or a pharmaceutically acceptable salt or solvate thereof, wherein $R_2$ is —CO$_2$CH$_3$. In some embodiments, provided herein is a compound of Formula (Ib), or a pharmaceutically acceptable salt or solvate thereof, wherein $R_2$ is —CO$_2$CH$_2$CH$_3$. In some embodiments, provided herein is a compound of Formula (Ib), or a pharmaceutically acceptable salt or solvate thereof, wherein $R_2$ is —CO$_2$H. In some embodiments, provided herein is a compound of Formula (Ib), or a pharmaceutically acceptable salt or solvate thereof, wherein $R_2$ is —C(=O)OR$_6$ and $R_6$ is $C_2$-$C_9$heterocycloalkyl optionally substituted with $C_1$-$C_6$alkyl. In some embodiments, provided herein is a compound of Formula (Ib), or a pharmaceutically acceptable salt or solvate thereof, wherein $R_2$ is —C(=O)OR$_6$ and $R_6$ is unsubstituted $C_2$-$C_9$heterocycloalkyl. In some embodiments, provided herein is a compound of Formula (Ib), or a pharmaceutically acceptable salt or solvate thereof, wherein $R_2$ is —C(=O)OR$_6$ and $R_6$ is —C$_1$-C$_6$alkyl-C$_2$-C$_9$heterocycloalkyl optionally substituted with $C_1$-$C_6$alkyl. In some embodiments, provided herein is a compound of Formula (Ib), or a pharmaceutically acceptable salt or solvate thereof, wherein $R_2$ is —C(=O)OR$_6$ and $R_6$ is unsubstituted —C$_1$-C$_6$alkyl-C$_2$-C$_9$heterocycloalkyl.

In some embodiments, provided herein is a compound of Formula (II'), or a pharmaceutically acceptable salt or solvate thereof:

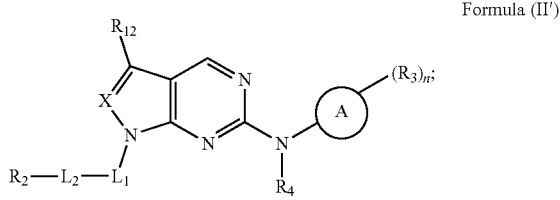

Formula (II')

wherein:

is a $C_2$-$C_9$heteroaryl ring;
X is C(R$_{11}$) or N;
$L_1$ is a bond or $C_1$-$C_6$alkyl;
$L_2$ is $C_1$-$C_6$alkyl, $C_2$-$C_9$heteroaryl, or —C(H)(phenyl)-;
$R_2$ is —C(=O)OR$_6$,

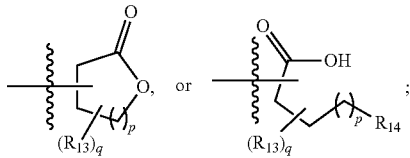

each $R_3$ is independently selected from halogen, $C_1$-$C_6$alkyl, $C_1$-$C_6$haloalkyl, $C_1$-$C_6$alkoxy, $C_1$-$C_6$heteroalkyl, —OR$_7$, —N(R$_7$)$_2$, —CN, —C(=O)R$_8$, —C(=O)OR$_7$, —C(=O)N(R$_7$)$_2$, —NR$_7$C(=O)R$_8$, —NR$_7$S(=O)$_2$R$_8$, —S(=O)$_2$R$_8$, and —S(=O)$_2$N(R$_7$)$_2$;
$R_4$ is hydrogen, $C_1$-$C_6$alkyl, or $C_1$-$C_6$heteroalkyl;
each $R_5$ is independently selected from halogen, oxo, $C_1$-$C_6$alkyl, $C_1$-$C_6$haloalkyl, $C_1$-$C_6$heteroalkyl, —OR$_7$, —N(R$_7$)$_2$, —CN, —C(=O)R$_8$, —C(=O)OR$_7$, —C(=O)N(R$_7$)$_2$, —NR$_7$C(=O)R$_8$, —NR$_7$S(=O)$_2$R$_8$, —S(=O)$_2$R$_8$, and —S(=O)$_2$N(R$_7$)$_2$;
$R_6$ is hydrogen, $C_1$-$C_6$alkyl optionally subsituted with 1 or 2 Y, $C_3$-$C_6$cycloalkyl optionally subsituted with 1 or 2 Y, $C_3$-$C_6$cycloalkyl optionally subsituted with 1 or 2 Y, $C_2$-$C_9$heterocycloalkyl optionally substituted with $C_1$-$C_6$alkyl, or —C$_1$-$C_6$alkyl-C$_2$-$C_9$heterocycloalkyl optionally substituted with $C_1$-$C_6$alkyl;
each Y is independently selected from —CN, —OR$_9$, —SR$_9$, and —N(R$_{10}$)$_2$;
each $R_7$ is independently selected from hydrogen, $C_1$-$C_6$alkyl, $C_2$-$C_6$alkenyl, $C_1$-$C_6$haloalkyl, and $C_1$-$C_6$heteroalkyl;
each $R_8$ is independently selected from $C_1$-$C_6$alkyl, $C_2$-$C_6$alkenyl, $C_1$-$C_6$heteroalkyl, $C_3$-$C_6$cycloalkyl, and $C_2$-$C_9$heterocycloalkyl;
each $R_9$ is independently selected from hydrogen and $C_1$-$C_6$alkyl;
each $R_{10}$ is independently selected from hydrogen and $C_1$-$C_6$alkyl;
$R_{11}$ is hydrogen or $C_1$-$C_6$alkyl optionally substituted with 1, 2, or 3 $R_5$;
$R_{12}$ is hydrogen, halogen, or $C_1$-$C_6$alkyl;
$R_{13}$ is $C_1$-$C_6$alkyl;
$R_{14}$ is —OH, —C(=O)H, or —C(=O)ORi5;
$R_{15}$ is hydrogen or $C_1$-$C_6$alkyl;
n is 0, 1, 2, or 3;
p is 0, 1, or 2; and
q is 0, 1, or 2.

In some embodiments, provided herein is a compound of Formula (II), or a pharmaceutically acceptable salt or solvate thereof:

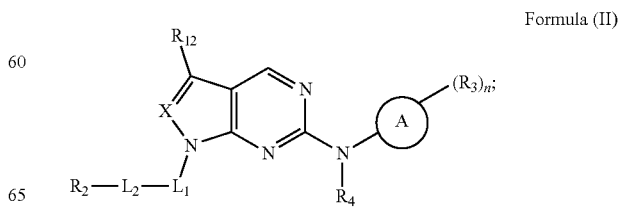

Formula (II)

wherein:

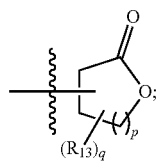

is a $C_2$-$C_9$heteroaryl ring;
$X$ is $C(R_{11})$ or $N$;
$L_1$ is a bond or $C_1$-$C_6$alkyl;
$L_2$ is $C_1$-$C_6$alkyl, $C_2$-$C_9$heteroaryl, or —C(H)(phenyl)-;
$R_2$ is —C(=O)OR$_6$ or each $R_3$ is independently selected from halogen, $C_1$-$C_6$alkyl, $C_1$-$C_6$haloalkyl, $C_1$-$C_6$alkoxy, $C_1$-$C_6$heteroalkyl, —OR$_7$, —N(R$_7$)$_2$, —CN, —C(=O)R$_8$, —C(=O)OR$_7$, —C(=O)N(R$_7$)$_2$, —NR$_7$C(=O)R$_8$, —NR$_7$S(=O)$_2$R$_8$, —S(=O)$_2$R$_8$, and —S(=O)$_2$N(R$_7$)$_2$;
$R_4$ is hydrogen, $C_1$-$C_6$alkyl, or $C_1$-$C_6$heteroalkyl;
each $R_5$ is independently selected from halogen, oxo, $C_1$-$C_6$alkyl, $C_1$-$C_6$haloalkyl, $C_1$-$C_6$heteroalkyl, —OR$_7$, —N(R$_7$)$_2$, —CN, —C(=O)R$_8$, —C(=O)OR$_7$, —C(=O)N(R$_7$)$_2$, —NR$_7$C(=O)R$_8$, —NR$_7$S(=O)$_2$R$_8$, —S(=O)$_2$R$_8$, and —S(=O)$_2$N(R$_7$)$_2$;
$R_6$ is hydrogen, $C_1$-$C_6$alkyl optionally subsituted with 1 or 2 Y, $C_3$-$C_6$cycloalkyl optionally subsituted with 1 or 2 Y, $C_2$-$C_9$heterocycloalkyl optionally substituted with $C_1$-$C_6$alkyl, or —$C_1$-$C_6$alkyl-$C_2$-$C_9$heterocycloalkyl optionally substituted with $C_1$-$C_6$alkyl;
each Y is independently selected from —CN, —OR$_9$, —SR$_9$, and —N(R$_{10}$)$_2$;
each $R_7$ is independently selected from hydrogen, $C_1$-$C_6$alkyl, $C_2$-$C_6$alkenyl, $C_1$-$C_6$haloalkyl, and $C_1$-$C_6$heteroalkyl;
each $R_8$ is independently selected from $C_1$-$C_6$alkyl, $C_2$-$C_6$alkenyl, $C_1$-$C_6$heteroalkyl, $C_3$-$C_6$cycloalkyl, and $C_2$-$C_9$heterocycloalkyl;
each $R_9$ is independently selected from hydrogen and $C_1$-$C_6$alkyl;
each $R_{10}$ is independently selected from hydrogen and $C_1$-$C_6$alkyl;
$R_{11}$ is hydrogen or $C_1$-$C_6$alkyl optionally substituted with 1, 2, or 3 $R_5$;
$R_{12}$ is hydrogen, halogen, or $C_1$-$C_6$alkyl;
$R_{13}$ is $C_1$-$C_6$alkyl;
n is 0, 1, 2, or 3;
p is 0, 1, or 2; and
q is 0, 1, or 2.

In some embodiments is a compound of Formula (II') or (II), or a pharmaceutically acceptable salt or solvate thereof, wherein X is C(R$_{11}$). In some embodiments is a compound of Formula (II') or (II), or a pharmaceutically acceptable salt or solvate thereof, wherein X is C(H). In some embodiments is a compound of Formula (II') or (II), or a pharmaceutically acceptable salt or solvate thereof, wherein X is N.

In some embodiments is a compound of Formula (II') or (II), or a pharmaceutically acceptable salt or solvate thereof, wherein

A is a $C_2$-$C_9$heteroaryl ring selected from oxazolyl, thiazolyl, pyrazolyl, furanyl, thienyl, pyrrolyl, imidazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl. In some embodiments is a compound of Formula (II') or (II), or a pharmaceutically acceptable salt or solvate thereof, wherein

A is a $C_2$-$C_9$heteroaryl ring selected from pyrazolyl, pyrrolyl, and imidazolyl. In some embodiments is a compound of Formula (II') or (II), or a pharmaceutically acceptable salt or solvate thereof, wherein

A is pyrazolyl. In some embodiments is a compound of Formula (II') or (II), or a pharmaceutically acceptable salt or solvate thereof, wherein

A is pyrrolyl. In some embodiments is a compound of Formula (II') or (II), or a pharmaceutically acceptable salt or solvate thereof, wherein

A is imidazolyl. In some embodiments is a compound of Formula (II') or (II), or a pharmaceutically acceptable salt or solvate thereof, wherein

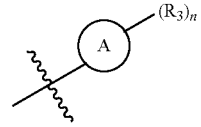

is selected from

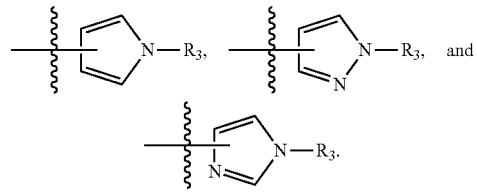

In some embodiments is a compound of Formula (II') or (II), or a pharmaceutically acceptable salt or solvate thereof, wherein

[Structure: A ring with $(R_3)_n$ is imidazole with $N-R_3$]

In some embodiments is a compound of Formula (II') or (II), or a pharmaceutically acceptable salt or solvate thereof, wherein

[Structure: A ring with $(R_3)_n$ is pyrazole with $N-R_3$]

In some embodiments is a compound of Formula (II') or (II), or a pharmaceutically acceptable salt or solvate thereof, wherein

[Structure: A ring with $(R_3)_n$ is imidazole isomer with $N-R_3$]

In some embodiments, provided herein is a compound of Formula (II') or (II), or a pharmaceutically acceptable salt or solvate thereof, wherein $L_1$ is a bond. In some embodiments, provided herein is a compound of Formula (II') or (II), or a pharmaceutically acceptable salt or solvate thereof, wherein $L_1$ is $C_1$-$C_6$alkyl. In some embodiments, provided herein is a compound of Formula (II') or (II), or a pharmaceutically acceptable salt or solvate thereof, wherein $L_1$ is —$CH_2$—. In some embodiments, provided herein is a compound of Formula (II') or (II), or a pharmaceutically acceptable salt or solvate thereof, wherein $L_1$ is —$CH_2CH_2$—. In some embodiments, provided herein is a compound of Formula (II') or (II), or a pharmaceutically acceptable salt or solvate thereof, wherein $L_1$ is —$CH_2CH_2CH_2$—.

In some embodiments, provided herein is a compound of Formula (II') or (II), or a pharmaceutically acceptable salt or solvate thereof, wherein $L_2$ is $C_1$-$C_6$alkyl. In some embodiments, provided herein is a compound of Formula (II') or (II), or a pharmaceutically acceptable salt or solvate thereof, wherein $L_2$ is —$CH_2$—. In some embodiments, provided herein is a compound of Formula (II') or (II), or a pharmaceutically acceptable salt or solvate thereof, wherein $L_2$ is —$CH_2CH_2$—. In some embodiments, provided herein is a compound of Formula (II') or (II), or a pharmaceutically acceptable salt or solvate thereof, wherein $L_2$ is —$CH_2CH_2CH_2$—. In some embodiments, provided herein is a compound of Formula (II') or (II), or a pharmaceutically acceptable salt or solvate thereof, wherein $L_2$ is $C_2$-$C_9$heteroaryl. In some embodiments, provided herein is a compound of Formula (II') or (II), or a pharmaceutically acceptable salt or solvate thereof, wherein $L_2$ is $C_2$-$C_9$heteroaryl selected from oxazolyl, thiazolyl, pyrazolyl, furanyl, thienyl, pyrrolyl, imidazolyl, triazolyl, tetrazolyl, isoxazolyl, isothiazolyl, oxadiazolyl, thiadiazolyl, pyridinyl, pyrimidinyl, pyrazinyl, pyridazinyl, and triazinyl. In some embodiments, provided herein is a compound of Formula (II') or (II), or a pharmaceutically acceptable salt or solvate thereof, wherein $L_2$ is $C_2$-$C_9$heteroaryl selected from oxazolyl, thiazolyl, pyrazolyl, thienyl, pyrrolyl, imidazolyl, and pyridinyl. In some embodiments, provided herein is a compound of Formula (II') or (II), or a pharmaceutically acceptable salt or solvate thereof, wherein $L_2$ is oxazolyl. In some embodiments, provided herein is a compound of Formula (II') or (II), or a pharmaceutically acceptable salt or solvate thereof, wherein $L_2$ is thiazolyl. In some embodiments, provided herein is a compound of Formula (II') or (II), or a pharmaceutically acceptable salt or solvate thereof, wherein $L_2$ is pyrazolyl. In some embodiments, provided herein is a compound of Formula (II') or (II), or a pharmaceutically acceptable salt or solvate thereof, wherein $L_2$ is thienyl. In some embodiments, provided herein is a compound of Formula (II') or (II), or a pharmaceutically acceptable salt or solvate thereof, wherein $L_2$ is pyrrolyl. In some embodiments, provided herein is a compound of Formula (II') or (II), or a pharmaceutically acceptable salt or solvate thereof, wherein $L_2$ is imidazolyl. In some embodiments, provided herein is a compound of Formula (II') or (II), or a pharmaceutically acceptable salt or solvate thereof, wherein $L_2$ is pyridinyl. In some embodiments, provided herein is a compound of Formula (II') or (II), or a pharmaceutically acceptable salt or solvate thereof, wherein $L_2$ is —$C(H)$(phenyl)-.

In some embodiments, provided herein is a compound of Formula (II') or (II), or a pharmaceutically acceptable salt or solvate thereof, wherein $R_2$ is —$C(=O)OR_6$. In some embodiments, provided herein is a compound of Formula (II') or (II), or a pharmaceutically acceptable salt or solvate thereof, wherein $R_2$ is —$C(=O)OR_6$ and $R_6$ is $C_1$-$C_6$alkyl optionally subsituted with 1 or 2 Y. In some embodiments, provided herein is a compound of Formula (II') or (II), or a pharmaceutically acceptable salt or solvate thereof, wherein $R_2$ is —$CO_2C_1$-$C_6$alkyl. In some embodiments, provided herein is a compound of Formula (II') or (II), or a pharmaceutically acceptable salt or solvate thereof, wherein $R_2$ is —$CO_2CH_3$. In some embodiments, provided herein is a compound of Formula (II') or (II), or a pharmaceutically acceptable salt or solvate thereof, wherein $R_2$ is —$CO_2CH_2CH_3$. In some embodiments, provided herein is a compound of Formula (II') or (II), or a pharmaceutically acceptable salt or solvate thereof, wherein $R_2$ is —$CO_2H$. In some embodiments, provided herein is a compound of Formula (II') or (II), or a pharmaceutically acceptable salt or solvate thereof, wherein $R_2$ is —$CO_2C_1$-$C_6$alkyl-Y. In some embodiments, provided herein is a compound of Formula (II') or (II), or a pharmaceutically acceptable salt or solvate thereof, wherein $R_2$ is —$CO_2C_1$-$C_6$alkyl-$OR_9$. In some embodiments, provided herein is a compound of Formula (II') or (II), or a pharmaceutically acceptable salt or solvate thereof, wherein $R_2$ is —$C(=O)OR_6$ and $R_6$ is $C_2$-$C_9$heterocycloalkyl optionally substituted with $C_1$-$C_6$alkyl. In some embodiments, provided herein is a compound of Formula (II') or (II), or a pharmaceutically acceptable salt or solvate thereof, wherein $R_2$ is —$C(=O)OR_6$ and $R_6$ is unsubstituted $C_2$-$C_9$heterocycloalkyl. In some embodiments, provided herein is a compound of Formula (II') or (II), or a pharmaceutically acceptable salt or solvate thereof, wherein $R_2$ is —$C(=O)OR_6$ and $R_6$ is —$C_1$-$C_6$alkyl-$C_2$-$C_9$heterocycloalkyl optionally substituted with $C_1$-$C_6$alkyl. In some embodiments, provided herein is a compound of Formula (II') or (II), or a pharmaceutically acceptable salt or solvate thereof, wherein $R_2$ is —C(=O)$OR_6$ and $R_6$ is unsubstituted —$C_1$-$C_6$alkyl-$C_2$-$C_9$heterocycloalkyl.

In some embodiments, provided herein is a compound of Formula (II') or (II), or a pharmaceutically acceptable salt or solvate thereof, wherein $R_2$ is

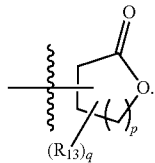

In some embodiments, provided herein is a compound of Formula (II') or (II), or a pharmaceutically acceptable salt or solvate thereof, wherein $R_2$ is

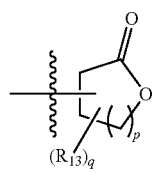

and p is 1. In some embodiments, provided herein is a compound of Formula (II') or (II), or a pharmaceutically acceptable salt or solvate thereof, wherein $R_2$ is

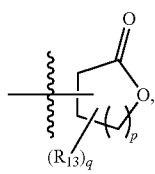

p is 1, and q is 0. In some embodiments, provided herein is a compound of Formula (II') or (II), or a pharmaceutically acceptable salt or solvate thereof, wherein $R_2$ is

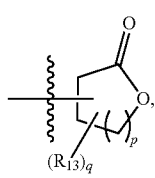

p is 1, and q is 2. In some embodiments, provided herein is a compound of Formula (II') or (II), or a pharmaceutically acceptable salt or solvate thereof, wherein $R_2$ is

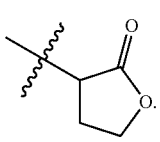 [SMILES: *C1CCOC1=O]

In some embodiments, provided herein is a compound of Formula (II') or (II), or a pharmaceutically acceptable salt or solvate thereof, wherein $R_2$ is

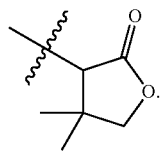

In some embodiments, provided herein is a compound of Formula (II') or (II), or a pharmaceutically acceptable salt or solvate thereof, wherein $R_2$ is

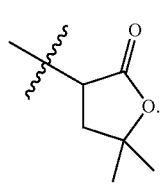 [SMILES: *C1CC(C)(C)OC1=O]

In some embodiments, provided herein is a compound of Formula (II'), or a pharmaceutically acceptable salt or solvate thereof, wherein $R_2$ is

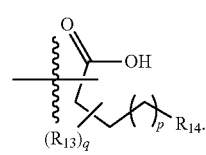

In some embodiments, provided herein is a compound of Formula (II'), or a pharmaceutically acceptable salt or solvate thereof, wherein $R_2$ is

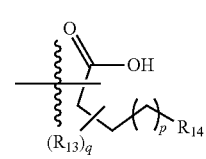

and p is 1. In some embodiments, provided herein is a compound of Formula (II'), or a pharmaceutically acceptable salt or solvate thereof, wherein $R_2$ is p is 1, and q is 0. In some embodiments, provided herein is a compound of Formula (II'), or a pharmaceutically acceptable salt or solvate thereof, wherein $R_2$ is

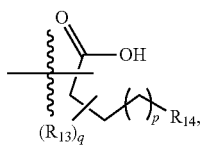

p is 1, and q is 2. In some embodiments, provided herein is a compound of Formula (II'), or a pharmaceutically acceptable salt or solvate thereof, wherein $R_{14}$ is —OH. In some embodiments, provided herein is a compound of Formula (II'), or a pharmaceutically acceptable salt or solvate thereof, wherein $R_{14}$ is —C(=O)H. In some embodiments, provided herein is a compound of Formula (II'), or a pharmaceutically acceptable salt or solvate thereof, wherein $R_{14}$ is —C(=O)OR$_{15}$. In some embodiments, provided herein is a compound of Formula (II'), or a pharmaceutically acceptable salt or solvate thereof, wherein $R_{14}$ is —C(=O)OR$_{15}$ and $R_{15}$ is hydrogen.

In some embodiments, provided herein is a compound of Formula (II') or (II), or a pharmaceutically acceptable salt or solvate thereof, wherein n is 0.

In some embodiments, provided herein is a compound of Formula (II') or (II), or a pharmaceutically acceptable salt or solvate thereof, wherein n is 1. In some embodiments, provided herein is a compound of Formula (II') or (II), or a pharmaceutically acceptable salt or solvate thereof, wherein n is 2. In some embodiments, provided herein is a compound of Formula (II') or (II), or a pharmaceutically acceptable salt or solvate thereof, wherein n is 3. In some embodiments, provided herein is a compound of Formula (II') or (II), or a pharmaceutically acceptable salt or solvate thereof, wherein n is 1 or 2 and each $R_3$ is independently selected from halogen, $C_1$-$C_6$alkyl, $C_1$-$C_6$haloalkyl, $C_1$-$C_6$heteroalkyl, —OR$_7$, —N(R$_7$)$_2$, —CN, —C(=O)R$_8$, —C(=O)OR$_7$, —C(=O)N(R$_7$)$_2$, —NR$_7$C(=O)R$_8$, —NR$_7$S(=O)$_2$R$_8$, —S(=O)$_2$R$_8$, and —S(=O)$_2$N(R$_7$)$_2$. In some embodiments, provided herein is a compound of Formula (II') or (II), or a pharmaceutically acceptable salt or solvate thereof, wherein n is 1 or 2 and each $R_3$ is independently selected from halogen, $C_1$-$C_6$alkyl, $C_1$-$C_6$haloalkyl, $C_1$-$C_6$heteroalkyl, —OR$_7$, —N(R$_7$)$_2$, —CN, —C(=O)R$_8$, —C(=O)OR$_7$, —C(=O)N(R$_7$)$_2$, —NR$_7$C(=O)R$_8$, —NR$_7$S(=O)$_2$R$_8$, —S(=O)$_2$R$_8$, and —S(=O)$_2$N(R$_7$)$_2$. In some embodiments, provided herein is a compound of Formula (II') or (II), or a pharmaceutically acceptable salt or solvate thereof, wherein n is 1 or 2 and each $R_3$ is independently selected from halogen, $C_1$-$C_6$alkyl, $C_1$-$C_6$haloalkyl, —OR$_7$, and —N(R$_7$)$_2$. In some embodiments, provided herein is a compound of Formula (II') or (II), or a pharmaceutically acceptable salt or solvate thereof, wherein n is 1 or 2 and each $R_3$ is independently selected from halogen and $C_1$-$C_6$alkyl. In some embodiments, provided herein is a compound of Formula (II') or (II), or a pharmaceutically acceptable salt or solvate thereof, wherein n is 1 and $R_3$ is selected from halogen, $C_1$-$C_6$alkyl, $C_1$-$C_6$haloalkyl, —OR$_7$, and —N(R$_7$)$_2$. In some embodiments, provided herein is a compound of Formula (II') or (II), or a pharmaceutically acceptable salt or solvate thereof, wherein n is 1 and $R_3$ is selected from halogen and $C_1$-$C_6$alkyl. In some embodiments, provided herein is a compound of Formula (II') or (II), or a pharmaceutically acceptable salt or solvate thereof, wherein n is 1 and $R_3$ is halogen. In some embodiments, provided herein is a compound of Formula (II') or (II), or a pharmaceutically acceptable salt or solvate thereof, wherein n is 1 and $R_3$ is $C_1$-$C_6$alkyl.

In some embodiments, provided herein is a compound of Formula (II') or (II), or a pharmaceutically acceptable salt or solvate thereof, wherein $R_4$ is hydrogen. In some embodiments, provided herein is a compound of Formula (II') or (II), or a pharmaceutically acceptable salt or solvate thereof, wherein $R_4$ is $C_1$-$C_6$alkyl. In some embodiments, provided herein is a compound of Formula (II') or (II), or a pharmaceutically acceptable salt or solvate thereof, wherein $R_4$ is —CH$_3$. In some embodiments, provided herein is a compound of Formula (II') or (II), or a pharmaceutically acceptable salt or solvate thereof, wherein $R_4$ is $C_1$-$C_6$heteroalkyl.

In some embodiments is a compound of Formula (II') or (II), or a pharmaceutically acceptable salt or solvate thereof, wherein $R_{12}$ is hydrogen. In some embodiments is a compound of Formula (II') or (II), or a pharmaceutically acceptable salt or solvate thereof, wherein $R_{12}$ is halogen. In some embodiments is a compound of Formula (II') or (II), or a pharmaceutically acceptable salt or solvate thereof, wherein $R_{12}$ is $C_1$-$C_6$alkyl. In some embodiments, provided herein is a compound of Formula (II') or (II), or a pharmaceutically acceptable salt or solvate thereof, wherein $R_{12}$ is —CH$_3$.

In some embodiments, provided herein is a compound of Formula (IIa), or a pharmaceutically acceptable salt or solvate thereof:

Formula (IIa)

wherein:
$L_1$ is a bond or $C_1$-$C_6$alkyl;
$L_2$ is $C_1$-$C_6$alkyl, $C_2$-$C_9$heteroaryl, or —C(H)(phenyl)-;
$R_2$ is —C(=O)OR$_6$ or

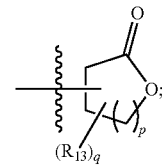

$R_3$ is selected from $C_1$-$C_6$alkyl, $C_1$-$C_6$haloalkyl, $C_1$-$C_6$heteroalkyl, —C(=O)R$_8$, —C(=O)OR$_7$, —C(=O)N(R$_7$)$_2$, —S(=O)$_2$R$_8$, and —S(=O)$_2$N(R$_7$)$_2$;
$R_6$ is hydrogen, $C_1$-$C_6$alkyl, $C_2$-$C_9$heterocycloalkyl optionally substituted with $C_1$-$C_6$alkyl, or —$C_1$-$C_6$alkyl-$C_2$-$C_9$heterocycloalkyl optionally substituted with $C_1$-$C_6$alkyl;
each $R_7$ is independently selected from hydrogen, $C_1$-$C_6$alkyl, $C_2$-$C_6$alkenyl, $C_1$-$C_6$haloalkyl, and $C_1$-$C_6$heteroalkyl; and
each $R_8$ is independently selected from $C_1$-$C_6$alkyl, $C_2$-$C_6$alkenyl, $C_1$-$C_6$heteroalkyl, $C_3$-$C_6$cycloalkyl, and $C_2$-$C_9$heterocycloalkyl;
$R_{13}$ is $C_1$-$C_6$alkyl;
p is 0, 1, or 2; and
q is 0, 1, or 2.

In some embodiments, provided herein is a compound of Formula (IIa), or a pharmaceutically acceptable salt or solvate thereof, wherein $L_1$ is a bond. In some embodiments, provided herein is a compound of Formula (IIa), or a pharmaceutically acceptable salt or solvate thereof, wherein $L_1$ is $C_1$-$C_6$alkyl. In some embodiments, provided herein is a compound of Formula (IIa), or a pharmaceutically acceptable salt or solvate thereof, wherein $L_1$ is —$CH_2$—. In some embodiments, provided herein is a compound of Formula (IIa), or a pharmaceutically acceptable salt or solvate thereof, wherein $L_1$ is —$CH_2CH_2$—. In some embodiments, provided herein is a compound of Formula (IIa), or a pharmaceutically acceptable salt or solvate thereof, wherein $L_1$ is —$CH_2CH_2CH_2$—.

In some embodiments, provided herein is a compound of Formula (IIa), or a pharmaceutically acceptable salt or solvate thereof, wherein $L_2$ is $C_1$-$C_6$alkyl. In some embodiments, provided herein is a compound of Formula (IIa), or a pharmaceutically acceptable salt or solvate thereof, wherein $L_2$ is —$CH_2$—. In some embodiments, provided herein is a compound of Formula (IIa), or a pharmaceutically acceptable salt or solvate thereof, wherein $L_2$ is —$CH_2CH_2$—. In some embodiments, provided herein is a compound of Formula (IIa), or a pharmaceutically acceptable salt or solvate thereof, wherein $L_2$ is —$CH_2CH_2CH_2$—. In some embodiments, provided herein is a compound of Formula (IIa), or a pharmaceutically acceptable salt or solvate thereof, wherein $L_2$ is $C_2$-$C_9$heteroaryl. In some embodiments, provided herein is a compound of Formula (IIa), or a pharmaceutically acceptable salt or solvate thereof, wherein $L_2$ is $C_2$-$C_9$heteroaryl selected from oxazolyl, thiazolyl, pyrazolyl, furanyl, thienyl, pyrrolyl, imidazolyl, triazolyl, tetrazolyl, isoxazolyl, isothiazolyl, oxadiazolyl, thiadiazolyl, pyridinyl, pyrimidinyl, pyrazinyl, pyridazinyl, and triazinyl. In some embodiments, provided herein is a compound of Formula (IIa), or a pharmaceutically acceptable salt or solvate thereof, wherein $L_2$ is $C_2$-$C_9$heteroaryl selected from oxazolyl, thiazolyl, pyrazolyl, thienyl, pyrrolyl, imidazolyl, and pyridinyl. In some embodiments, provided herein is a compound of Formula (IIa), or a pharmaceutically acceptable salt or solvate thereof, wherein $L_2$ is oxazolyl. In some embodiments, provided herein is a compound of Formula (IIa), or a pharmaceutically acceptable salt or solvate thereof, wherein $L_2$ is thiazolyl. In some embodiments, provided herein is a compound of Formula (IIa), or a pharmaceutically acceptable salt or solvate thereof, wherein $L_2$ is pyrazolyl. In some embodiments, provided herein is a compound of Formula (IIa), or a pharmaceutically acceptable salt or solvate thereof, wherein $L_2$ is thienyl. In some embodiments, provided herein is a compound of Formula (IIa), or a pharmaceutically acceptable salt or solvate thereof, wherein $L_2$ is pyrrolyl. In some embodiments, provided herein is a compound of Formula (IIa), or a pharmaceutically acceptable salt or solvate thereof, wherein $L_2$ is imidazolyl. In some embodiments, provided herein is a compound of Formula (IIa), or a pharmaceutically acceptable salt or solvate thereof, wherein $L_2$ is pyridinyl. In some embodiments, provided herein is a compound of Formula (IIa), or a pharmaceutically acceptable salt or solvate thereof, wherein $L_2$ is —C(H)(phenyl)-.

In some embodiments, provided herein is a compound of Formula (IIa), or a pharmaceutically acceptable salt or solvate thereof, wherein $R_2$ is —C(=O)$OR_6$. In some embodiments, provided herein is a compound of Formula (IIa), or a pharmaceutically acceptable salt or solvate thereof, wherein $R_2$ is —C(=O)$OR_6$ and $R_6$ is $C_1$-$C_6$alkyl optionally substituted with 1 or 2 Y. In some embodiments, provided herein is a compound of Formula (IIa), or a pharmaceutically acceptable salt or solvate thereof, wherein $R_2$ is —$CO_2C_1$-$C_6$alkyl. In some embodiments, provided herein is a compound of Formula (IIa), or a pharmaceutically acceptable salt or solvate thereof, wherein $R_2$ is —$CO_2CH_3$. In some embodiments, provided herein is a compound of Formula (IIa), or a pharmaceutically acceptable salt or solvate thereof, wherein $R_2$ is —$CO_2CH_2CH_3$. In some embodiments, provided herein is a compound of Formula (IIa), or a pharmaceutically acceptable salt or solvate thereof, wherein $R_2$ is —$CO_2H$. In some embodiments, provided herein is a compound of Formula (IIa), or a pharmaceutically acceptable salt or solvate thereof, wherein $R_2$ is —C(=O)$OR_6$ and $R_6$ is $C_2$-$C_9$heterocycloalkyl optionally substituted with $C_1$-$C_6$alkyl. In some embodiments, provided herein is a compound of Formula (IIa), or a pharmaceutically acceptable salt or solvate thereof, wherein $R_2$ is —C(=O)$OR_6$ and $R_6$ is unsubstituted $C_2$-$C_9$heterocycloalkyl. In some embodiments, provided herein is a compound of Formula (IIa), or a pharmaceutically acceptable salt or solvate thereof, wherein $R_2$ is —C(=O)$OR_6$ and $R_6$ is —$C_1$-$C_6$alkyl-$C_2$-$C_9$heterocycloalkyl optionally substituted with $C_1$-$C_6$alkyl. In some embodiments, provided herein is a compound of Formula (IIa), or a pharmaceutically acceptable salt or solvate thereof, wherein $R_2$ is —C(=O)$OR_6$ and $R_6$ is unsubstituted —$C_1$-$C_6$alkyl-$C_2$-$C_9$heterocycloalkyl.

In some embodiments, provided herein is a compound of Formula (IIa), or a pharmaceutically acceptable salt or solvate thereof, wherein $R_2$ is

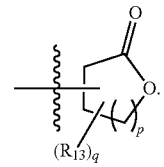

In some embodiments, provided herein is a compound of Formula (IIa), or a pharmaceutically acceptable salt or solvate thereof, wherein $R_2$ is

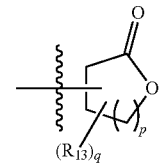

and p is 1. In some embodiments, provided herein is a compound of Formula (IIa), or a pharmaceutically acceptable salt or solvate thereof, wherein $R_2$ is

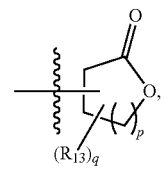

p is 1, and q is 0. In some embodiments, provided herein is a compound of Formula (IIa), or a pharmaceutically acceptable salt or solvate thereof, wherein $R_2$ is

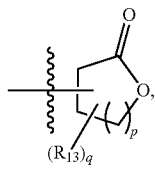

p is 1, and q is 2. In some embodiments, provided herein is a compound of Formula (IIa), or a pharmaceutically acceptable salt or solvate thereof, wherein $R_2$ is

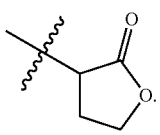 [SMILES: *C1CCOC1=O]

In some embodiments, provided herein is a compound of Formula (IIa), or a pharmaceutically acceptable salt or solvate thereof, wherein $R_2$ is

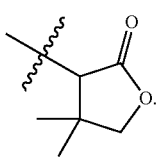 [SMILES: *C1C(=O)OCC1(C)C]

In some embodiments, provided herein is a compound of Formula (IIa), or a pharmaceutically acceptable salt or solvate thereof, wherein $R_2$ is

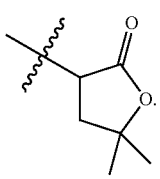 [SMILES: *C1CC(C)(C)OC1=O]

In some embodiments, provided herein is a compound of Formula (IIa), or a pharmaceutically acceptable salt or solvate thereof, wherein $R_3$ is selected from $C_1$-$C_6$alkyl, $C_1$-$C_6$haloalkyl, $C_1$-$C_6$heteroalkyl, —C(=O)$R_8$, —C(=O)O$R_7$, —C(=O)N($R_7$)$_2$, and —S(=O)$_2$$R_8$. In some embodiments, provided herein is a compound of Formula (IIa), or a pharmaceutically acceptable salt or solvate thereof, wherein $R_3$ is selected from $C_1$-$C_6$alkyl, $C_1$-$C_6$haloalkyl, $C_1$-$C_6$heteroalkyl, —C(=O)$R_8$, and —S(=O)$_2$$R_8$. In some embodiments, provided herein is a compound of Formula (IIa), or a pharmaceutically acceptable salt or solvate thereof, wherein $R_3$ is selected from $C_1$-$C_6$alkyl and $C_1$-$C_6$heteroalkyl. In some embodiments, provided herein is a compound of Formula (IIa), or a pharmaceutically acceptable salt or solvate thereof, wherein $R_3$ is $C_1$-$C_6$alkyl. In some embodiments, provided herein is a compound of Formula (IIa), or a pharmaceutically acceptable salt or solvate thereof, wherein $R_3$ is selected from $C_1$-$C_6$haloalkyl. In some embodiments, provided herein is a compound of Formula (IIa), or a pharmaceutically acceptable salt or solvate thereof, wherein $R_3$ is $C_1$-$C_6$heteroalkyl. In some embodiments, provided herein is a compound of Formula (IIa), or a pharmaceutically acceptable salt or solvate thereof, wherein $R_3$ is —C(=O)$R_8$. In some embodiments, provided herein is a compound of Formula (IIa), or a pharmaceutically acceptable salt or solvate thereof, wherein $R_3$ is —S(=O)$_2$$R_8$.

In some embodiments, provided herein is a compound of Formula (III), or a pharmaceutically acceptable salt or solvate thereof:

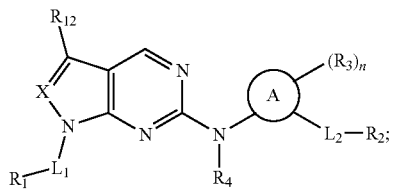

Formula (III)

wherein:

is phenyl or a $C_2$-$C_9$heteroaryl ring;
X is C($R_{11}$) or N;
$L_1$ is $C_1$-$C_6$alkyl or $C_1$-$C_6$heteroalkyl;
$L_2$ is a bond, $C_1$-$C_6$alkyl, or $C_1$-$C_6$heteroalkyl;
$R_1$ is $C_3$-$C_9$alkyl, $C_2$-$C_6$alkenyl, $C_2$-$C_6$alkynyl, $C_3$-$C_6$cycloalkyl, $C_2$-$C_9$heterocycloalkyl, or $C_2$-$C_9$heteroaryl, wherein $C_3$-$C_9$alkyl, $C_2$-$C_6$alkenyl, $C_2$-$C_6$alkynyl, $C_3$-$C_6$cycloalkyl, $C_2$-$C_9$heterocycloalkyl, or $C_2$-$C_9$heteroaryl are optionally substituted with 1, 2, or 3 $R_5$;
$R_2$ is

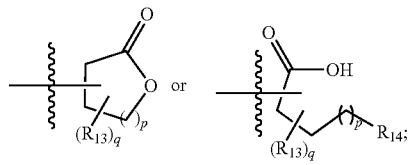

each $R_3$ is independently selected from halogen, $C_1$-$C_6$alkyl, $C_1$-$C_6$haloalkyl, $C_1$-$C_6$heteroalkyl, —O$R_7$, —N($R_7$)$_2$, —CN, —C(=O)$R_8$, —C(=O)O$R_7$, —C(=O)N($R_7$)$_2$, —N$R_7$C(=O)$R_8$, —N$R_7$S(=O)$_2$$R_8$, —S(=O)$_2$$R_8$, and —S(=O)$_2$N($R_7$)$_2$;
$R_4$ is hydrogen, $C_1$-$C_6$alkyl, or $C_1$-$C_6$heteroalkyl;
each $R_5$ is independently selected from halogen, oxo, $C_1$-$C_6$alkyl, $C_1$-$C_6$haloalkyl, $C_1$-$C_6$heteroalkyl, —O$R_7$, —N($R_7$)$_2$, —CN, —C(=O)$R_8$, —C(=O)O$R_7$, —C(=O)N($R_7$)$_2$, —N$R_7$C(=O)$R_8$, —N$R_7$S(=O)$_2$$R_8$, —S(=O)$_2$$R_8$, and —S(=O)$_2$N($R_7$)$_2$;
each $R_7$ is independently selected from hydrogen, $C_1$-$C_6$alkyl, $C_2$-$C_6$alkenyl, $C_1$-$C_6$haloalkyl, and $C_1$-$C_6$heteroalkyl;
each $R_8$ is independently selected from $C_1$-$C_6$alkyl, $C_2$-$C_6$alkenyl, $C_1$-$C_6$heteroalkyl, $C_3$-$C_6$cycloalkyl, and $C_2$-$C_9$heterocycloalkyl;
$R_{11}$ is hydrogen or $C_1$-$C_6$alkyl optionally substituted with 1, 2, or 3 $R_5$;
$R_{12}$ is hydrogen, halogen, or $C_1$-$C_6$alkyl;
$R_{13}$ is $C_1$-$C_6$alkyl;

$R_{14}$ is —OH, —C(=O)H, or —C(=O)OR$_{15}$;
$R_{15}$ is hydrogen or $C_1$-$C_6$alkyl;
n is 0, 1, 2, or 3;
p is 0, 1, or 2; and
q is 0, 1, or 2.

In some embodiments is a compound of Formula (III), or a pharmaceutically acceptable salt or solvate thereof, wherein X is C(R$_{11}$). In some embodiments is a compound of Formula (III), or a pharmaceutically acceptable salt or solvate thereof, wherein X is C(H). In some embodiments is a compound of Formula (III), or a pharmaceutically acceptable salt or solvate thereof, wherein X is N.

In some embodiments is a compound of Formula (III), or a pharmaceutically acceptable salt or solvate thereof, wherein

is phenyl.

In some embodiments is a compound of Formula (III), or a pharmaceutically acceptable salt or solvate thereof, wherein

is a $C_2$-$C_9$heteroaryl ring. In some embodiments is a compound of Formula (III), or a pharmaceutically acceptable salt or solvate thereof, wherein

is a $C_2$-$C_9$heteroaryl ring selected from oxazolyl, thiazolyl, pyrazolyl, furanyl, thienyl, pyrrolyl, imidazolyl, triazolyl, tetrazolyl, isoxazolyl, isothiazolyl, oxadiazolyl, thiadiazolyl, pyridinyl, pyrimidinyl, pyrazinyl, pyridazinyl, and triazinyl. In some embodiments is a compound of Formula (III), or a pharmaceutically acceptable salt or solvate thereof, wherein

is a $C_2$-$C_9$heteroaryl ring selected from pyrazolyl, pyrrolyl, and imidazolyl. In some embodiments is a compound of Formula (III), or a pharmaceutically acceptable salt or solvate thereof, wherein

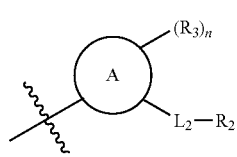

is a $C_2$-$C_9$heteroaryl ring selected from

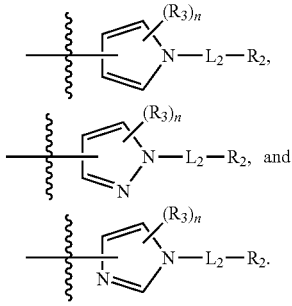

In some embodiments is a compound of Formula (III), or a pharmaceutically acceptable salt or solvate thereof, wherein

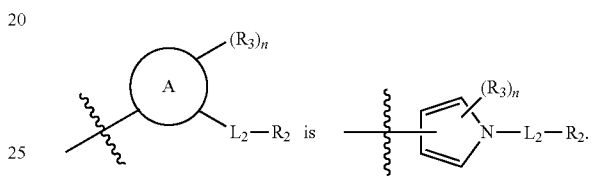

In some embodiments is a compound of Formula (III), or a pharmaceutically acceptable salt or solvate thereof, wherein

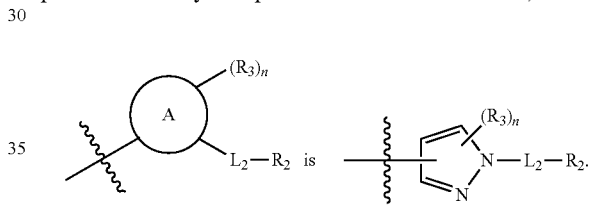

In some embodiments is a compound of Formula (III), or a pharmaceutically acceptable salt or solvate thereof, wherein

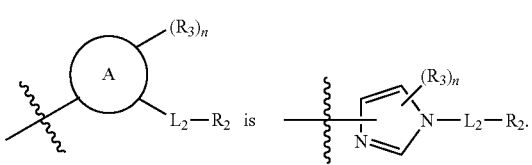

In some embodiments, provided herein is a compound of Formula (III), or a pharmaceutically acceptable salt or solvate thereof, wherein $L_1$ is $C_1$-$C_6$alkyl. In some embodiments, provided herein is a compound of Formula (III), or a pharmaceutically acceptable salt or solvate thereof, wherein $L_1$ is —CH$_2$—. In some embodiments, provided herein is a compound of Formula (III), or a pharmaceutically acceptable salt or solvate thereof, wherein $L_1$ is —CH$_2$CH$_2$—. In some embodiments, provided herein is a compound of Formula (III), or a pharmaceutically acceptable salt or solvate thereof, wherein $L_1$ is $C_1$-$C_6$heteroalkyl.

In some embodiments, provided herein is a compound of Formula (III), or a pharmaceutically acceptable salt or solvate thereof, wherein $R_1$ is $C_3$-$C_9$alkyl optionally substituted with 1, 2, or 3 $R_5$. In some embodiments, provided herein is a compound of Formula (III), or a pharmaceutically acceptable salt or solvate thereof, wherein $R_1$ is unsubstituted $C_3$-$C_9$alkyl. In some embodiments, provided herein is a compound of Formula (III), or a pharmaceutically acceptable salt or solvate thereof, wherein $R_1$ is $C_3$-$C_6$cycloalkyl optionally substituted with 1, 2, or 3 $R_5$. In some embodiments, provided herein is a compound of Formula (III), or a pharmaceutically acceptable salt or solvate thereof, wherein $R_1$ is $C_3$-$C_6$cycloalkyl optionally substituted with 1, 2, or 3 $R_5$, wherein each $R_5$ is independently selected from halogen, $C_1$-$C_6$alkyl, $C_1$-$C_6$haloalkyl, —$OR_7$, and —$N(R_7)_2$. In some embodiments, provided herein is a compound of Formula (III), or a pharmaceutically acceptable salt or solvate thereof, wherein $R_1$ is $C_3$-$C_6$cycloalkyl optionally substituted with 1, 2, or 3 $R_5$, wherein each $R_5$ is independently selected from halogen and $C_1$-$C_6$alkyl. In some embodiments, provided herein is a compound of Formula (III), or a pharmaceutically acceptable salt or solvate thereof, wherein $R_1$ is unsubstituted $C_3$-$C_6$cycloalkyl. In some embodiments, provided herein is a compound of Formula (III), or a pharmaceutically acceptable salt or solvate thereof, wherein $R_1$ is $C_2$-$C_9$heterocycloalkyl optionally substituted with 1, 2, or 3 $R_5$. In some embodiments, provided herein is a compound of Formula (III), or a pharmaceutically acceptable salt or solvate thereof, wherein $R_1$ is $C_2$-$C_9$heterocycloalkyl optionally substituted with 1, 2, or 3 $R_5$, wherein each $R_5$ is independently selected from halogen, $C_1$-$C_6$alkyl, $C_1$-$C_6$haloalkyl, —$OR_7$, and —$N(R_7)_2$. In some embodiments, provided herein is a compound of Formula (III), or a pharmaceutically acceptable salt or solvate thereof, wherein $R_1$ is $C_2$-$C_9$heterocycloalkyl optionally substituted with 1, 2, or 3 $R_5$, wherein each $R_5$ is independently selected from halogen and $C_1$-$C_6$alkyl. In some embodiments, provided herein is a compound of Formula (III), or a pharmaceutically acceptable salt or solvate thereof, wherein $R_1$ is unsubstituted $C_2$-$C_9$heterocycloalkyl. In some embodiments, provided herein is a compound of Formula (III), or a pharmaceutically acceptable salt or solvate thereof, wherein $R_1$ is $C_2$-$C_9$heteroaryl optionally substituted with 1, 2, or 3 $R_5$. In some embodiments, provided herein is a compound of Formula (III), or a pharmaceutically acceptable salt or solvate thereof, wherein $R_1$ is $C_2$-$C_9$heteroaryl optionally substituted with 1, 2, or 3 $R_5$, wherein each $R_5$ is independently selected from halogen, $C_1$-$C_6$alkyl, $C_1$-$C_6$haloalkyl, —$OR_7$, and —$N(R_7)_2$. In some embodiments, provided herein is a compound of Formula (III), or a pharmaceutically acceptable salt or solvate thereof, wherein $R_1$ is $C_2$-$C_9$heteroaryl optionally substituted with 1, 2, or 3 $R_5$, wherein each $R_5$ is independently selected from halogen and $C_1$-$C_6$alkyl. In some embodiments, provided herein is a compound of Formula (III), or a pharmaceutically acceptable salt or solvate thereof, wherein $R_1$ is unsubstituted $C_2$-$C_9$heteroaryl. In some embodiments, provided herein is a compound of Formula (III), or a pharmaceutically acceptable salt or solvate thereof, wherein $C_2$-$C_9$heteroaryl is selected from oxazolyl, thiazolyl, pyrazolyl, furanyl, thienyl, pyrrolyl, imidazolyl, triazolyl, tetrazolyl, isoxazolyl, isothiazolyl, oxadiazolyl, and thiadiazolyl.

In some embodiments, provided herein is a compound of Formula (III), or a pharmaceutically acceptable salt or solvate thereof, wherein $L_2$ is a bond. In some embodiments, provided herein is a compound of Formula (III), or a pharmaceutically acceptable salt or solvate thereof, wherein $L_2$ is $C_1$-$C_6$alkyl. In some embodiments, provided herein is a compound of Formula (III), or a pharmaceutically acceptable salt or solvate thereof, wherein $L_2$ is —$CH_2$—. In some embodiments, provided herein is a compound of Formula (III), or a pharmaceutically acceptable salt or solvate thereof, wherein $L_2$ is —$CH_2CH_2$—. In some embodiments, provided herein is a compound of Formula (III), or a pharmaceutically acceptable salt or solvate thereof, wherein $L_2$ is —$CH_2CH_2CH_2$—. In some embodiments, provided herein is a compound of Formula (III), or a pharmaceutically acceptable salt or solvate thereof, wherein $L_2$ is $C_1$-$C_6$heteroalkyl.

In some embodiments, provided herein is a compound of Formula (III), or a pharmaceutically acceptable salt or solvate thereof, wherein $R_2$ is

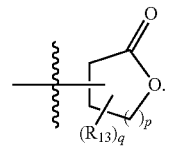

In some embodiments, provided herein is a compound of Formula (III), or a pharmaceutically acceptable salt or solvate thereof, wherein $R_2$ is

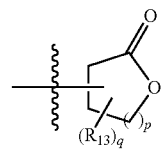

and p is 1. In some embodiments, provided herein is a compound of Formula (III), or a pharmaceutically acceptable salt or solvate thereof, wherein $R_2$ is

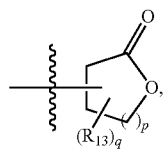

p is 1, and q is 0. In some embodiments, provided herein is a compound of Formula (III), or a pharmaceutically acceptable salt or solvate thereof, wherein $R_2$ is

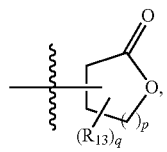

p is 1, and q is 2. In some embodiments, provided herein is a compound of Formula (III), or a pharmaceutically acceptable salt or solvate thereof, wherein $R_2$ is

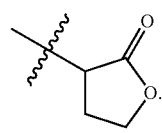 [SMILES: *C1CCOC1=O]

In some embodiments, provided herein is a compound of Formula (III), or a pharmaceutically acceptable salt or solvate thereof, wherein $R_2$ is

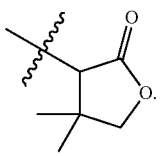

In some embodiments, provided herein is a compound of Formula (III), or a pharmaceutically acceptable salt or solvate thereof, wherein $R_2$ is

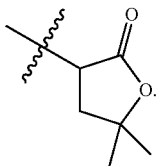 [SMILES: *C1CC(C)(C)OC1=O]

In some embodiments, provided herein is a compound of Formula (III), or a pharmaceutically acceptable salt or solvate thereof, wherein $R_2$ is

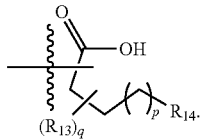

In some embodiments, provided herein is a compound of Formula (III), or a pharmaceutically acceptable salt or solvate thereof, wherein $R_2$ is

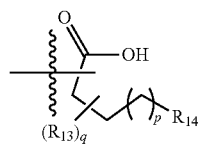

and p is 1. In some embodiments, provided herein is a compound of Formula (III), or a pharmaceutically acceptable salt or solvate thereof, wherein $R_2$ is

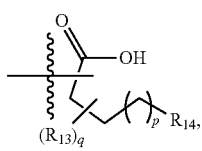

p is 1, and q is 0. In some embodiments, provided herein is a compound of Formula (III), or a pharmaceutically acceptable salt or solvate thereof, wherein $R_2$ is

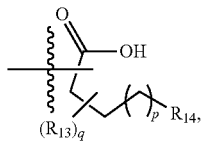

p is 1, and q is 2. In some embodiments, provided herein is a compound of Formula (III), or a pharmaceutically acceptable salt or solvate thereof, wherein $R_{14}$ is —OH. In some embodiments, provided herein is a compound of Formula (III), or a pharmaceutically acceptable salt or solvate thereof, wherein $R_{14}$ is —C(=O)H. In some embodiments, provided herein is a compound of Formula (III), or a pharmaceutically acceptable salt or solvate thereof, wherein $R_{14}$ is —C(=O)OR$_{15}$. In some embodiments, provided herein is a compound of Formula (III), or a pharmaceutically acceptable salt or solvate thereof, wherein $R_{14}$ is —C(=O)OR$_{15}$ and $R_{15}$ is hydrogen.

In some embodiments, provided herein is a compound of Formula (III), or a pharmaceutically acceptable salt or solvate thereof, wherein n is 0.

In some embodiments, provided herein is a compound of Formula (III), or a pharmaceutically acceptable salt or solvate thereof, wherein n is 1. In some embodiments, provided herein is a compound of Formula (III), or a pharmaceutically acceptable salt or solvate thereof, wherein n is 2. In some embodiments, provided herein is a compound of Formula (III), or a pharmaceutically acceptable salt or solvate thereof, wherein n is 3. In some embodiments, provided herein is a compound of Formula (III), or a pharmaceutically acceptable salt or solvate thereof, wherein n is 1 or 2 and each $R_3$ is independently selected from halogen, $C_1$-$C_6$alkyl, $C_1$-$C_6$haloalkyl, $C_1$-$C_6$heteroalkyl, —OR$_7$, —N(R$_7$)$_2$, —CN, —C(=O)R$_8$, —C(=O)OR$_7$, —C(=O)N(R$_7$)$_2$, —NR$_7$C(=O)R$_8$, —NR$_7$S(=O)$_2$R$_8$, —S(=O)$_2$R$_8$, and —S(=O)$_2$N(R$_7$)$_2$. In some embodiments, provided herein is a compound of Formula (III), or a pharmaceutically acceptable salt or solvate thereof, wherein n is 1 or 2 and each $R_3$ is independently selected from halogen, $C_1$-$C_6$alkyl, $C_1$-$C_6$haloalkyl, $C_1$-$C_6$heteroalkyl, —OR$_7$, —N(R$_7$)$_2$, —CN, —C(=O)R$_8$, —C(=O)OR$_7$, —C(=O)N(R$_7$)$_2$, —NR$_7$C(=O)R$_8$, —NR$_7$S(=O)$_2$R$_8$, —S(=O)$_2$R$_8$, and —S(=O)$_2$N(R$_7$)$_2$. In some embodiments, provided herein is a compound of Formula (III), or a pharmaceutically acceptable salt or solvate thereof, wherein n is 1 or 2 and each $R_3$ is independently selected from halogen, $C_1$-$C_6$alkyl, $C_1$-$C_6$haloalkyl, —OR$_7$, and —N(R$_7$)$_2$. In some embodiments, provided herein is a compound of Formula (III), or a pharmaceutically acceptable salt or solvate thereof, wherein n is 1 or 2 and each $R_3$ is independently selected from halogen and $C_1$-$C_6$alkyl. In some embodiments, provided herein is a compound of Formula (III), or a pharmaceutically acceptable salt or solvate thereof, wherein n is 1 and $R_3$ is selected from halogen, $C_1$-$C_6$alkyl, $C_1$-$C_6$haloalkyl, —OR$_7$, and —N(R$_7$)$_2$. In some embodiments, provided herein is a compound of Formula (III), or a pharmaceutically acceptable salt or solvate thereof, wherein n is 1 and $R_3$ is selected from halogen and $C_1$-$C_6$alkyl. In some embodiments, provided herein is a compound of Formula (III), or a pharmaceutically acceptable salt or solvate thereof, wherein n is 1 and $R_3$ is halogen. In some embodiments, provided herein is a compound of Formula (III), or a pharmaceutically acceptable salt or solvate thereof, wherein n is 1 and $R_3$ is $C_1$-$C_6$alkyl.

In some embodiments, provided herein is a compound of Formula (III), or a pharmaceutically acceptable salt or solvate thereof, wherein $R_4$ is hydrogen. In some embodiments, provided herein is a compound of Formula (III), or a pharmaceutically acceptable salt or solvate thereof, wherein $R_4$ is $C_1$-$C_6$alkyl. In some embodiments, provided herein is a compound of Formula (III), or a pharmaceutically acceptable salt or solvate thereof, wherein $R_4$ is —$CH_3$. In some embodiments, provided herein is a compound of Formula (III), or a pharmaceutically acceptable salt or solvate thereof, wherein $R_4$ is $C_1$-$C_6$heteroalkyl.

In some embodiments is a compound of Formula (III), or a pharmaceutically acceptable salt or solvate thereof, wherein $R_{12}$ is hydrogen. In some embodiments is a compound of Formula (III), or a pharmaceutically acceptable salt or solvate thereof, wherein $R_{12}$ is halogen. In some embodiments is a compound of Formula (III), or a pharmaceutically acceptable salt or solvate thereof, wherein $R_{12}$ is $C_1$-$C_6$alkyl. In some embodiments, provided herein is a compound of Formula (III), or a pharmaceutically acceptable salt or solvate thereof, wherein $R_{12}$ is —$CH_3$.

In some embodiments, provided herein is a compound of Formula (IIa), or a pharmaceutically acceptable salt or solvate thereof:

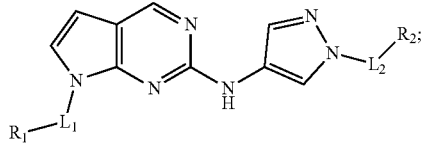

Formula (IIIa)

wherein:
$L_1$ is a bond or $C_1$-$C_6$alkyl;
$L_2$ is $C_1$-$C_6$alkyl;
$R_1$ is $C_1$-$C_9$alkyl, $C_3$-$C_6$cycloalkyl, $C_2$-$C_9$heterocycloalkyl, or $C_2$-$C_9$heteroaryl, wherein $C_1$-$C_9$alkyl, $C_3$-$C_6$cycloalkyl, $C_2$-$C_9$heterocycloalkyl, or $C_2$-$C_9$heteroaryl are optionally substituted with 1, 2, or 3 $R_5$;
$R_2$ is

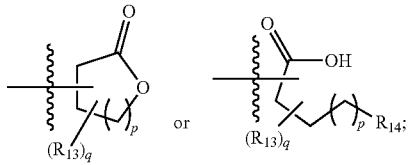

each $R_5$ is independently selected from halogen, $C_1$-$C_6$alkyl, $C_1$-$C_6$haloalkyl, $C_1$-$C_6$heteroalkyl, —$OR_7$, —$N(R_7)_2$, —CN, —C(=O)$R_8$, —C(=O)$OR_7$, —C(=O)N$(R_7)_2$, —$NR_7$C(=O)$R_8$, —$NR_7$S(=O)$_2R_8$, —S(=O)$_2R_8$, and —S(=O)$_2$N$(R_7)_2$;
each $R_7$ is independently selected from hydrogen, $C_1$-$C_6$alkyl, $C_2$-$C_6$alkenyl, $C_1$-$C_6$haloalkyl, and $C_1$-$C_6$heteroalkyl;
each $R_8$ is independently selected from $C_1$-$C_6$alkyl, $C_2$-$C_6$alkenyl, $C_1$-$C_6$heteroalkyl, $C_3$-$C_6$cycloalkyl, and $C_2$-$C_9$heterocycloalkyl;
$R_{13}$ is $C_1$-$C_6$alkyl;
$R_1$ is —OH, —C(=O)H, or —C(=O)$OR_{15}$;
$R_{15}$ is hydrogen or $C_1$-$C_6$alkyl;
p is 0, 1, or 2; and
q is 0, 1, or 2.

In some embodiments, provided herein is a compound of Formula (IIa), or a pharmaceutically acceptable salt or solvate thereof, wherein $L_1$ is $C_1$-$C_6$alkyl. In some embodiments, provided herein is a compound of Formula (IIIa), or a pharmaceutically acceptable salt or solvate thereof, wherein $L_1$ is —$CH_2$—. In some embodiments, provided herein is a compound of Formula (IIIa), or a pharmaceutically acceptable salt or solvate thereof, wherein $L_1$ is —$CH_2CH_2$—. In some embodiments, provided herein is a compound of Formula (IIIa), or a pharmaceutically acceptable salt or solvate thereof, wherein $L_1$ is a bond.

In some embodiments, provided herein is a compound of Formula (IIa), or a pharmaceutically acceptable salt or solvate thereof, wherein $R_1$ is $C_1$-$C_9$alkyl optionally substituted with 1, 2, or 3 $R_5$. In some embodiments, provided herein is a compound of Formula (IIa), or a pharmaceutically acceptable salt or solvate thereof, wherein $R_1$ is $C_3$-$C_9$alkyl optionally substituted with 1, 2, or 3 $R_5$. In some embodiments, provided herein is a compound of Formula (IIa), or a pharmaceutically acceptable salt or solvate thereof, wherein $R_1$ is unsubstituted $C_1$-$C_9$alkyl. In some embodiments, provided herein is a compound of Formula (IIIa), or a pharmaceutically acceptable salt or solvate thereof, wherein $R_1$ is unsubstituted $C_3$-$C_9$alkyl. In some embodiments, provided herein is a compound of Formula (IIIa), or a pharmaceutically acceptable salt or solvate thereof, wherein $R_1$ is $C_3$-$C_6$cycloalkyl optionally substituted with 1, 2, or 3 $R_5$. In some embodiments, provided herein is a compound of Formula (IIIa), or a pharmaceutically acceptable salt or solvate thereof, wherein $R_1$ is $C_3$-$C_6$cycloalkyl optionally substituted with 1, 2, or 3 $R_5$, wherein each $R_5$ is independently selected from halogen, $C_1$-$C_6$alkyl, $C_1$-$C_6$haloalkyl, —$OR_7$, and —$N(R_7)_2$. In some embodiments, provided herein is a compound of Formula (IIIa), or a pharmaceutically acceptable salt or solvate thereof, wherein $R_1$ is $C_3$-$C_6$cycloalkyl optionally substituted with 1, 2, or 3 $R_5$, wherein each $R_5$ is independently selected from halogen and $C_1$-$C_6$alkyl. In some embodiments, provided herein is a compound of Formula (IIa), or a pharmaceutically acceptable salt or solvate thereof, wherein $R_1$ is unsubstituted $C_3$-$C_6$cycloalkyl. In some embodiments, provided herein is a compound of Formula (IIIa), or a pharmaceutically acceptable salt or solvate thereof, wherein $R_1$ is $C_2$-$C_9$heterocycloalkyl optionally substituted with 1, 2, or 3 $R_5$. In some embodiments, provided herein is a compound of Formula (IIIa), or a pharmaceutically acceptable salt or solvate thereof, wherein $R_1$ is $C_2$-$C_9$heterocycloalkyl optionally substituted with 1, 2, or 3 $R_5$, wherein each $R_5$ is independently selected from halogen, $C_1$-$C_6$alkyl, $C_1$-$C_6$haloalkyl, —$OR_7$, and —$N(R_7)_2$. In some embodiments, provided herein is a compound of Formula (IIIa), or a pharmaceutically acceptable salt or solvate thereof, wherein $R_1$ is $C_2$-$C_9$heterocycloalkyl optionally substituted with 1, 2, or 3 $R_5$, wherein each $R_5$ is independently selected from halogen and $C_1$-$C_6$alkyl. In some embodiments, provided herein is a compound of Formula (IIIa), or a pharmaceutically acceptable salt or solvate thereof, wherein $R_1$ is unsubstituted $C_2$-$C_9$heterocycloalkyl. In some embodiments, provided herein is a compound of Formula (IIIa), or a pharmaceutically acceptable salt or solvate thereof, wherein $R_1$ is $C_2$-$C_9$heteroaryl optionally substituted with 1, 2, or 3 $R_5$. In some embodiments, provided herein is a compound of Formula (IIIa), or a pharmaceutically acceptable salt or solvate thereof, wherein $R_1$ is $C_2$-$C_9$heteroaryl optionally substituted with 1, 2, or 3 $R_5$, wherein each $R_5$ is independently selected from halogen, $C_1$-$C_6$alkyl, $C_1$-$C_6$haloalkyl, —$OR_7$, and —$N(R_7)_2$. In some embodiments, provided herein is a compound of Formula (IIIa), or a pharmaceutically acceptable salt or solvate thereof, wherein $R_1$ is $C_2$-$C_9$heteroaryl optionally substituted with 1, 2, or 3 $R_5$, wherein each $R_5$ is independently selected from halogen and $C_1$-$C_6$alkyl. In some embodiments, provided herein is a compound of Formula (IIIa), or a pharmaceutically acceptable salt or solvate thereof, wherein $R_1$ is unsubstituted $C_2$-$C_9$heteroaryl. In some embodiments, provided herein is a compound of Formula (IIIa), or a pharmaceutically acceptable salt or solvate thereof, wherein $C_2$-$C_9$heteroaryl is selected from oxazolyl, thiazolyl, pyrazolyl, furanyl, thienyl, pyrrolyl, imidazolyl, triazolyl, tetrazolyl, isoxazolyl, isothiazolyl, oxadiazolyl, and thiadiazolyl.

In some embodiments, provided herein is a compound of Formula (IIa), or a pharmaceutically acceptable salt or solvate thereof, wherein $L_2$ is —$CH_2$—. In some embodiments, provided herein is a compound of Formula (IIIa), or a pharmaceutically acceptable salt or solvate thereof, wherein $L_2$ is —$CH_2CH_2$—. In some embodiments, provided herein is a compound of Formula (IIIa), or a pharmaceutically acceptable salt or solvate thereof, wherein $L_2$ is —$CH_2CH_2CH_2$—.

In some embodiments, provided herein is a compound of Formula (IIa), or a pharmaceutically acceptable salt or solvate thereof, wherein $R_2$ is

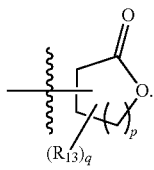

In some embodiments, provided herein is a compound of Formula (IIIa), or a pharmaceutically acceptable salt or solvate thereof, wherein $R_2$ is

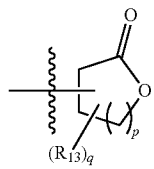

and p is 1. In some embodiments, provided herein is a compound of Formula (IIIa), or a pharmaceutically acceptable salt or solvate thereof, wherein $R_2$ is

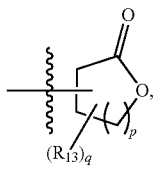

p is 1, and q is 0. In some embodiments, provided herein is a compound of Formula (IIIa), or a pharmaceutically acceptable salt or solvate thereof, wherein $R_2$ is

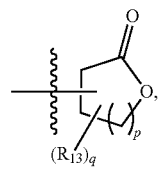

p is 1, and q is 2. In some embodiments, provided herein is a compound of Formula (IIIa), or a pharmaceutically acceptable salt or solvate thereof, wherein $R_2$ is

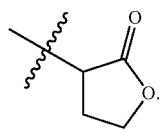 [SMILES: *C1CCOC1=O]

In some embodiments, provided herein is a compound of Formula (IIIa), or a pharmaceutically acceptable salt or solvate thereof, wherein $R_2$ is

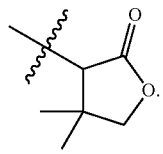

In some embodiments, provided herein is a compound of Formula (IIIa), or a pharmaceutically acceptable salt or solvate thereof, wherein $R_2$ is

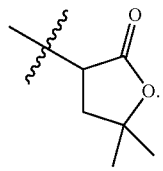 [SMILES: *C1CC(C)(C)OC1=O]

In some embodiments, provided herein is a compound of Formula (IIa), or a pharmaceutically acceptable salt or solvate thereof, wherein $R_2$ is

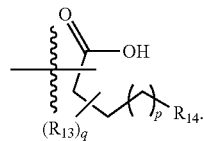

In some embodiments, provided herein is a compound of Formula (IIIa), or a pharmaceutically acceptable salt or solvate thereof, wherein $R_2$ is

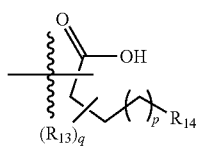

p is 1. In some embodiments, provided herein is a compound of Formula (IIIa), or a pharmaceutically acceptable salt or solvate thereof, wherein $R_2$ is

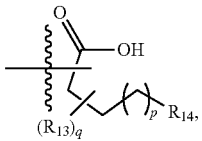

p is 1, and q is 0. In some embodiments, provided herein is a compound of Formula (IIIa), or a pharmaceutically acceptable salt or solvate thereof, wherein $R_2$ is

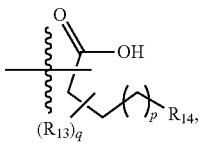

p is 1, and q is 2. In some embodiments, provided herein is a compound of Formula (IIIa), or a pharmaceutically acceptable salt or solvate thereof, wherein $R_{14}$ is —OH. In some embodiments, provided herein is a compound of Formula (IIIa), or a pharmaceutically acceptable salt or solvate thereof, wherein $R_{14}$ is —C(=O)H. In some embodiments, provided herein is a compound of Formula (IIa), or a pharmaceutically acceptable salt or solvate thereof, wherein $R_{14}$ is —C(=O)$OR_{15}$. In some embodiments, provided herein is a compound of Formula (IIIa), or a pharmaceutically acceptable salt or solvate thereof, wherein $R_{14}$ is —C(=O)$OR_{15}$ and $R_{15}$ is hydrogen.

In some embodiments, provided herein is a compound of Formula (IV), or a pharmaceutically acceptable salt or solvate thereof:

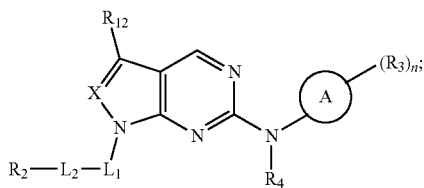

Formula (IV)

wherein:

is a $C_2$-$C_9$heteroaryl ring;
X is $C(R_{11})$ or N;
$L_1$ is a bond or $C_1$-$C_6$alkyl;
$L_2$ is $C_1$-$C_6$alkyl, $C_2$-$C_9$heteroaryl, or —C(H)(phenyl)-;
$R_2$ is

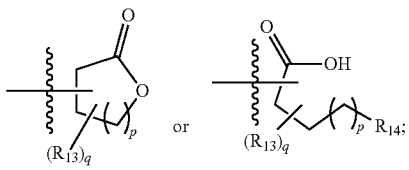

each $R_3$ is independently selected from halogen, $C_1$-$C_6$alkyl, $C_1$-$C_6$haloalkyl, $C_1$-$C_6$alkoxy, $C_1$-$C_6$heteroalkyl, —$OR_7$, —$N(R_7)_2$, —CN, —C(=O)$R_8$, —C(=O)$OR_7$, —C(=O)$N(R_7)_2$, —$NR_7$C(=O)$R_8$, —$NR_7$S(=O)$_2R_8$, —S(=O)$_2R_8$, and —S(=O)$_2N(R_7)_2$;
$R_4$ is hydrogen, $C_1$-$C_6$alkyl, or $C_1$-$C_6$heteroalkyl;
each $R_5$ is independently selected from halogen, oxo, $C_1$-$C_6$alkyl, $C_1$-$C_6$haloalkyl, $C_1$-$C_6$heteroalkyl, —$OR_7$, —$N(R_7)_2$, —CN, —C(=O)$R_8$, —C(=O)$OR_7$, —C(=O)$N(R_7)_2$, —$NR_7$C(=O)$R_8$, —$NR_7$S(=O)$_2R_8$, —S(=O)$_2R_8$, and —S(=O)$_2N(R_7)_2$;
each $R_7$ is independently selected from hydrogen, $C_1$-$C_6$alkyl, $C_2$-$C_6$alkenyl, $C_1$-$C_6$haloalkyl, and $C_1$-$C_6$heteroalkyl;
each $R_8$ is independently selected from $C_1$-$C_6$alkyl, $C_2$-$C_6$alkenyl, $C_1$-$C_6$heteroalkyl, $C_3$-$C_6$cycloalkyl, and $C_2$-$C_9$heterocycloalkyl;
$R_{11}$ is hydrogen or $C_1$-$C_6$alkyl optionally substituted with 1, 2, or 3 $R_5$;
$R_{12}$ is hydrogen, halogen, or $C_1$-$C_6$alkyl;
$R_{13}$ is $C_1$-$C_6$alkyl;
$R_{14}$ is —OH, —C(=O)H, or —C(=O)$OR_{15}$;
$R_{15}$ is hydrogen or $C_1$-$C_6$alkyl;
n is 0, 1, 2, or 3;
p is 0, 1, or 2; and
q is 0, 1, or 2.
In some embodiments is a compound of Formula (IV), or a pharmaceutically acceptable salt or solvate thereof, wherein X is $C(R_{11})$. In some embodiments is a compound of Formula (IV), or a pharmaceutically acceptable salt or solvate thereof, wherein X is C(H). In some embodiments is a compound of Formula (IV), or a pharmaceutically acceptable salt or solvate thereof, wherein X is N.

In some embodiments is a compound of Formula (IV), or a pharmaceutically acceptable salt or solvate thereof, wherein

is a $C_2$-$C_9$heteroaryl ring selected from oxazolyl, thiazolyl, pyrazolyl, furanyl, thienyl, pyrrolyl, imidazolyl, triazolyl, tetrazolyl, isoxazolyl, isothiazolyl, oxadiazolyl, thiadiazolyl, pyridinyl, pyrimidinyl, pyrazinyl, pyridazinyl, or triazinyl.

In some embodiments is a compound of Formula (IV), or a pharmaceutically acceptable salt or solvate thereof, wherein

is a $C_2$-$C_9$heteroaryl ring selected from pyrazolyl, pyrrolyl, and imidazolyl. In some embodiments is a compound of Formula (IV), or a pharmaceutically acceptable salt or solvate thereof, wherein

is pyrazolyl. In some embodiments is a compound of Formula (IV), or a pharmaceutically acceptable salt or solvate thereof, wherein

is pyrrolyl. In some embodiments is a compound of Formula (IV), or a pharmaceutically acceptable salt or solvate thereof, wherein

is imidazolyl. In some embodiments is a compound of Formula (IV), or a pharmaceutically acceptable salt or solvate thereof, wherein

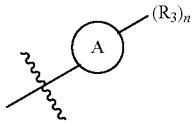

is selected from

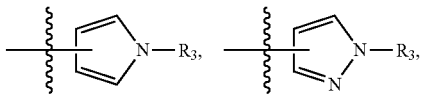

and

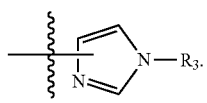

In some embodiments is a compound of Formula (IV), or a pharmaceutically acceptable salt or solvate thereof, wherein

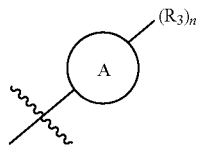 is 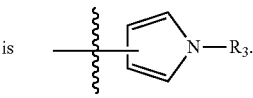

In some embodiments is a compound of Formula (IV), or a pharmaceutically acceptable salt or solvate thereof, wherein

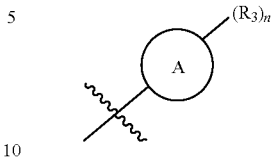 is 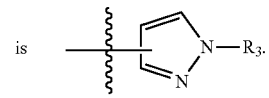

In some embodiments is a compound of Formula (IV), or a pharmaceutically acceptable salt or solvate thereof, wherein

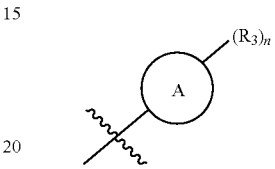 is 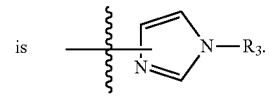

In some embodiments, provided herein is a compound of Formula (IV), or a pharmaceutically acceptable salt or solvate thereof, wherein $L_1$ is a bond. In some embodiments, provided herein is a compound of Formula (IV), or a pharmaceutically acceptable salt or solvate thereof, wherein $L_1$ is $C_1$-$C_6$alkyl. In some embodiments, provided herein is a compound of Formula (IV), or a pharmaceutically acceptable salt or solvate thereof, wherein $L_1$ is —$CH_2$—. In some embodiments, provided herein is a compound of Formula (IV), or a pharmaceutically acceptable salt or solvate thereof, wherein $L_1$ is —$CH_2CH_2$—. In some embodiments, provided herein is a compound of Formula (IV), or a pharmaceutically acceptable salt or solvate thereof, wherein $L_1$ is —$CH_2CH_2CH_2$—.

In some embodiments, provided herein is a compound of Formula (IV), or a pharmaceutically acceptable salt or solvate thereof, wherein $L_2$ is $C_1$-$C_6$alkyl. In some embodiments, provided herein is a compound of Formula (IV), or a pharmaceutically acceptable salt or solvate thereof, wherein $L_2$ is —$CH_2$—. In some embodiments, provided herein is a compound of Formula (IV), or a pharmaceutically acceptable salt or solvate thereof, wherein $L_2$ is —$CH_2CH_2$—. In some embodiments, provided herein is a compound of Formula (IV), or a pharmaceutically acceptable salt or solvate thereof, wherein $L_2$ is —$CH_2CH_2CH_2$—. In some embodiments, provided herein is a compound of Formula (IV), or a pharmaceutically acceptable salt or solvate thereof, wherein $L_2$ is $C_2$-$C_9$heteroaryl. In some embodiments, provided herein is a compound of Formula (IV), or a pharmaceutically acceptable salt or solvate thereof, wherein $L_2$ is $C_2$-$C_9$heteroaryl selected from oxazolyl, thiazolyl, pyrazolyl, furanyl, thienyl, pyrrolyl, imidazolyl, triazolyl, tetrazolyl, isoxazolyl, isothiazolyl, oxadiazolyl, thiadiazolyl, pyridinyl, pyrimidinyl, pyrazinyl, pyridazinyl, and triazinyl. In some embodiments, provided herein is a compound of Formula (IV), or a pharmaceutically acceptable salt or solvate thereof, wherein $L_2$ is $C_2$-$C_9$heteroaryl selected from oxazolyl, thiazolyl, pyrazolyl, thienyl, pyrrolyl, imidazolyl, and pyridinyl. In some embodiments, provided herein is a compound of Formula (IV), or a pharmaceutically acceptable salt or solvate thereof, wherein $L_2$ is oxazolyl. In some embodiments, provided herein is a compound of Formula (IV), or a pharmaceutically acceptable salt or solvate thereof, wherein $L_2$ is thiazolyl. In some embodiments, provided herein is a compound of Formula (IV), or a pharmaceutically acceptable salt or solvate thereof, wherein $L_2$ is pyrazolyl. In some embodiments, provided herein is a compound of Formula (IV), or a pharmaceutically acceptable salt or solvate thereof, wherein $L_2$ is thienyl. In some embodiments, provided herein is a compound of Formula (IV), or a pharmaceutically acceptable salt or solvate thereof, wherein $L_2$ is pyrrolyl. In some embodiments, provided herein is a compound of Formula (IV), or a pharmaceutically acceptable salt or solvate thereof, wherein $L_2$ is imidazolyl. In some embodiments, provided herein is a compound of Formula (IV), or a pharmaceutically acceptable salt or solvate thereof, wherein $L_2$ is pyridinyl. In some embodiments, provided herein is a compound of Formula (IV), or a pharmaceutically acceptable salt or solvate thereof, wherein $L_2$ is —C(H)(phenyl)-.

In some embodiments, provided herein is a compound of Formula (IV), or a pharmaceutically acceptable salt or solvate thereof, wherein $R_2$ is

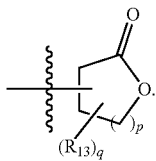

In some embodiments, provided herein is a compound of Formula (IV), or a pharmaceutically acceptable salt or solvate thereof, wherein $R_2$ is

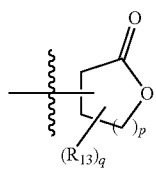

and p is 1. In some embodiments, provided herein is a compound of Formula (IV), or a pharmaceutically acceptable salt or solvate thereof, wherein $R_2$ is

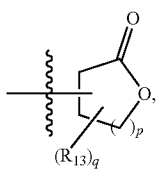

p is 1, and q is 0. In some embodiments, provided herein is a compound of Formula (IV), or a pharmaceutically acceptable salt or solvate thereof, wherein $R_2$ is

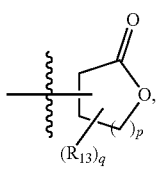

p is 1, and q is 2. In some embodiments, provided herein is a compound of Formula (IV), or a pharmaceutically acceptable salt or solvate thereof, wherein $R_2$ is

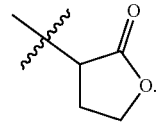 [SMILES: *C1CCOC1=O]

In some embodiments, provided herein is a compound of Formula (IV), or a pharmaceutically acceptable salt or solvate thereof, wherein $R_2$ is

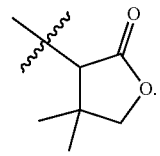 [SMILES: *C1C(=O)OCC1(C)C]

In some embodiments, provided herein is a compound of Formula (IV), or a pharmaceutically acceptable salt or solvate thereof, wherein $R_2$ is

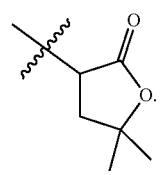 [SMILES: *C1CC(C)(C)OC1=O]

In some embodiments, provided herein is a compound of Formula (IV), or a pharmaceutically acceptable salt or solvate thereof, wherein $R_2$ is

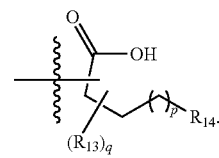

In some embodiments, provided herein is a compound of Formula (IV), or a pharmaceutically acceptable salt or solvate thereof, wherein $R_2$ is

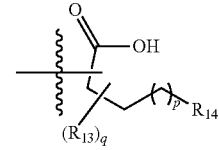

and p is 1. In some embodiments, provided herein is a compound of Formula (IV), or a pharmaceutically acceptable salt or solvate thereof, wherein $R_2$ is

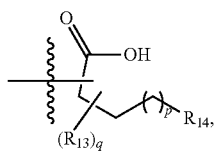

p is 1, and q is 0. In some embodiments, provided herein is a compound of Formula (IV), or a pharmaceutically acceptable salt or solvate thereof, wherein R$_2$ is

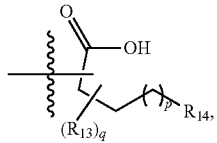

p is 1, and q is 2. In some embodiments, provided herein is a compound of Formula (IV), or a pharmaceutically acceptable salt or solvate thereof, wherein R$_{14}$ is —OH. In some embodiments, provided herein is a compound of Formula (IV), or a pharmaceutically acceptable salt or solvate thereof, wherein R$_{14}$ is —C(=O)H. In some embodiments, provided herein is a compound of Formula (IV), or a pharmaceutically acceptable salt or solvate thereof, wherein R$_{14}$ is —C(=O)OR$_{15}$. In some embodiments, provided herein is a compound of Formula (IV), or a pharmaceutically acceptable salt or solvate thereof, wherein R$_{14}$ is —C(=O)OR$_{15}$ and R$_{15}$ is hydrogen.

In some embodiments, provided herein is a compound of Formula (IV), or a pharmaceutically acceptable salt or solvate thereof, wherein n is 0.

In some embodiments, provided herein is a compound of Formula (IV), or a pharmaceutically acceptable salt or solvate thereof, wherein n is 1. In some embodiments, provided herein is a compound of Formula (IV), or a pharmaceutically acceptable salt or solvate thereof, wherein n is 2. In some embodiments, provided herein is a compound of Formula (IV), or a pharmaceutically acceptable salt or solvate thereof, wherein n is 3. In some embodiments, provided herein is a compound of Formula (IV), or a pharmaceutically acceptable salt or solvate thereof, wherein n is 1 or 2 and each R$_3$ is independently selected from halogen, C$_1$-C$_6$alkyl, C$_1$-C$_6$haloalkyl, C$_1$-C$_6$heteroalkyl, —OR$_7$, —N(R$_7$)$_2$, —CN, —C(=O)R$_8$, —C(=O)OR$_7$, —C(=O)N(R$_7$)$_2$, —NR$_7$C(=O)R$_8$, —NR$_7$S(=O)$_2$R$_8$, —S(=O)$_2$R$_8$, and —S(=O)$_2$N(R$_7$)$_2$. In some embodiments, provided herein is a compound of Formula (IV), or a pharmaceutically acceptable salt or solvate thereof, wherein n is 1 or 2 and each R$_3$ is independently selected from halogen, C$_1$-C$_6$alkyl, C$_1$-C$_6$haloalkyl, C$_1$-C$_6$heteroalkyl, —OR$_7$, —N(R$_7$)$_2$, —CN, —C(=O)R$_8$, —C(=O)OR$_7$, —C(=O)N(R$_7$)$_2$, —NR$_7$C(=O)R$_8$, —NR$_7$S(=O)$_2$R$_8$, —S(=O)$_2$R$_8$, and —S(=O)$_2$N(R$_7$)$_2$. In some embodiments, provided herein is a compound of Formula (IV), or a pharmaceutically acceptable salt or solvate thereof, wherein n is 1 or 2 and each R$_3$ is independently selected from halogen, C$_1$-C$_6$alkyl, C$_1$-C$_6$haloalkyl, —OR$_7$, and —N(R$_7$)$_2$. In some embodiments, provided herein is a compound of Formula (IV), or a pharmaceutically acceptable salt or solvate thereof, wherein n is 1 or 2 and each R$_3$ is independently selected from halogen and C$_1$-C$_6$alkyl. In some embodiments, provided herein is a compound of Formula (IV), or a pharmaceutically acceptable salt or solvate thereof, wherein n is 1 and R$_3$ is selected from halogen, C$_1$-C$_6$alkyl, C$_1$-C$_6$haloalkyl, —OR$_7$, and —N(R$_7$)$_2$. In some embodiments, provided herein is a compound of Formula (IV), or a pharmaceutically acceptable salt or solvate thereof, wherein n is 1 and R$_3$ is selected from halogen and C$_1$-C$_6$alkyl. In some embodiments, provided herein is a compound of Formula (IV), or a pharmaceutically acceptable salt or solvate thereof, wherein n is 1 and R$_3$ is halogen. In some embodiments, provided herein is a compound of Formula (IV), or a pharmaceutically acceptable salt or solvate thereof, wherein n is 1 and R$_3$ is C$_1$-C$_6$alkyl.

In some embodiments, provided herein is a compound of Formula (IV), or a pharmaceutically acceptable salt or solvate thereof, wherein R$_4$ is hydrogen. In some embodiments, provided herein is a compound of Formula (IV), or a pharmaceutically acceptable salt or solvate thereof, wherein R$_4$ is C$_1$-C$_6$alkyl. In some embodiments, provided herein is a compound of Formula (IV), or a pharmaceutically acceptable salt or solvate thereof, wherein R$_4$ is —CH$_3$. In some embodiments, provided herein is a compound of Formula (IV), or a pharmaceutically acceptable salt or solvate thereof, wherein R$_4$ is C$_1$-C$_6$heteroalkyl.

In some embodiments is a compound of Formula (IV), or a pharmaceutically acceptable salt or solvate thereof, wherein R$_{12}$ is hydrogen. In some embodiments is a compound of Formula (IV), or a pharmaceutically acceptable salt or solvate thereof, wherein R$_{12}$ is halogen. In some embodiments is a compound of Formula (IV), or a pharmaceutically acceptable salt or solvate thereof, wherein R$_{12}$ is C$_1$-C$_6$alkyl. In some embodiments, provided herein is a compound of Formula (IV), or a pharmaceutically acceptable salt or solvate thereof, wherein R$_{12}$ is —CH$_3$.

In some embodiments, provided herein is a compound selected from:

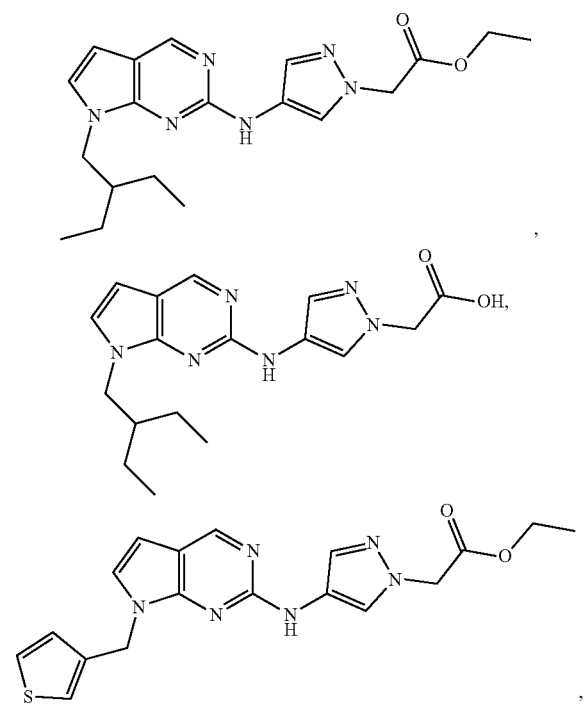

67
-continued
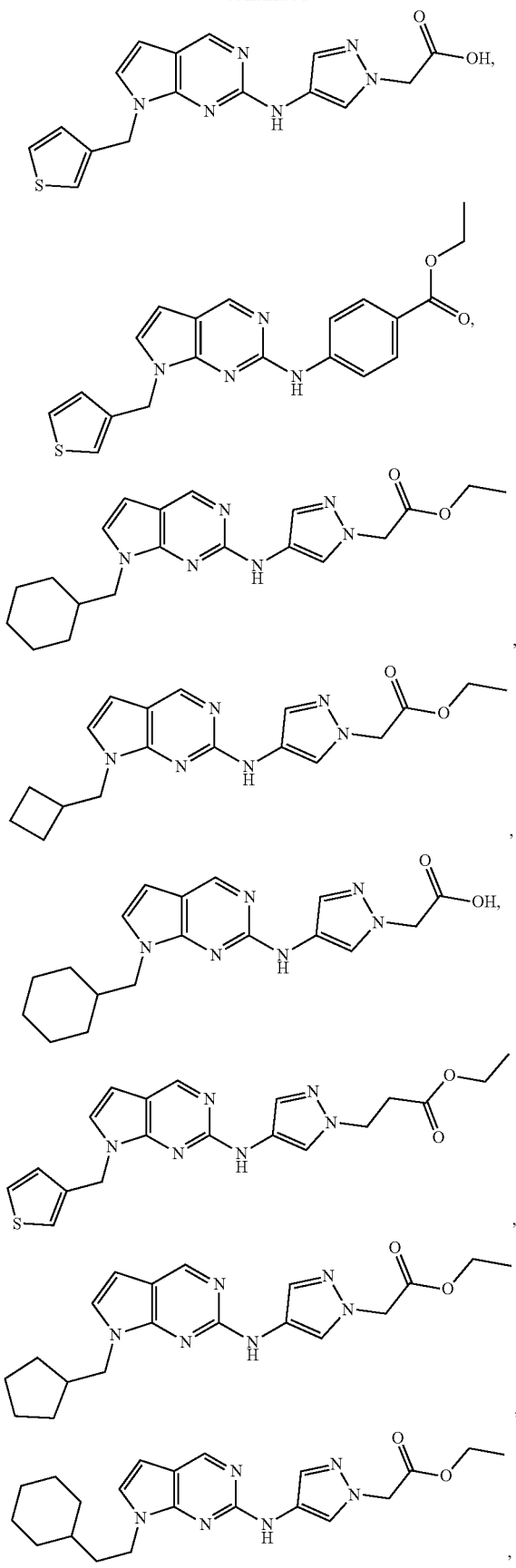
68
-continued
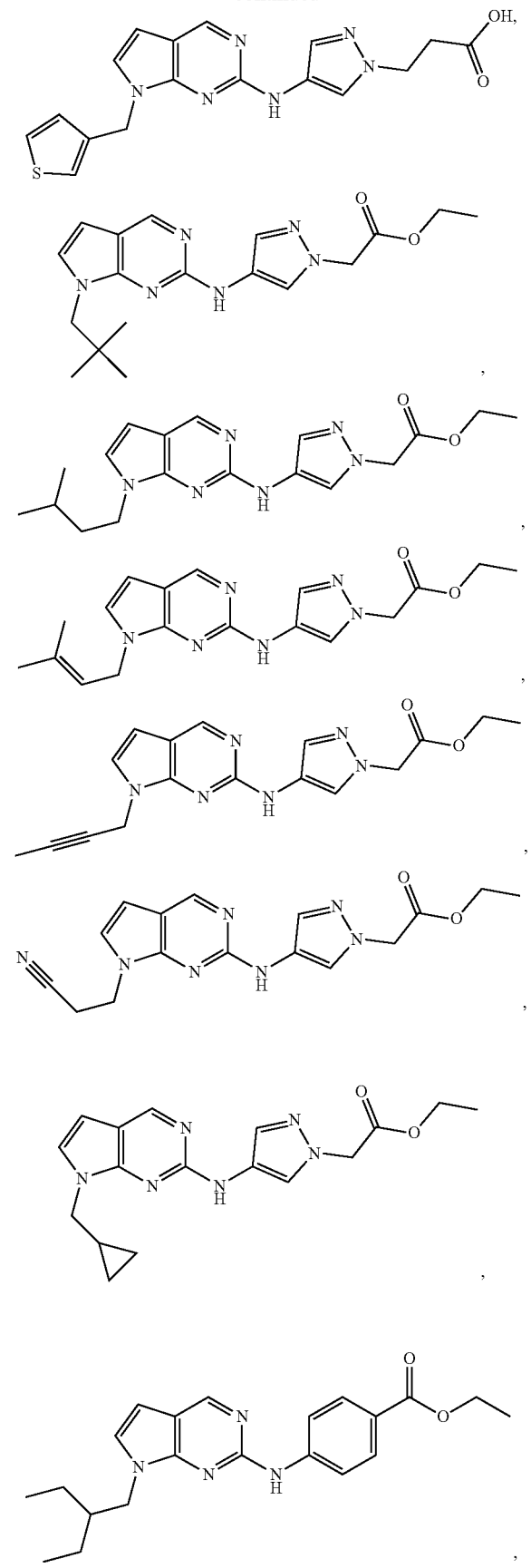

69
-continued
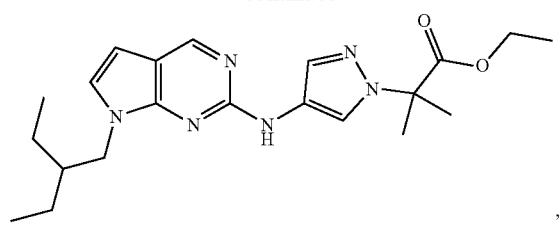
,
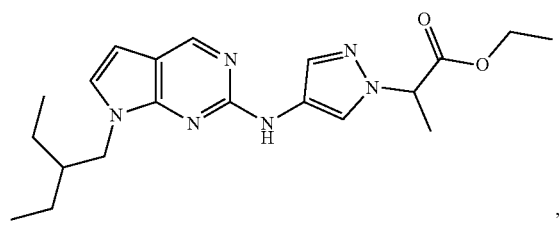
,
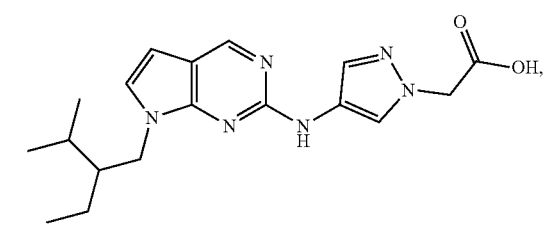
,
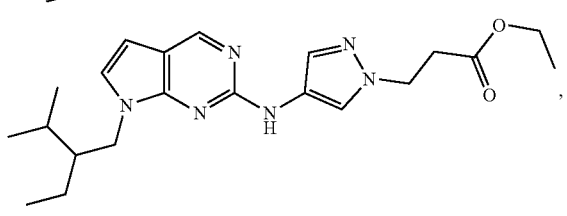
,
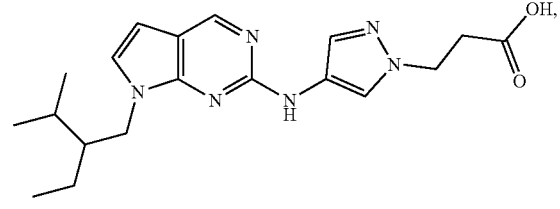
,
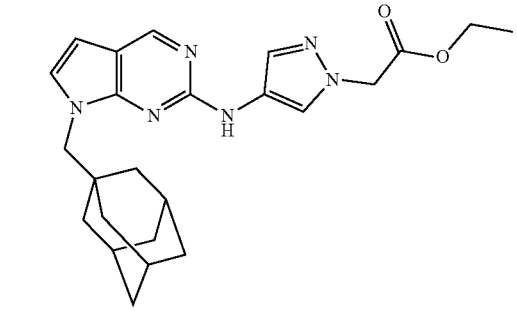
,
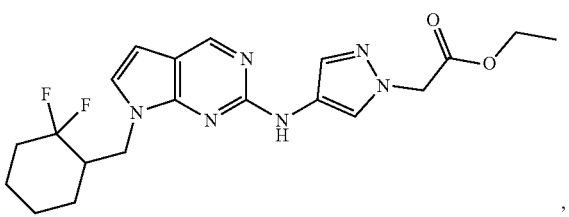
,
70
-continued
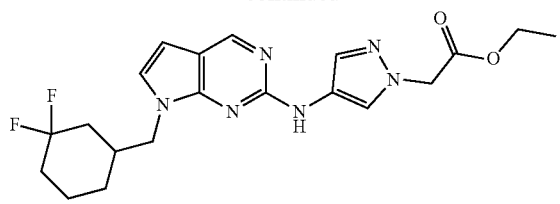
,
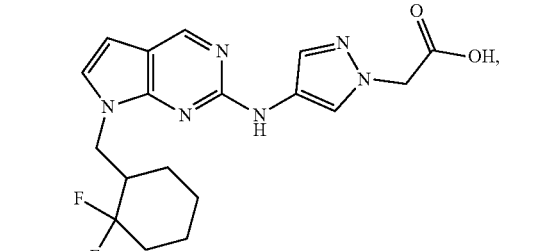
,
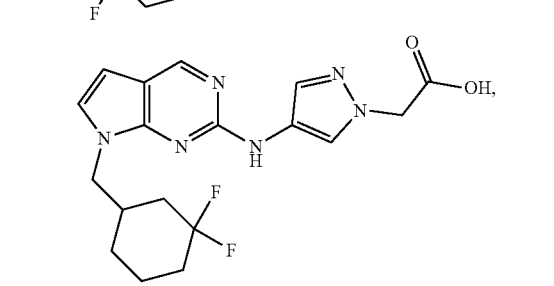
,
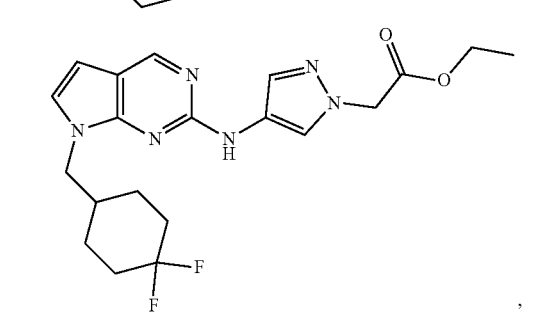
,
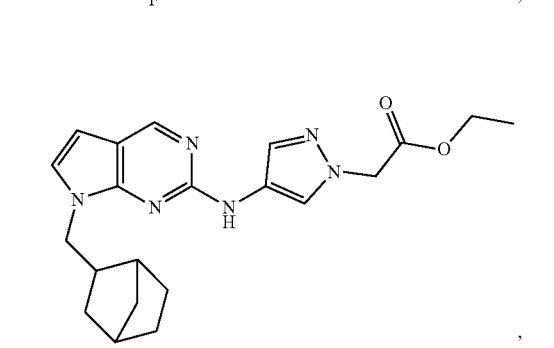
,
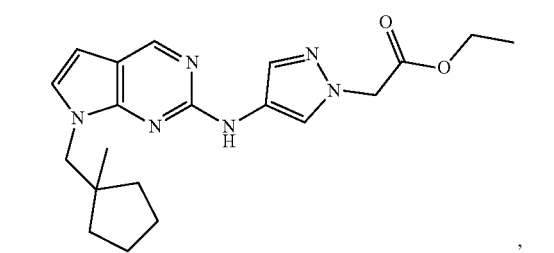
,

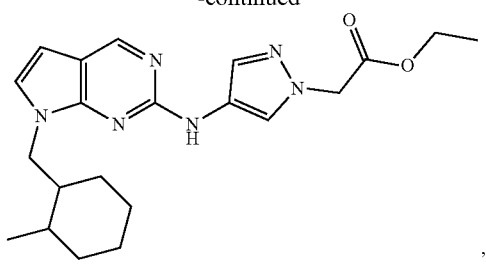
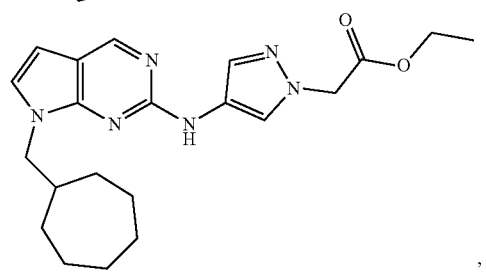
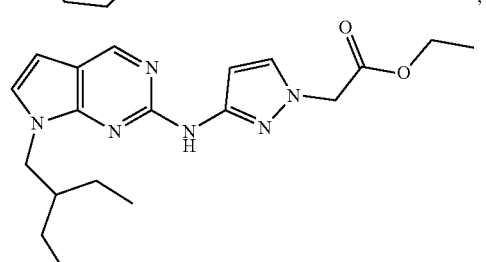
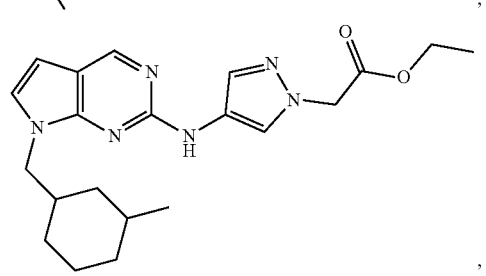
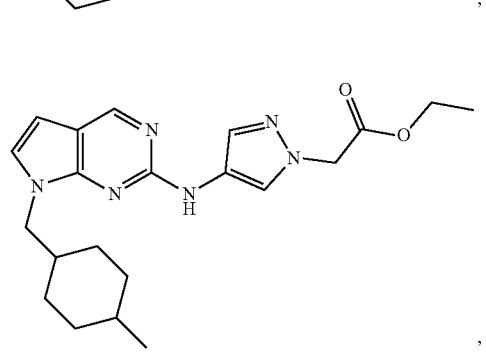
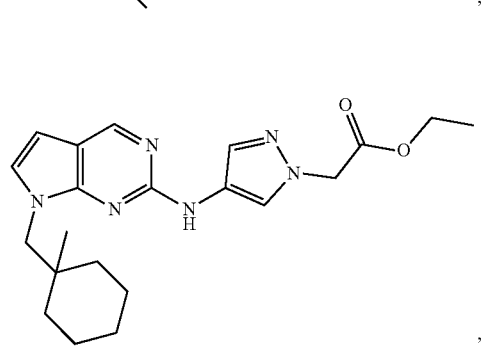
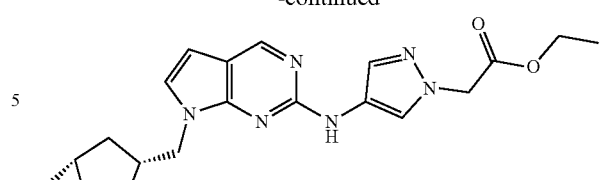
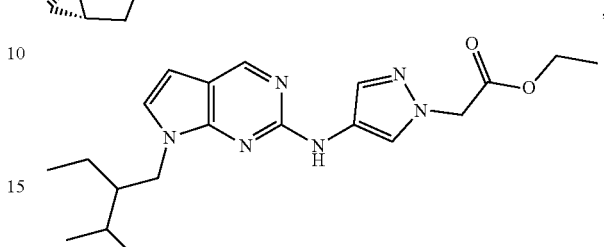
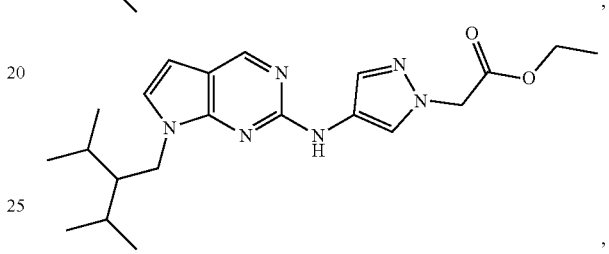
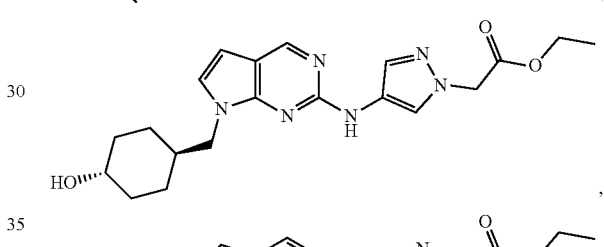
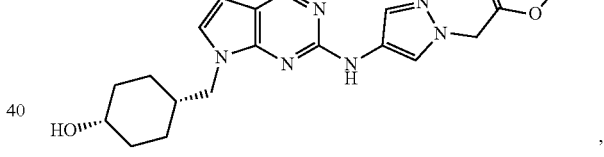
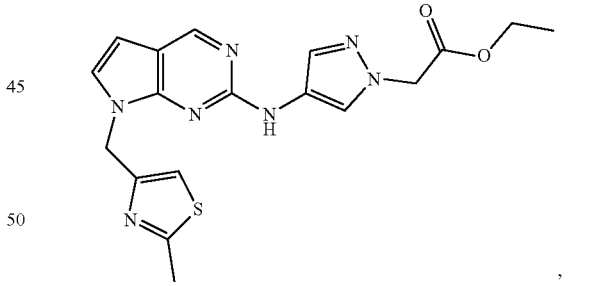
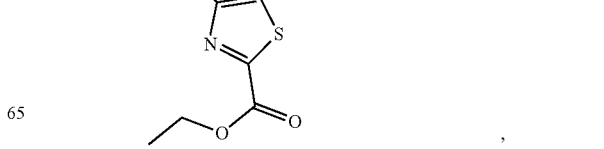

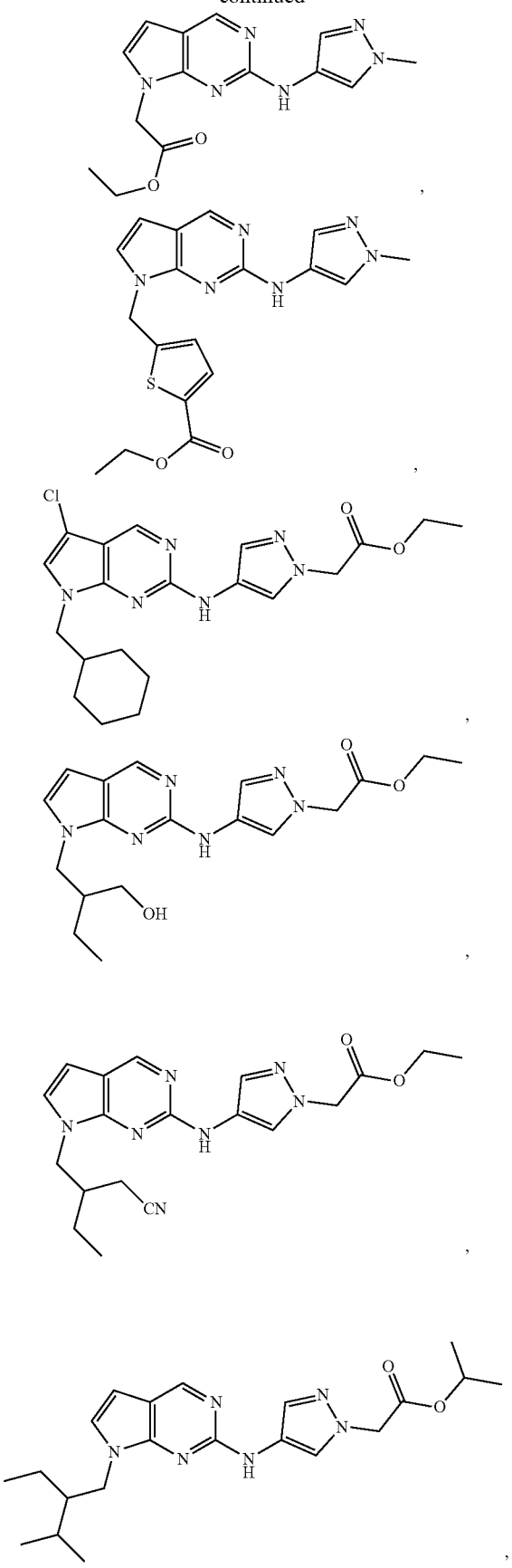
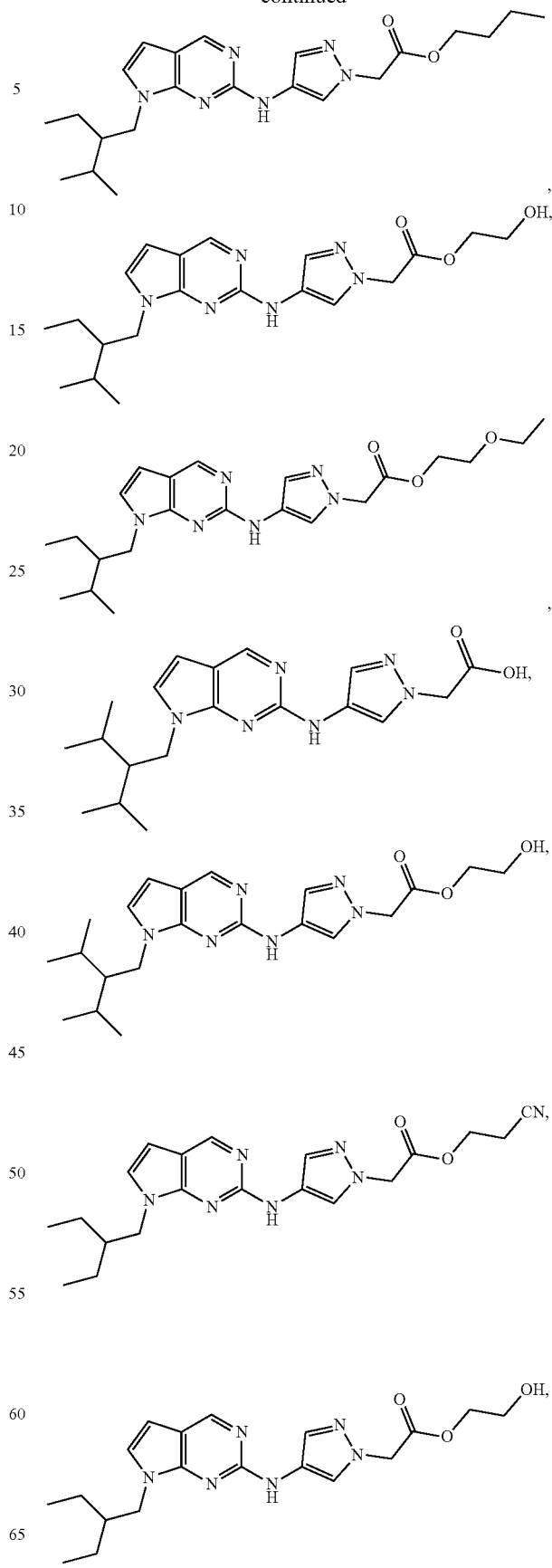

75
-continued
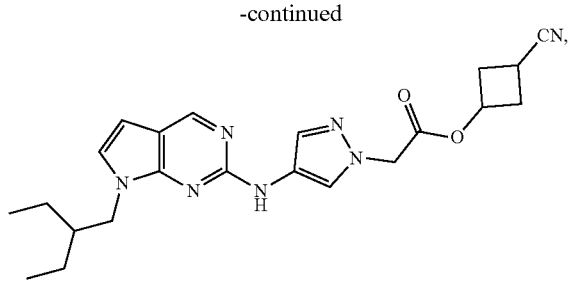
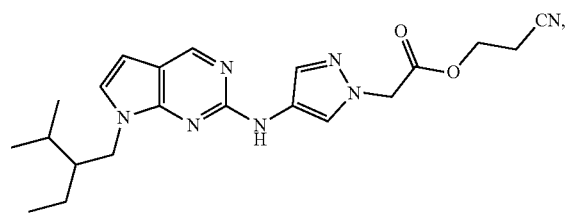
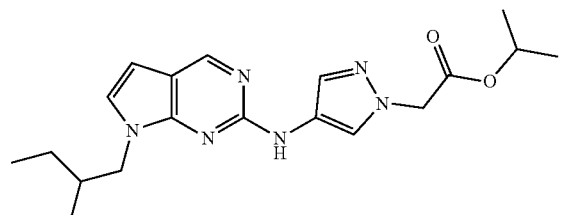
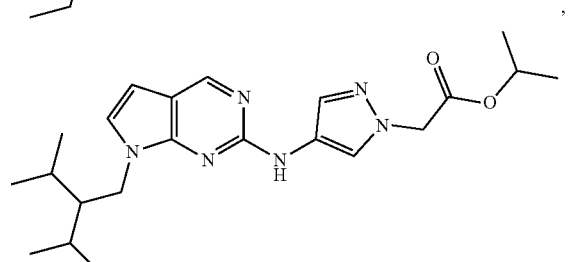
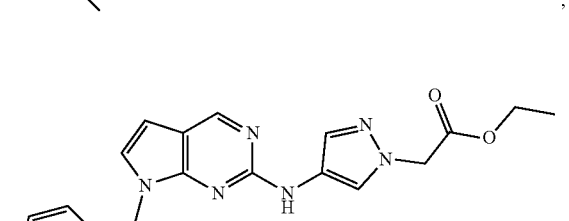
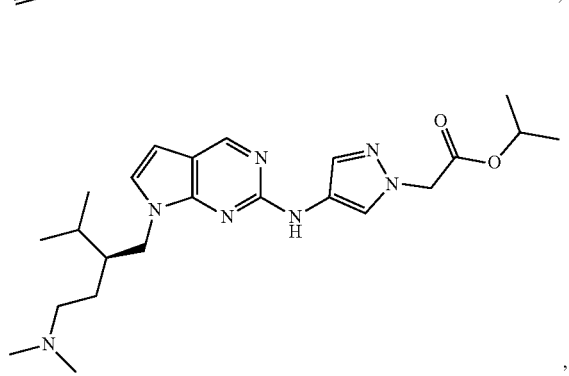
76
-continued
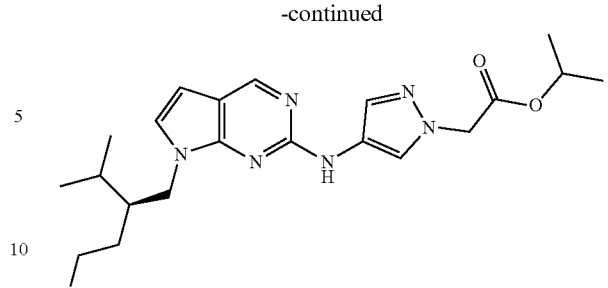
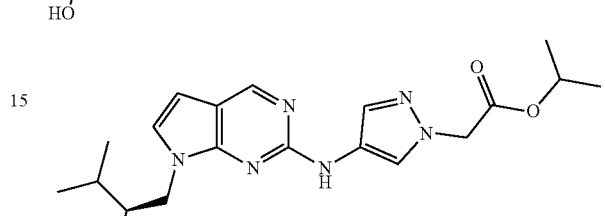
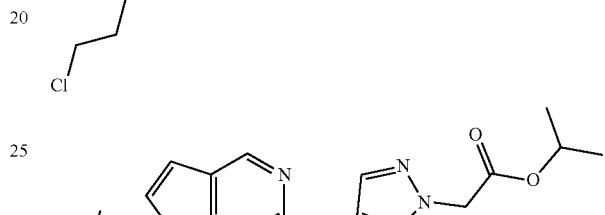
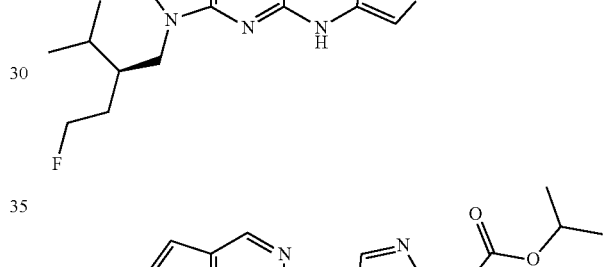
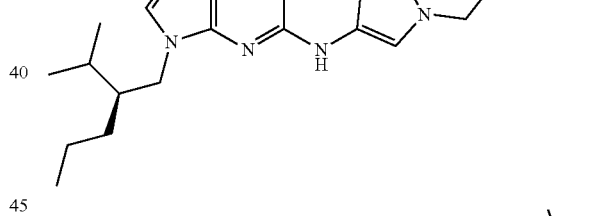
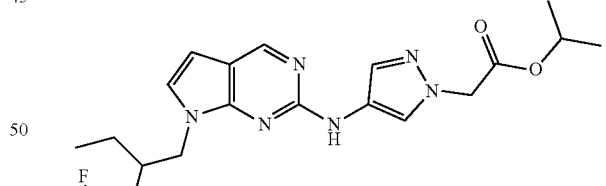
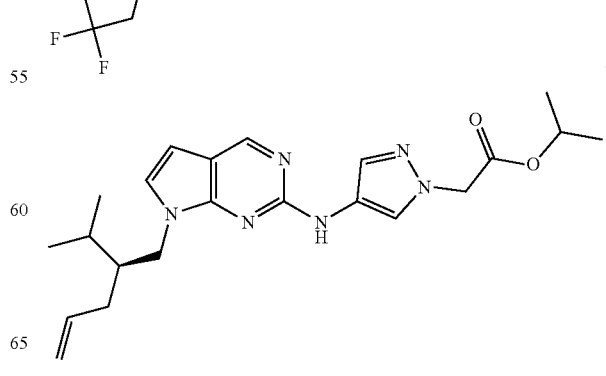

77
-continued
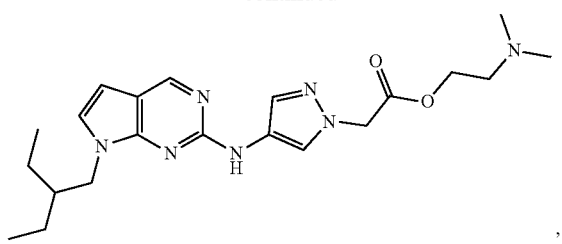
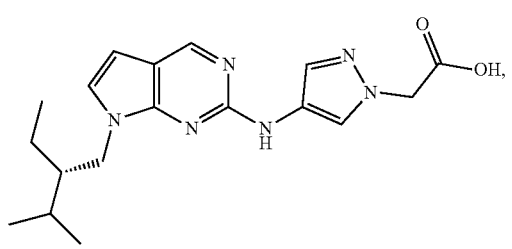
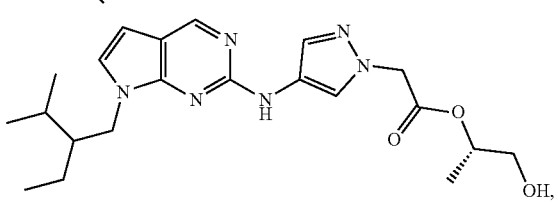
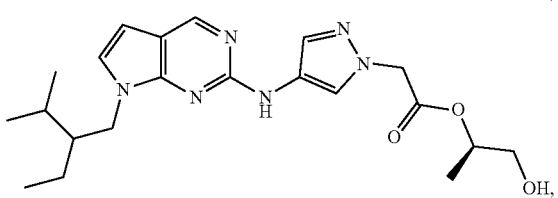
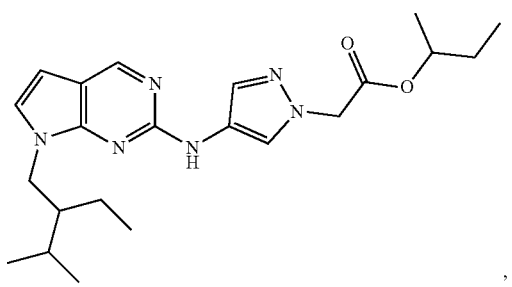
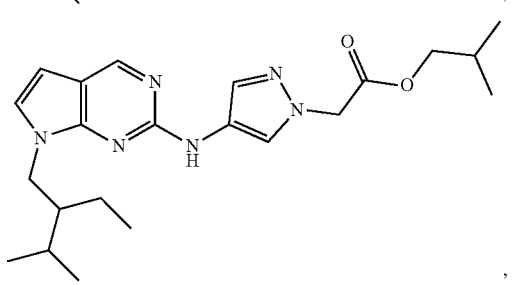
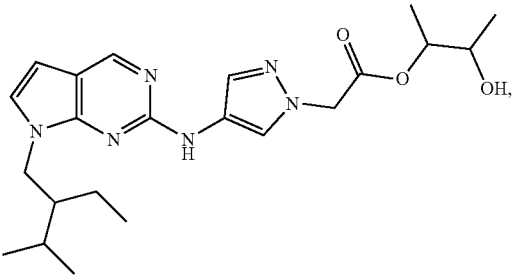
78
-continued
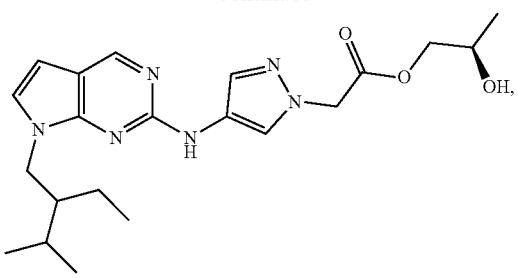
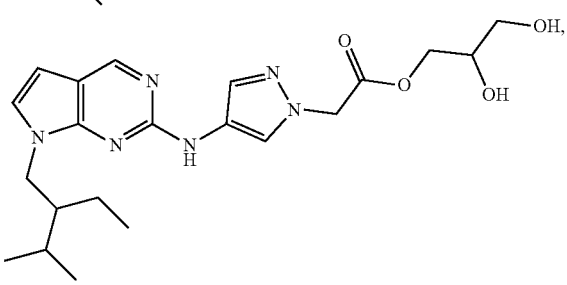
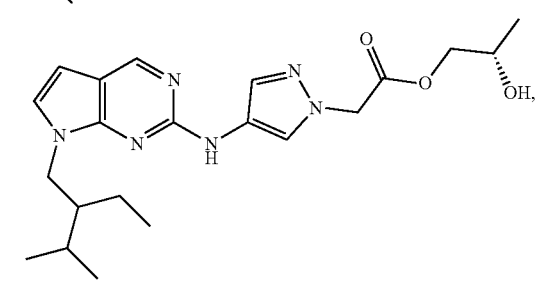
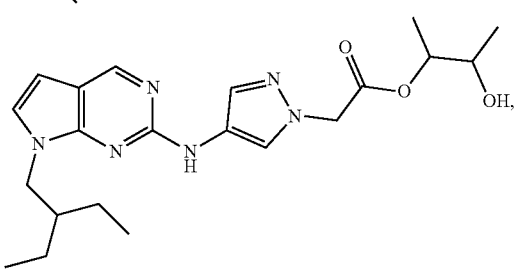
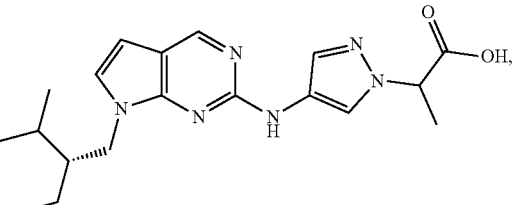
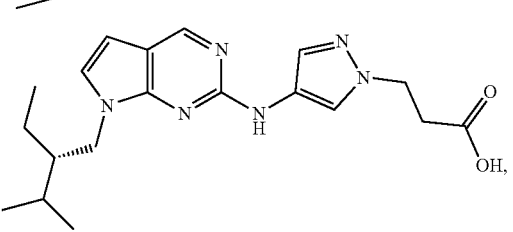
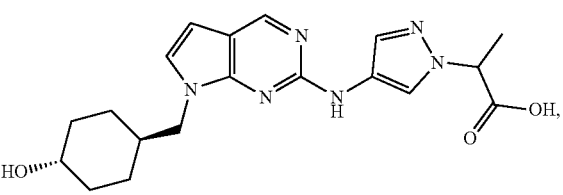

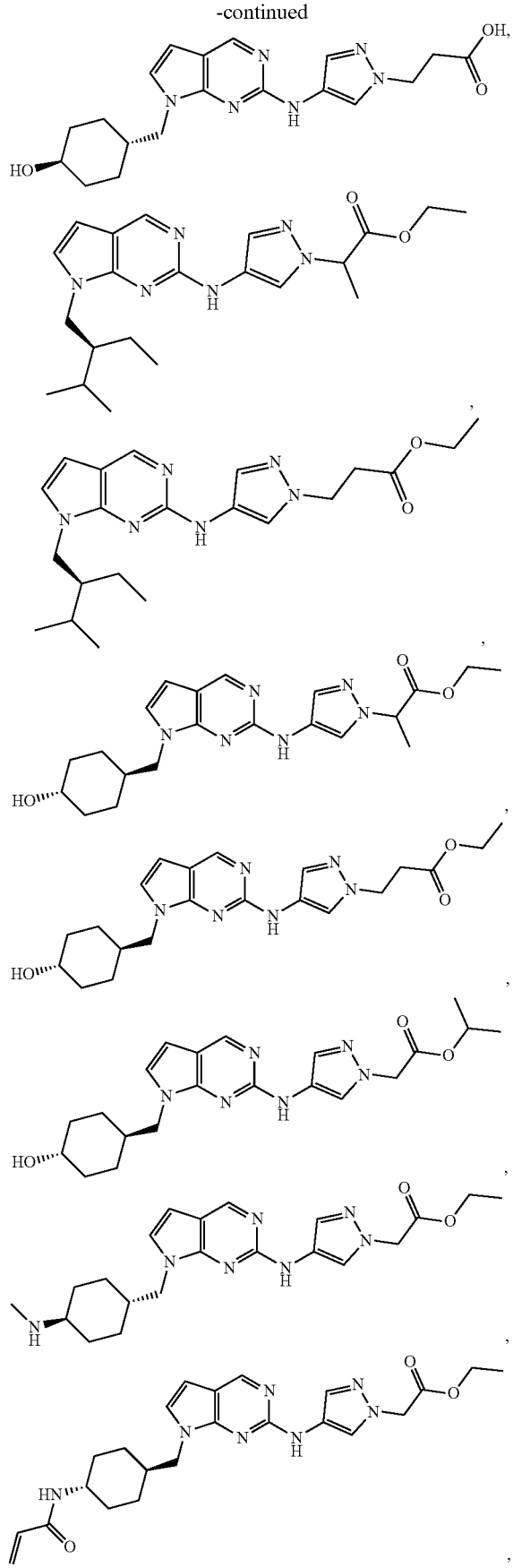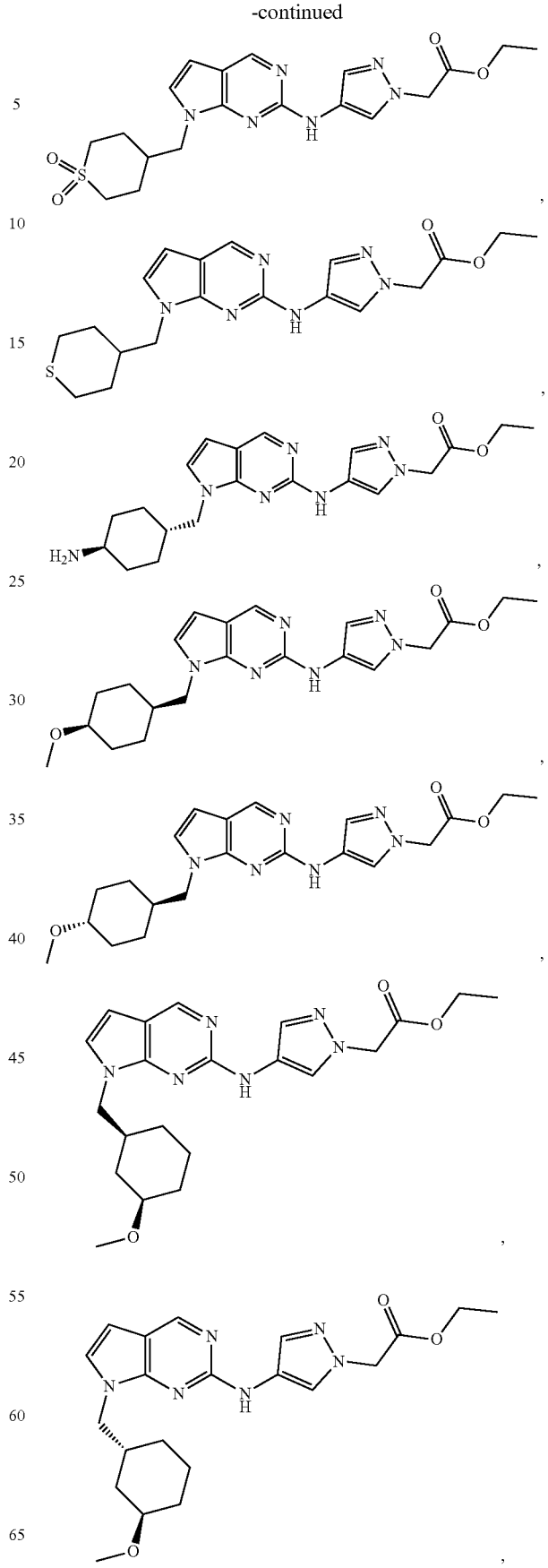

-continued
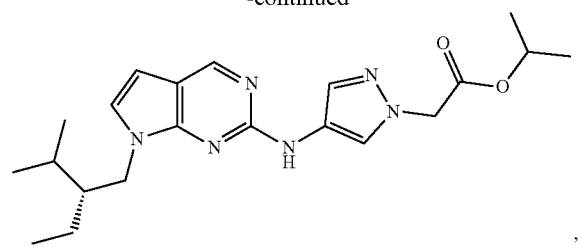
,
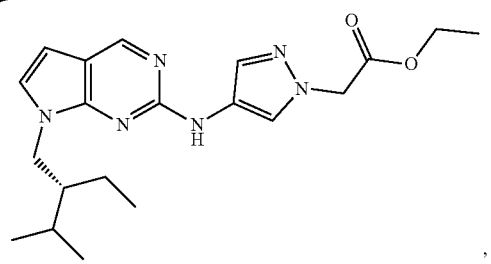
,
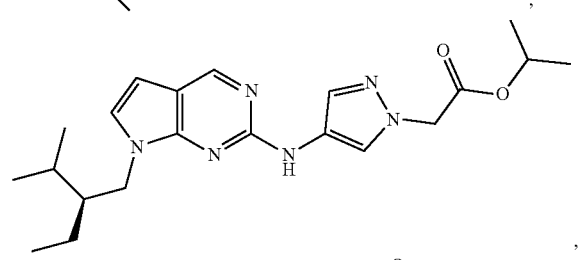
,
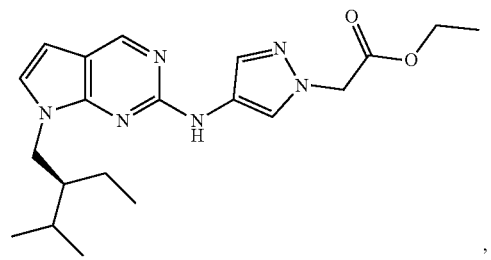
,
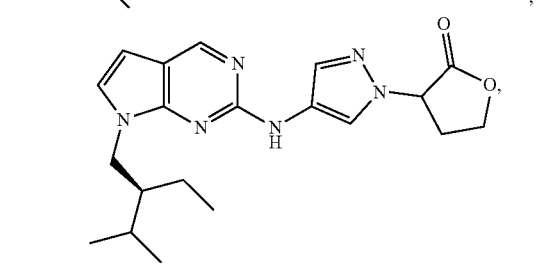
,
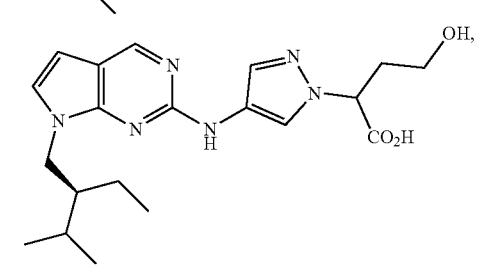
,
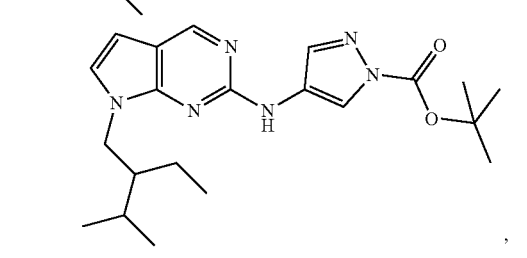
,
-continued
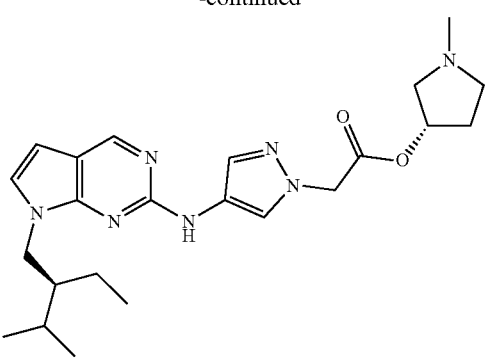
,
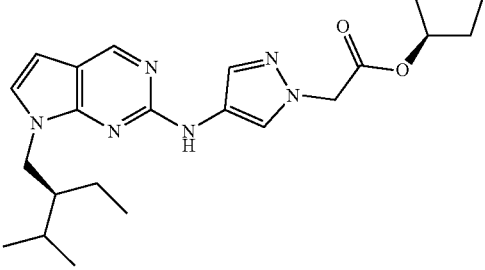
,
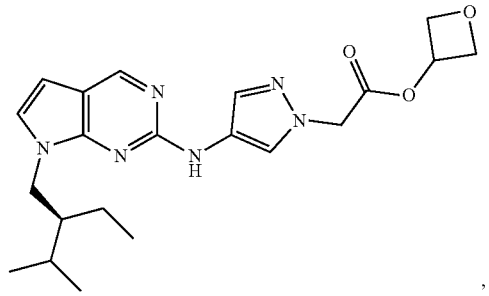
,
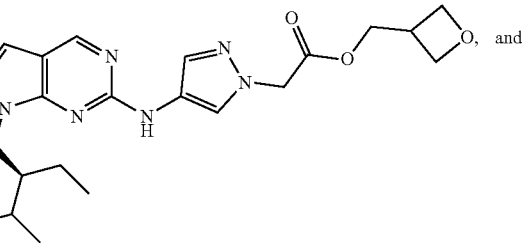
, and
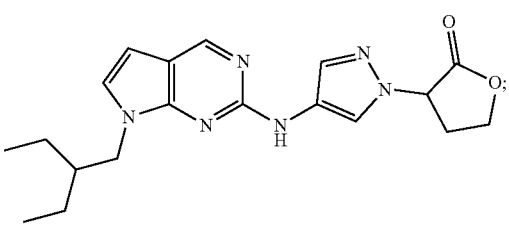
;
or a pharmaceutically acceptable salt or solvate thereof.

In some embodiments provided herein is a compound selected from:

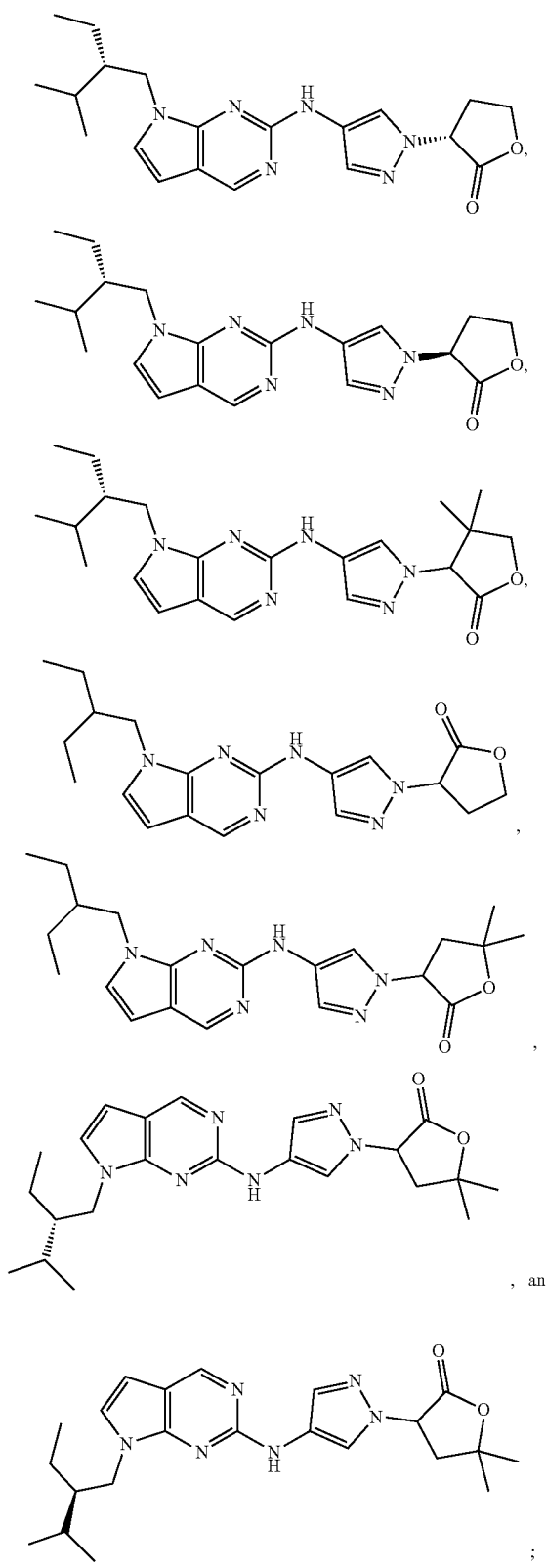

or a pharmaceutically acceptable salt or solvate thereof.

In some embodiments, provided herein is a compound selected from:

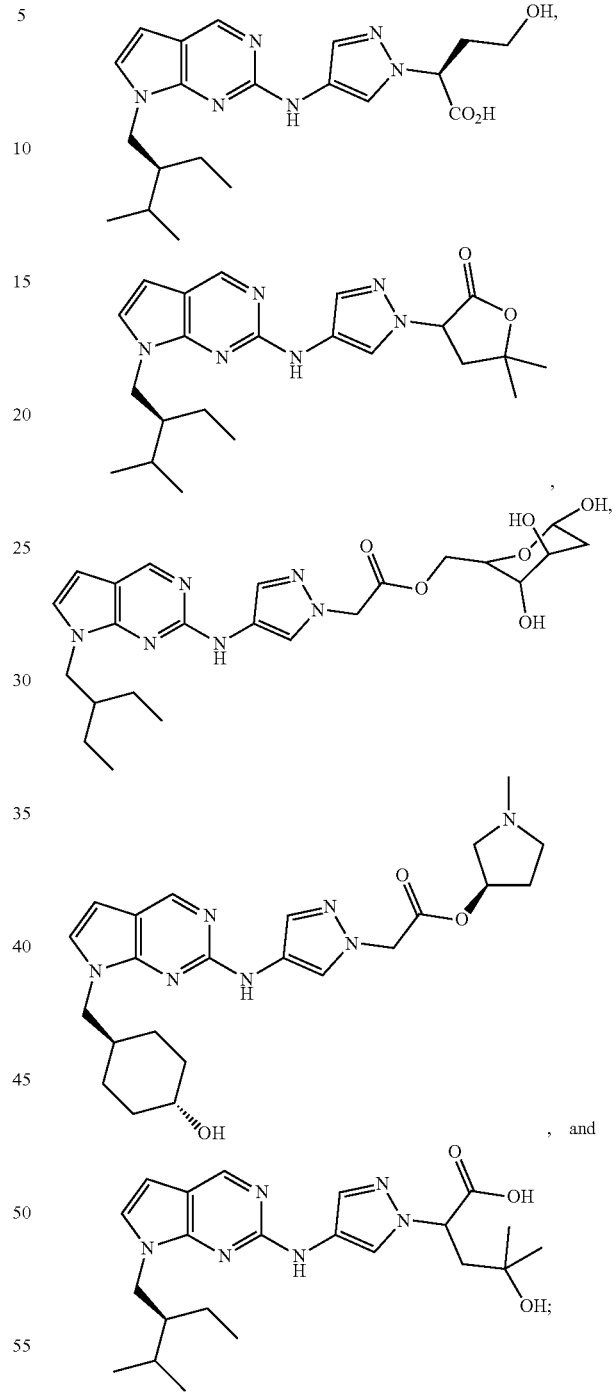

or a pharmaceutically acceptable salt or solvate thereof.

In some embodiments, the compounds provided herein have $IC_{50}$s of about or less than 50 nM in the JAK/TYK2 assay. In some embodiments, the compounds provided herein have $IC_{50}$s of about or less than 100 nM in the JAK/TYK2 assay. In some embodiments, the compounds provided herein have $IC_{50}$s of about 10 nM or less, about 20 nM or less, about 25 nM or less, about 50 nM or less, about 100 nM or less, about 250 nM or less, or about 500 nM or less in the JAK/TYK2 assay. In another embodiment, the compounds provided herein inhibit JAK1 selectively over JAK2, JAK3, and TYK2. In another embodiment, the compounds provided herein inhibit JAK2 selectively over JAK1, JAK3, and TYK2. In another embodiment, the compounds provided herein inhibit JAK3 selectively over JAK1, JAK2, and TYK2. In another embodiment, the compounds provided herein inhibit TYK2 selectively over JAK1, JAK2, and JAK3. In another embodiment, the compounds provided herein inhibit JAK1 and JAK2 selectively over JAK3 and TYK2. In another embodiment, the compounds provided herein inhibit JAK1 and JAK3 selectively over JAK2 and TYK2. In another embodiment, the compounds provided herein inhibit JAK1 and TYK2 selectively over JAK2 and JAK3. In another embodiment, the compounds provided herein inhibit JAK2 and JAK3 selectively over JAK1 and TYK2. In another embodiment, the compounds provided herein inhibit JAK2 and TYK2 selectively over JAK1 and JAK3. In another embodiment, the compounds provided herein inhibit JAK3 and TYK2 selectively over JAK1 and JAK2. In another embodiment, the compounds provided herein inhibit JAK1, JAK2, and JAK3 selectively over TYK2. In another embodiment, the compounds provided herein inhibit JAK1, JAK2, and TYK2 selectively over JAK3. In another embodiment, the compounds provided herein inhibit JAK1, JAK3, and TYK2 selectively over JAK2. In another embodiment, the compounds provided herein inhibit JAK2, JAK3, and TYK2 selectively over JAK1.

Any combination of the groups described above for the various variables is contemplated herein. Throughout the specification, groups and substituents thereof can be chosen by one skilled in the field to provide stable moieties and compounds.

In some embodiments, the therapeutic agent(s) (e.g. compound of Formula (I'), (I), (Ia'), (Ia), (Ib), (II'), (II), (IIa), (III), (IIIa), or (IV)) is present in the pharmaceutical composition as a pharmaceutically acceptable salt. In some embodiments, any compound described above is suitable for any method or composition described herein.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion, are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine, and chloride, such as $^2$H, $^3$H, $^{13}$C, $^{14}$C, $^{15}$N, $^{17}$O, $^{18}$O, $^{31}$P, $^{32}$P, $^{35}$S, $^{18}$F, and $^{36}$Cl, respectively. Compounds described herein, and pharmaceutically acceptable salts, esters, solvate, hydrates, or derivatives thereof which contain the aforementioned isotopes and/or other isotopes of other atoms are within the scope of this invention. Certain isotopically-labeled compounds, for example those into which radioactive isotopes such as $^3$H and $^{14}$C are incorporated, are useful in drug and/or substrate tissue distribution assays. Tritiated, i. e., $^3$H and carbon-14, i.e., $^{14}$C, isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Solvates

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or MeOH. In addition, the compounds provided herein exist in unsolvated as well as solvated forms. In general, the solvated forms are considered equivalent to the unsolvated forms for the purposes of the compounds and methods provided herein.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, FischerScientific (Fischer Chemicals), and AcrosOrganics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4$^{th}$ Ed., Vols. A and B (Plenum 2000, 2001), and Green and Wuts, Protective Groups in Organic Synthesis 3$^{rd}$ Ed., (Wiley 1999) (all of which are incorporated by reference for such disclosure). General methods for the preparation of compound as disclosed herein may be derived from reactions and the reactions may be modified by the use of appropriate reagents and conditions, for the introduction of the various moieties found in the formulae as provided herein. As a guide the following synthetic methods may be utilized.

Use of Protecting Groups

In the reactions described, it may be necessary to protect reactive functional groups, for example hydroxy, amino, imino, thio or carboxy groups, where these are desired in the final product, in order to avoid their unwanted participation in reactions. Protecting groups are used to block some or all of the reactive moieties and prevent such groups from participating in chemical reactions until the protective group is removed. It is preferred that each protective group be removable by a different means. Protective groups that are cleaved under totally disparate reaction conditions fulfill the requirement of differential removal.

Protective groups can be removed by acid, base, reducing conditions (such as, for example, hydrogenolysis), and/or oxidative conditions. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, which include conversion to alkyl esters, or they may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a Pd$^0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

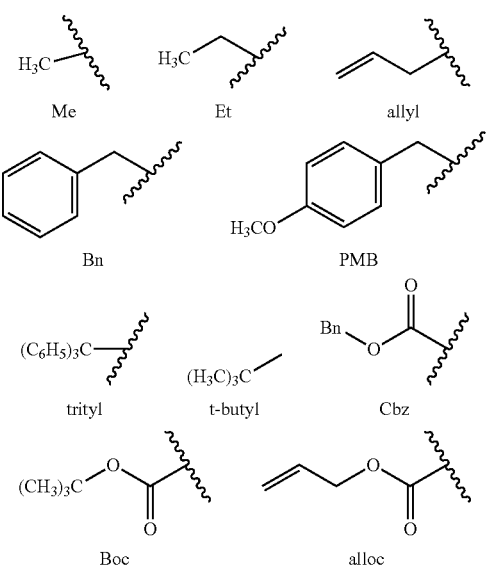

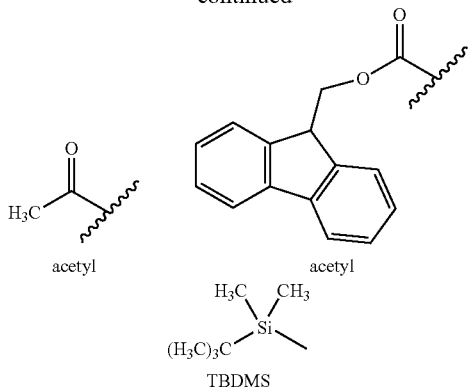

acetyl    acetyl

TBDMS

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

Methods of Treatment and Prevention

In some embodiments is a method of treating an inflammatory or autoimmune disease in a patient in need thereof, comprising administering to the patient a therapeutically effective amount of a compound Formula (I'), (I), (Ia'), (Ia), (Ib), (II'), (II), (IIa), (III), (IIIa), or (IV), or a pharmaceutically acceptable salt or solvate thereof. In some embodiments is a method of treating an inflammatory disease in a patient in need thereof, comprising administering to the patient a therapeutically effective amount of a compound Formula (I'), (I), (Ia'), (Ia), (Ib), (II'), (II), (IIa), (III), (IIIa), or (IV), or a pharmaceutically acceptable salt or solvate thereof. In some embodiments is a method of treating an autoimmune disease in a patient in need thereof, comprising administering to the patient a therapeutically effective amount of a compound Formula (I'), (I), (Ia'), (Ia), (Ib), (II'), (II), (IIa), (III), (IIIa), or (IV), or a pharmaceutically acceptable salt or solvate thereof. In some embodiments is a method of treating an inflammatory or autoimmune disease in a patient in need thereof, comprising administering to the patient a therapeutically effective amount of a compound Formula (I'), (I), (Ia'), (Ia), (Ib), (II'), (II), (IIa), (III), (IIIa), or (IV), or a pharmaceutically acceptable salt or solvate thereof, wherein the disease, disorder, or condition is selected from rheumatoid arthritis, multiple sclerosis, psoriasis, lupus, intestinal bowel disease, Crohn's disease, ulcerative colitis, ankylosing spondylitis, vitiligo, and atopic dermatitis. In some embodiments is a method of treating an inflammatory or autoimmune disease in a patient in need thereof, comprising administering to the patient a therapeutically effective amount of a compound Formula (I'), (I), (Ia'), (Ia), (Ib), (II'), (II), (IIa), (III), (IIIa), or (IV), or a pharmaceutically acceptable salt or solvate thereof, wherein the disease, disorder, or condition is rheumatoid arthritis. In some embodiments is a method of treating an inflammatory or autoimmune disease in a patient in need thereof, comprising administering to the patient a therapeutically effective amount of a compound Formula (I'), (I), (Ia'), (Ia), (Ib), (II'), (II), (IIa), (III), (IIIa), or (IV), or a pharmaceutically acceptable salt or solvate thereof, wherein the disease, disorder, or condition is multiple sclerosis. In some embodiments is a method of treating an inflammatory or autoimmune disease in a patient in need thereof, comprising administering to the patient a therapeutically effective amount of a compound Formula (I'), (I), (Ia'), (Ia), (Ib), (II'), (II), (IIa), (III), (IIIa), or (IV), or a pharmaceutically acceptable salt or solvate thereof, wherein the disease, disorder, or condition is psoriasis. In some embodiments is a method of treating an inflammatory or autoimmune disease in a patient in need thereof, comprising administering to the patient a therapeutically effective amount of a compound Formula (I'), (I), (Ia'), (Ia), (Ib), (II'), (II), (IIa), (III), (IIIa), or (IV), or a pharmaceutically acceptable salt or solvate thereof, wherein the disease, disorder, or condition is lupus. In some embodiments is a method of treating an inflammatory or autoimmune disease in a patient in need thereof, comprising administering to the patient a therapeutically effective amount of a compound Formula (I'), (I), (Ia'), (Ia), (Ib), (II'), (II), (IIa), (III), (IIIa), or (IV), or a pharmaceutically acceptable salt or solvate thereof, wherein the disease, disorder, or condition is intestinal bowel disease. In some embodiments is a method of treating an inflammatory or autoimmune disease in a patient in need thereof, comprising administering to the patient a therapeutically effective amount of a compound Formula (I'), (I), (Ia'), (Ia), (Ib), (II'), (II), (IIa), (III), (IIIa), or (IV), or a pharmaceutically acceptable salt or solvate thereof, wherein the disease, disorder, or condition is Crohn's disease. In some embodiments is a method of treating an inflammatory or autoimmune disease in a patient in need thereof, comprising administering to the patient a therapeutically effective amount of a compound Formula (I'), (I), (Ia'), (Ia), (Ib), (II'), (II), (IIa), (III), (IIIa), or (IV), or a pharmaceutically acceptable salt or solvate thereof, wherein the disease, disorder, or condition is ulcerative colitis. In some embodiments is a method of treating an inflammatory or autoimmune disease in a patient in need thereof, comprising administering to the patient a therapeutically effective amount of a compound Formula (I'), (I), (Ia'), (Ia), (Ib), (II'), (II), (IIa), (III), (IIIa), or (IV), or a pharmaceutically acceptable salt or solvate thereof, wherein the disease, disorder, or condition is ankylosing spondylitis. In some embodiments is a method of treating an inflammatory or autoimmune disease in a patient in need thereof, comprising administering to the patient a therapeutically effective amount of a compound Formula (I'), (I), (Ia'), (Ia), (Ib), (II'), (II), (IIa), (III), (IIIa), or (IV), or a pharmaceutically acceptable salt or solvate thereof, wherein the disease, disorder, or condition is vitiligo. In some embodiments is a method of treating an inflammatory or autoimmune disease in a patient in need thereof, comprising administering to the patient a therapeutically effective amount of a compound Formula (I'), (I), (Ia'), (Ia), (Ib), (II'), (II), (IIa), (III), (IIIa), or (IV), or a pharmaceutically acceptable salt or solvate thereof, wherein the disease, disorder, or condition is atopic dermatitis.

Pharmaceutical Compositions and Methods of Administration

JAK inhibitors described herein are administered to subjects in a biologically compatible form suitable for administration to treat or prevent diseases, disorders or conditions. Administration of JAK inhibitors as described herein can be in any pharmacological form including a therapeutically effective amount of a JAK inhibitor alone or in combination with a pharmaceutically acceptable carrier.

In certain embodiments, the compounds described herein are administered as a pure chemical. In other embodiments, the compounds described herein are combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21st Ed. Mack Pub. Co., Easton, Pa. (2005)).

Accordingly, provided herein is a pharmaceutical composition comprising at least one compound described herein, or a pharmaceutically acceptable salt, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

In some embodiments is a pharmaceutical composition comprising a pharmaceutically acceptable carrier and a compound of Formula (I'), (I), (Ia'), (Ia), (Ib), (II'), (II), (IIa), (III), (IIIa), or (IV), or a pharmaceutically acceptable salt or solvate thereof. In some embodiments is a pharmaceutical composition comprising a pharmaceutically acceptable carrier and a compound of Formula (I), or a pharmaceutically acceptable salt or solvate thereof. In some embodiments is a pharmaceutical composition comprising a pharmaceutically acceptable carrier and a compound of Formula (Ia), or a pharmaceutically acceptable salt or solvate thereof. In some embodiments is a pharmaceutical composition comprising a pharmaceutically acceptable carrier and a compound of Formula (Ib), or a pharmaceutically acceptable salt or solvate thereof. In some embodiments is a pharmaceutical composition comprising a pharmaceutically acceptable carrier and a compound of Formula (II), or a pharmaceutically acceptable salt or solvate thereof. In some embodiments is a pharmaceutical composition comprising a pharmaceutically acceptable carrier and a compound of Formula (IIa), or a pharmaceutically acceptable salt or solvate thereof.

Another embodiment provides a pharmaceutical composition consisting essentially of a pharmaceutically acceptable carrier and a compound of Formula (I'), (I), (Ia'), (Ia), (Ib), (II'), (II), (IIa), (III), (IIIa), or (IV), or a pharmaceutically acceptable salt or solvate thereof. In some embodiments is a pharmaceutical composition consisting essentially of a pharmaceutically acceptable carrier and a compound of Formula (I), or a pharmaceutically acceptable salt or solvate thereof. In some embodiments is a pharmaceutical composition consisting essentially of a pharmaceutically acceptable carrier and a compound of Formula (Ia), or a pharmaceutically acceptable salt or solvate thereof. In some embodiments is a pharmaceutical composition consisting essentially of a pharmaceutically acceptable carrier and a compound of Formula (Ib), or a pharmaceutically acceptable salt or solvate thereof. In some embodiments is a pharmaceutical composition consisting essentially of a pharmaceutically acceptable carrier and a compound of Formula (II), or a pharmaceutically acceptable salt or solvate thereof. In some embodiments is a pharmaceutical composition consisting essentially of a pharmaceutically acceptable carrier and a compound of Formula (IIa), or a pharmaceutically acceptable salt or solvate thereof.

In certain embodiments, the compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, topical, buccal, parenteral (e.g., subcutaneous, intramuscular, intradermal, or intravenous), or aerosol administration.

Exemplary pharmaceutical compositions are used in the form of a pharmaceutical preparation, for example, in solid, semisolid or liquid form, which includes one or more of a disclosed compound, as an active ingredient, in a mixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments, JAK inhibitors described herein are administered to subjects in a biologically compatible form suitable for topical administration to treat or prevent dermal diseases, disorders, or conditions. By "biologically compatible form suitable for topical administration" is meant a form of the JAK inhibitor to be administered in which any toxic effects are outweighed by the therapeutic effects of the inhibitor. Administration of JAK inhibitors as described herein can be in any pharmacological form including a therapeutically effective amount of a JAK inhibitor alone or in combination with a pharmaceutically acceptable carrier.

Topical administration of a JAK inhibitor may be presented in the form of an aerosol, a semi-solid pharmaceutical composition, a powder, or a solution. By the term "a semi-solid composition" is meant an ointment, cream, salve, jelly, or other pharmaceutical composition of substantially similar consistency suitable for application to the skin. Examples of semi-solid compositions are given in Chapter 17 of The Theory and Practice of Industrial Pharmacy, Lachman, Lieberman and Kanig, published by Lea and Febiger (1970) and in Chapter 67 of Remington's Pharmaceutical Sciences, 15th Edition (1975) published by Mack Publishing Company.

Dermal or skin patches are another method for transdermal delivery of the therapeutic or pharmaceutical compositions described herein. Patches can provide an absorption enhancer such as DMSO to increase the absorption of the compounds. Patches can include those that control the rate of drug delivery to the skin. Patches may provide a variety of dosing systems including a reservoir system or a monolithic system, respectively. The reservoir design may, for example, have four layers: the adhesive layer that directly contacts the skin, the control membrane, which controls the diffusion of drug molecules, the reservoir of drug molecules, and a water-resistant backing. Such a design delivers uniform amounts of the drug over a specified time period, the rate of delivery has to be less than the saturation limit of different types of skin. The monolithic design, for example, typically has only three layers: the adhesive layer, a polymer matrix containing the compound, and a water-proof backing. This design brings a saturating amount of drug to the skin. Thereby, delivery is controlled by the skin. As the drug amount decreases in the patch to below the saturating level, the delivery rate falls.

In one embodiment, the topical composition may, for example, take the form of hydrogel based on polyacrylic acid or polyacrylamide; as an ointment, for example with polyethyleneglycol (PEG) as the carrier, like the standard ointment DAB 8 (50% PEG 300, 50% PEG 1500); or as an emulsion, especially a microemulsion based on water-in-oil or oil-in-water, optionally with added liposomes. Suitable permeation accelerators (entraining agents) include sulphoxide derivatives such as dimethylsulphoxide (DMSO) or decylmethylsulphoxide (decyl-MSO) and transcutol (diethyleneglycolmonoethylether) or cyclodextrin; as well as pyrrolidones, for example 2-pyrrolidone, N-methyl-2-pyrrolidone, 2-pyrrolidone-5-carboxylic acid, or the biodegradable N-(2-hydroxyethyl)-2-pyrrolidone and the fatty acid esters thereof; urea derivatives such as dodecylurea, 1,3-didodecylurea, and 1,3-diphenylurea; and terpenes, for example D-limonene, menthone, a-terpinol, carvol, limonene oxide, or 1,8-cineol.

Ointments, pastes, creams and gels also can contain excipients, such as starch, tragacanth, cellulose derivatives, polyethylene glycols, silicones, bentonites, silicic acid, and talc, or mixtures thereof. Powders and sprays also can contain excipients such as lactose, talc, silicic acid, aluminum hydroxide, calcium silicates and polyamide powder, or mixtures of these substances. Solutions of nanocrystalline antimicrobial metals can be converted into aerosols or sprays by any of the known means routinely used for making aerosol pharmaceuticals. In general, such methods comprise pressurizing or providing a means for pressurizing a container of the solution, usually with an inert carrier gas, and passing the pressurized gas through a small orifice. Sprays can additionally contain customary propellants, such a chlorofluorohydrocarbons and volatile unsubstituted hydrocarbons, such as butane and propane.

The carrier can also contain other pharmaceutically-acceptable excipients for modifying or maintaining the pH, osmolarity, viscosity, clarity, color, sterility, stability, rate of dissolution, or odor of the formulation. The anti-skin aging compositions can also further comprise antioxidants, sun screens, natural retinoids (e.g., retinol), and other additives commonly found in skin treatment compositions.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills and granules, are scored or prepared with coatings and shells, such as enteric coatings and other coatings.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

In some embodiments, powders and sprays contain, in addition to a subject composition, excipients such as lactose, talc, silicic acid, aluminum hydroxide, calcium silicates, and polyamide powder, or mixtures of these substances. In some embodiments, sprays additionally contain customary propellants, such as chlorofluorohydrocarbons and volatile unsubstituted hydrocarbons, such as butane and propane.

Compositions and compounds disclosed herein alternatively are administered by aerosol. This is accomplished by preparing an aqueous aerosol, liposomal preparation, or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient, or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity is maintained, for example, by the use of coating materials, such as lecithin, by the maintenance of the required particle size in the case of dispersions, and by the use of surfactants The dose of the composition comprising at least one compound described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Dose administration can be repeated depending upon the pharmacokinetic parameters of the dosage formulation and the route of administration used.

It is especially advantageous to formulate compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the JAK inhibitor and the particular therapeutic effect to be achieved and (b) the limitations inherent in the art of compounding such an active compound for the treatment of sensitivity in individuals. The specific dose can be readily calculated by one of ordinary skill in the art, e.g., according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the JAK inhibitor activities disclosed herein in assay preparations of target cells. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration.

Toxicity and therapeutic efficacy of such JAK inhibitors can be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. JA K inhibitors that exhibit large therapeutic indices are preferred. While JAK inhibitors that exhibit toxic side effects may be used, care should be taken to design a delivery system that targets such inhibitors to the site of affected tissue in order to minimize potential damage to uninfected cells and, thereby, reduce side effects.

The data obtained from the cell culture assays and animal studies can be used in formulating a range of dosage for use in humans. The dosage of such JAK inhibitors lies preferably within a range of circulating concentrations that include the $ED_{50}$ with little or no toxicity. The dosage may vary within this range depending upon the dosage form employed and the route of administration utilized. For any JAK inhibitor used in a method described herein, the therapeutically effective dose can be estimated initially from cell culture assays. A dose may be formulated in animal models to achieve a circulating plasma concentration range that includes the $IC_{50}$ (i.e., the concentration of JAK inhibitor that achieves a half-maximal inhibition of symptoms) as determined in cell culture. Such information can be used to more accurately determine useful doses in humans. Levels in plasma may be measured, for example, by high performance liquid chromatography.

EXAMPLES

The following examples are offered for purposes of illustration and are not intended to limit the scope of the claims provided herein. All literature citations in these examples and throughout this specification are incorporated herein by references for all legal purposes to be served thereby. The starting materials and reagents used for the synthesis of the compounds described herein may be synthesized or can be obtained from commercial sources, such as, but not limited to, Sigma-Aldrich, Acros Organics, Fluka, and Fischer Scientific.

Standard abbreviations and acronyms as defined in *J. Org. Chem.* 2007 72(1): 23A-24A are used herein. Other abbreviations and acronyms used herein are as follows:

| | |
|---|---|
| AcOH | acetic acid |
| DMF | dimethylformamide |
| DMP | Dess-Martin periodinane |
| dppf | (diphenylphosphino)ferrocene |
| EtOAc | ethyl acetate |

-continued

| EtOH | ethanol |
| --- | --- |
| eq | equivalent |
| HBTU | N,N,N',N'-tetramethyl-O-(1H-benzotriazol-1-yl)uronium hexafluorophosphate |
| LC-MS | liquid chromatography-mass spectrometry |
| MeOH | methanol |
| TEA | triethylamine |
| rt | room temperature |

General Synthetic Scheme:

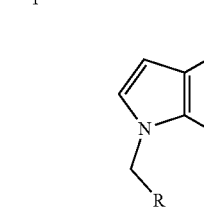
1

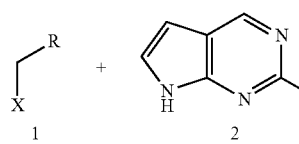 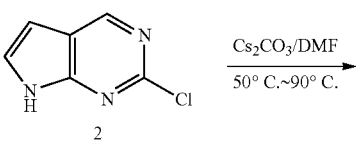

$X = Cl, Br, $—$OMs, $—$OTs$

General Procedure

To a solution of 2 (1.0 eq) in DMF was added $Cs_2CO_3$ (2.5 eq). The mixture was stirred at room temperature for 5 mins under $N_2$. 1 (1.5 eq) was then added to the reaction mixture. The resulting mixture was heated at 50° C. to 90° C. to afford 3.

3 (1.0 eq) and 4 (HCl salt, 1.4 eq) were combined in dry EtOH. The mixture was heated at 120° C. in a sealed-tube for 20 hrs to 48 hrs to provide 5.

Example A: Synthesis of Intermediate 1

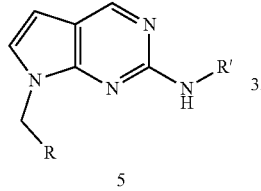

The alcohol was dissolved in DCM and pyridine (5 eq). To the solution was added MsCl (1.5 eq) or TsCl (1.5 eq) at 0° C. The reaction mixture was stirred at RT for 2 hrs to afford 1.

Example B: Synthesis of Intermediates 4-a, 4-b, 4-c, 4-d, 4-e

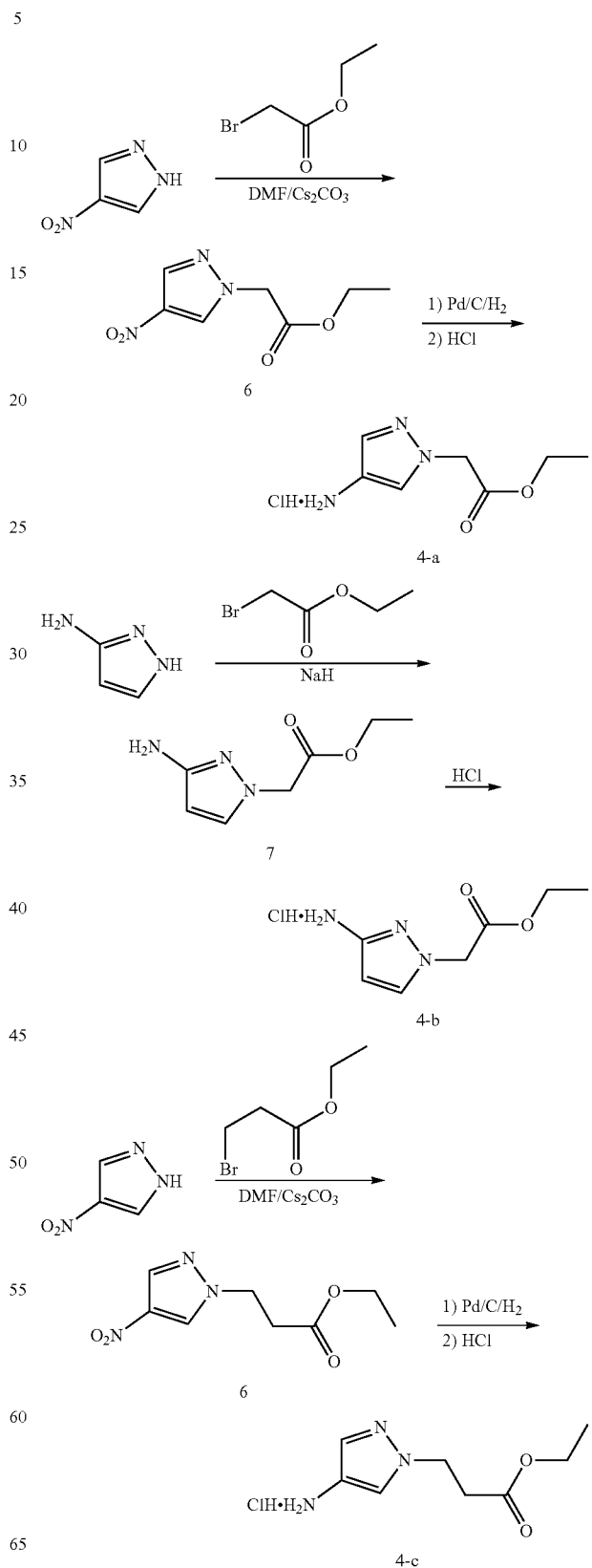

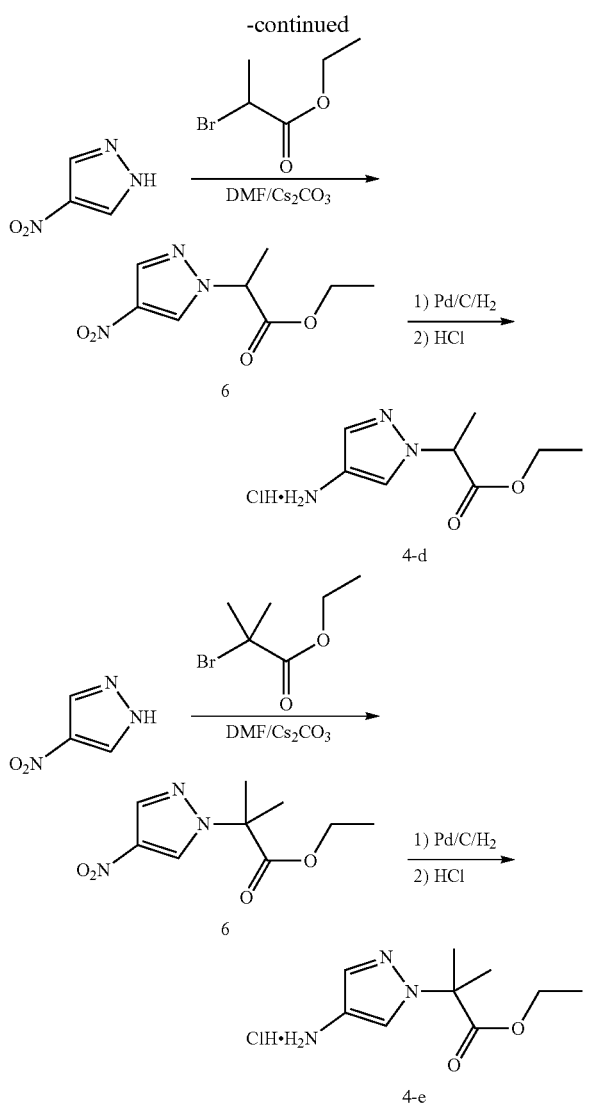

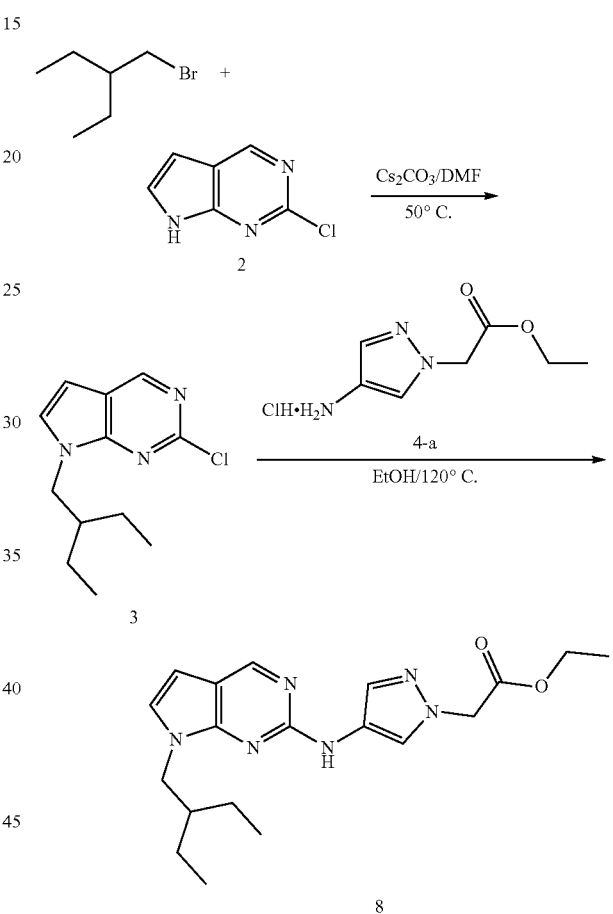

added dropwise at 0° C. The mixture was stirred at 0° C. for 30 mins. Bromoacetate (2.0 g, 1.0 eq) was added dropwise. The resulting mixture was stirred at 0° C. for 1 hr and then at room temperature overnight. The precipitate was removed by filtration, the filtrate was concentrated in vacuo to afford oil which was purified on ISCO silica gel column directly to afford 7 (0.28 g). 7 was treated with 2N HCl in ether to afford 4-b as an HCl salt.

Example 1: Synthesis of ethyl 2-(4-((7-(2-ethylbutyl)-7H-pyrrolo[2,3-d]pyrimidin-2-yl)amino)-1H-pyrazol-1-yl)acetate (8)

To a solution of 2-chloro-7H-pyrrolo[2,3-d]pyrimidine (2) (100 mg, 1.0 eq) in DMF (5 mL) was added Cs$_2$CO$_3$ (530 mg, 2.5 eq). The mixture was stirred at room temperature for 5 mins under N$_2$. 3-(bromomethyl)pentane (162 mg, 1.5 eq) was added to the reaction mixture. The resulting mixture was heated at 50° C. overnight. The reaction mixture was diluted with 30 mL ethyl acetate and 10 mL hexane, washed with 3×20 mL water and 30 mL brine. The crude mixture was purified on ISCO silica-gel column to afford 2-chloro-7-(2-ethylbutyl)-7H-pyrrolo[2,3-d]pyrimidine (3) (139 mg, yield 90%) as an oil.

2-chloro-7-(2-ethylbutyl)-7H-pyrrolo[2,3-d]pyrimidine (3) (100 mg, 1.0 eq) and 4-a (122 mg, 1.4 eq) were combined in dry EtOH (4 mL). The resulting mixture was heated at 120° C. in a sealed-tube for 28 hrs. The solvent was removed in vacuo, the residue was dissolved in 30 mL ethyl acetate and washed with saturated NaHCO$_3$. The crude mixture was Synthesis of 4-a To a solution of 4-nitropyrazole (1.13 g, 1.0 eq) in dry DMF (15 mL) was added Cs$_2$CO$_3$ (8.13 g, 2.5 eq). The mixture was stirred at RT for 30 mins under N$_2$, and then bromoacetate (2 g, 1.2 eq) was added into reaction. The resulting mixture was stirred at RT overnight. The reaction mixture was diluted with 50 mL ethyl acetate and 10 mL hexane. The inorganic was removed by filtration. The filtrate was washed with 3×30 mL water and brine. The crude was purified on ISCO silica gel to afford 6 (1.65 g, yield 83%) white solid.

To a solution of Intermediate 6 (1.65 g) in ethyl acetate (40 mL) was added Pd/C (10% Pd on Carbon, 165 mg). The mixture was hydrogenated at 30 psi for 2 hrs. The catalyst was removed by filtration. To the acetate solution was added 2N HCl in ether (10 mL), and stirred at RT for 5 mins. Removal solvent in vacuo gave 4-a as HCl salt.

4-c, 4-d, and 4-e were prepared in a similar manner as described for 4-a.

Synthesis of Intermediate 4-b

NaH (60% in mineral oil, 0.48 g, 1.0 eq) was suspended into dry THF (15 mL) at 0° C. under N$_2$. A solution of 3-aminopyrazole (1.0 g, 1.0 eq) in dry THF (5 mL) was purified on ISCO silica-gel column to afford ethyl 2-(4-((7-(2-ethylbutyl)-7H-pyrrolo[2,3-d]pyrimidin-2-yl)amino)-1H-pyrazol-1-yl)acetate (8) (75 mg, yield 48%). MS: 371.6 [M+H]$^+$.

Example 2: Synthesis of 2-(4-((7-(2-ethylbutyl)-7H-pyrrolo[2,3-d]pyrimidin-2-yl)amino)-1H-pyrazol-1-yl)acetic acid (9)

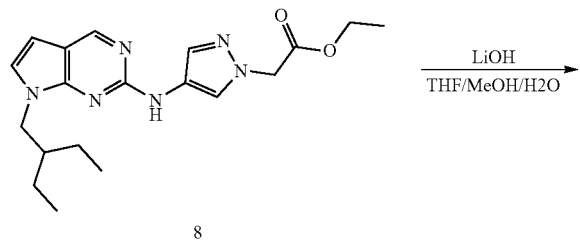

8

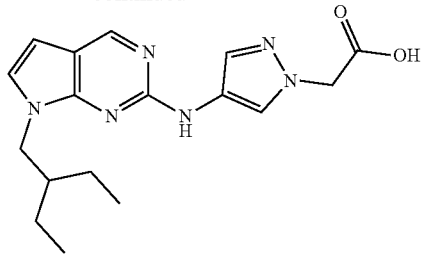

9

To a solution of 8 (20 mg, 1.0 eq) in THF (2 mL) and MeOH (2 mL) was added a solution of LiOH.H$_2$O (2.3 mg) in water (1.5 mL). The resulting mixture was stirred at room temperature overnight. The solvent was removed in vacuo. The residue was treated with 1N HCl to pH 5 to afford 2-(4-((7-(2-ethylbutyl)-7H-pyrrolo[2,3-d]pyrimidin-2-yl)amino)-1H-pyrazol-1-yl)acetic acid (9)(14 mg, yield 78%). MS: 343.1[M+H]$^+$.

Compounds 10-33 were prepared by similar procedures as described in Example 1 or Example 2.

| Compound | Structure | Name | MS [M + H]$^+$ |
|---|---|---|---|
| 10 | 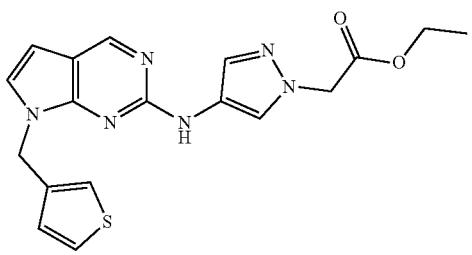 | ethyl 2-(4-((7-(thiophen-3-ylmethyl)-7H-pyrrolo[2,3-d]pyrimidin-2-yl)amino)-1H-pyrazol-1-yl)acetate | 383.3 |
| 11 | 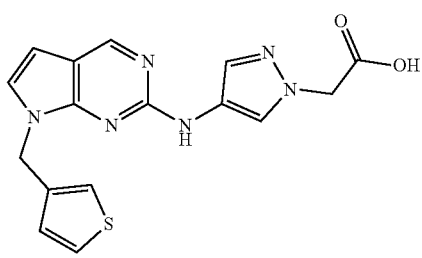 | 2-(4-((7-(thiophen-3-ylmethyl)-7H-pyrrolo[2,3-d]pyrimidin-2-yl)amino)-1H-pyrazol-1-yl)acetic acid | 355.4 |
| 12 | 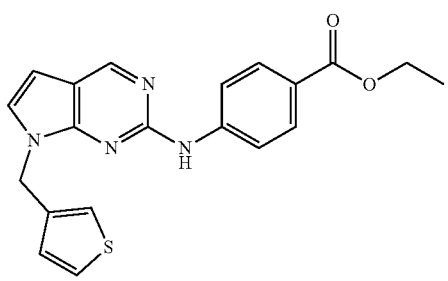 | ethyl 4-((7-(thiophen-3-ylmethyl)-7H-pyrrolo[2,3-d]pyrimidin-2-yl)amino)benzoate | 379 |

-continued

| Compound | Structure | Name | MS [M + H]+ |
|---|---|---|---|
| 13 | 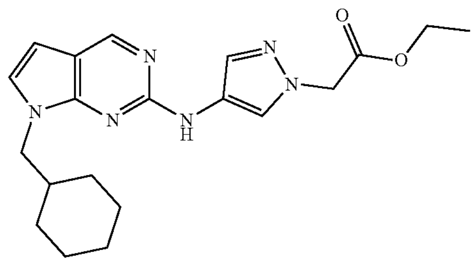 | ethyl 2-(4-((7-(cyclohexylmethyl)-7H-pyrrolo[2,3-d]pyrimidin-2-yl)amino)-1H-pyrazol-1-yl)acetate | 383.5 |
| 14 | 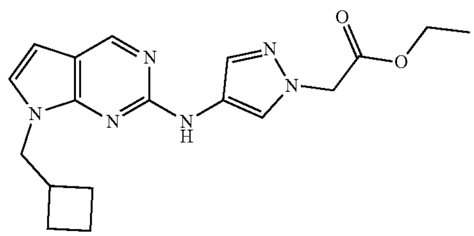 | ethyl 2-(4-((7-(cyclobutylmethyl)-7H-pyrrolo[2,3-d]pyrimidin-2-yl)amino)-1H-pyrazol-1-yl)acetate | 355.4 |
| 15 | 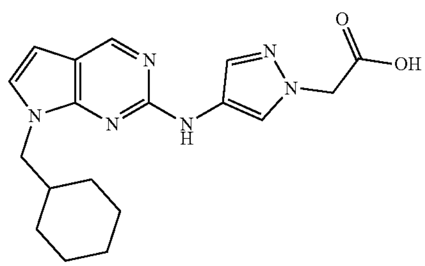 | 2-(4-((7-(cyclohexylmethyl)-7H-pyrrolo[2,3-d]pyrimidin-2-yl)amino)-1H-pyrazol-1-yl)acetic acid | 355.4 |
| 16 | 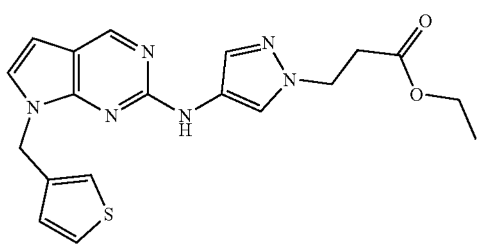 | ethyl 3-(4-((7-(thiophen-3-ylmethyl)-7H-pyrrolo[2,3-d]pyrimidin-2-yl)amino)-1H-pyrazol-1-yl)propanoate | 397.3 |
| 17 | 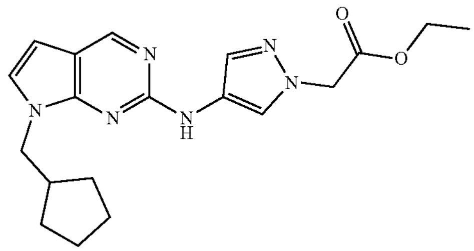 | ethyl 2-(4-((7-(cyclopentylmethyl)-7H-pyrrolo[2,3-d]pyrimidin-2-yl)amino)-1H-pyrazol-1-yl)acetate | 369.1 |

-continued

| Compound | Structure | Name | MS [M + H]+ |
|---|---|---|---|
| 18 | 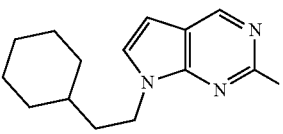 | ethyl 2-(4-((7-(2-cyclohexylethyl)-7H-pyrrolo[2,3-d]pyrimidin-2-yl)amino)-1H-pyrazol-1-yl)acetate | 397.4 |
| 19 | 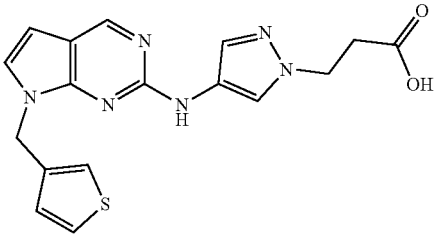 | 3-(4-((7-(thiophen-3-ylmethyl)-7H-pyrrolo[2,3-d]pyrimidin-2-yl)amino)-1H-pyrazol-1-yl)propanoic acid | 369.2 |
| 20 | 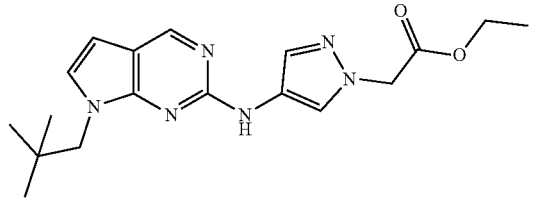 | ethyl 2-(4-((7-neopentyl-7H-pyrrolo[2,3-d]pyrimidin-2-yl)amino)-1H-pyrazol-1-yl)acetate | 357.5 |
| 21 | 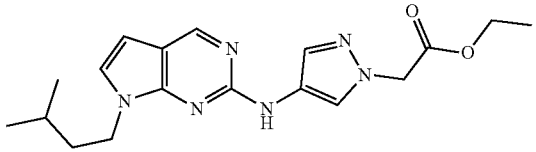 | ethyl 2-(4-((7-isopentyl-7H-pyrrolo[2,3-d]pyrimidin-2-yl)amino)-1H-pyrazol-1-yl)acetate | 357.4 |
| 22 | 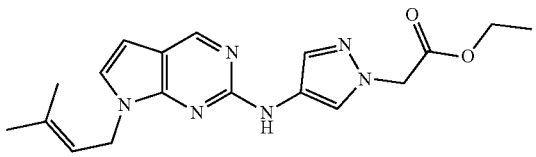 | ethyl 2-(4-((7-(3-methylbut-2-en-1-yl)-7H-pyrrolo[2,3-d]pyrimidin-2-yl)amino)-1H-pyrazol-1-yl)acetate | 355.3 |
| 23 | 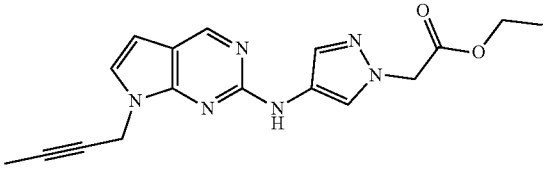 | ethyl 2-(4-((7-(but-2-yn-1-yl)-7H-pyrrolo[2,3-d]pyrimidin-2-yl)amino)-1H-pyrazol-1-yl)acetate | 339.5 |
| 24 | 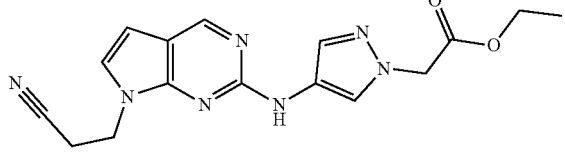 | ethyl 2-(4-((7-(2-cyanoethyl)-7H-pyrrolo[2,3-d]pyrimidin-2-yl)amino)-1H-pyrazol-1-yl)acetate | 340.6 |

| Compound | Name | MS [M + H]+ |
|---|---|---|
| 25 | ethyl 2-(4-((7-(cyclopropylmethyl)-7H-pyrrolo[2,3-d]pyrimidin-2-yl)amino)-1H-pyrazol-1-yl)acetate | 341.5 |
| 26 | ethyl 4-((7-(2-ethylbutyl)-7H-pyrrolo[2,3-d]pyrimidin-2-yl)amino)benzoate | 367.4 |
| 27 | ethyl 2-(4-((7-(2-ethylbutyl)-7H-pyrrolo[2,3-d]pyrimidin-2-yl)amino)-1H-pyrazol-1-yl)-2-methylpropanoate | 399.5 |
| 28 | ethyl 2-(4-((7-(2-ethylbutyl)-7H-pyrrolo[2,3-d]pyrimidin-2-yl)amino)-1H-pyrazol-1-yl)propanoate | 385.4 |
| 29 | 2-(4-((7-(2-ethyl-3-methylbutyl)-7H-pyrrolo[2,3-d]pyrimidin-2-yl)amino)-1H-pyrazol-1-yl)acetic acid | 357.4 |
| 30 | ethyl 3-(4-((7-(2-ethyl-3-methylbutyl)-7H-pyrrolo[2,3-d]pyrimidin-2-yl)amino)-1H-pyrazol-1-yl)propanoate | 399.2 |

| Compound | Structure | Name | MS [M + H]+ |
|---|---|---|---|
| 31 | 31 | 3-(4-((7-(2-ethyl-3-methylbutyl)-7H-pyrrolo[2,3-d]pyrimidin-2-yl)amino)-1H-pyrazol-1-yl)propanoic acid | 371.2 |

Example 3: Synthesis of ethyl 2-(4-((7-(((s,3s)-adamantan-1-yl)methyl)-7H-pyrrolo[2,3-d]pyrimidin-2-yl)amino)-1H-pyrazol-1-yl)acetate (34)

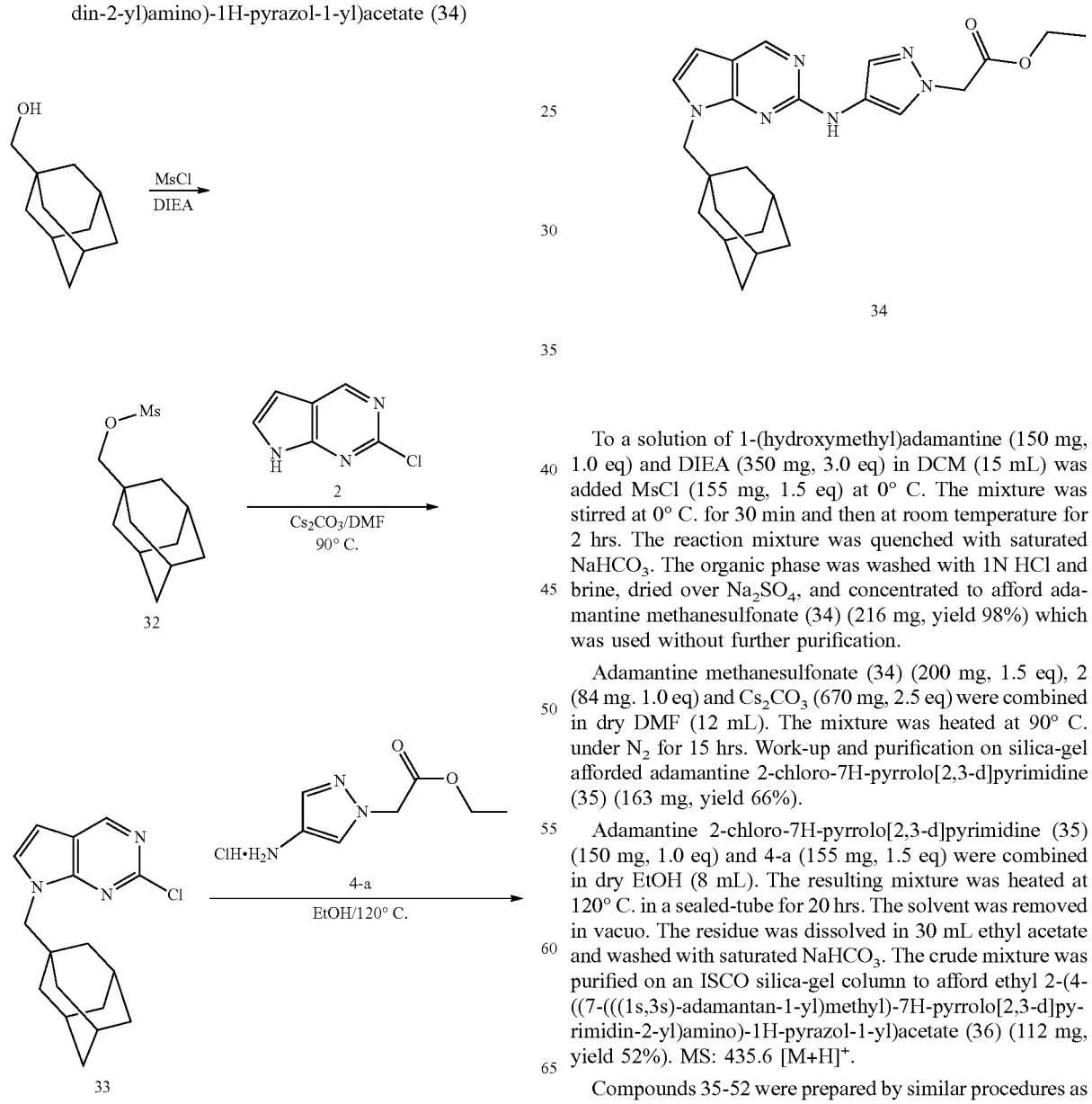

To a solution of 1-(hydroxymethyl)adamantine (150 mg, 1.0 eq) and DIEA (350 mg, 3.0 eq) in DCM (15 mL) was added MsCl (155 mg, 1.5 eq) at 0° C. The mixture was stirred at 0° C. for 30 min and then at room temperature for 2 hrs. The reaction mixture was quenched with saturated NaHCO₃. The organic phase was washed with 1N HCl and brine, dried over Na₂SO₄, and concentrated to afford adamantine methanesulfonate (34) (216 mg, yield 98%) which was used without further purification.

Adamantine methanesulfonate (34) (200 mg, 1.5 eq), 2 (84 mg. 1.0 eq) and Cs₂CO₃ (670 mg, 2.5 eq) were combined in dry DMF (12 mL). The mixture was heated at 90° C. under N₂ for 15 hrs. Work-up and purification on silica-gel afforded adamantine 2-chloro-7H-pyrrolo[2,3-d]pyrimidine (35) (163 mg, yield 66%).

Adamantine 2-chloro-7H-pyrrolo[2,3-d]pyrimidine (35) (150 mg, 1.0 eq) and 4-a (155 mg, 1.5 eq) were combined in dry EtOH (8 mL). The resulting mixture was heated at 120° C. in a sealed-tube for 20 hrs. The solvent was removed in vacuo. The residue was dissolved in 30 mL ethyl acetate and washed with saturated NaHCO₃. The crude mixture was purified on an ISCO silica-gel column to afford ethyl 2-(4-((7-(((1s,3s)-adamantan-1-yl)methyl)-7H-pyrrolo[2,3-d]pyrimidin-2-yl)amino)-1H-pyrazol-1-yl)acetate (36) (112 mg, yield 52%). MS: 435.6 [M+H]⁺.

Compounds 35-52 were prepared by similar procedures as described in Example 3 or Example 2.

| Compound | Structure | Name | MS [M + H]+ |
|---|---|---|---|
| 35 | 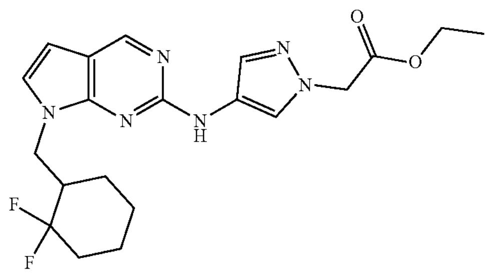 | ethyl 2-(4-((7-((2,2-difluorocyclohexyl)methyl)-7H-pyrrolo[2,3-d]pyrimidin-2-yl)amino)-1H-pyrazol-1-yl)acetate | 419.5 |
| 36 | 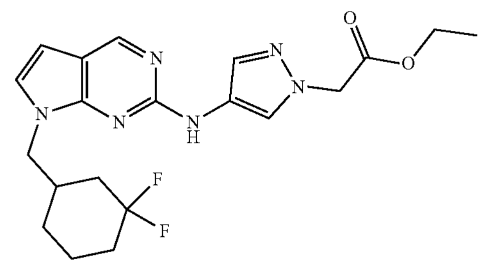 | ethyl 2-(4-((7-((3,3-difluorocyclohexyl)methyl)-7H-pyrrolo[2,3-d]pyrimidin-2-yl)amino)-1H-pyrazol-1-yl)acetate | 419.2 |
| 37 | 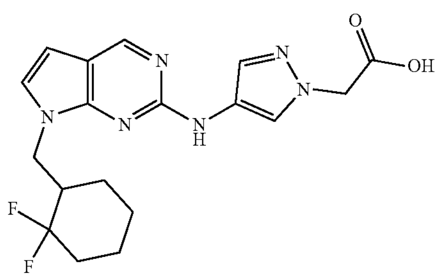 | 2-(4-((7-((2,2-difluorocyclohexyl)methyl)-7H-pyrrolo[2,3-d]pyrimidin-2-yl)amino)-1H-pyrazol-1-yl)acetic acid | 391.5 |
| 38 | 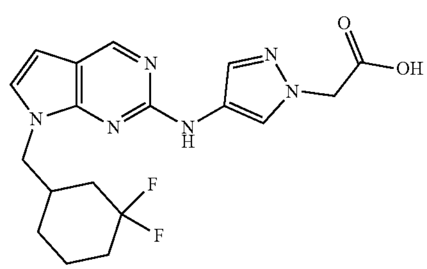 | 2-(4-((7-((3,3-difluorocyclohexyl)methyl)-7H-pyrrolo[2,3-d]pyrimidin-2-yl)amino)-1H-pyrazol-1-yl)acetic acid | 391 |
| 39 | 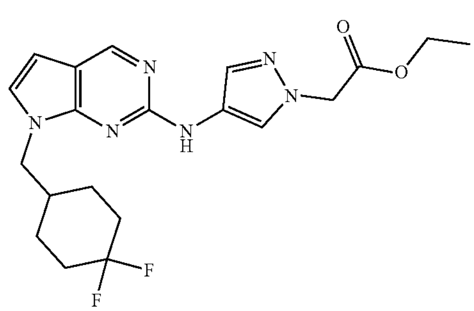 | ethyl 2-(4-((7-((4,4-difluorocyclohexyl)methyl)-7H-pyrrolo[2,3-d]pyrimidin-2-yl)amino)-1H-pyrazol-1-yl)acetate | 419.6 |

| Compound | Structure | Name | MS [M + H]+ |
|---|---|---|---|
| 40 | 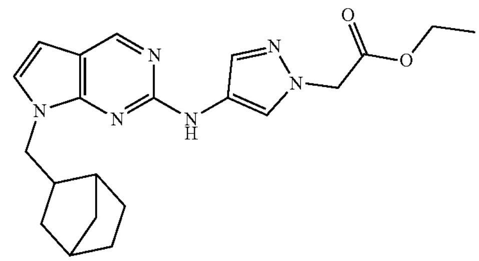 | ethyl 2-(4-((7-(bicyclo[2.2.1]heptan-2-ylmethyl)-7H-pyrrolo[2,3-d]pyrimidin-2-yl)amino)-1H-pyrazol-1-yl)acetate | 395 |
| 41 | 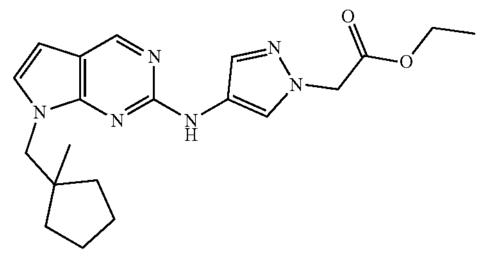 | ethyl 2-(4-((7-((1-methylcyclopentyl)methyl)-7H-pyrrolo[2,3-d]pyrimidin-2-yl)amino)-1H-pyrazol-1-yl)acetate | 383.4 |
| 42 | 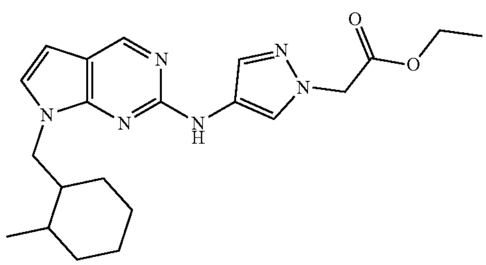 | ethyl 2-(4-((7-((2-methylcyclohexyl)methyl)-7H-pyrrolo[2,3-d]pyrimidin-2-yl)amino)-1H-pyrazol-1-yl)acetate | 397.5 |
| 43 | 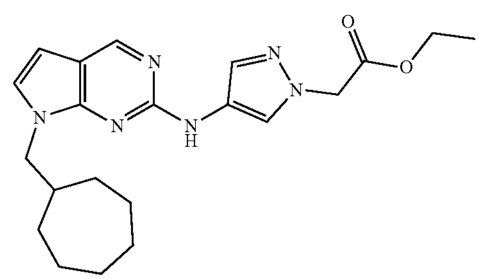 | ethyl 2-(4-((7-(cycloheptylmethyl)-7H-pyrrolo[2,3-d]pyrimidin-2-yl)amino)-1H-pyrazol-1-yl)acetate | 397.1 |
| 44 | 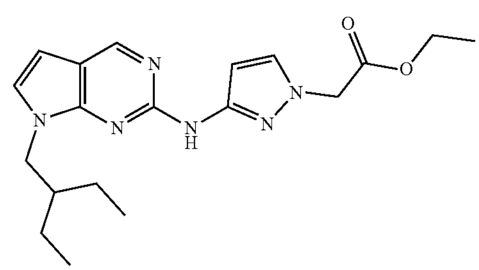 | ethyl 2-(3-((7-(2-ethylbutyl)-7H-pyrrolo[2,3-d]pyrimidin-2-yl)amino)-1H-pyrazol-1-yl)acetate | 371.5 |

-continued

| Compound | Structure | Name | MS [M + H]+ |
|---|---|---|---|
| 45 | 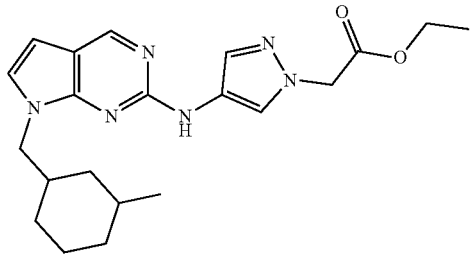 | ethyl 2-(4-((7-((3-methylcyclohexyl)methyl)-7H-pyrrolo[2,3-d]pyrimidin-2-yl)amino)-1H-pyrazol-1-yl)acetate | 397.4 |
| 46 | 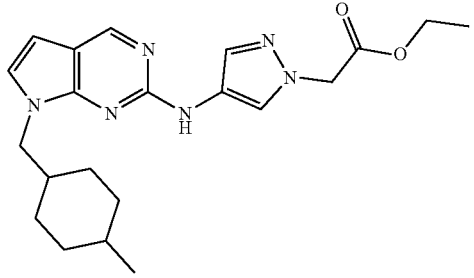 [SMILES: CCOC(=O)Cn1cc(Nc2ncc3ccn(CC4CCCCC4)c3n2)cn1 ; "13"] | ethyl 2-(4-((7-((4-methylcyclohexyl)methyl)-7H-pyrrolo[2,3-d]pyrimidin-2-yl)amino)-1H-pyrazol-1-yl)acetate | 397 |
| 47 | 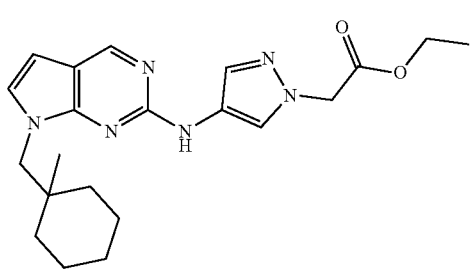 | ethyl 2-(4-((7-((1-methylcyclohexyl)methyl)-7H-pyrrolo[2,3-d]pyrimidin-2-yl)amino)-1H-pyrazol-1-yl)acetate | 397.2 |
| 48 | 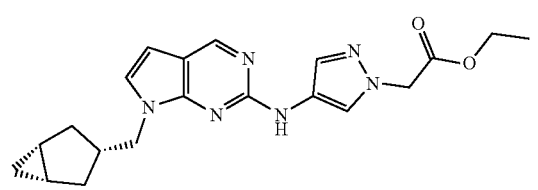 | ethyl 2-(4-((7-(((1R,3r,5S)-bicyclo[3.1.0]hexan-3-yl)methyl)-7H-pyrrolo[2,3-d]pyrimidin-2-yl)amino)-1H-pyrazol-1-yl)acetate | 381.5 |
| 49 | 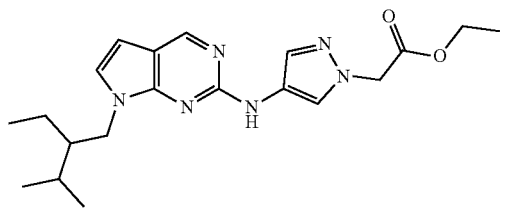 | ethyl 2-(4-((7-(2-ethyl-3-methylbutyl)-7H-pyrrolo[2,3-d]pyrimidin-2-yl)amino)-1H-pyrazol-1-yl)acetate | 385.4 |

| Compound | Structure | Name | MS [M + H]+ |
|---|---|---|---|
| 50 | 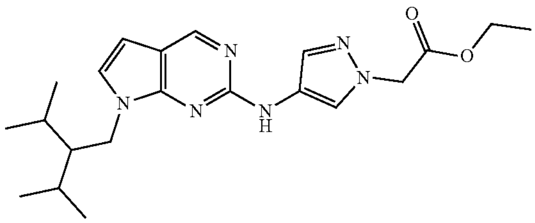 | ethyl 2-(4-((7-(2-isopropyl-3-methylbutyl)-7H-pyrrolo[2,3-d]pyrimidin-2-yl)amino)-1H-pyrazol-1-yl)acetate | 399.3 |
| 51 | 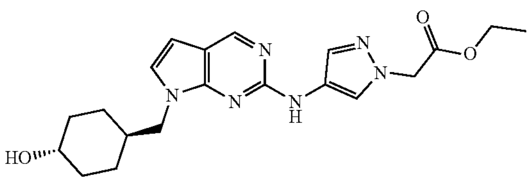 | ethyl 2-(4-((7-(((1r,4r)-4-hydroxycyclohexyl)methyl)-7H-pyrrolo[2,3-d]pyrimidin-2-yl)amino)-1H-pyrazol-1-yl)acetate | 399.4 |
| 52 | 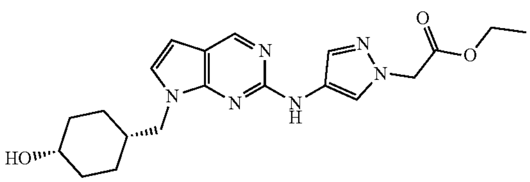 | ethyl 2-(4-((7-(((1s,4s)-4-hydroxycyclohexyl)methyl)-7H-pyrrolo[2,3-d]pyrimidin-2-yl)amino)-1H-pyrazol-1-yl)acetate | 399.1 |

Example 4: Synthesis of 7-(cyclohexylmethyl)-N-(1-methyl-1H-pyrazol-4-yl)-7H-pyrrolo[2,3-d]pyrimidin-2-amine (54)

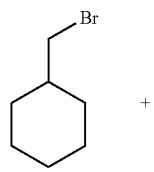

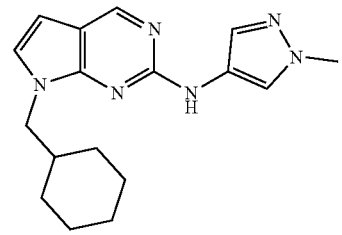

2 (60 mg, 1.0 eq), (bromomethyl)cyclohexane (104 mg, 1.5 eq) and Cs₂CO₃ (318 mg, 2.5 eq) were combined in dry DMF (10 mL). The mixture was heated at 50° C. under N₂ for 15 hrs. Work-up and purification on silica-gel afforded 2-chloro-7-(cyclohexylmethyl)-7H-pyrrolo[2,3-d]pyrimidine (53) (90 mg, yield 92%).

2-chloro-7-(cyclohexylmethyl)-7H-pyrrolo[2,3-d]pyrimidine (53) (90 mg, 1.0 eq) and 4 (72 mg, 1.5 eq) were combined in dry EtOH (5 mL). The resulting mixture was heated at 120° C. in a sealed-tube for 20 hrs. The solvent was removed in vacuo. The residue was dissolved in 30 mL ethyl acetate and washed with saturated NaHCO₃. The crude mixture was purified on ISCO silica-gel column to afford 7-(cyclohexylmethyl)-N-(1-methyl-H-pyrazol-4-yl)-7H-pyrrolo[2,3-d]pyrimidin-2-amine (54) (60 mg, yield 54%). MS: 311.5 [M+H]+.

Compounds 55-58 were prepared by similar procedures as described in Example 4.

| Compound | Structure | Name | MS [M + H]+ |
|---|---|---|---|
| 55 | 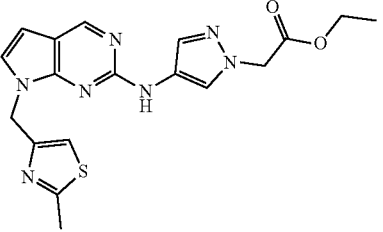 | ethyl 2-(4-((7-((2-methylthiazol-4-yl)methyl)-7H-pyrrolo[2,3-d]pyrimidin-2-yl)amino)-1H-pyrazol-1-yl)acetate | 398.4 |
| 56 | 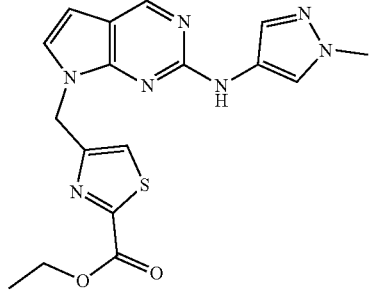 | ethyl 4-((2-((1-methyl-1H-pyrazol-4-yl)amino)-7H-pyrrolo[2,3-d]pyrimidin-7-yl)methyl)thiazole-2-carboxylate | 384.3 |
| 57 | 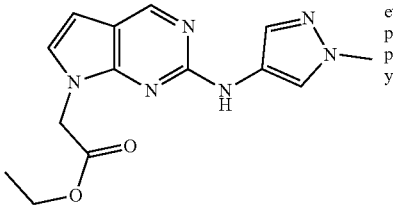 | ethyl 2-(2-((1-methyl-1H-pyrazol-4-yl)amino)-7H-pyrrolo[2,3-d]pyrimidin-7-yl)acetate | 301.3 |
| 58 | 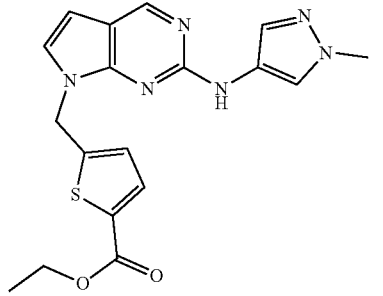 | ethyl 5-((2-((1-methyl-1H-pyrazol-4-yl)amino)-7H-pyrrolo[2,3-d]pyrimidin-7-yl)methyl)thiophene-2-carboxylate | 369.2 |

Example 5: Synthesis of ethyl 2-(4-((5-chloro-7-(cyclohexylmethyl)-7H-pyrrolo[2,3-d]pyrimidin-2-yl)amino)-1H-pyrazol-1-yl)acetate (60)

Example 6: Synthesis of ethyl 2-(4-((7-(2-(hydroxymethyl)butyl)-7H-pyrrolo[2,3-d]pyrimidin-2-yl)amino)-1H-pyrazol-1-yl)acetate (65)

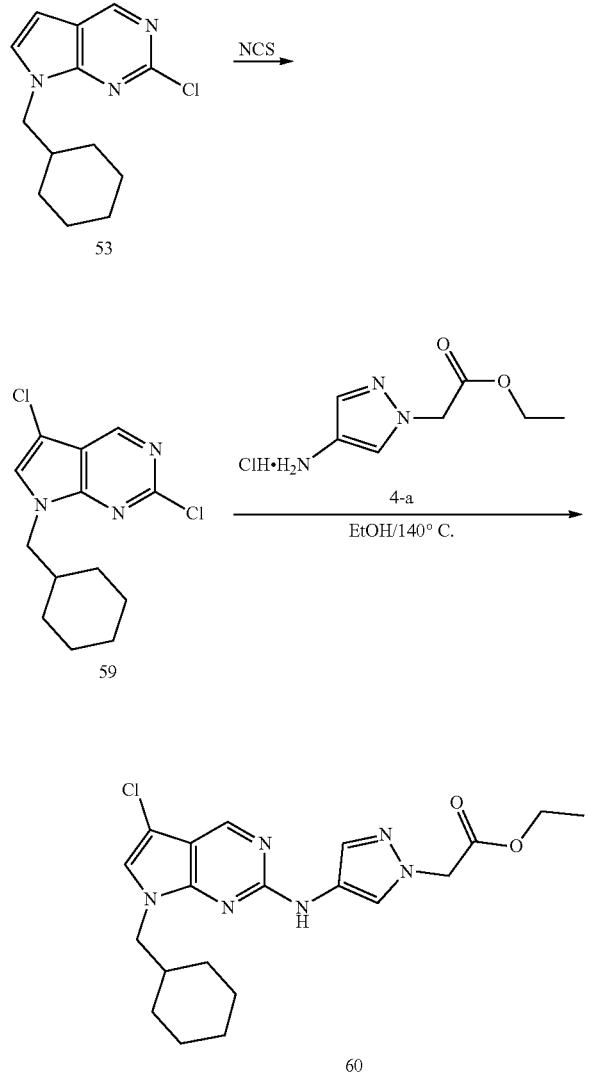

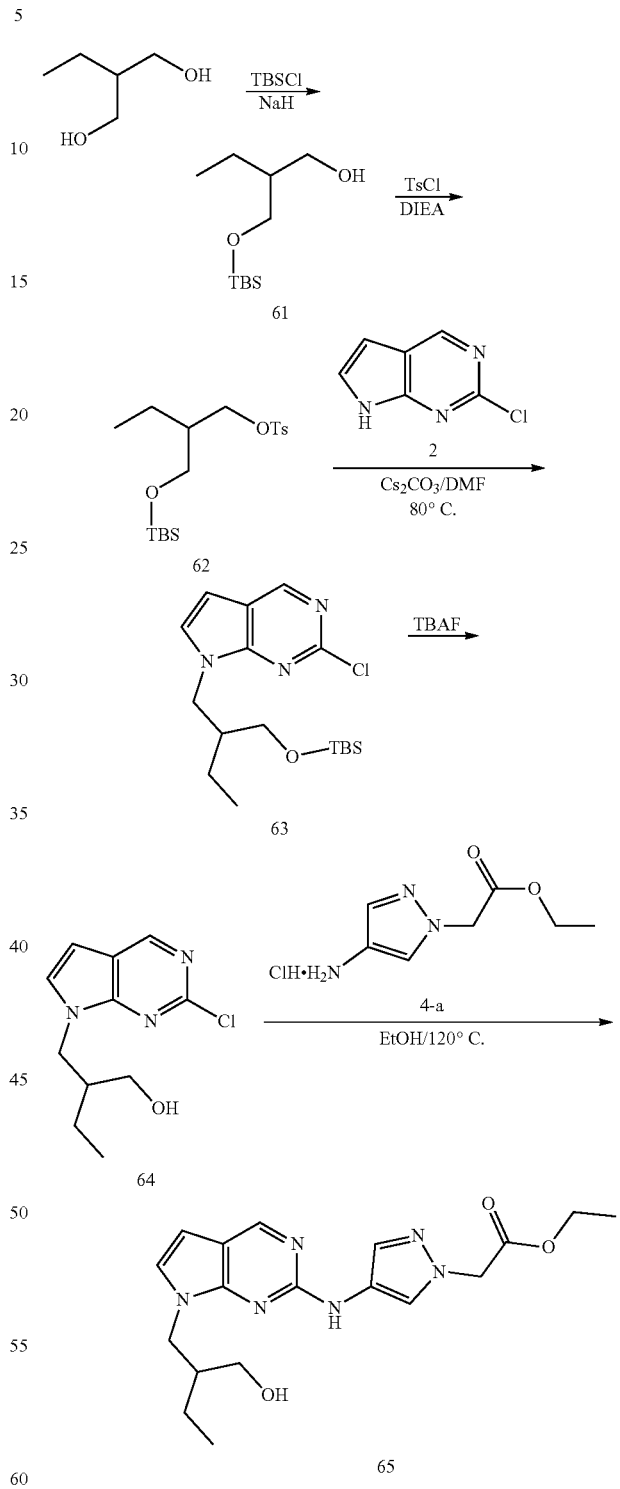

To a solution of 2-chloro-7-(cyclohexylmethyl)-7H-pyrrolo[2,3-d]pyrimidine (53) (100 mg, 1.0 eq) in dry THF (8 mL) was added N-chlorosuccinimide (64 mg, 1.2 eq) at 0° C. The resulting mixture was stirred at room temperature for 18 hrs. The crude mixture was purified on ISCO to afford 2,5-dichloro-7-(cyclohexylmethyl)-7H-pyrrolo[2,3-d]pyrimidine (59) (82 mg, yield 73%).

To 2,5-dichloro-7-(cyclohexylmethyl)-7H-pyrrolo[2,3-d]pyrimidine (59) (40 mg, 1.0 eq) and 4-a (43 mg, 1.5 eq) were combined in dry EtOH (3 mL). The resulting mixture was heated at 140° C. in microwave reactor for 2 hrs. The solvent was removed in vacuo. The residue was dissolved in 30 mL ethyl acetate and washed with saturated NaHCO$_3$. The crude mixture was purified on ISCO silica-gel column to afford ethyl 2-(4-((5-chloro-7-(cyclohexylmethyl)-7H-pyrrolo[2,3-d]pyrimidin-2-yl)amino)-1H-pyrazol-1-yl)acetate (60) (22 mg, yield 38%). MS: 417.1 [M+H]$^+$.

To a suspension solution of NaH (60%,170 mg, 1.0 eq) in dry THF (10 mL) was added 2-ethylpropane-1,3-diol (500 mg, 1.0 eq) in dry THF (10 mL) dropwise. The mixture was stirred at room temperature for 1 hr. To the reaction was added tert-butylchlorodimethylsilane (640 mg, 1.0 eq). The resulting mixture was stirred at room temperature overnight.

The solvent was removed in vacuo, the residue was purified on silica gel column to afford 2-(((tert-butyldimethylsilyl)oxy)methyl)butan-1-ol (61) (995 mg, yield 95%).

To a solution of 2-(((tert-butyldimethylsilyl)oxy)methyl)butan-1-ol (61) (500 mg, 1.0 eq) in DCM (15 mL) was added DIEA (3.0 eq) and then TsCl (660 mg, 1.5 eq). The mixture was stirred at room temperature overnight. The mixture was washed with 1N HCl and brine. The crude was purified on silica gel column to afford 2-(((tert-butyldimethylsilyl)oxy)methyl)butyl 4-methylbenzenesulfonate (62) (546 mg, yield 64%).

2-(((tert-butyldimethylsilyl)oxy)methyl)butyl 4-methylbenzenesulfonate (62) (200 mg, 1.5 eq), 2 (55 mg, 1.0 eq), and $Cs_2CO_3$ (300 mg, 2.5 eq) were combined in dry DMF (8 mL). The mixture was heated at 80° C. under $N_2$ for 15 hrs. Work-up and purification on silica-gel afforded 7-(2-(((tert-butyldimethylsilyl)oxy)methyl)butyl)-2-chloro-7H-pyrrolo[2,3-d]pyrimidine (63) (99 mg, yield 78%).

To a solution of 7-(2-(((tert-butyldimethylsilyl)oxy)methyl)butyl)-2-chloro-7H-pyrrolo[2,3-d]pyrimidine (63) (99 mg) in THF (5 mL) was added a solution of TABF (1N in THF, 2.8 mL, 10 eq). The mixture was stirred at room temperature for 3 hrs. The reaction was diluted with 30 mL ethyl acetate, washed with saturated $NH_4Cl$ and brine, and concentrated. The residue was purified on a silica gel column to provide 2-((2-chloro-7H-pyrrolo[2,3-d]pyrimidin-7-yl)methyl)butan-1-ol (64) (60 mg, yield 90%).

2-((2-chloro-7H-pyrrolo[2,3-d]pyrimidin-7-yl)methyl)butan-1-ol (64) (60 mg, 1.0 eq) and 4-a (73 mg, 1.4 eq) were combined in dry EtOH (3 mL). The resulting mixture was heated at 140° C. in a microwave reactor for 2 hrs. The solvent was removed in vacuo, the residue was dissolved in 30 mL ethyl acetate and washed with saturated $NaHCO_3$. The crude mixture was purified on ISCO silica gel column to afford ethyl 2-(4-((7-(2-(hydroxymethyl)butyl)-7H-pyrrolo[2,3-d]pyrimidin-2-yl)amino)-1H-pyrazol-1-yl)acetate (65) (57 mg, yield 61%). MS: 387.4 $[M+H]^+$.

Example 7: Synthesis of ethyl 2-(4-((7-(2-(cyanomethyl)butyl)-7H-pyrrolo[2,3-d]pyrimidin-2-yl)amino)-1H-pyrazol-1-yl)acetate (70)

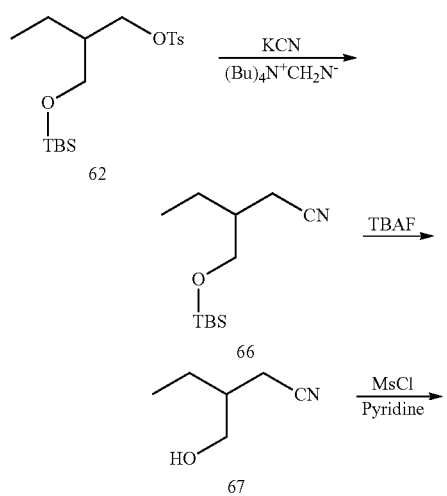

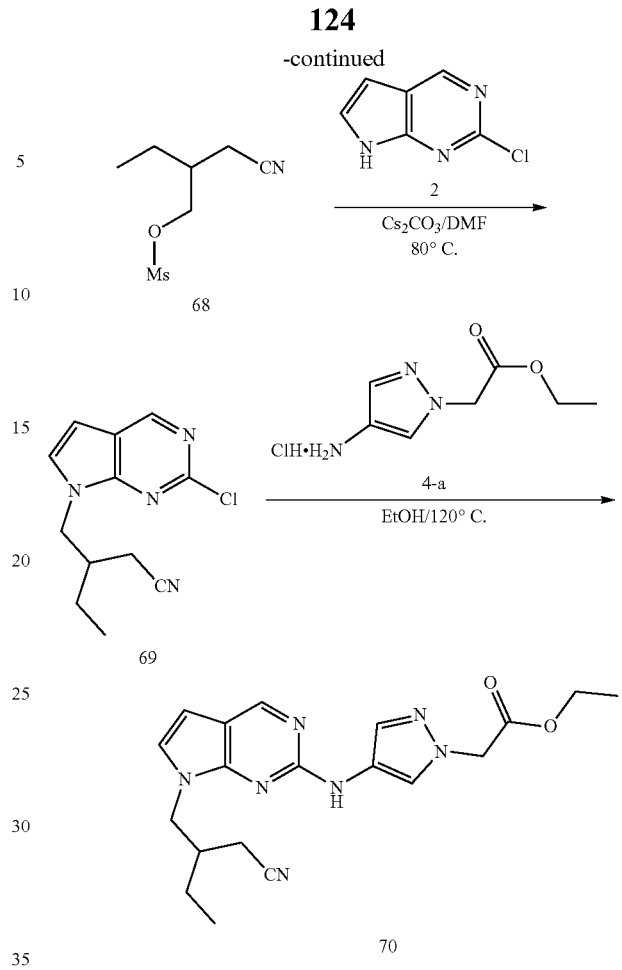

2-(((tert-butyldimethylsilyl)oxy)methyl)butyl 4-methylbenzenesulfonate (62) (500 mg, 1.0 eq), KCN (175 mg, 2.0 eq) and $(Bu)_4N^+CN^-$ (20 mg) were combined in dry $CH_3CN$ (30 mL). The resulting mixture was heated at 90° C. in a sealed-tube for 24 hrs. $CH_3CN$ was removed in vacuo and the residue was purified on silica-gel column directly to afford 3-(((tert-butyldimethylsilyl)oxy)methyl)pentanenitrile (66) (210 mg, yield 69%).

3-(((tert-butyldimethylsilyl)oxy)methyl)pentanenitrile (66) (210 mg) in THF (10 mL) was treated with 1N TABF (10 eq) at room temperature for 3 hrs. The crude mixture was purified on a silica gel column to afford 3-(hydroxymethyl)pentanenitrile (67) (74 mg, yield 70%).

To a solution of 3-(hydroxymethyl)pentanenitrile (67) (70 mg, 1.0 eq) in DCM (5 mL) was added DIEA (2.5 eq). The mixture was cooled in an ice-water bath. MsCl (1.5 eq) was added dropwise. The resulting mixture was stirred at 0° C. for hr. The reaction was quenched with 1N HCl. The crude mixture was purified on silica gel column to afford 2-(cyanomethyl)butyl methanesulfonate (68) (109 mg, yield 92%).

2-(cyanomethyl)butyl methanesulfonate (68) (108 mg, 1.2 eq), 2 (98 mg. 1.0 eq) and $Cs_2CO_3$ (390 mg, 2.5 eq) were combined in dry DMF (8 mL). The mixture was heated at 80° C. under $N_2$ for 15 hrs. Work-up and purification on silica gel afforded 3-((2-chloro-7H-pyrrolo[2,3-d]pyrimidin-7-yl)methyl)pentanenitrile (69) (87 mg, yield 74%).

3-((2-chloro-7H-pyrrolo[2,3-d]pyrimidin-7-yl)methyl)pentanenitrile (69) (70 mg, 1.0 eq) and 4-a (87 mg, 1.5 eq) were combined in dry EtOH (5 mL). The resulting mixture was heated at 140° C. in a microwave reactor for 2 hrs. The solvent was removed in vacuo. The residue was dissolved in ethyl acetate (30 mL) and washed with saturated NaHCO₃. The crude mixture was purified on ISCO silica-gel column to afford ethyl 2-(4-((7-(2-(cyanomethyl)butyl)-7H-pyrrolo [2,3-d]pyrimidin-2-yl)amino)-1H-pyrazol-1-yl)acetate (70) (71 mg, yield 66%).

Example 8: Synthesis of 3-(4-((7-((S)-2-ethyl-3-methylbutyl)-7H-pyrrolo[2,3-d]pyrimidin-2-yl) amino)-1H-pyrazol-1-yl)dihydrofuran-2(3H)-one (82), (R)-3-(4-((7-((S)-2-ethyl-3-methylbutyl)-7H-pyrrolo[2,3-d]pyrimidin-2-yl)amino)-1H-pyrazol-1-yl)dihydrofuran-2(3H)-one (82a) and (S)-3-(4-((7-((S)-2-ethyl-3-methylbutyl)-7H-pyrrolo[2,3-d] pyrimidin-2-yl)amino)-1H-pyrazol-1-yl)dihydrofuran-2(3H)-one (82b)

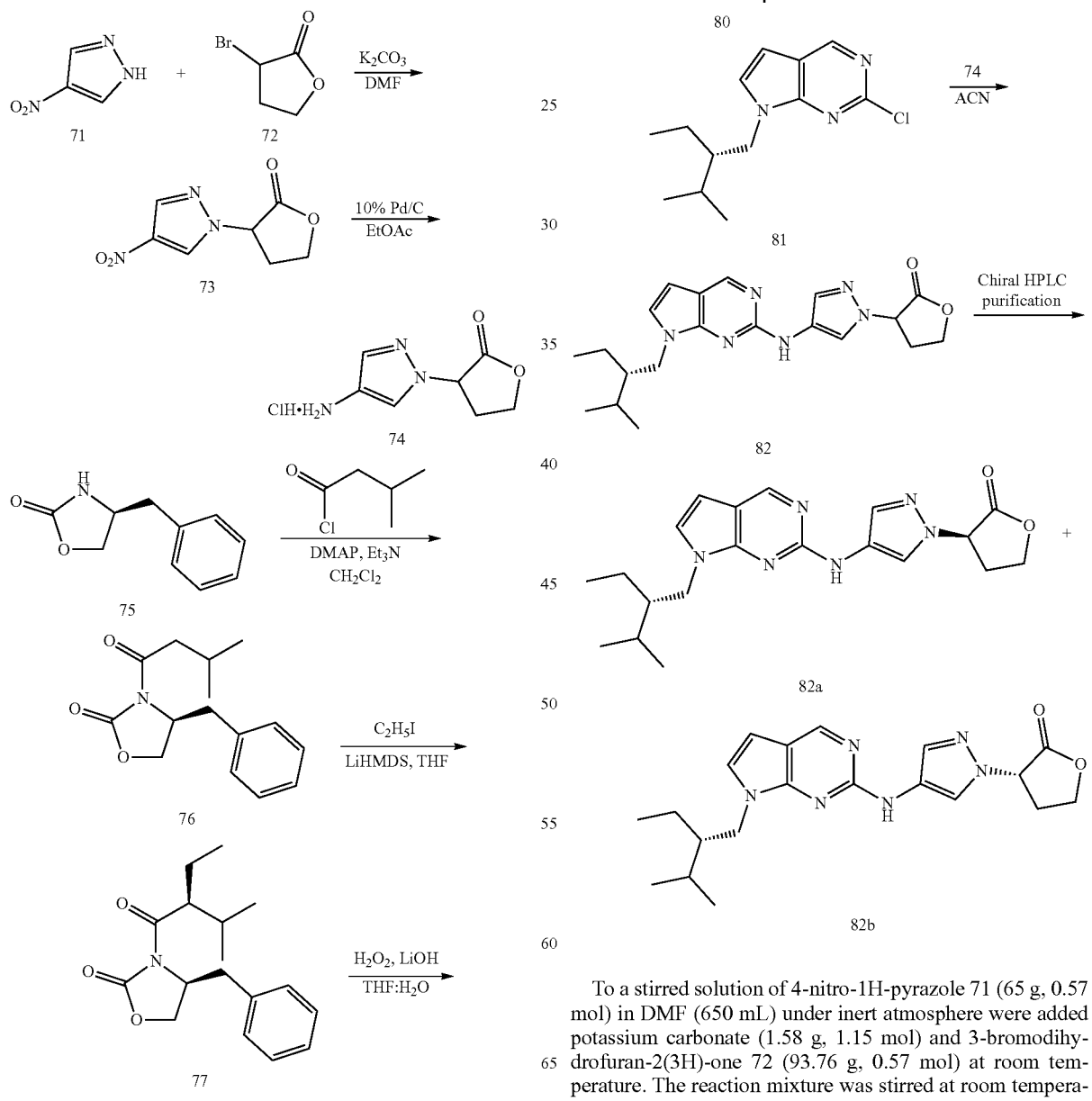

To a stirred solution of 4-nitro-1H-pyrazole 71 (65 g, 0.57 mol) in DMF (650 mL) under inert atmosphere were added potassium carbonate (1.58 g, 1.15 mol) and 3-bromodihydrofuran-2(3H)-one 72 (93.76 g, 0.57 mol) at room temperature. The reaction mixture was stirred at room temperature for 16 h. The reaction mixture was diluted with ethyl acetate (2 L) and n-hexane (650 mL). The reaction mixture was filtered and washed with EtOAc (800 mL). The organic extract was washed with water (3×1 L) and brine (1 L). The organic solution was dried over anhydrous Na$_2$SO$_4$, filtered, and concentrated under reduced pressure. The crude product was washed with 3% EtOAc/Hexane (500 mL) to obtain the solid. The solid was dried under vacuum to afford 3-(4-nitro-1H-pyrazol-1-yl) dihydrofuran-2 (3H)-one 73 (80 g, 70%) as an off white solid. $^1$H NMR (400 MHz, DMSO-d$_6$) δ 9.13 (s, 1H), 8.38 (s, 1H), 5.66 (t, J=9.7 Hz, 1H), 4.59-4.54 (m, 1H), 4.46-4.38 (m, 1H), 3.05-2.59 (m, 2H).

To a stirred solution of 3-(4-nitro-1H-pyrazol-1-yl) dihydrofuran-2 (3H)-one 73 (110 g, 558.37 mol) in EtOAc (1.1 L) under inert atmosphere was added 10% Pd/C (22 g, 50% wet) at room temperature. The reaction mixture was stirred at room temperature for 12 h under hydrogen atmosphere (55 psi). The reaction mixture was filtered through a Celite pad, washed with CH$_2$C$_{12}$ (2×100 mL), and concentrated under reduced pressure. To the above amine in CH$_2$Cl$_2$ (1.23 L) was added HCl (492 mL, 2.0N in Et$_2$O) at 0° C. The reaction mixture was stirred for 10 min and then hexane (1.64 L) was added. The mixture was stirred for 20 min. The precipitated solid was filtered and dried under high vacuum to afford 3-(4-amino-1H-pyrazol-1-yl) dihydrofuran-2 (3H)-one hydrochloride 74 (82 g) as a pale brown solid. $^1$H NMR (400 MHz, DMSO-d$_6$) δ 7.14 (s, 1H), 7.01 (s, 1H), 5.27 (t, J=9.5 Hz, 1H), 4.50-4.45 (m, 1H), 4.37-4.12 (m, 1H), 3.91 (brs, 2H), 2.68-2.58 (m, 2H).

To a stirred solution of (S)-4-benzyloxazolidin-2-one 75 (300 g, 1.69 mol) in CH$_2$Cl$_2$ (2.1 L) under inert atmosphere were added 4-dimethylaminopyridine (20.6 g, 0.16 mol), triethylamine (256.7 g, 2.54 mol) followed by solution of 3-methylbutanoyl chloride (224.4 g, 1.86 mol) in CH$_2$C$_{12}$ (900 mL) at 0° C. The reaction mixture was stirred at room temperature for 2 h. The reaction mixture was quenched with water (2 L) and extracted with CH$_2$Cl$_2$ (2×1 L). The combined organic extracts were washed with sat. sodium bicarbonate solution (1.0 L), water (1.0 L), 2.0N aq HCl solution (1 L), and brine (1 L). The organic solution was dried over anhydrous Na$_2$SO$_4$, filtered, and concentrated under reduced pressure. The residue was dissolved in n-hexane (1.5 L), cooled to 0° C., and stirred for 1 h to obtain a solid. The solid was filtered and dried under vacuum to afford (S)-4-benzyl-3-(3-methylbutanoyl) oxazolidin-2-one 76 (402 g, 1.54 mol, 91%) as an off-white solid. $^1$H NMR (500 MHz, DMSO-d$_6$) δ 7.37-7.16 (m, 5H), 4.74-4.57 (m, 1H), 4.32 (t, J=8.7 Hz, 1H), 4.17 (dd, J=8.7, 2.9 Hz, 1H), 3.06-2.98 (m, 1H), 2.96-2.89 (m, 1H), 2.82-2.73 (m, 1H), 2.69-2.58 (m, 1H), 2.13-2.07 (m, 1H), 0.98-0.92 (m, 6H).

To a stirred solution of LiHMDS (1.724 mL, 1.14 mol) in THF (2.1 L) under inert atmosphere was added (S)-4-benzyl-3-(3-methylbutanoyl) oxazolidin-2-one 76 (300 g, 1.14 mol) in THF (900 mL) portion wise over period of 20 min at −78° C. The mixture was stirred for 1.5 h. Ethyl iodide (712.6 g, 4.59 mol) was added at −78° C. The reaction mixture was stirred for 2 h at −78° C. and then stirred at about −5° C. for 4 h. The reaction mixture was warmed to room temperature and stirred for 16 h. The reaction mixture was diluted with sat. ammonium chloride solution (3 L) and extracted with EtOAc (2×1 L). The combined organic extracts were washed with 1.0M aq HCl solution (500 mL) and saturated sodium bicarbonate solution (500 mL). The organic solution was dried over anhydrous Na$_2$SO$_4$, filtered, and concentrated under reduced pressure. The crude product was purified by silica gel flash column chromatography (eluent: 2% EtOAc/Hexane) to afford (S)-4-benzyl-3-((S)-2-ethyl-3-methylbutanoyl) oxazolidin-2-one 77 (120 g, 36%) as a colorless oil. $^1$H NMR (500 MHz, DMSO-d$_6$) δ 7.34-7.18 (m, 5H), 4.72-4.68 (m, 1H), 4.30 (t, J=8.4 Hz, 1H), 4.15 (dd, J=8.7, 2.7 Hz, 1H), 3.54-3.50 (m, 1H), 3.05 (dd, J=13.4, 3.4 Hz, 1H), 2.91-2.86 (m, 1H), 1.98-1.72 (m, 1H), 1.69-1.51 (m, 2H), 0.89-0.79 (m, 9H).

To a stirred solution of (S)-4-benzyl-3-((S)-2-ethyl-3-methylbutanoyl) oxazolidin-2-one 77 (98 g, 0.33 mol) in THF (1.5 L) and water (400 mL) under inert atmosphere were added 30% aq H$_2$O$_2$ (225 mL) and lithium hydroxide monohydrate (28 g, 0.67 mol) in 200 mL of water at 0° C. The reaction mixture was stirred at room temperature for 5 h. The reaction mixture was quenched with 2.0M aq Na$_2$SO$_3$ solution (800 mL) at 0° C. and volatiles were evaporated under reduced pressure. The residue was basified with 2.0M aq NaOH solution to pH~12-13 and extracted with EtOAc (2×500 mL). The combined organic extracts were dried over anhydrous Na$_2$SO$_4$, filtered, and concentrated under reduced pressure to obtain (S)-2-ethyl-3-methylbutanoic acid 78 (44 g, crude) as a pale yellow solid. $^1$H NMR (400 MHz, CDCl$_3$) δ 11.23-10.31 (m, 1H), 2.12-2.00 (m, 1H), 1.93-1.78 (m, 1H), 1.68-1.55 (m, 2H), 0.99-0.90 (m, 9H).

To a stirred solution of (S)-2-ethyl-3-methylbutanoic acid 78 (44 g, 0.33 mol) in THF (1.5 L) under inert atmosphere was added lithium aluminium hydride (1.01 L, 1.01 mol, 1.0M in THF) at 0° C. The reaction mixture was stirred for 16 h. The reaction mixture was diluted with 2.0N aq HCl solution to pH~1 and extracted with CH$_2$Cl$_2$ (2×1 L). The combined organic extracts were dried over anhydrous Na$_2$SO$_4$, filtered, and concentrated under reduced pressure to afford (S)-2-ethyl-3-methylbutan-1-ol 79 (38 g, crude) as colorless syrup which was used in the next step without further purification. $^1$H NMR (500 MHz, CDCl$_3$) δ 3.66-3.54 (m, 2H), 1.88-1.76 (m, 1H), 1.47-1.37 (m, 1H), 1.32-1.20 (m, 3H), 0.94-0.88 (m, 9H).

To a stirred solution of (S)-2-ethyl-3-methylbutan-1-ol 79 (38 g, 0.32 mol) in CH$_2$Cl$_2$ (400 mL) under inert atmosphere were added diisopropyl ethyl amine (126.77 g, 0.98 mol) and methane sulfonyl chloride (56 g, 0.50 mol) at 0° C. The reaction mixture was stirred at room temperature for 2 h. The reaction mixture was quenched with 1.0N HCl solution (2×300 mL) and extracted with CH$_2$C$_{12}$ (2×1 L). The combined organic extracts were washed with saturated sodium bicarbonate solution (1 L), dried over anhydrous Na$_2$SO$_4$, filtered, and concentrated under reduced pressure to obtain (S)-2-ethyl-3-methylbutyl methanesulfonate 80 (63 g, crude) as a pale yellow syrup.

To a stirred solution of (S)-2-ethyl-3-methylbutyl methanesulfonate 80 (63 g, 0.32 mol) in DMF (1.3 L) under inert atmosphere were added cesium carbonate (263 g, 0.81 mol) and 2-chloro-7H-pyrrolo [2, 3-d] pyrimidine (49.68 g 0.32 mol) at room temperature. The reaction mixture was stirred at 50° C. for 16 h. The reaction mixture was diluted with water (500 mL) and extracted with EtOAc (2×500 mL). The combined organic extracts were washed with brine (200 mL), dried over anhydrous Na$_2$SO$_4$, filtered, and concentrated under reduced pressure. The crude product was purified by silica gel flash column chromatography (eluent: 10% EtOAc/Hexane) to afford (S)-2-chloro-7-(2-ethyl-3-methylbutyl)-7H-pyrrolo [2, 3-d] pyrimidine 81 (52 g, 64%) as a colorless oil. H NMR (400 MHz, CDCl$_3$) δ 8.77 (s, 1H), 7.19 (d, J=3.7 Hz, 1H), 6.56 (d, J=3.5 Hz, 1H), 4.24-4.07 (m, 2H), 1.82-1.71 (m, 1H), 1.44-1.28 (m, 1H), 1.44-1.27 (m, 1H), 1.23-1.13 (m, 1H), 0.96-0.92 (m, 6H), 0.87 (t, J=7.5 Hz, 3H).

To a stirred solution of (S)-2-chloro-7-(2-ethyl-3-methylbutyl)-7H-pyrrolo [2, 3-d]pyrimidine 81 (10 g, 39.84 mmol) in acetonitrile (100 mL) under inert atmosphere were added 3-(4-amino-1H-pyrazol-1-yl) dihydrofuran-2 (3H)-one hydrochloride 74 (12.13 g, 59.76 mmol) and sodium iodide (593 mg, 3.98 mmol) at room temperature. The reaction mixture was heated to 130° C. and stirred for 18 h in a sealed tube. The reaction mixture was cooled to room temperature and volatiles were evaporated under reduced pressure. The residue was diluted with saturated sodium bicarbonate solution (100 mL) and extracted with EtOAc (2×100 mL). The combined organic extracts were washed with brine (100 mL), dried over anhydrous $Na_2SO_4$, filtered, and concentrated under reduced pressure. The residue was purified by silica gel flash column chromatography (eluent: 60% EtOH/Hexanes) to afford 3-(4-((7-((S)-2-ethyl-3-methylbutyl)-7H-pyrrolo [2, 3-d] pyrimidin-2-yl) amino)-1H-pyrazol-1-yl) dihydrofuran-2(3H)-one 82 (6.0 g, 40%) as an off-white solid. $^1$H NMR (400 MHz, DMSO-$d_6$) δ 9.24 (s, 1H), 8.61 (s, 1H), 8.10 (s, 1H), 7.71 (s, 1H), 7.18 (d, J=3.5 Hz, 1H), 6.40 (d, J=3.5 Hz, 1H), 5.45 (t, J=9.5 Hz, 1H), 4.55-4.50 (m, 1H), 4.43-4.30 (m, 1H), 4.16-3.99 (m, 2H), 2.78-2.67 (m, 2H), 1.83-1.79 (m, 1H), 1.65-1.60 (m, 1H), 1.35-1.22 (m, 1H), 1.21-1.06 (m, 1H), 0.90 (t, J=7.2 Hz, 6H), 0.82 (t, J=7.4 Hz, 3H); LCMS: 383.3 (M+H)$^+$.

Chiral HPLC purification of 40 g of 82 afforded 15 g of 82a and 15 g of 82b. 82a: $^1$H NMR (400 MHz, DMSO-$d_6$) δ 9.24 (s, 1H), 8.61 (s, 1H), 8.10 (s, 1H), 7.71 (s, 1H), 7.18 (d, J=3.5 Hz, 1H), 6.40 (d, J=3.5 Hz, 1H), 5.45 (t, J=9.5 Hz, 1H), 4.55-4.50 (m, 1H), 4.43-4.30 (m, 1H), 4.16-3.99 (m, 2H), 2.78-2.67 (m, 2H), 1.83-1.79 (m, 1H), 1.65-1.60 (m, 1H), 1.35-1.22 (m, 1H), 1.21-1.06 (m, 1H), 0.90 (t, J=7.2 Hz, 6H), 0.82 (t, J=7.4 Hz, 3H); LCMS: 383.3 (M+H)$^+$; chiral HPLC (purity): 100% (column; Chiralpak IC-3 (150×4.6 mm, 3.5 m); RT 16.49 min; mobile Phase: n-heptane; EtOAc; MTBE (60:35:5); flow rate: 0.7 mL/min). 82b: $^1$H NM/R (400 MHz, DMSO-$d_6$) δ9.24 (s, 1H), 8.61 (s, 1H), 8.10 (s, 1H), 7.71 (s, 1H), 7.18 (d, J=3.5 Hz, 1H), 6.40 (d, J=3.5 Hz, 1H), 5.45 (t, J=9.5 Hz, 1H), 4.55-4.50 (m, 1H), 4.43-4.30 (m, 1H), 4.16-3.99 (m, 2H), 2.78-2.67 (m, 2H), 1.83-1.79 (m, 1H), 1.65-1.60 (m, 1H), 1.35-1.22 (m, 1H), 1.21-1.06 (m, 1H), 0.90 (t, J=7.2 Hz, 6H), 0.82 (t, J=7.4 Hz, 3H); LCMS: 383.3 (M+H)$^+$; chiral HPLC (purity): 100%: (column; Chiralpak IC-3 (150×4.6 mm, 3.5 μm); RT 19.03 min; mobile Phase: n-heptane; EtOAc; MTBE (60:35:5); flow rate: 0.7 mL/min).

Compounds 83-147 were prepared by similar procedures as described in the preceding Examples.

| Compound | Structure | Name | MS [M + H]$^+$ |
|---|---|---|---|
| 83 | 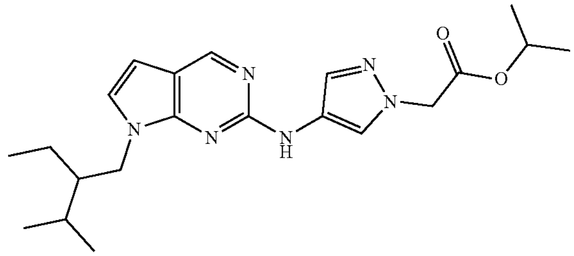 | isopropyl 2-(4-((7-(2-ethyl-3-methylbutyl)-7H-pyrrolo[2,3-d]pyrimidin-2-yl)amino)-1H-pyrazol-1-yl)acetate | 399.2 |
| 84 | 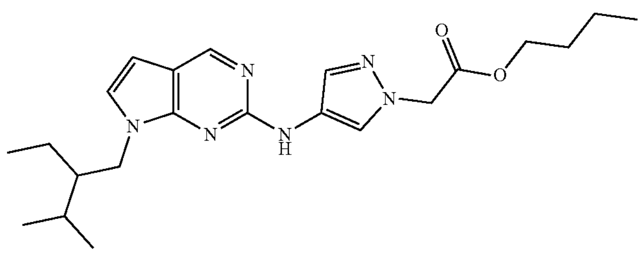 | butyl 2-(4-((7-(2-ethyl-3-methylbutyl)-7H-pyrrolo[2,3-d]pyrimidin-2-yl)amino)-1H-pyrazol-1-yl)acetate | 413.5 |
| 85 | 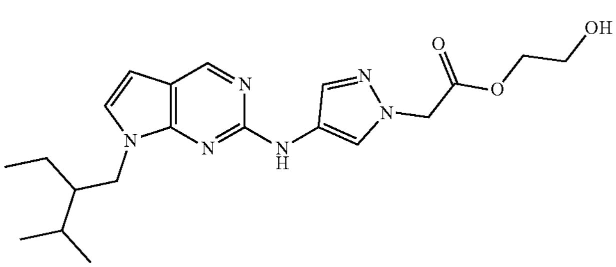 | 2-hydroxyethyl 2-(4-((7-(2-ethyl-3-methylbutyl)-7H-pyrrolo[2,3-d]pyrimidin-2-yl)amino)-1H-pyrazol-1-yl)acetate | 401.2 |

-continued

| Compound | Structure | Name | MS [M + H]+ |
|---|---|---|---|
| 86 | 86 | 2-ethoxyethyl 2-(4-((7-(2-ethyl-3-methylbutyl)-7H-pyrrolo[2,3-d]pyrimidin-2-yl)amino)-1H-pyrazol-1-yl)acetate | 429.1 |
| 87 | 87 | 2-(4-((7-(2-isopropyl-3-methylbutyl)-7H-pyrrolo[2,3-d]pyrimidin-2-yl)amino)-1H-pyrazol-1-yl)acetic acid | 371.2 |
| 88 | 88 | 2-hydroxyethyl 2-(4-((7-(2-isopropyl-3-methylbutyl)-7H-pyrrolo[2,3-d]pyrimidin-2-yl)amino)-1H-pyrazol-1-yl)acetate | 415.2 |
| 89 | 89 | 2-cyanoethyl 2-(4-((7-(2-ethylbutyl)-7H-pyrrolo[2,3-d]pyrimidin-2-yl)amino)-1H-pyrazol-1-yl)acetate | 396.3 |
| 90 | 90 | 2-hydroxyethyl 2-(4-((7-(2-ethylbutyl)-7H-pyrrolo[2,3-d]pyrimidin-2-yl)amino)-1H-pyrazol-1-yl)acetate | 387.3 |

-continued

| Compound | Structure | Name | MS [M + H]+ |
|---|---|---|---|
| 91 | 91 | 3-cyanocyclobutyl 2-(4-((7-(2-ethylbutyl)-7H-pyrrolo[2,3-d]pyrimidin-2-yl)amino)-1H-pyrazol-1-yl)acetate | 422.1 |
| 92 | 92 | 2-cyanoethyl 2-(4-((7-(2-ethyl-3-methylbutyl)-7H-pyrrolo[2,3-d]pyrimidin-2-yl)amino)-1H-pyrazol-1-yl)acetate | 410.3 |
| 93 | 93 | isopropyl 2-(4-((7-(2-ethylbutyl)-7H-pyrrolo[2,3-d]pyrimidin-2-yl)amino)-1H-pyrazol-1-yl)acetate | 385.2 |
| 94 | 94 | isopropyl 2-(4-((7-(2-isopropyl-3-methylbutyl)-7H-pyrrolo[2,3-d]pyrimidin-2-yl)amino)-1H-pyrazol-1-yl)acetate | 413.2 |

-continued

| Compound | Structure | Name | MS [M + H]+ |
|---|---|---|---|
| 95 | 95 | ethyl 2-(4-((7-(3-acrylamidobenzyl)-7H-pyrrolo[2,3-d]pyrimidin-2-yl)amino)-1H-pyrazol-1-yl)acetate | 446.5 |
| 96 | 96 | isopropyl (S)-2-(4-((7-(4-(dimethylamino)-2-isopropylbutyl)-7H-pyrrolo[2,3-d]pyrimidin-2-yl)amino)-1H-pyrazol-1-yl)acetate | 442.3 |
| 97 | 97 | isopropyl (S)-2-(4-((7-(4-hydroxy-2-isopropylbutyl)-7H-pyrrolo[2,3-d]pyrimidin-2-yl)amino)-1H-pyrazol-1-yl)acetate | 415.1 |
| 98 | 98 | isopropyl (S)-2-(4-((7-(4-chloro-2-isopropylbutyl)-7H-pyrrolo[2,3-d]pyrimidin-2-yl)amino)-1H-pyrazol-1-yl)acetate | 433.3 |

-continued

| Compound | Structure | Name | MS [M + H]+ |
|---|---|---|---|
| 99 | 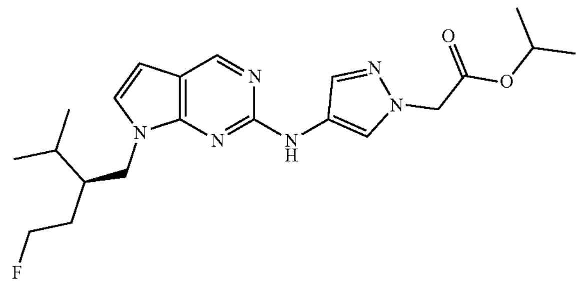 | isopropyl (S)-2-(4-((7-(4-fluoro-2-isopropylbutyl)-7H-pyrrolo[2,3-d]pyrimidin-2-yl)amino)-1H-pyrazol-1-yl)acetate | 417.1 |
| 100 | 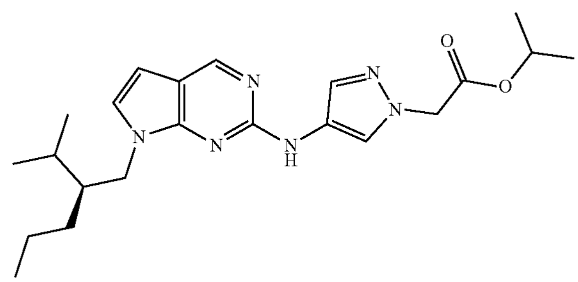 | isopropyl (S)-2-(4-((7-(2-isopropylpentyl)-7H-pyrrolo[2,3-d]pyrimidin-2-yl)amino)-1H-pyrazol-1-yl)acetate | 413.2 |
| 101 | 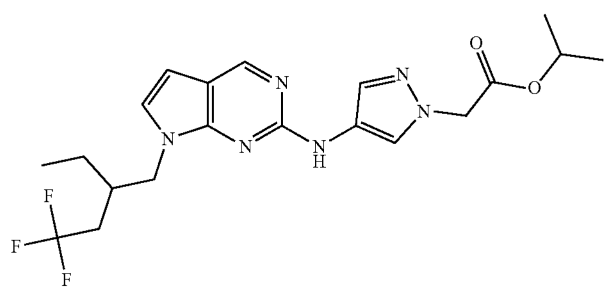 | isopropyl 2-(4-((7-(2-ethyl-4,4,4-trifluorobutyl)-7H-pyrrolo[2,3-d]pyrimidin-2-yl)amino)-1H-pyrazol-1-yl)acetate | 439.3 |
| 102 | 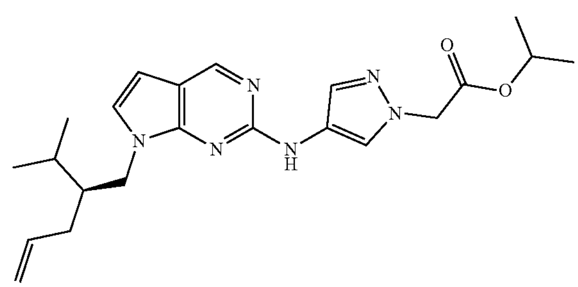 | isopropyl (S)-2-(4-((7-(2-isopropylpent-4-en-1-yl)-7H-pyrrolo[2,3-d]pyrimidin-2-yl)amino)-1H-pyrazol-1-yl)acetate | 411.2 |
| 103 | 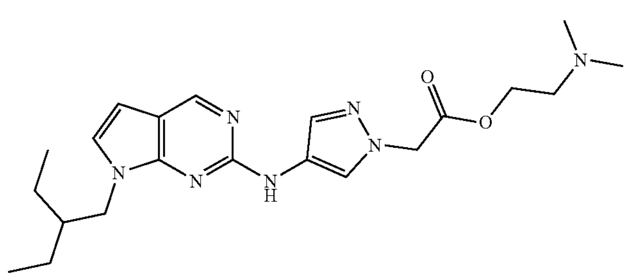 | 2-(dimethylamino)ethyl 2-(4-((7-(2-ethylbutyl)-7H-pyrrolo[2,3-d]pyrimidin-2-yl)amino)-1H-pyrazol-1-yl)acetate | 414.5 |

-continued

| Compound | Structure | Name | MS [M + H]+ |
|---|---|---|---|
| 104 | 104 | (S)-2-(4-((7-(2-ethyl-3-methylbutyl)-7H-pyrrolo[2,3-d]pyrimidin-2-yl)amino)-1H-pyrazol-1-yl)acetic acid | 357.1 |
| 105 | 105 | (S)-1-hydroxypropan-2-yl 2-(4-((7-(2-ethyl-3-methylbutyl)-7H-pyrrolo[2,3-d]pyrimidin-2-yl)amino)-1H-pyrazol-1-yl)acetate | 415.1 |
| 106 | 106 | (R)-1-hydroxypropan-2-yl 2-(4-((7-(2-ethyl-3-methylbutyl)-7H-pyrrolo[2,3-d]pyrimidin-2-yl)amino)-1H-pyrazol-1-yl)acetate | 415.1 |
| 107 | 107 | sec-butyl 2-(4-((7-(2-ethyl-3-methylbutyl)-7H-pyrrolo[2,3-d]pyrimidin-2-yl)amino)-1H-pyrazol-1-yl)acetate | 413.0 |
| 108 | 108 | isobutyl 2-(4-((7-(2-ethyl-3-methylbutyl)-7H-pyrrolo[2,3-d]pyrimidin-2-yl)amino)-1H-pyrazol-1-yl)acetate | 413.3 |

-continued

| Compound | Structure | Name | MS [M + H]+ |
|---|---|---|---|
| 109 | 109 | 3-hydroxybutan-2-yl 2-(4-((7-(2-ethyl-3-methylbutyl)-7H-pyrrolo[2,3-d]pyrimidin-2-yl)amino)-1H-pyrazol-1-yl)acetate | 429.1 |
| 110 | 110 | (R)-2-hydroxypropyl 2-(4-((7-(2-ethyl-3-methylbutyl)-7H-pyrrolo[2,3-d]pyrimidin-2-yl)amino)-1H-pyrazol-1-yl)acetate | 415.2 |
| 111 | 111 | 2,3-dihydroxypropyl 2-(4-((7-(2-ethyl-3-methylbutyl)-7H-pyrrolo[2,3-d]pyrimidin-2-yl)amino)-1H-pyrazol-1-yl)acetate | 431.2 |
| 112 | 112 | (S)-2-hydroxypropyl 2-(4-((7-(2-ethyl-3-methylbutyl)-7H-pyrrolo[2,3-d]pyrimidin-2-yl)amino)-1H-pyrazol-1-yl)acetate | 415.2 |
| 113 | 113 | 3-hydroxybutan-2-yl 2-(4-((7-(2-ethylbutyl)-7H-pyrrolo[2,3-d]pyrimidin-2-yl)amino)-1H-pyrazol-1-yl)acetate | 415.1 |

-continued

| Compound | Structure | Name | MS [M + H]+ |
|---|---|---|---|
| 114 | 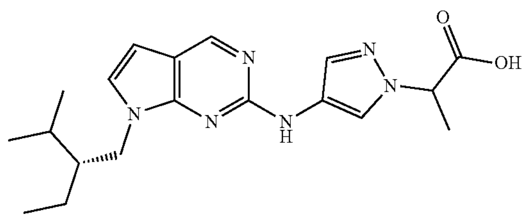 | 2-(4-((7-((R)-2-ethyl-3-methylbutyl)-7H-pyrrolo[2,3-d]pyrimidin-2-yl)amino)-1H-pyrazol-1-yl)propanoic acid | 371.0 |
| 115 | 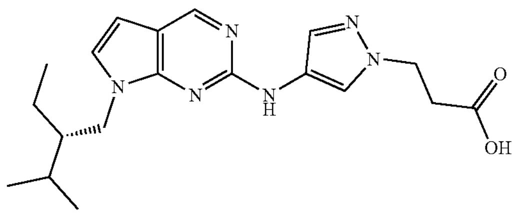 | (S)-3-(4-((7-(2-ethyl-3-methylbutyl)-7H-pyrrolo[2,3-d]pyrimidin-2-yl)amino)-1H-pyrazol-1-yl)propanoic acid | 371.2 |
| 116 | 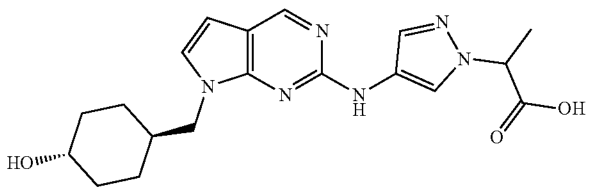 | 2-(4-((7-(((1r,4r)-4-hydroxycyclohexyl)methyl)-7H-pyrrolo[2,3-d]pyrimidin-2-yl)amino)-1H-pyrazol-1-yl)propanoic acid | 385.2 |
| 117 | 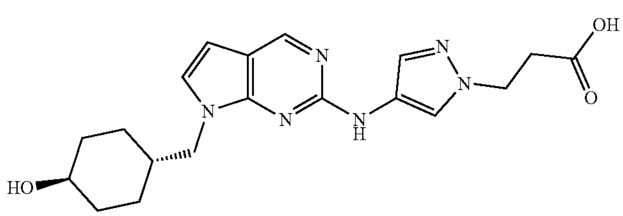 | 3-(4-((7-(((1r,4r)-4-hydroxycyclohexyl)methyl)-7H-pyrrolo[2,3-d]pyrimidin-2-yl)amino)-1H-pyrazol-1-yl)propanoic acid | 385.2 |
| 118 | 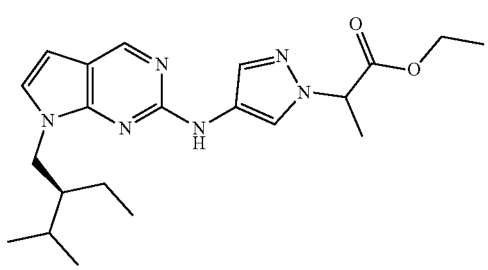 | ethyl 2-(4-((7-((S)-2-ethyl-3-methylbutyl)-7H-pyrrolo[2,3-d]pyrimidin-2-yl)amino)-1H-pyrazol-1-yl)propanoate | 399.0 |

-continued

| Compound | Structure | Name | MS [M + H]+ |
|---|---|---|---|
| 119 | 119 | ethyl (S)-3-(4-((7-(2-ethyl-3-methylbutyl)-7H-pyrrolo[2,3-d]pyrimidin-2-yl)amino)-1H-pyrazol-1-yl)propanoate | 399.0 |
| 120 | 120 | ethyl 2-(4-((7-(((1r,4r)-4-hydroxycyclohexyl)methyl)-7H-pyrrolo[2,3-d]pyrimidin-2-yl)amino)-1H-pyrazol-1-yl)propanoate | 413.6 |
| 121 | 121 | ethyl 3-(4-((7-(((1r,4r)-4-hydroxycyclohexyl)methyl)-7H-pyrrolo[2,3-d]pyrimidin-2-yl)amino)-1H-pyrazol-1-yl)propanoate | 413.1 |
| 122 | 122 | isopropyl 2-(4-((7-(((1r,4r)-4-hydroxycyclohexyl)methyl)-7H-pyrrolo[2,3-d]pyrimidin-2-yl)amino)-1H-pyrazol-1-yl)acetate | 413.0 |
| 123 | 123 | ethyl 2-(4-((7-(((1r,4r)-4-(methylamino)cyclohexyl)methyl)-7H-pyrrolo[2,3-d]pyrimidin-2-yl)amino)-1H-pyrazol-1-yl(acetate | 412.3 |

-continued

| Compound | Structure | Name | MS [M + H]+ |
|---|---|---|---|
| 124 | 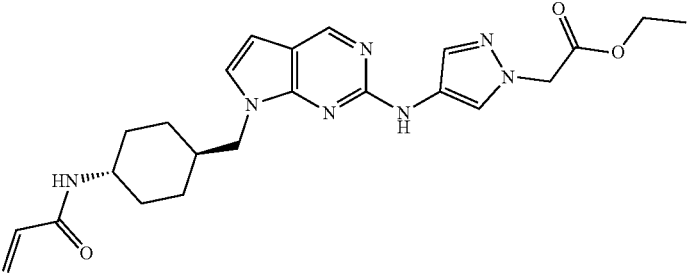 | ethyl 2-(4-((7-(((1r,4r)-4-acrylamidocyclohexyl)methyl)-7H-pyrrolo[2,3-d]pyrimidin-2-yl)amino)-1H-pyrazol-1-yl)acetate | 452.0 |
| 125 | 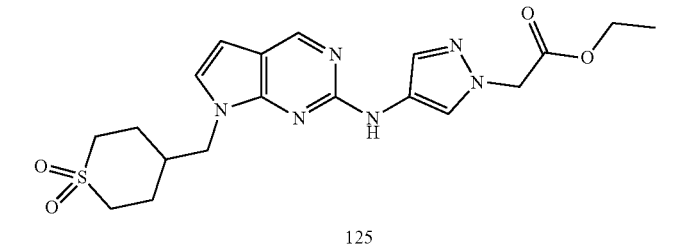 [SMILES: CCOC(=O)Cn1cc(Nc2ncc3ccn(CC4CCS(=O)(=O)CC4)c3n2)cn1] | ethyl 2-(4-((7-((1,1-dioxidotetrahydro-2H-thiopyran-4-yl)methyl)-7H-pyrrolo[2,3-d]pyrimidin-2-yl)amino)-1H-pyrazol-1-yl)acetate | 433.3 |
| 126 | 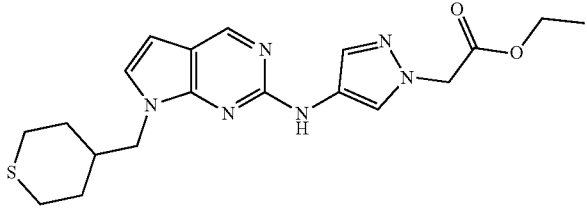 | ethyl 2-(4-((7-((tetrahydro-2H-thiopyran-4-yl)methyl)-7H-pyrrolo[2,3-d]pyrimidin-2-yl)amino)-1H-pyrazol-1-yl)acetate | 401.3 |
| 127 | 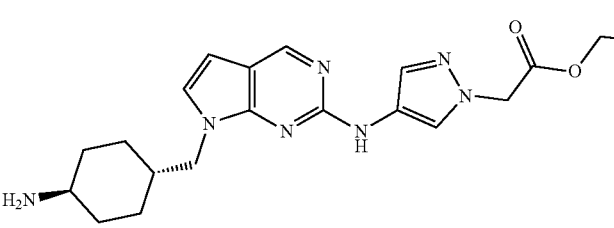 | ethyl 2-(4-((7-(((1r,4r)-4-aminocyclohexyl)methyl)-7H-pyrrolo[2,3-d]pyrimidin-2-yl)amino)-1H-pyrazol-1-yl)acetate | 398.3 |
| 128 | 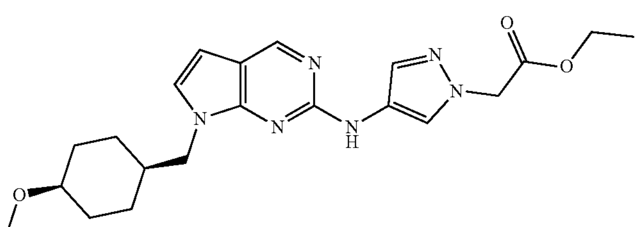 | ethyl 2-(4-((7-(((1s,4s)-4-methoxycyclohexyl)methyl)-7H-pyrrolo[2,3-d]pyrimidin-2-yl)amino)-1H-pyrazol-1-yl)acetate | 413.4 |

-continued

| Compound | Structure | Name | MS [M + H]+ |
|---|---|---|---|
| 129 | 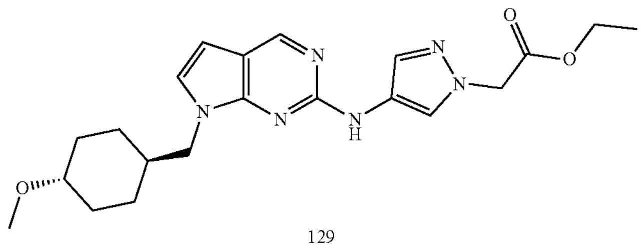 [SMILES: CCOC(=O)Cn1cc(Nc2ncc3ccn(C[C@H]4CC[C@H](OC)CC4)c3n2)cn1] | ethyl 2-(4-((7-(((1r,4r)-4-methoxycyclohexyl)methyl)-7H-pyrrolo[2,3-d]pyrimidin-2-yl)amino)-1H-pyrazol-1-yl)acetate | 413.1 |
| 130 | 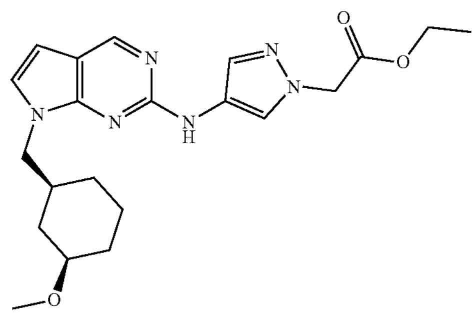 | ethyl 2-(4-((7-(((1S,3R)-3-methoxycyclohexyl)methyl)-7H-pyrrolo[2,3-d]pyrimidin-2-yl)amino)-1H-pyrazol-1-yl)acetate | 413.0 |
| 131 | 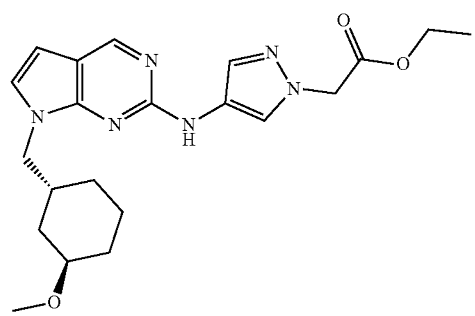 | ethyl 2-(4-((7-(((1R,3R)-3-methoxycyclohexyl)methyl)-7H-pyrrolo[2,3-d]pyrimidin-2-yl)amino)-1H-pyrazol-1-yl)acetate | 413.5 |
| 132 | 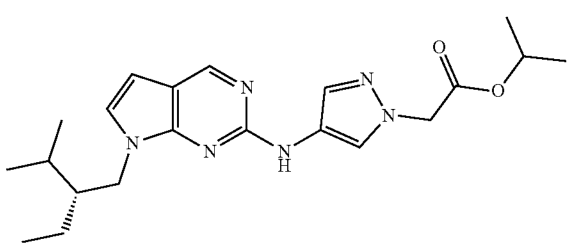 | isopropyl (R)-2-(4-((7-(2-ethyl-3-methylbutyl)-7H-pyrrolo[2,3-d]pyrimidin-2-yl)amino)-1H-pyrazol-1-yl)acetate | 399.0 |
| 133 | 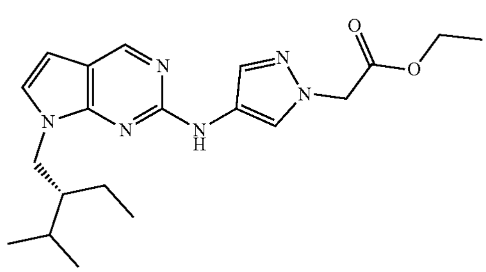 | ethyl (R)-2-(4-((7-(2-ethyl-3-methylbutyl)-7H-pyrrolo[2,3-d]pyrimidin-2-yl)amino)-1H-pyrazol-1-yl)acetate | 385.1 |

-continued

| Compound | Structure | Name | MS [M + H]+ |
|---|---|---|---|
| 134 | 134 | isopropyl (S)-2-(4-((7-(2-ethyl-3-methylbutyl)-7H-pyrrolo[2,3-d]pyrimidin-2-yl)amino)-1H-pyrazol-1-yl)acetate | 399.1 |
| 135 | 135 | ethyl (S)-2-(4-((7-(2-ethyl-3-methylbutyl)-7H-pyrrolo[2,3-d]pyrimidin-2-yl)amino)-1H-pyrazol-1-yl)acetate | 385.0 |
| 136 | 136 | 2-(4-((7-((S)-2-ethyl-3-methylbutyl)-7H-pyrrolo[2,3-d]pyrimidin-2-yl)amino)-1H-pyrazol-1-yl)-4-hydroxybutanoic acid | 401.1 |
| 137 | 137 | tert-butyl 4-((7-(2-ethyl-3-methylbutyl)-7H-pyrrolo[2,3-d]pyrimidin-2-yl)amino)-1H-pyrazole-1-carboxylate | 399.4 |
| 138 | 138 | (S)-1-methylpyrrolidin-3-yl 2-(4-((7-((S)-2-ethyl-3-methylbutyl)-7H-pyrrolo[2,3-d]pyrimidin-2-yl)amino)-1H-pyrazol-1-yl)acetate | 440.3 |

-continued

| Compound | Structure | Name | MS [M + H]+ |
|---|---|---|---|
| 139 | 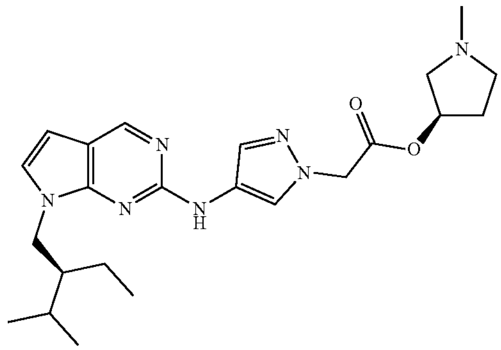 | (R)-1-methylpyrrolidin-3-yl 2-(4-((7-((S)-2-ethyl-3-methylbutyl)-7H-pyrrolo[2,3-d]pyrimidin-2-yl)amino)-1H-pyrazol-1-yl)acetate | 440.5 |
| 140 | 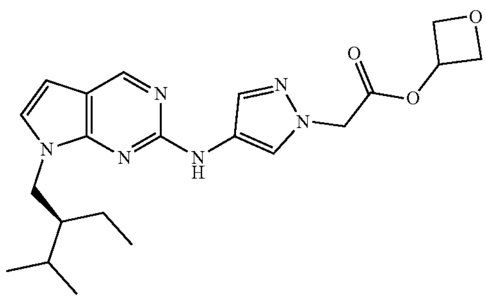 | oxetan-3-yl (S)-2-(4-((7-(2-ethyl-3-methylbutyl)-7H-pyrrolo[2,3-d]pyrimidin-2-yl)amino)-1H-pyrazol-1-yl)acetate | 413.4 |
| 141 | 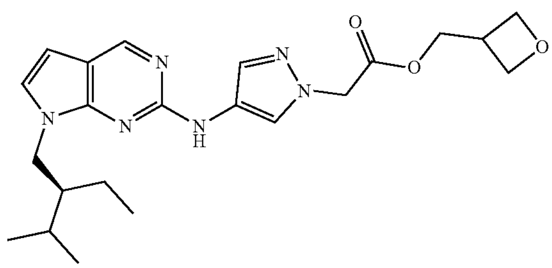 | oxetan-3-ylmethyl (S)-2-(4-((7-(2-ethyl-3-methylbutyl)-7H-pyrrolo[2,3-d]pyrimidin-2-yl)amino)-1H-pyrazol-1-yl)acetate | 427.4 |
| 142 | 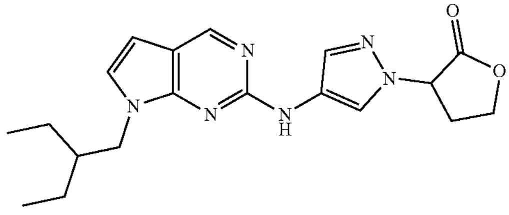 | 3-(4-((7-(2-ethylbutyl)-7H-pyrrolo[2,3-d]pyrimidin-2-yl)amino)-1H-pyrazol-1-yl)dihydrofuran-2(3H)-one | 369.3 |
| 143 | 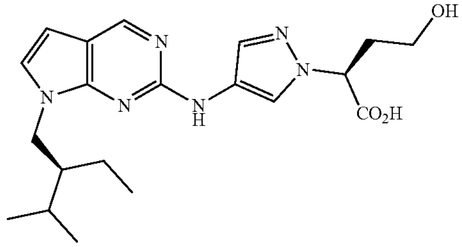 | (S)-2-(4-((7-((S)-2-ethyl-3-methylbutyl)-7H-pyrrolo[2,3-d]pyrimidin-2-yl)amino)-1H-pyrazol-1-yl)-4-hydroxybutanoic acid | 400.2 |

| Compound | Structure | Name | MS [M + H]+ |
|---|---|---|---|
| 144 | 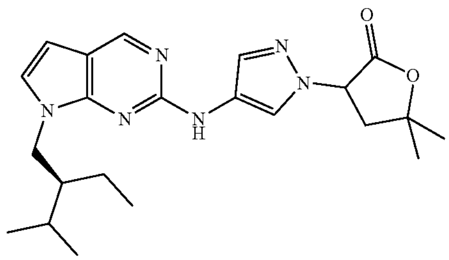 | 3-(4-((7-((S)-2-ethyl-3-methylbutyl)-7H-pyrrolo[2,3-d]pyrimidin-2-yl)amino)-1H-pyrazol-1-yl)-5,5-dimethyldihydrofuran-2(3H)-one | 411.1 |
| 145 | 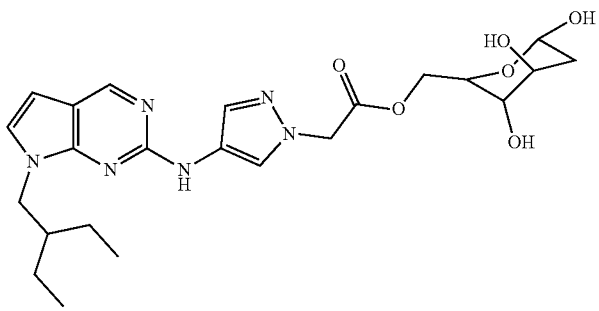 | ((3S,4R,6S)-3,4,6-trihydroxytetrahydro-2H-pyran-2-yl)methyl 2-(4-((7-92-ethylbutyl)-7H-pyrrolo[2,3-d]pyrimidin-2-yl)amino)-1H-pyrazol-1-yl)acetate | 488.2 |
| 146 | 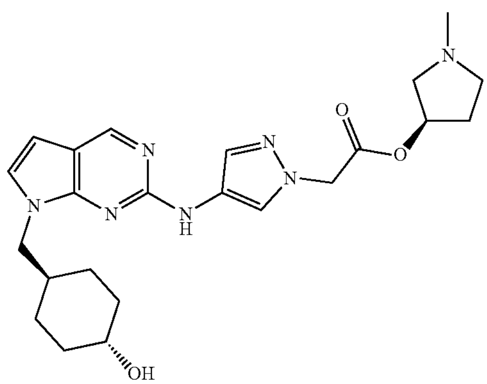 | (R)-1-methylpyrrolidin-3-yl 2-(4-((7-(((1r,4r)-4-hydroxycyclohexyl)methyl)-7H-pyrrolo[2,3-d]pyrimidin-2-yl)amino)-1H-pyrazol-1-yl)acetate | 454.3 |
| 147 | 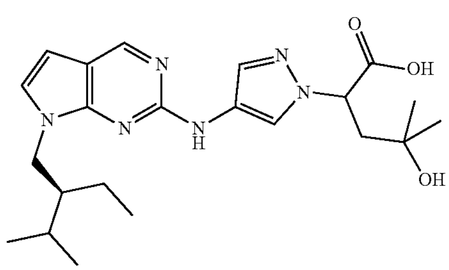 | 2-(4-((7-((S)-2-ethyl-3-methylbutyl)-7H-pyrrolo[2,3-d]pyrimidin-2-yl)amino)-1H-pyrazol-1-yl)-4-hydroxy-4-methylpentanoic acid | 429.1 |

Example 9: JAK/TYK2 Assay 10 mM test compound stock or 1 mM control compound stock (tofocitinib, ruxolitinib or staurosporine) in DMSO was diluted to 0.4 mM in DMSO. A 3-fold series dilution was then performed in DMSO to generate 10 different compound concentrations. The assay was carried out in 384-well white plate. 0.5 uL of 40× compound DMSO solution at different concentrations was mixed with 10 uL 2× enzyme prepared in reaction buffer (20 mM HEPES, 10 mM MgCl$_2$, 0.01% Tween, 1 mM DTT, pH 7.5). 10 uL 2× substrate mixture prepared in reaction buffer was then added to start the reaction. A short spin was done to settle down all solutions to the bottom of the plate. Final concentrations of test compound in the reaction mixture were 10000, 3333, 1111, 370, 123, 41.2, 13.7, 4.57, 1.52 and 0.51 nM. Concentrations of control compound were ten times less. Enzymatic reaction was conducted at 25° C. for 1-2 hours. 10 uL of Kinase Glo Reagents was added to stop the reaction and generate the luminescent signal which was measured using Envision. Luminescence signal was inversely related to kinase activity. Reaction mixture which did not contain enzyme served as negative control. The mixture without any compound was the positive control. Final concentration of enzymes and substrates and incubation time are summarized in the table below.

|  | [enz] | [ATP] | [sub] | time |
|---|---|---|---|---|
| JAK1 | 7.5 nM | 2 uM | 30 uM (IRS-1) | 1 hr |
| JAK2 | 0.8 nM | 2 uM | 4 uM (pEY) | 1 hr |
| JAK3 | 1.5 nM | 2 uM | 4 uM (pEY) | 1 hr |
| TYK2 | 9 nM | 2 uM | 30 uM (IRS-1) | 1 hr |

$IC_{50}$ values are shown in the table below.

| Compound | JAK1 ($IC_{50}$) | JAK2 ($IC_{50}$) | JAK3 ($IC_{50}$) | TYK2 ($IC_{50}$) | Compound | JAK1 ($IC_{50}$) | JAK2 ($IC_{50}$) | JAK3 ($IC_{50}$) | TYK2 ($IC_{50}$) |
|---|---|---|---|---|---|---|---|---|---|
| 8 | A | A | A | A | 9 | A | A | A | A |
| 10 | A | A | A | A | 11 | B | A | A | A |
| 12 | NT | NT | B | NT | 13 | A | A | A | A |
| 14 | NT | NT | A | NT | 15 | A | A | A | A |
| 16 | B | A | A | A | 17 | A | A | A | A |
| 18 | D | B | A | A | 19 | A | A | A | A |
| 20 | B | B | A | A | 21 | A | A | A | A |
| 22 | B | A | A | A | 23 | B | B | A | B |
| 24 | C | B | B | B | 25 | B | B | A | B |
| 26 | B | B | B | B | 27 | A | A | A | A |
| 28 | A | A | A | A | 29 | A | A | A | A |
| 30 | A | A | A | A | 31 | A | A | A | A |
| 34 | B | A | A | A | 35 | A | A | A | A |
| 36 | A | A | A | A | 37 | A | A | A | A |
| 38 | A | A | A | A | 39 | B | B | B | B |
| 40 | A | A | A | A | 41 | A | A | A | A |
| 42 | A | A | A | A | 43 | B | A | A | A |
| 44 | C | B | B | B | 45 | A | A | A | A |
| 46 | A | A | A | A | 47 | A | A | A | A |
| 48 | A | A | A | A | 49 | A | A | A | A |
| 50 | A | A | A | A | 51 | A | A | A | A |
| 52 | B | A | A | A | 55 | B | A | A | B |
| 56 | C | C | C | NT | 57 | C | B | C | NT |
| 58 | NT | NT | C | NT | 60 | NT | NT | A | NT |
| 65 | A | A | A | A | 70 | A | A | A | A |
| 82 | A | A | A | A | 82A | A | A | A | A |
| 82B | A | A | A | A | 83 | A | A | A | A |
| 84 | A | A | A | A | 85 | A | A | A | A |
| 86 | A | A | A | A | 87 | A | A | A | A |
| 88 | A | A | A | A | 89 | A | A | A | A |
| 90 | A | A | A | A | 91 | A | A | A | A |
| 92 | A | A | A | A | 93 | A | A | A | A |
| 94 | A | A | A | A | 95 | B | B | B | NT |
| 96 | B | B | B | B | 97 | A | A | A | A |
| 98 | A | A | A | A | 99 | A | A | A | A |
| 100 | A | A | A | A | 101 | A | A | A | A |
| 102 | A | A | A | A | 103 | A | A | A | A |
| 104 | A | A | A | A | 105 | A | A | A | A |
| 106 | A | A | A | A | 107 | A | A | A | A |
| 108 | A | A | A | A | 109 | A | A | A | A |
| 110 | A | A | A | A | 111 | A | A | A | A |
| 112 | A | A | A | A | 113 | A | A | A | A |
| 114 | A | A | A | A | 115 | A | A | A | A |
| 116 | A | A | A | A | 117 | A | A | A | A |
| 118 | A | A | A | A | 119 | A | A | A | A |
| 120 | A | A | A | A | 121 | A | A | A | A |
| 122 | A | A | A | A | 123 | B | A | NT | A |
| 124 | B | B | NT | B | 125 | C | C | NT | B |
| 126 | B | A | NT | A | 127 | A | A | A | A |
| 128 | C | B | B | B | 129 | B | A | A | A |
| 130 | A | A | A | A | 131 | B | A | A | A |
| 132 | A | A | A | A | 133 | A | A | A | A |
| 134 | A | A | A | A | 135 | A | A | A | A |
| 136 | A | A | A | A | 137 | A | A | A | A |
| 138 | A | A | A | A | 139 | A | A | A | A |
| 140 | A | A | A | A | 141 | A | A | A | A |
| 142 | A | A | A | A | 143 | A | A | A | A |
| 144 | A | A | A | A | 145 | A | A | A | A |
| 146 | A | A | A | A | 147 | A | A | A | A |

A: $IC_{50} < 100$ nM; B: $IC_{50} \geq 100$ nM and $< 1$ uM; C: $IC_{50} \geq 1$ uM and $\leq 10$ uM; D: $IC_{50} > 10$ uM; NT = not tested Example 10: JAK1/JAK3: IL-2 Stimulated STAT5 Phosphorylation in PBMCs Assay Human PBMCs: (Precision Biomedicine)

Thaw as per instructions. Thaw frozen PBMCs in 37° C. water bath. Transfer cell suspension to 9 mL of pre-warmed complete media (RPMI+10% FBS+L-Glu+Pen/Strep). Centrifuge at 400×g for 5 min and wash cells with 10 mL of complete media. Resuspend pellet for acell-count of 3×106 cell s/mL.

Compound and Cytokine Treatment

Seed cells into 96-deep well at 80 uL/well based on experimental plate layout. Add 10 μL of (10× conc.) of different concentrations of compounds to all wells except controls (unstimulated) and mix it with 200 uL multichannel pipet. Add 10 uL of complete RPMI media with same % DMSO in controls. For dilution of compounds and dilution range please refer to appendix. Incubate in 5% $CO_2$ incubator for 1 hour at 37° C. Add 10 μL of (10× conc.) IL-2 (final conc. 50 ng/mL) to each well except unstimulated and unstained controls and incubate further for 20 minutes in water bath at 37° C.

Fixation

Add 900 μL of prewarmed 1× Fix/Lyse solution (Appendix) and mix it properly using 1000 μL multichannel pipet; incubate further on water bath at 37° C. for 10 minutes. Centrifuge at 800×g for 5 minutes, remove 900 uL of supernatant, and add 1000 μL of freshly prepared wash buffer or 1×PBS. Centrifuge at 800×g for 5 minutes, remove 900 μL of supernatant, and resuspend the pellet in remaining buffer.

Permeabilization

Disrupt the pellet by gentle tapping and add 1000 μL of ice cold BD Phosflow Perm Buffer III and incubate further on ice for 30 minutes. Centrifuge at 800×g for 5 minutes. Wash two more times with 1000 μL of BD Stain buffer, remove supernatant except 100 uL of buffer after the last wash.

Antibody Treatment

Disrupt the pellet by gentle tapping, add 100 uL of stain buffer and 5 μL of pSTAT5_Alex488 (pY701) in all appropriate wells and mix properly using 200 μL multichannel pipet. Incubate plate overnight at 40° C. Add 900 μL of BD stain buffer and centrifuge at 800×g for 5 minutes. Wash one additional time with 1000 μL of buffer. Finally resuspend the pellet in 300 uL of BD stain buffer. Transfer the cells to 96-well v-bottom plate and acquire the cells in Beckman Coulter Cytoflex. Acquiring cells in Flow Cytometer: Keep the threshold value to 250. Acquire at least 8,000-10,000 cells.

Preparation of Reagents

RPMI 1640 Complete Medium: RPMI 1640 media+10% FBS.

Cytokine dilution: 1) IL-2 Stock at 100 ug/mL. Prepare a 0.5 ug/mL dilution by adding 5 uL of stock into 995 uL of cRPMI. Keep it on ice until used.

Lyse/Fix buffer preparation: Dilute 5× Lyse/Fix buffer to 1× using MQ water and keep at 37° C. until used.

BD Phosflow perm buffer III: Keep on ice/fridge.

Compound Dilution

| Sample | Final concentration, nM | 10X concentration | Dilution |
|---|---|---|---|
| 1 | 10,000 | 100,000 | 2 µL of 10 mM compound + 198 µL of cRPMI media |
| 2 | 3333.3 | 33,333 | 60 µL of A + 120 µL of cRPMI media |
| 3 | 1111.1 | 11,111 | 60 µL of B + 120 µL of cRPMI media |
| 4 | 370.4 | 3,704 | 60 µL of C + 120 µL of cRPMI media |
| 5 | 123.5 | 1,235 | 60 µL of D + 120 µL of cRPMI media |
| 6 | 41.2 | 412 | 60 µL of E + 120 µL of cRPMI media |
| 7 | 13.7 | 137 | 60 µL of F + 120 µL of cRPMI media |
| 8 | 4.6 | 46 | 60 µL of G + 120 µL of cRPMI media |
| 9 | 0 | 0 | 2 µL of DMSO + 198 µL of cRPMI media |

Example 11: Co-Stimulation Assay in Lysed Whole Blood; JAK2: GM-CSF Stimulated STAT5 Phosphorylation and JAK1/TYK2 Stimulated STAT1 Phosphorylation Assay Human Blood Lysis Using Abcam's RBC Lysis Buffer Dilute RBC lysis buffer to 1× in distilled water. Add 2 mL blood to 38 mL of 1×RBC-lysis buffer. Incubate for 15 mins at RT, in dark. Spin at 300 g, 5 mins, to collect the pellet. Re-lyse if necessary. Re-suspend pellet in 5 mL of cRPMI.

Compound and Cytokine treatment

Aliquot 80 µL of lysed human blood into wells of 96deep-well plate. Add 10 µl of (OX conc.) of different concentrations of compounds to all wells except controls (unstained and unstimulated) and mix it with the help of 100 uL multichannel. Add 10 uL of RPMI media in controls. For dilution of compounds and dilution range please refer Appendix. Incubate on water bath or CO$_2$ incubator for 1 hour at 37° C. Add 10 µl of (10× conc.) of cytokine mix (GM-CSF and IFNa) (final conc. 10 ng/mL of GM-CSF and 100 ng/mL of IFNa) to each well except unstimulated and unstained controls and incubate further for 20 minutes on water bath at 37° C.

RBC Lysis and Fixation

Add 900 µL of prewarmed 1× Fix/Lyse solution (Appendix) and mix it properly using 1000 µl multichannel, incubate further on water bath at 37° C. for 10 minutes (which includes time of addition). Centrifuge at 800×g for 5 minutes at 40° C.; remove 900 uL of supernatant and add 900 µL of 1×PBS. Centrifuge at 800×g for 5 minutes at 40° C., remove 900 L of supernatant. Wash one more time with 900 µL of PBS (optional) and resuspend pellets in 100 uL of PBS.

Permeabilization

Disrupt the pellet by gentle tapping and resuspend in 1000 µL of BD Phosflow Perm Buffer III and incubate plate on ice for 30 minutes. Centrifuge plate at 800×g for 5 minutes at 40° C. Wash two more times with 1000 L of BD Pharmingen Stain Buffer.

Antibody Treatment

Disrupt the pellet by gentle tapping. Resuspend pellets in 100 uL of Stain Buffer and add 5 µL of pSTAT5_AF488 Ab and 5 uL of pSTAT1_PE in all wells except unstained control and mix properly using 200 µl multichannel, incubate overnight at 40° C. Add 900 µL of wash buffer and centrifuge at 1800 rpm for 3 minutes at 40° C. Wash one more time with 1000 µL of BD Pharmingen Stain Buffer. Finally resuspend the pellet in 300 uL of BD Pharmingen Stain Buffer. Transfer the cells to 96-well v-bottom plate and acquire the cells in Beckman Coulter CytExpert. Acquiring cells in Flow Cytometer: Keep the threshold value to 250 and cell concentration should not exceed 100-500 cells/µL. Acquire at least 5,000-10,000 cells.

Preparation of Reagents

RPMI 1640 Complete Medium: RPMI 1640 media+10% FBS.

Cytokine dilution: 1) GM-CSF Stock at 100 ug/mL. Prepare an intermediate dilution of 1 ug/mL by adding 2 uL of stock into 198 uL of cRPMI. Further dilute to 100 ng/mL by adding 100 uL of the intermediate stock to 900 uL of cRPMI. 2) IFNa Stock at 200 ug/mL. Dilute IFNa stock 1:200 by adding 5 uL of stock into the 1000 uL of 100 ng/mL GM-CSF working stock as above to give a combined working stock of 1000 ng/mL of IFNa and 100 ng/mL GM-CSF (10×). Keep it on ice until used.

Lyse/Fix buffer preparation: Dilute 5× Lyse/Fix buffer to 1× using MQ water and keep at 37° C. until used.

BD Phosflow perm buffer III: Keep on ice/fridge.

Compound Dilution

| Sample | Final concentration, nM | 10X concentration, nM | Dilution |
|---|---|---|---|
| 1 | 10,000 | 100,000 | 2 µL of 10 mM compound + 198 µL of cRPMI media |
| 2 | 3333.3 | 33,333 | 60 µL of A + 120 µL of cRPMI media |
| 3 | 1111.1 | 11,111 | 60 µL of B + 120 µL of cRPMI media |
| 4 | 370.4 | 3,704 | 60 µL of C + 120 µL of cRPMI media |
| 5 | 123.5 | 1,235 | 60 µL of D + 120 µL of cRPMI media |
| 6 | 41.2 | 412 | 60 µL of E + 120 µL of cRPMI media |
| 7 | 13.7 | 137 | 60 µL of F + 120 µL of cRPMI media |
| 8 | 4.6 | 46 | 60 µL of G + 120 µL of cRPMI media |
| 9 | 0 | 0 | 2 µL of DMSO + 198 µL of cRPMI media |

The examples and embodiments described herein are for illustrative purposes only and in some embodiments, various modifications or changes are to be included within the purview of disclosure and scope of the appended claims.

What is claimed is:

1. A compound of Formula (I'):

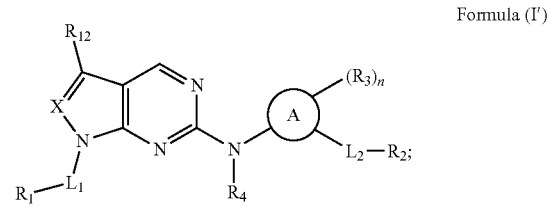

Formula (I')

wherein:

is phenyl or a $C_2$-$C_9$heteroaryl ring;
X is $C(R_{11})$ or N;
$L_1$ is $C_1$-$C_6$alkyl or $C_1$-$C_6$heteroalkyl;
$L_2$ is a bond, $C_1$-$C_6$alkyl, or $C_1$-$C_6$heteroalkyl;
$R_1$ is $C_3$-$C_9$alkyl, $C_2$-$C_6$alkenyl, $C_2$-$C_6$alkynyl, $C_3$-$C_6$cycloalkyl, $C_2$-$C_9$heterocycloalkyl, or $C_2$-$C_9$heteroaryl, wherein $C_3$-$C_9$alkyl, $C_2$-$C_6$alkenyl, $C_2$-$C_6$alkynyl, $C_3$-$C_6$cycloalkyl, $C_2$-$C_9$heterocycloalkyl, or $C_2$-$C_9$heteroaryl are optionally substituted with 1, 2, or 3 $R_5$;
$R_2$ is —C(=O)$OR_6$,

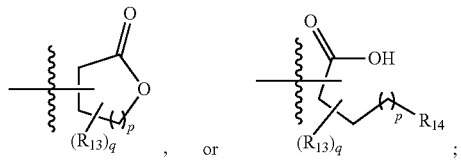

each $R_3$ is independently selected from halogen, $C_1$-$C_6$alkyl, $C_1$-$C_6$haloalkyl, $C_1$-$C_6$heteroalkyl, —$OR_7$, —$N(R_7)_2$, —CN, —C(=O)$R_8$, —C(=O)$OR_7$, —C(=O)$N(R_7)_2$, —$NR_7$C(=O)$R_8$, —$NR_7$S(=O)$_2R_8$, —S(=O)$_2R_8$, and —S(=O)$_2N(R_7)_2$;
$R_4$ is hydrogen, $C_1$-$C_6$alkyl, or $C_1$-$C_6$heteroalkyl;
each $R_5$ is independently selected from halogen, oxo, $C_1$-$C_6$alkyl, $C_1$-$C_6$haloalkyl, $C_1$-$C_6$heteroalkyl, —$OR_7$, —$N(R_7)_2$, —CN, —C(=O)$R_8$, —C(=O)$OR_7$, —C(=O)$N(R_7)_2$, —$NR_7$C(=O)$R_8$, —$NR_7$S(=O)$_2R_8$, —S(=O)$_2R_8$, and —S(=O)$_2N(R_7)_2$;
$R_6$ is hydrogen, $C_1$-$C_6$alkyl optionally substituted with 1 or 2 Y, $C_3$-$C_6$cycloalkyl optionally substituted with 1 or 2 Y, $C_2$-$C_9$heterocycloalkyl optionally substituted with $C_1$-$C_6$alkyl, or —$C_1$-$C_6$alkyl-$C_2$-$C_9$heterocycloalkyl optionally substituted with $C_1$-$C_6$alkyl;
each Y is independently selected from —CN, —$OR_9$, —$SR_9$, and —$N(R_{10})_2$;
each $R_7$ is independently selected from hydrogen, $C_1$-$C_6$alkyl, $C_2$-$C_6$alkenyl, $C_1$-$C_6$haloalkyl, and $C_1$-$C_6$heteroalkyl;
each $R_8$ is independently selected from $C_1$-$C_6$alkyl, $C_2$-$C_6$alkenyl, $C_1$-$C_6$heteroalkyl, $C_3$-$C_6$cycloalkyl, and $C_2$-$C_9$heterocycloalkyl;
each $R_9$ is independently selected from hydrogen and $C_1$-$C_6$alkyl;
each $R_{10}$ is independently selected from hydrogen and $C_1$-$C_6$alkyl;
$R_{11}$ is hydrogen or $C_1$-$C_6$alkyl optionally substituted with 1, 2, or 3 $R_5$;
$R_{12}$ is hydrogen, halogen, or $C_1$-$C_6$alkyl;
$R_{13}$ is $C_1$-$C_6$alkyl;
$R_{14}$ is —OH, —C(=O)H, or —C(=O)$OR_{15}$;
$R_{15}$ is hydrogen or $C_1$-$C_6$alkyl;
n is 0, 1, 2, or 3;
p is 0, 1, or 2; and
q is 0, 1, or 2;
or a pharmaceutically acceptable salt or solvate thereof.

2. The compound of claim 1 or a pharmaceutically acceptable salt or solvate thereof, wherein

is a $C_2$-$C_9$heteroaryl ring.

3. The compound of claim 2, or a pharmaceutically acceptable salt or solvate thereof, wherein

is selected from pyrazolyl, pyrrolyl, and imidazolyl.

4. The compound of claim 3, or a pharmaceutically acceptable salt or solvate thereof, wherein

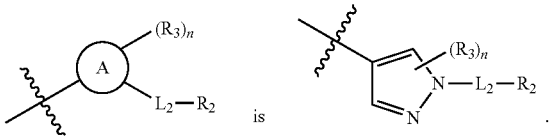

5. The compound of claim 1 or a pharmaceutically acceptable salt or solvate thereof, wherein $L_2$ is $C_1$-$C_6$alkyl.

6. The compound of claim 1 or a pharmaceutically acceptable salt or solvate thereof, wherein $L_1$ is $C_1$-$C_6$alkyl.

7. The compound of claim 1 or a pharmaceutically acceptable salt or solvate thereof, wherein $R_1$ is $C_3$-$C_9$alkyl, $C_3$-$C_6$cycloalkyl, or $C_2$-$C_9$heteroaryl, wherein $C_3$-$C_9$alkyl, $C_3$-$C_6$cycloalkyl, or $C_2$-$C_9$heteroaryl are optionally substituted with 1, 2, or 3 $R_5$ and the $C_2$-$C_9$heteroaryl is selected from oxazolyl, thiazolyl, pyrazolyl, furanyl, thienyl, pyrrolyl, imidazolyl, triazolyl, tetrazolyl, isoxazolyl, isothiazolyl, oxadiazolyl, and thiadiazolyl.

8. The compound of claim 7 or a pharmaceutically acceptable salt or solvate thereof, wherein $R_1$ is unsubstituted $C_3$-$C_9$alkyl, unsubstituted $C_3$-$C_6$cycloalkyl, or unsubstituted $C_2$-$C_9$heteroaryl.

9. The compound of claim 1 or a pharmaceutically acceptable salt or solvate thereof, wherein $R_4$ is hydrogen.

10. The compound of claim 1 or a pharmaceutically acceptable salt or solvate thereof, wherein $R_{12}$ is hydrogen.

11. The compound of claim 1 or a pharmaceutically acceptable salt or solvate thereof, wherein n is 0.

12. The compound of claim 1, or a pharmaceutically acceptable salt or solvate thereof, wherein X is C(H).

13. The compound of claim 1, or a pharmaceutically acceptable salt or solvate thereof, wherein $R_2$ is —C(=O)$OR_6$.

14. The compound of claim 13, or a pharmaceutically acceptable salt or solvate thereof, wherein $R_6$ is unsubstituted $C_1$-$C_6$alkyl.

15. The compound of claim 1 or a pharmaceutically acceptable salt or solvate thereof, wherein $R_2$ is
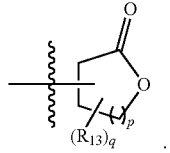
16. The compound of claim 1 or a pharmaceutically acceptable salt or solvate thereof, wherein $R_2$ is
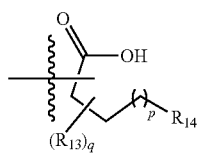
17. A compound selected from:
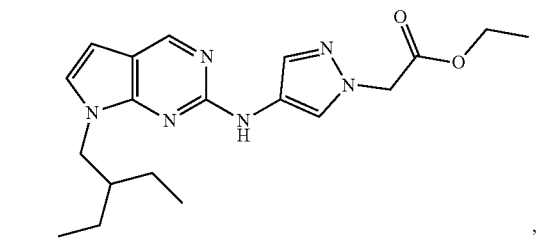
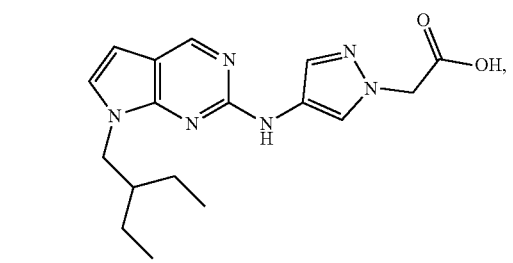
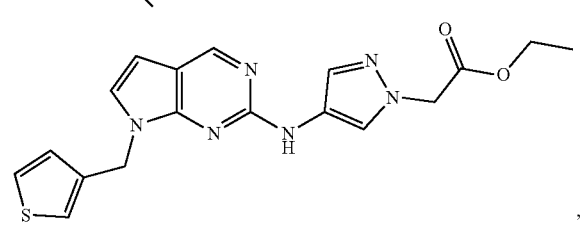
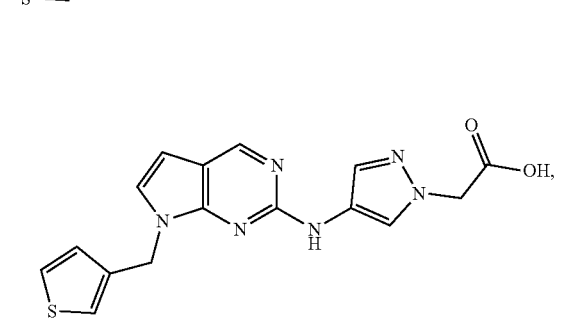
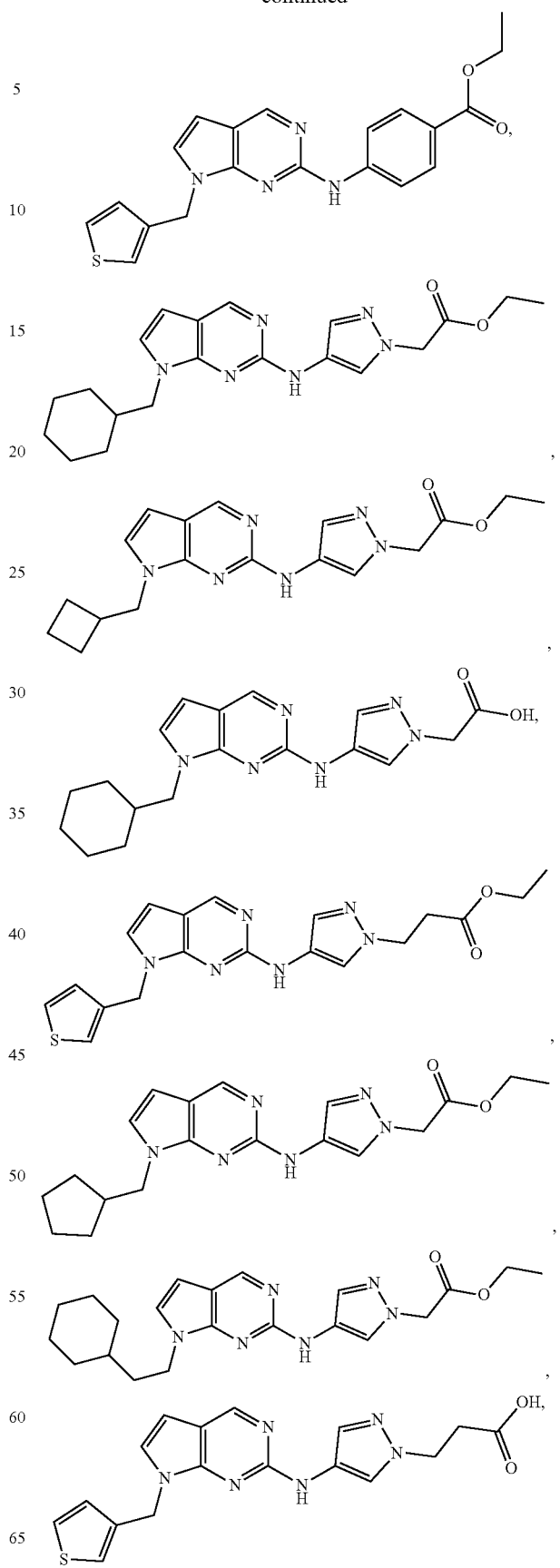

165
-continued
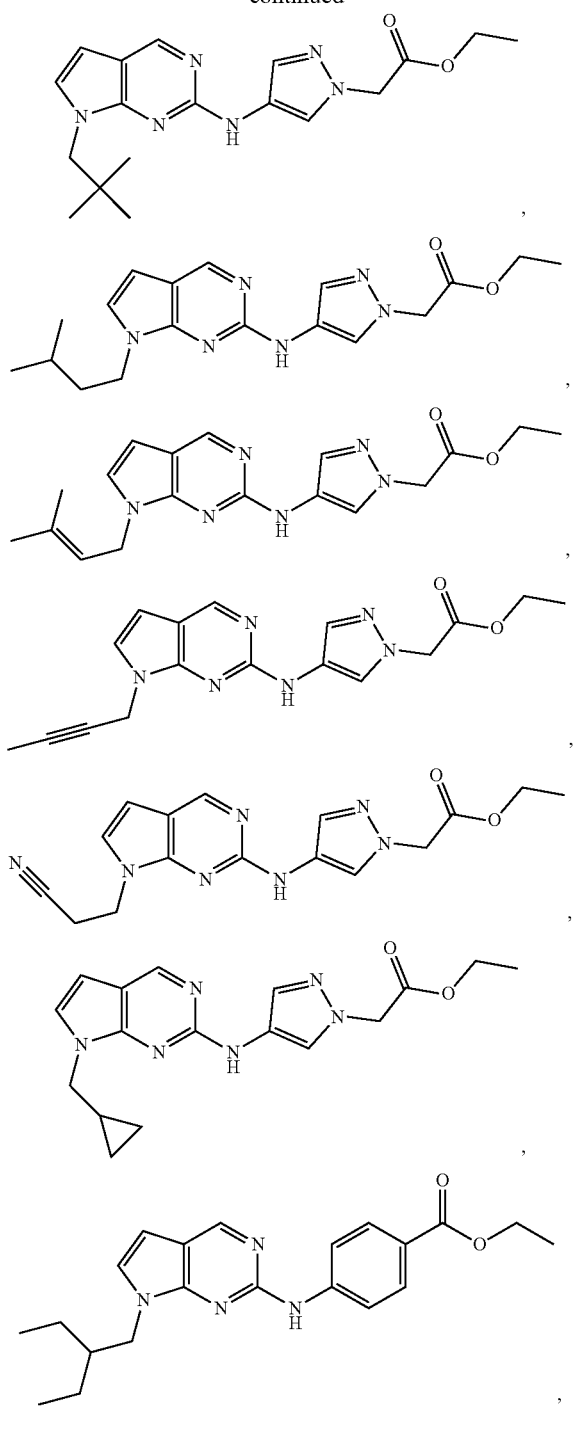
166
-continued
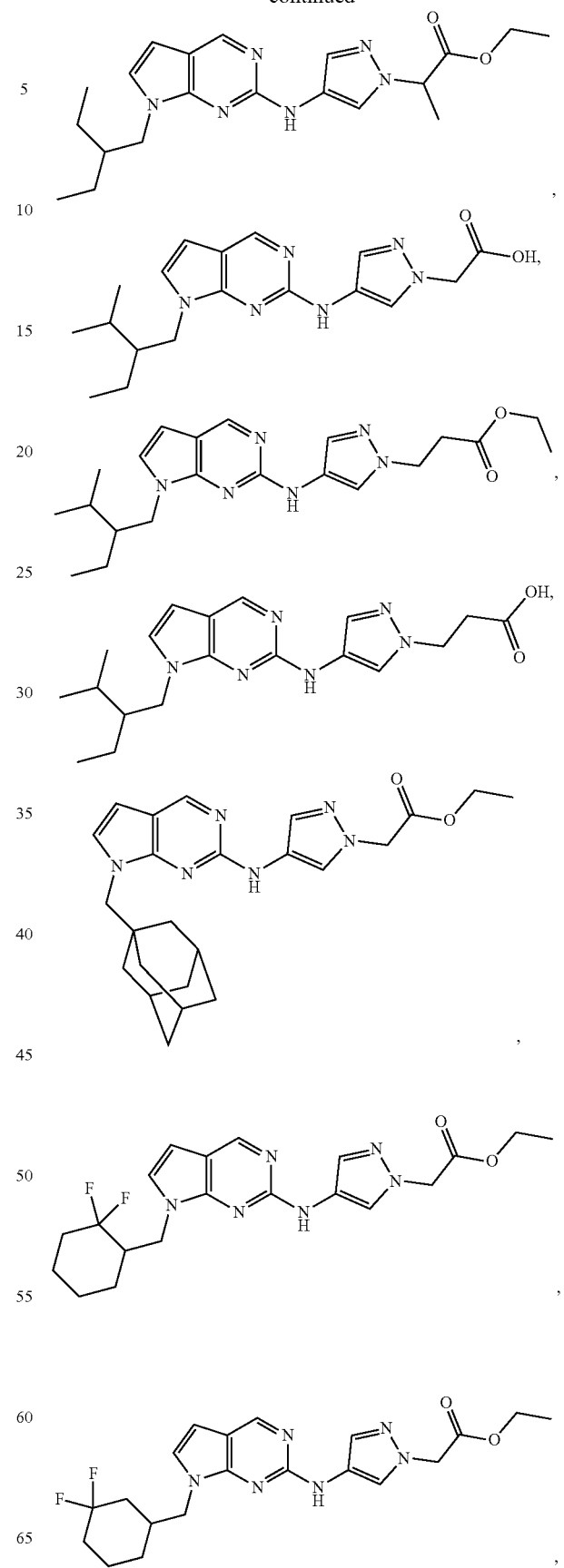

167
-continued
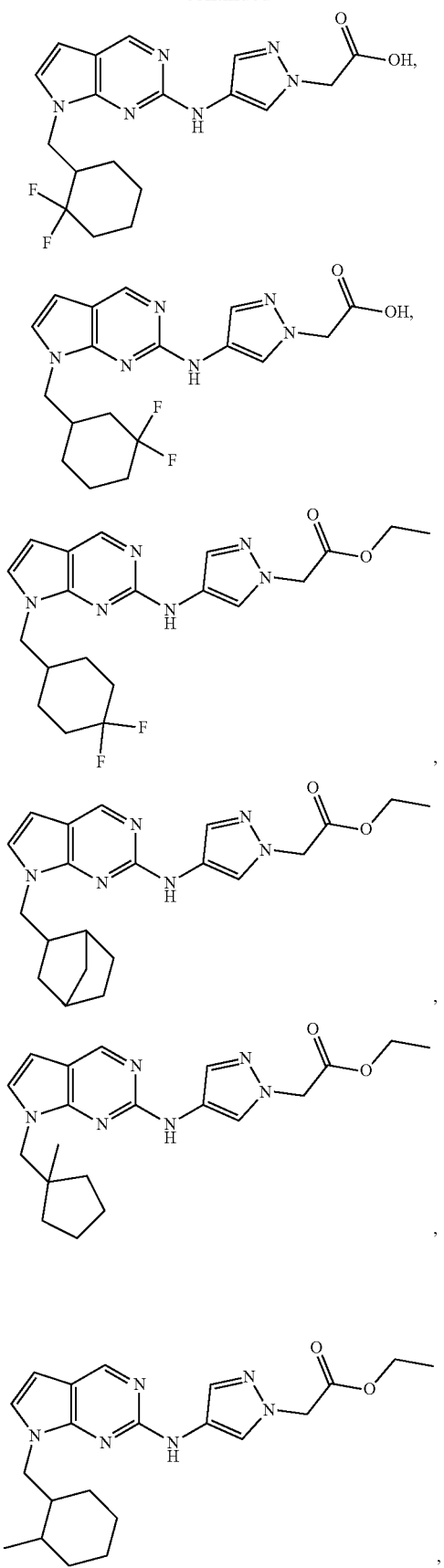
168
-continued
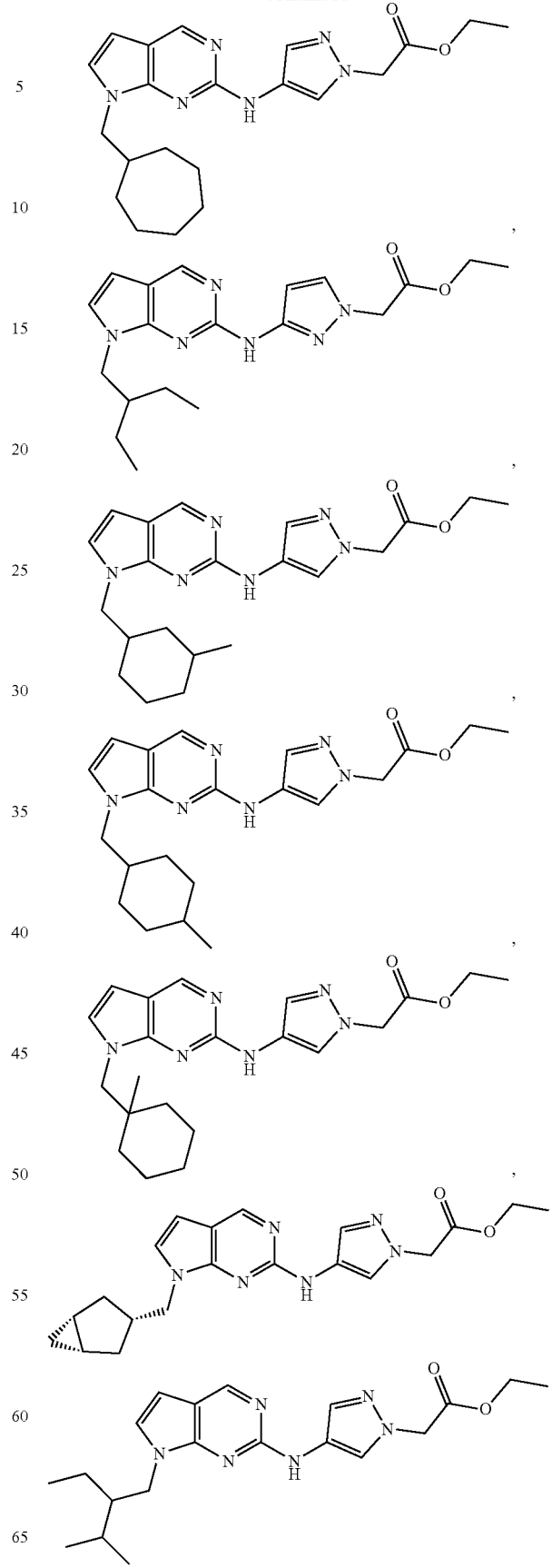

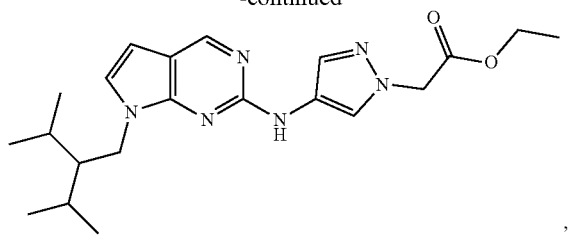,
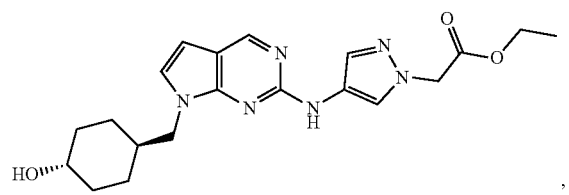,
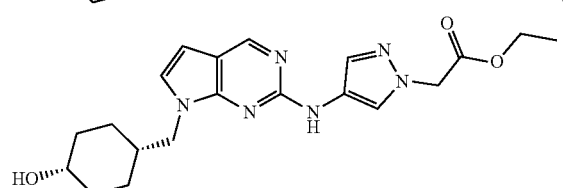,
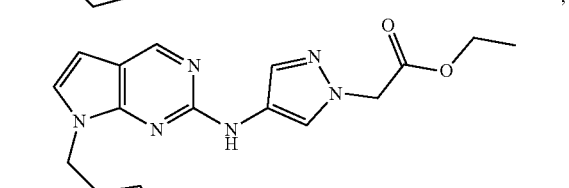,
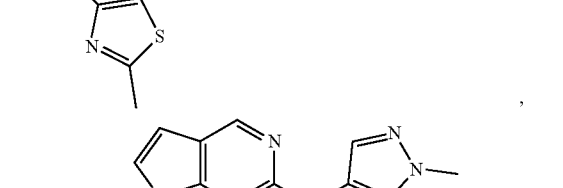,
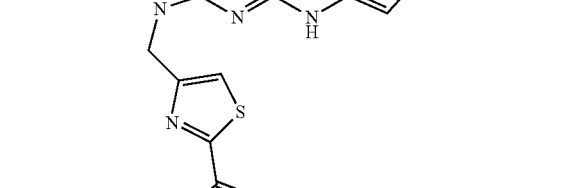,
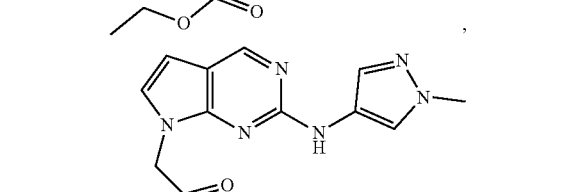,
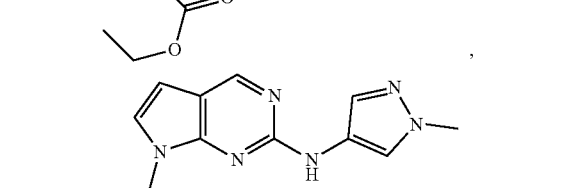,
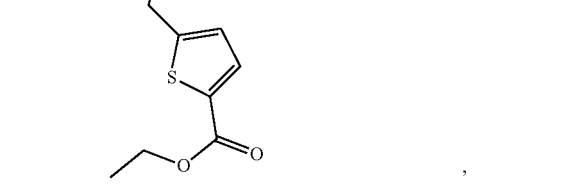,
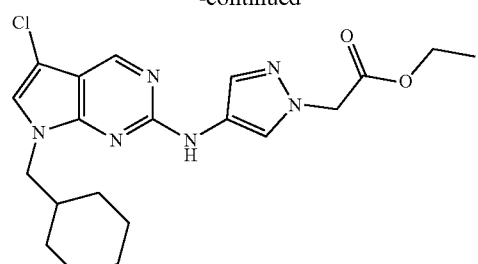,
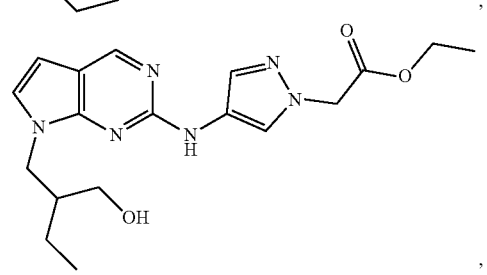,
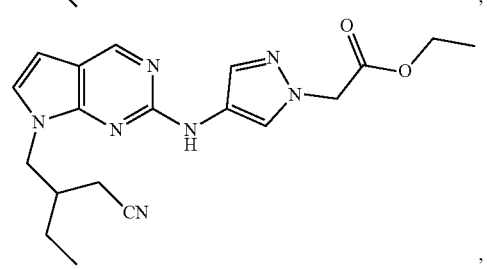,
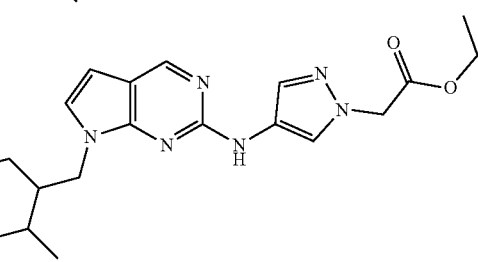,
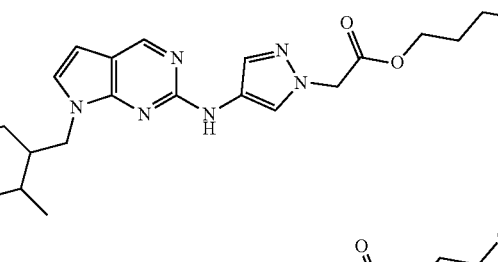,
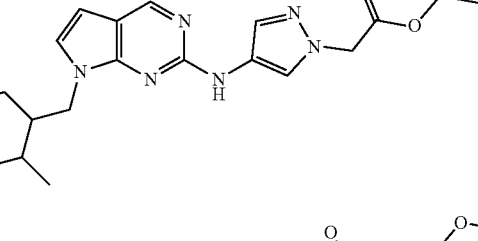,
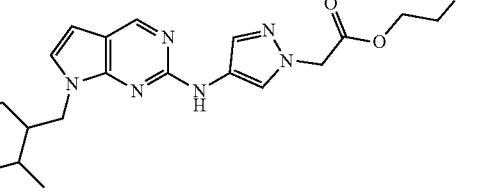, 171
-continued
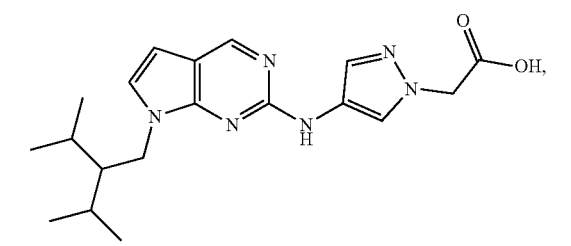
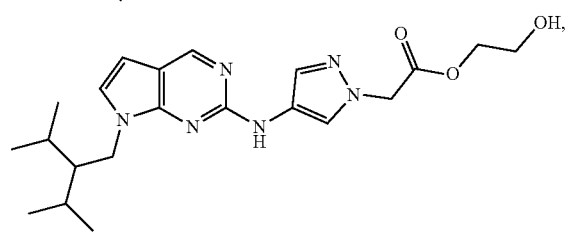
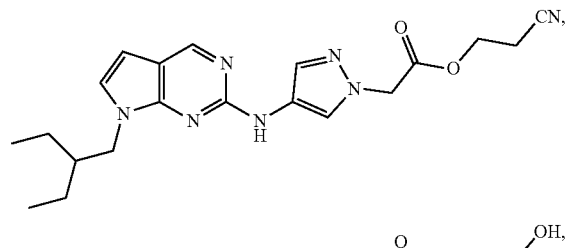
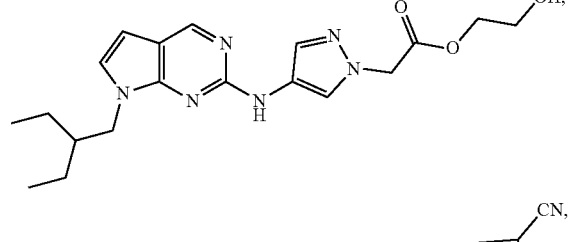
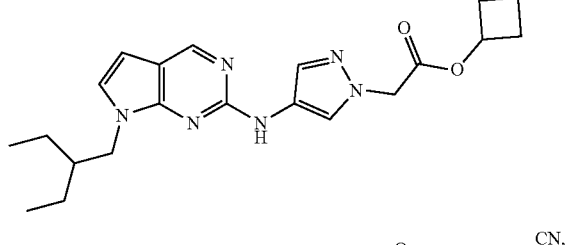
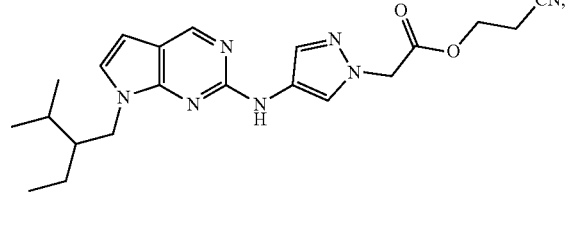
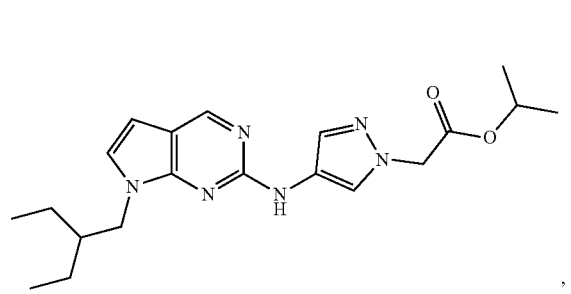
172
-continued
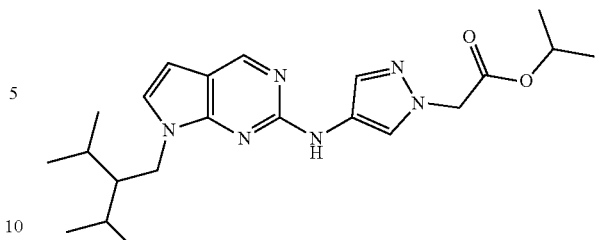
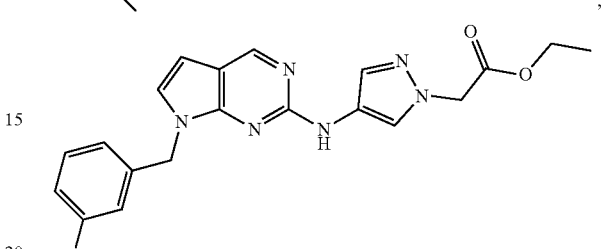
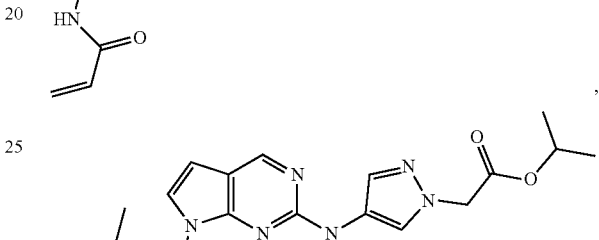
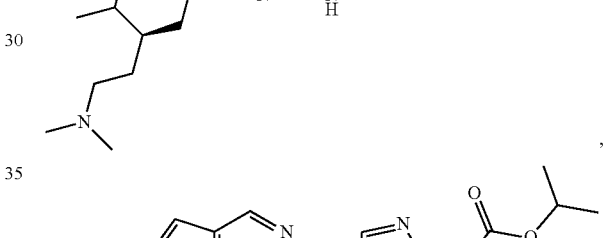
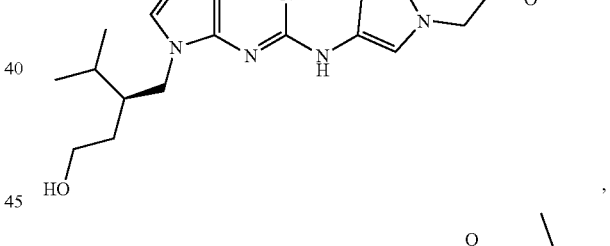
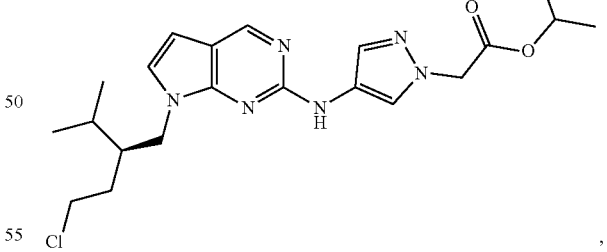
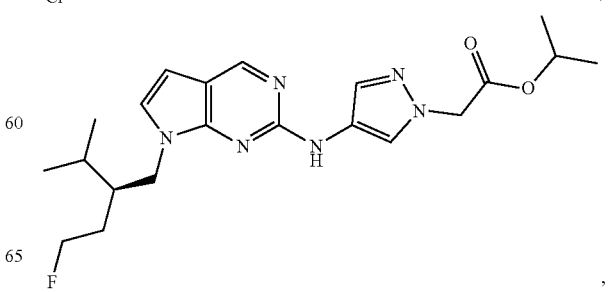

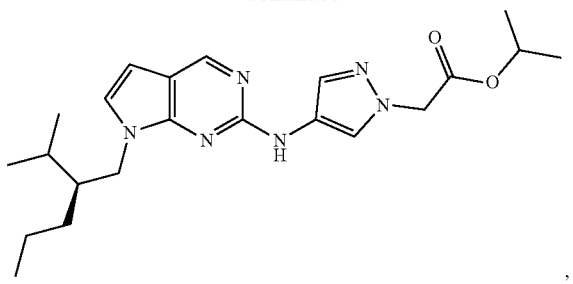
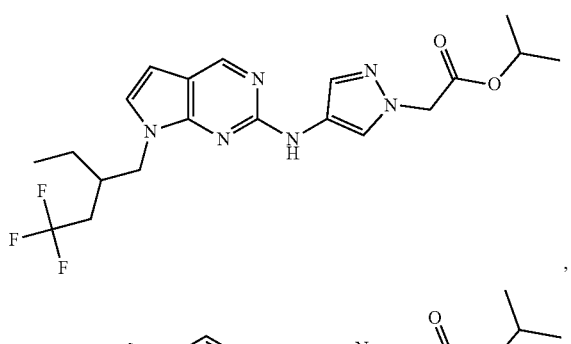
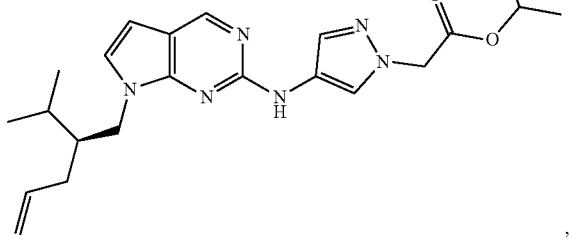
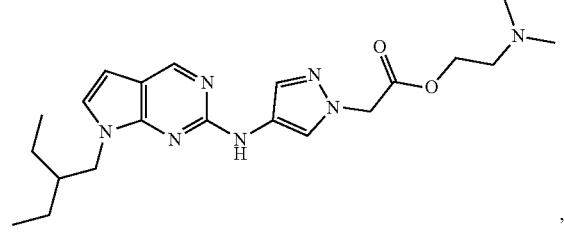
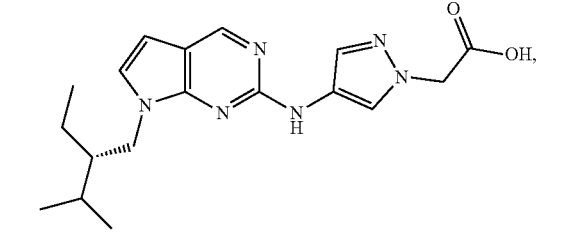
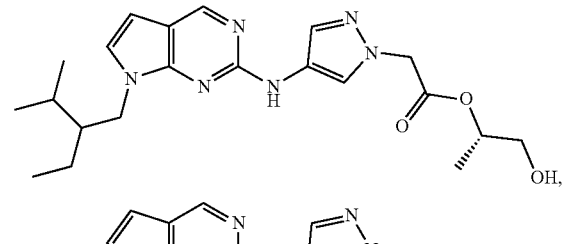
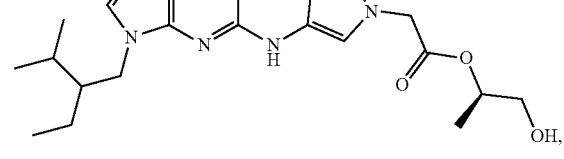
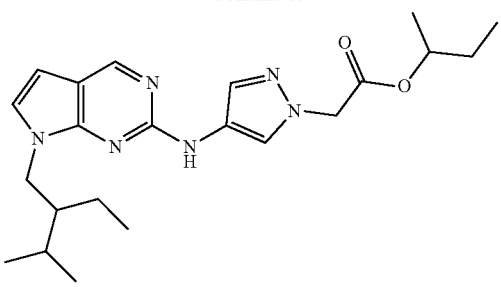
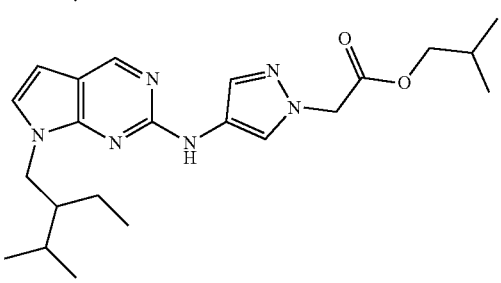
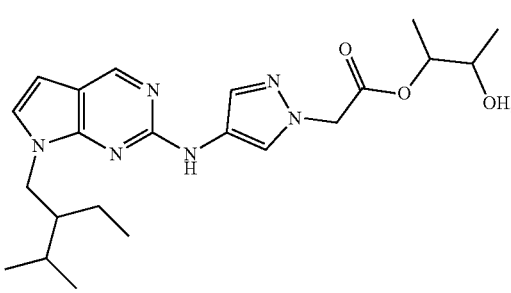
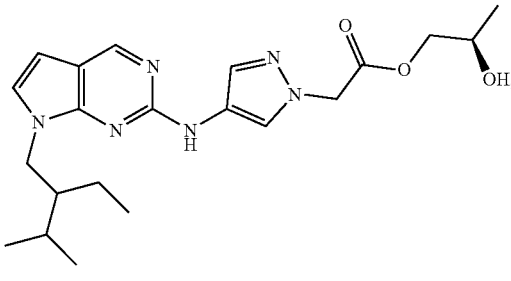
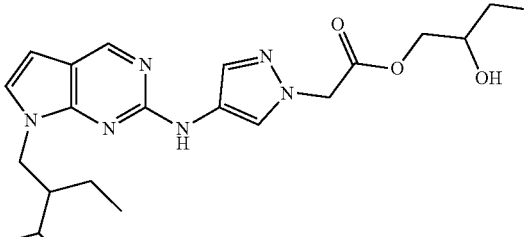
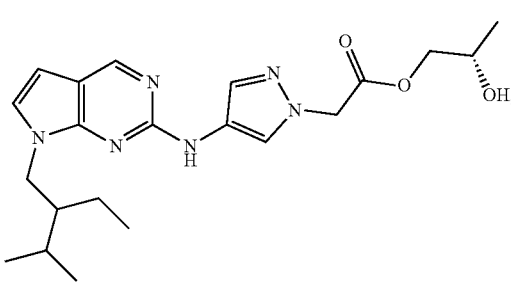

175
-continued
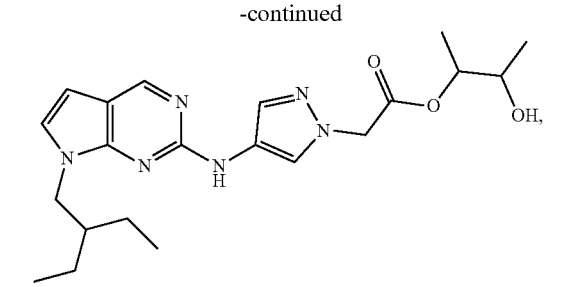
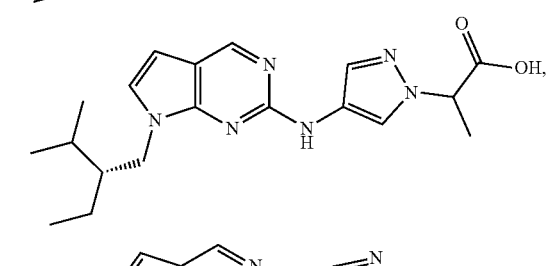
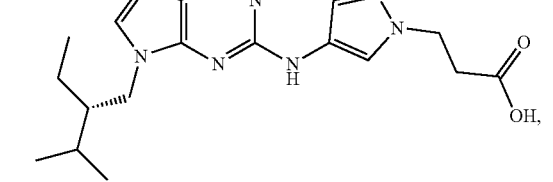
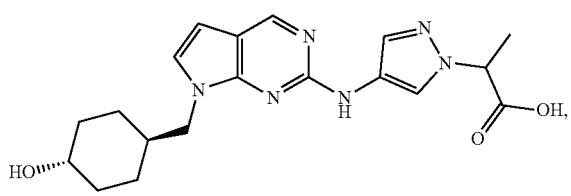
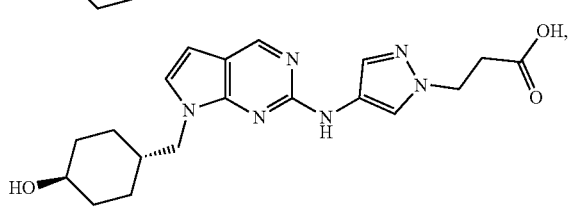
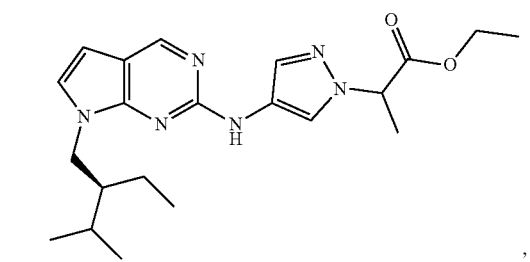
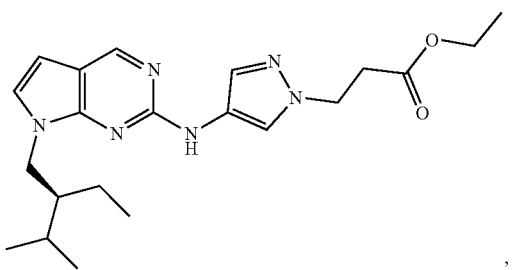
176
-continued
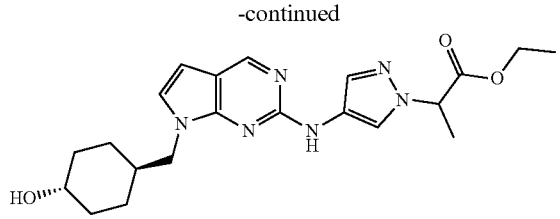
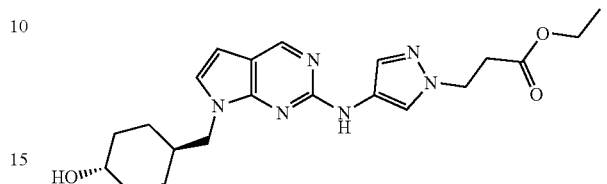
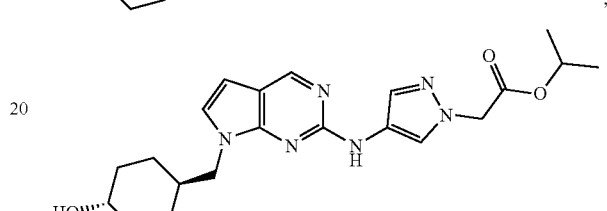
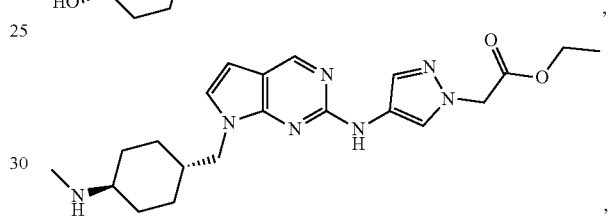
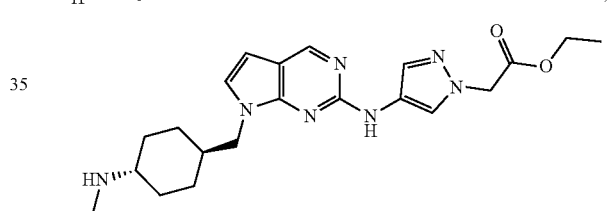
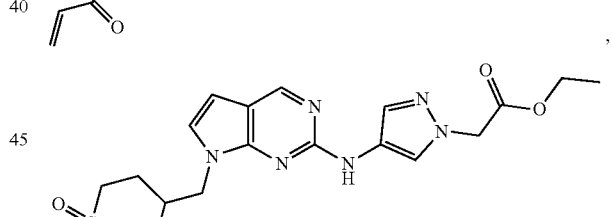
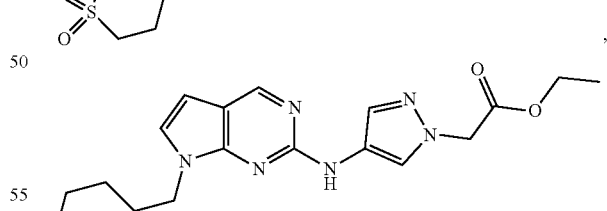
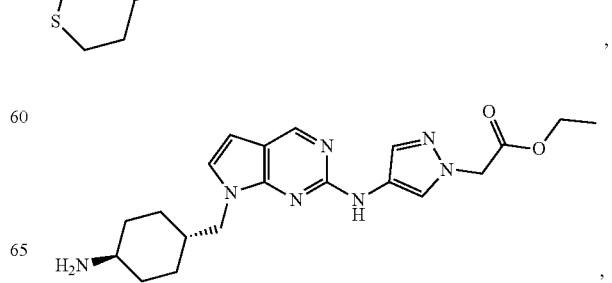

177
-continued
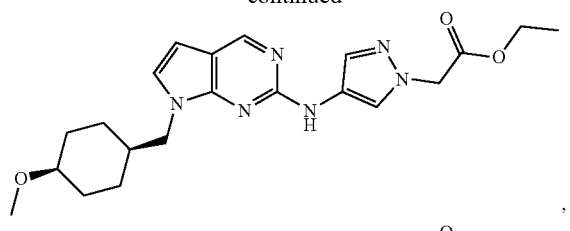
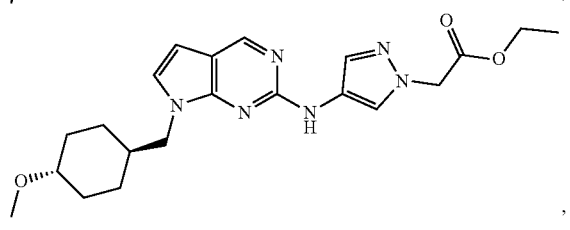
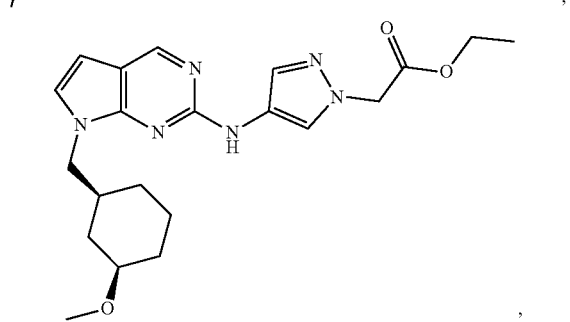
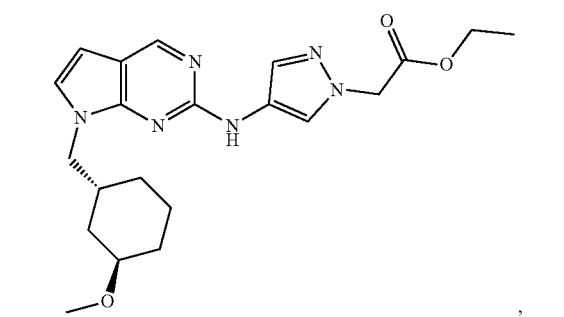
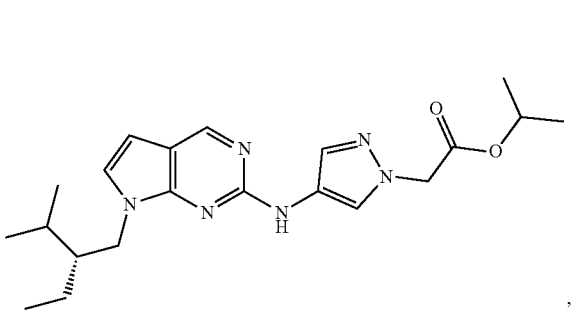
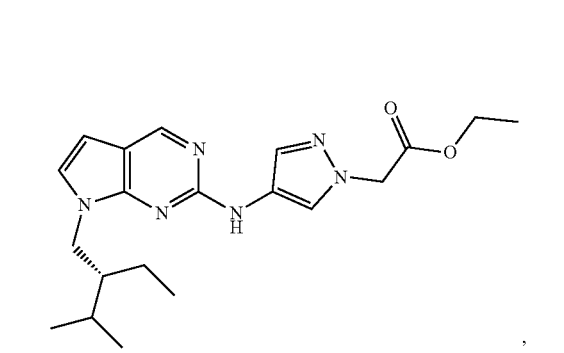
178
-continued
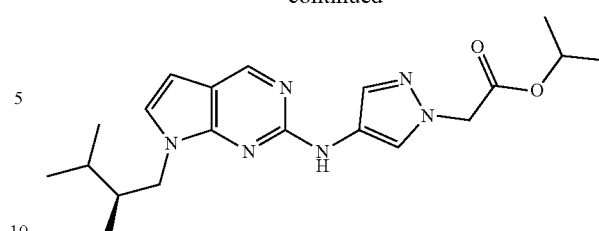
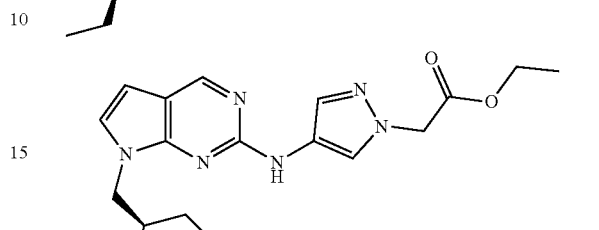
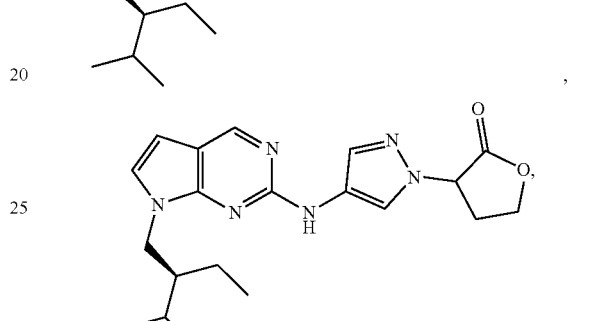
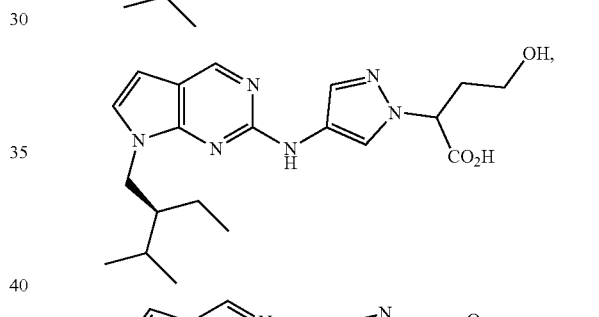
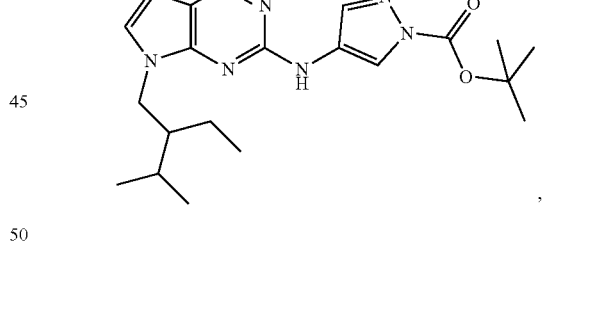
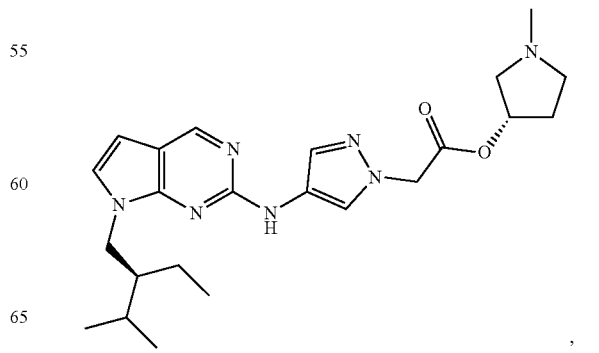

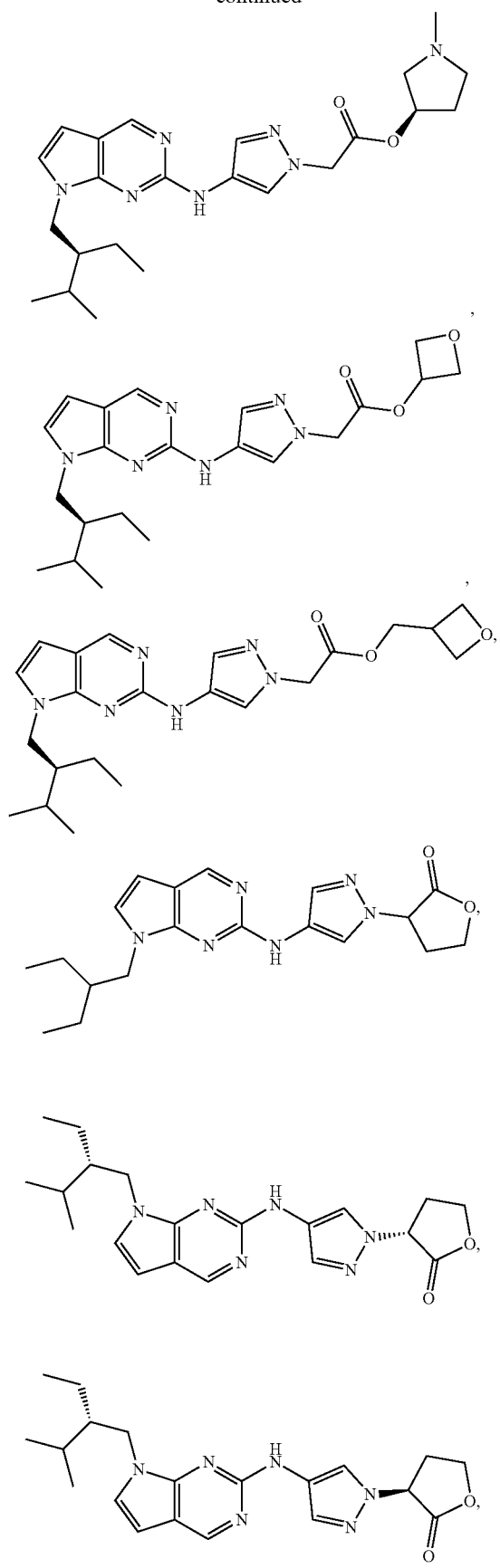
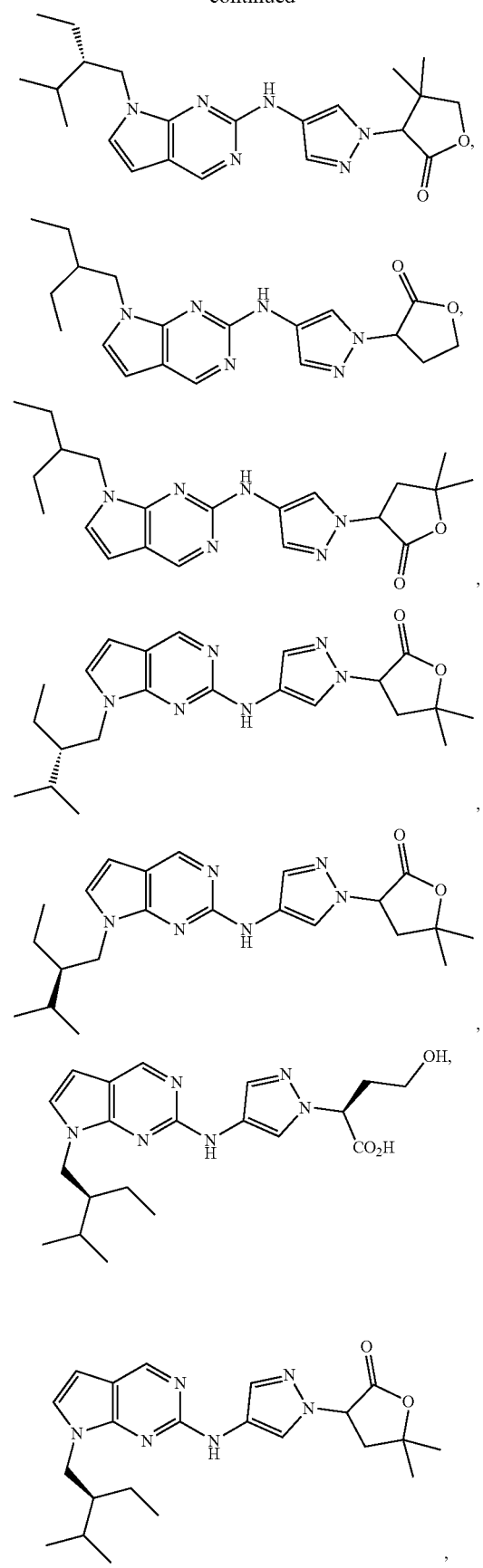

181
-continued

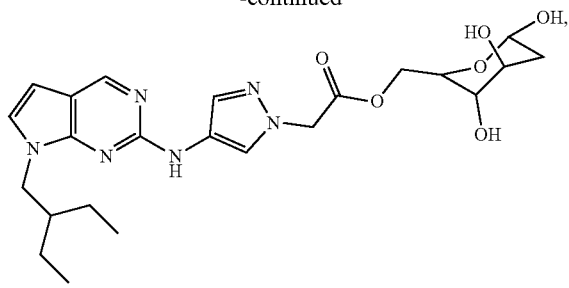

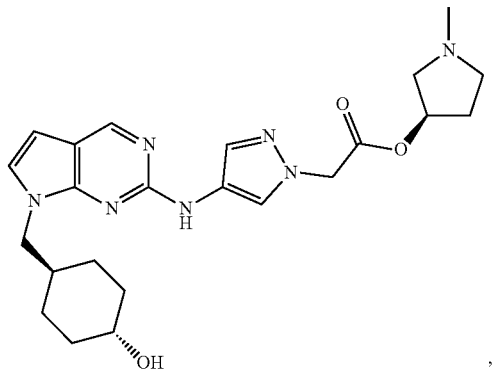
, and

182
-continued

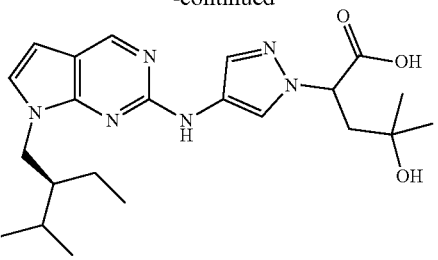
;

or a pharmaceutically acceptable salt or solvate thereof.

18. A pharmaceutical composition comprising a compound of claim 1 or a pharmaceutically acceptable salt or solvate thereof, and a pharmaceutically acceptable excipient.

19. A method of treating an inflammatory or autoimmune disease in a patient in need thereof, comprising administering to the patient a therapeutically effective amount of a compound of claim 1, or a pharmaceutically acceptable salt or solvate thereof; wherein the inflammatory or autoimmune disease is selected from rheumatoid arthritis, multiple sclerosis, psoriasis, lupus, intestinal bowel disease, Crohn's disease, ulcerative colitis, ankylosing spondylitis, vitiligo, and atopic dermatitis.

* * * * *